United States Patent
Ahmad et al.

(10) Patent No.: US 9,636,044 B2
(45) Date of Patent: May 2, 2017

(54) BREATH ANALYZER WITH EXPANDABLE RANGE OF MEASUREMENT

(71) Applicant: INVOY TECHNOLOGIES, LLC, Chandler, AZ (US)

(72) Inventors: Lubna M. Ahmad, Chandler, AZ (US); Zachary Smith, Phoenix, AZ (US); Salman A. Ahmad, Chandler, AZ (US); Brent C. Satterfield, Bountiful, UT (US); Rhett L. Martineau, Chandler, AZ (US)

(73) Assignee: Invoy Technologies, LLC, Aliso Viejo, CA (US)

( * ) Notice: Subject to any disclaimer, the term of this patent is extended or adjusted under 35 U.S.C. 154(b) by 1 day.

(21) Appl. No.: 15/040,838

(22) Filed: Feb. 10, 2016

(65) Prior Publication Data
US 2016/0345910 A1    Dec. 1, 2016

Related U.S. Application Data

(63) Continuation-in-part of application No. 14/206,347, filed on Mar. 12, 2014, which is a continuation of
(Continued)

(51) Int. Cl.
| | | |
|---|---|---|
| *A61B 5/097* | (2006.01) | |
| *A61B 5/08* | (2006.01) | |
| *A61B 5/00* | (2006.01) | |

(52) U.S. Cl.
CPC ............ *A61B 5/097* (2013.01); *A61B 5/0059* (2013.01); *A61B 5/082* (2013.01); *A61B 5/742* (2013.01);
(Continued)

(58) Field of Classification Search
CPC ....... A61B 5/7246; A61B 5/097; A61B 5/082; A61B 5/742; A61B 2560/0223
See application file for complete search history.

(56) References Cited

U.S. PATENT DOCUMENTS

| | | |
|---|---|---|
| 4,278,636 A | 7/1981 | Voigt et al. |
| 4,789,526 A | 12/1988 | Matkovich |

(Continued)

FOREIGN PATENT DOCUMENTS

| | | | |
|---|---|---|---|
| WO | WO 2005/082234 | 9/2005 | |
| WO | WO 2013115933 A1 * | 8/2013 | ............ A61B 5/0059 |
| WO | WO 2013160424 A1 * | 10/2013 | ............ G01N 21/274 |

OTHER PUBLICATIONS

International Search Report dated Jun. 17, 2013 from corresponding International Application No. PCT/US2013/000026 filed Feb. 1, 2013, 3 pages.
(Continued)

*Primary Examiner* — Meredith Weare
(74) *Attorney, Agent, or Firm* — Knobbe, Martens, Olson & Bear, LLP

(57) ABSTRACT

A method for extending an effective working range of an analyzer for measuring an analyte in a breath sample. The method includes initiating a reaction in the analyzer that produces an optically discernable reaction product having an optical property that is indicative of a concentration of the analyte in the breath sample, taking a first reading of the optical property at a first time, and comparing the first reading to a reference. If the comparison yields a first state, the method includes determining the concentration using the first reading. If it yields a second state different from the first state, the method includes taking a second reading of the optical property at a second time, and determining the
(Continued)

concentration of the analyte using the second reading. Other methods are provided as well.

23 Claims, 85 Drawing Sheets

Related U.S. Application Data application No. PCT/US2013/000026, filed on Feb. 1, 2013.

(60) Provisional application No. 61/593,862, filed on Feb. 1, 2012, provisional application No. 61/800,081, filed on Mar. 15, 2013, provisional application No. 62/173,958, filed on Jun. 11, 2015.

(52) U.S. Cl.
CPC ..... *A61B 5/7475* (2013.01); *A61B 2560/0223* (2013.01); *A61B 2560/0242* (2013.01); *A61B 2562/08* (2013.01)

(56) References Cited

U.S. PATENT DOCUMENTS

| | | | |
|---|---|---|---|
| 4,947,339 A | 8/1990 | Czekajewski et al. | |
| 5,174,959 A | 12/1992 | Kundu et al. | |
| 5,451,214 A | 9/1995 | Hajishoreh | |
| 6,609,068 B2 | 8/2003 | Cranley et al. | |
| 6,723,289 B2 | 4/2004 | Iheme et al. | |
| 7,364,551 B2 | 4/2008 | Allen et al. | |
| 7,533,558 B2 | 5/2009 | Flaherty et al. | |
| 7,837,936 B1 | 11/2010 | Martin | |
| 7,992,422 B2 | 8/2011 | Leddy et al. | |
| 8,181,502 B2 | 5/2012 | Loodberg | |
| 2004/0017570 A1 | 1/2004 | Parikh | |
| 2005/0083527 A1 | 4/2005 | Flaherty et al. | |
| 2007/0048756 A1 | 3/2007 | Mei et al. | |
| 2007/0116752 A1 | 5/2007 | Chowdhury | |
| 2007/0245810 A1 | 10/2007 | Carter et al. | |
| 2007/0261472 A1 | 11/2007 | Flaherty et al. | |
| 2008/0004542 A1 | 1/2008 | Allen et al. | |
| 2008/0064975 A1 | 3/2008 | Hancock et al. | |
| 2008/0110562 A1 | 5/2008 | Mayer | |
| 2009/0076738 A1* | 3/2009 | Kayihan | G01N 27/3273 702/25 |
| 2009/0188794 A1 | 7/2009 | Simon et al. | |
| 2009/0260418 A1 | 10/2009 | Flaherty et al. | |
| 2010/0268200 A1 | 10/2010 | Banister et al. | |
| 2011/0098590 A1 | 4/2011 | Garbutt et al. | |
| 2012/0071737 A1 | 3/2012 | Landini et al. | |
| 2012/0094387 A1 | 4/2012 | Haas et al. | |
| 2012/0231548 A1 | 9/2012 | Akers, Jr. | |
| 2012/0302907 A1 | 11/2012 | Palmskog et al. | |
| 2014/0276100 A1* | 9/2014 | Satterfield | A61B 5/082 600/476 |
| 2015/0044780 A1* | 2/2015 | Kurz | G01N 21/274 436/501 |

OTHER PUBLICATIONS

International Preliminary Report on Patentability dated Jun. 17, 2013 from corresponding International Application No. PCT/US2013/000026 filed Feb. 1, 2013, 6 pages.

Written Opinion of the International Searching Authority dated Jun. 17, 2013 from corresponding International Application No. PCT/US2013/000026 filed Feb. 1, 2013, 5 pages.

* cited by examiner

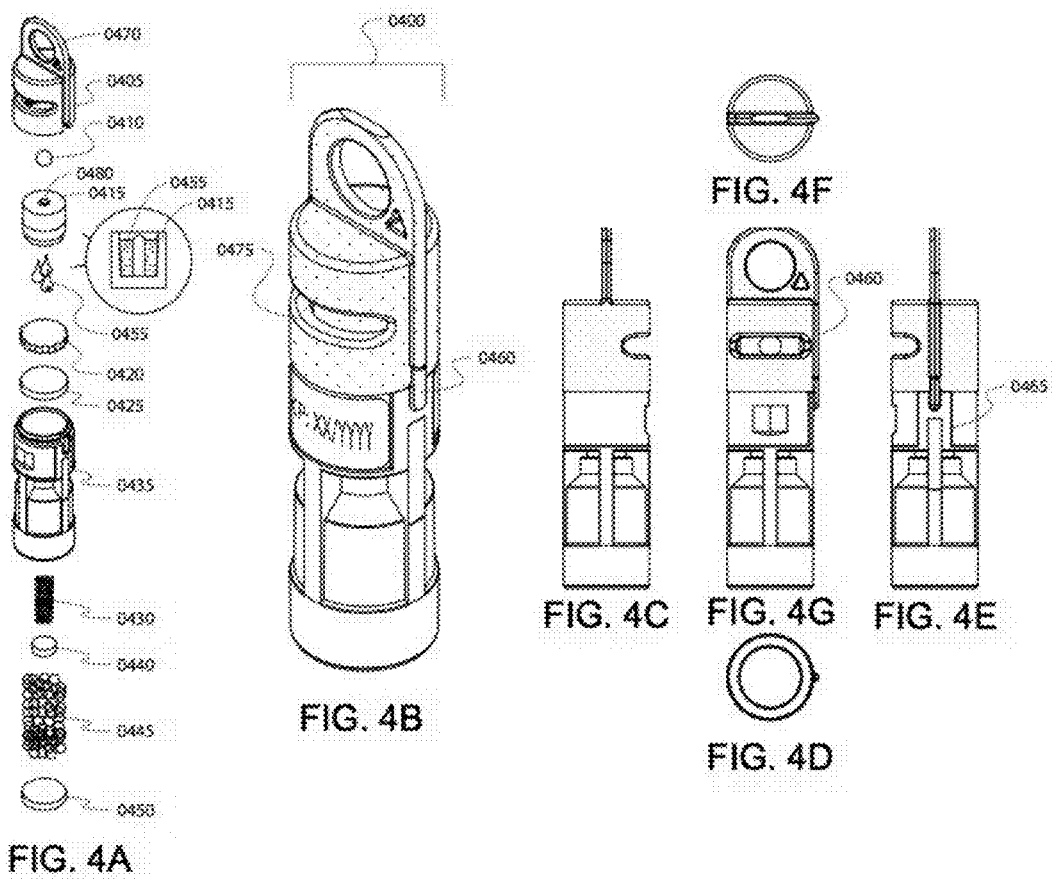

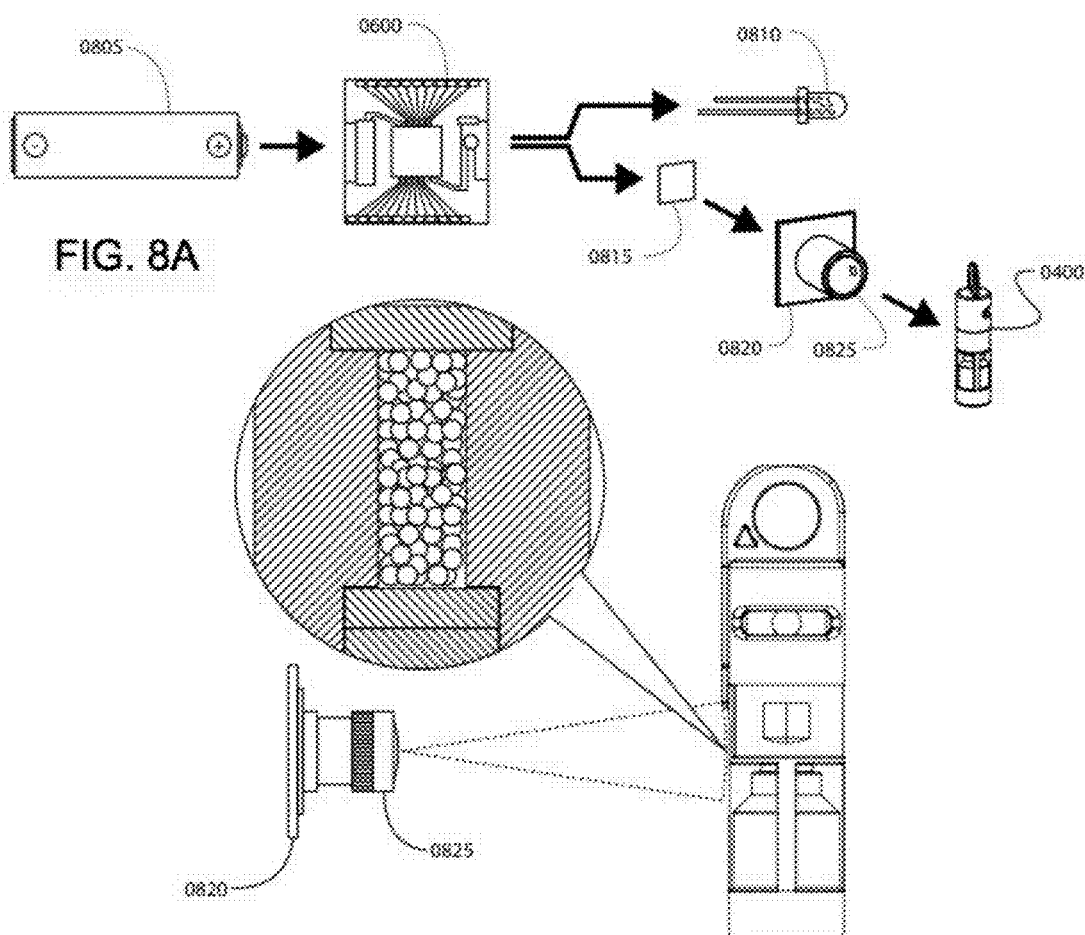

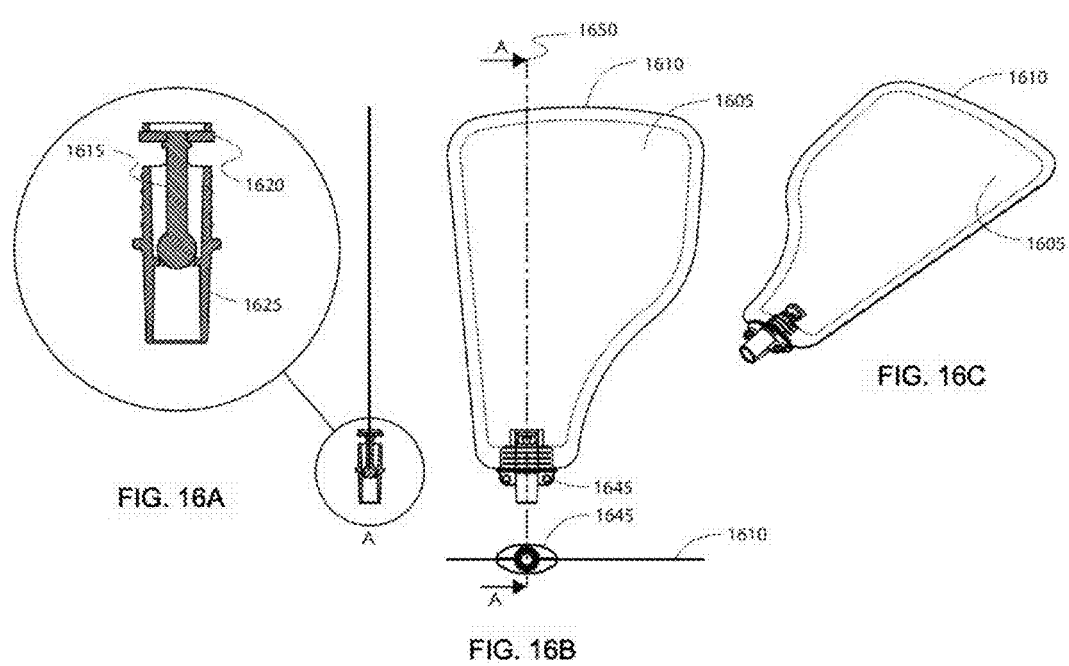

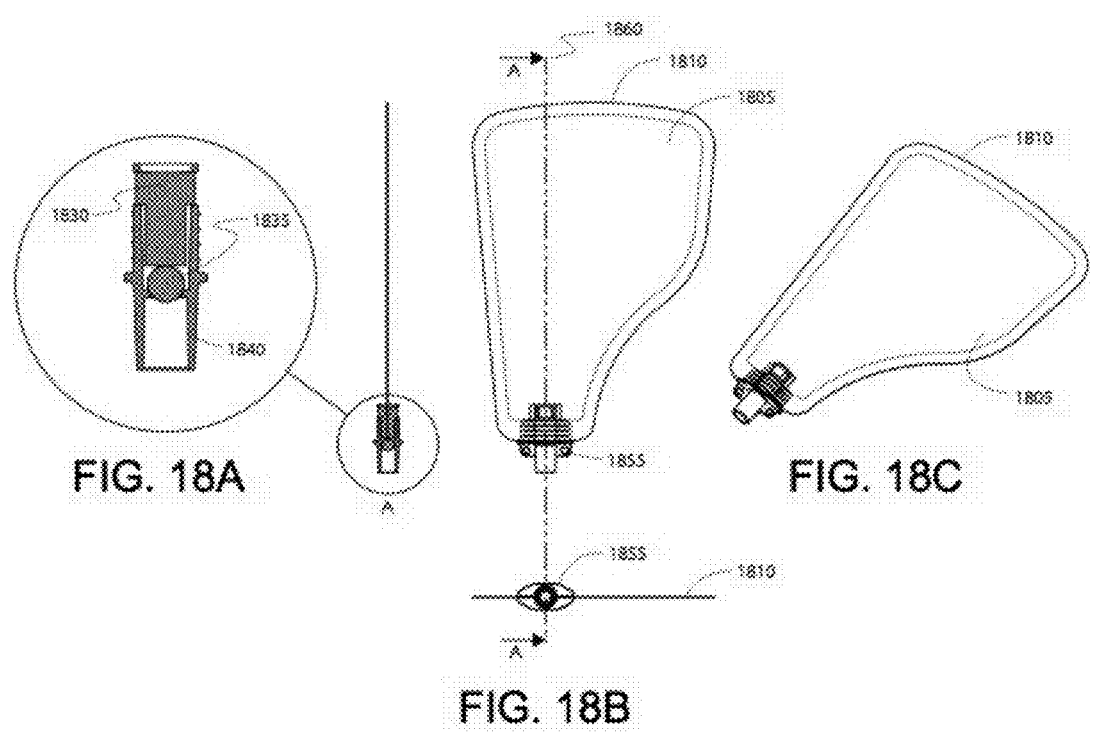

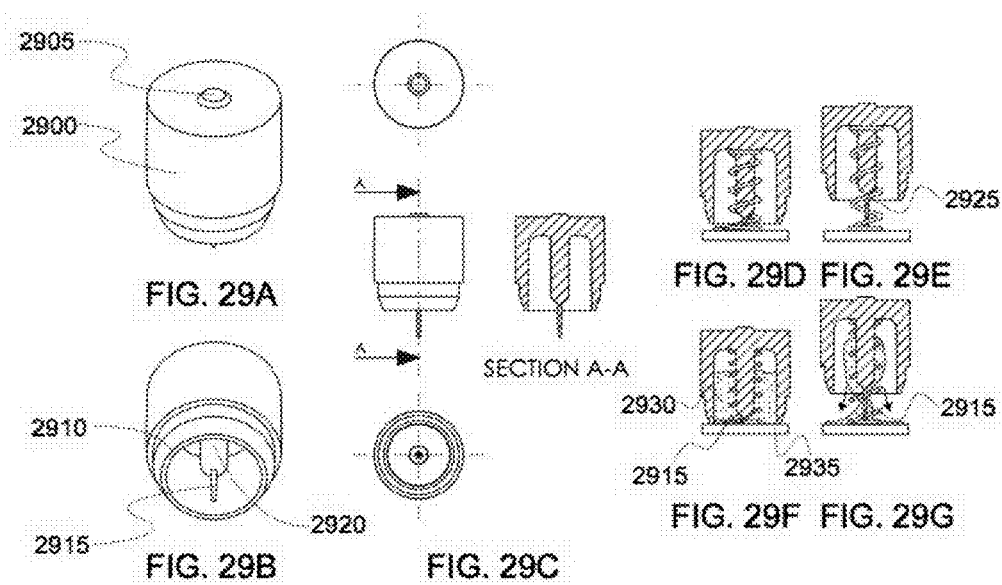

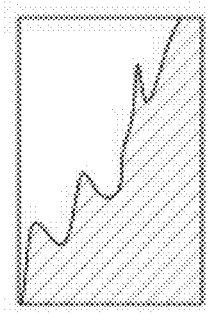 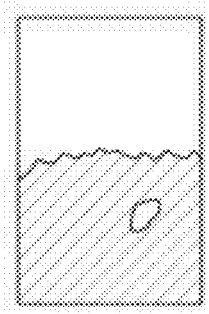 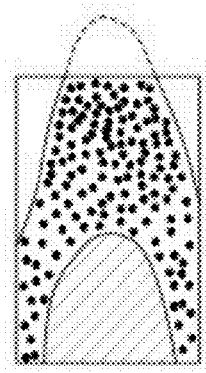
FIG. 50A      FIG. 50B      FIG. 50C
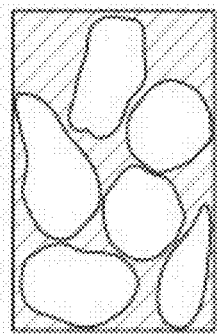 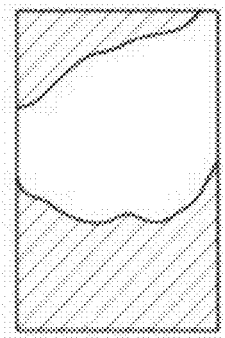
FIG. 50D      FIG. 50E

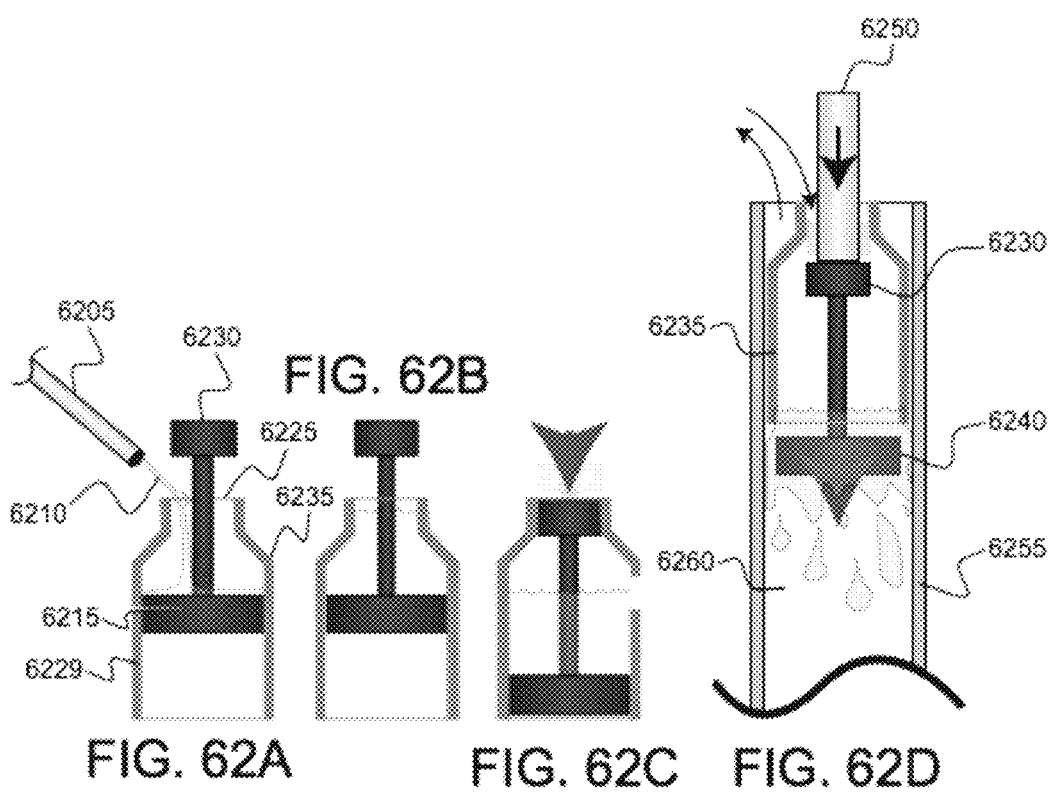

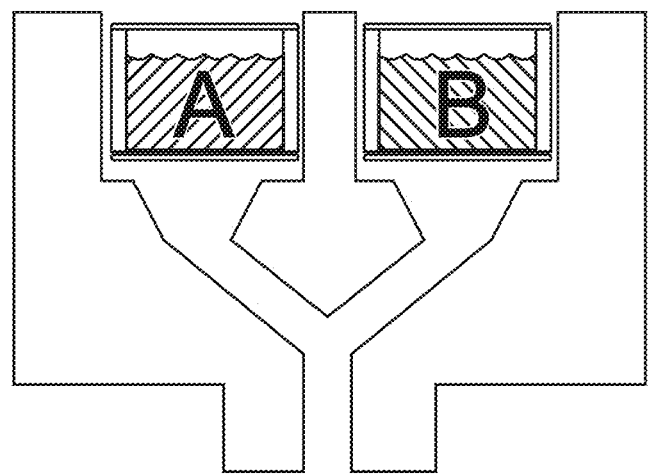
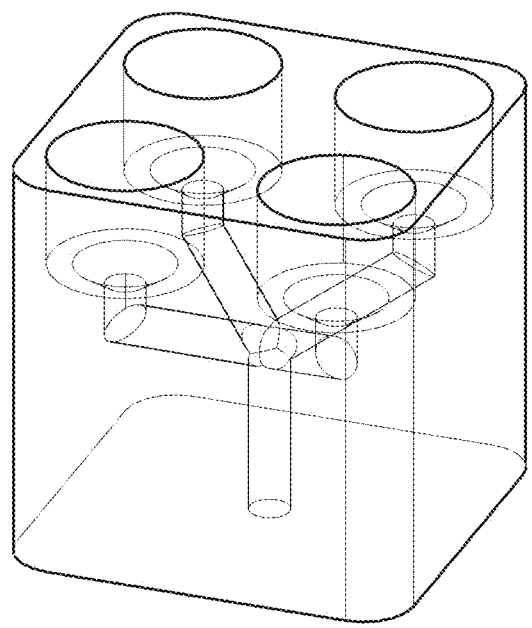
FIG. 63

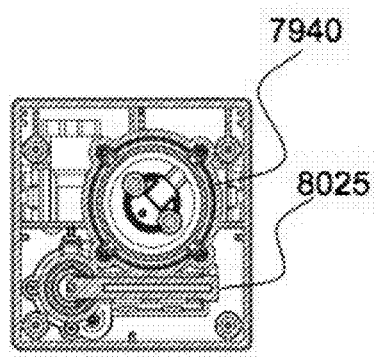
FIG. 82A
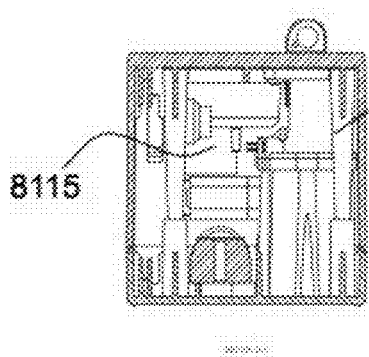
FIG. 82B
FIG. 82C
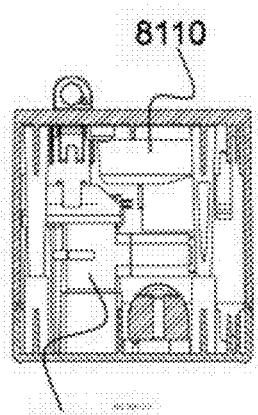
FIG. 82D

BREATH ANALYZER WITH EXPANDABLE RANGE OF MEASUREMENT

CROSS-REFERENCE TO RELATED APPLICATIONS

This application is a continuation-in-part of U.S. patent application Ser. No. 14/206,347, filed Mar. 12, 2014, which is a continuation-in-part of PCT International Application Number PCT/US2013/000026, filed Feb. 1, 2013, which claims the benefit of priority to U.S. Provisional Application No. 61/593,862, filed Feb. 1, 2012. U.S. patent application Ser. No. 14/206,347, filed Mar. 12, 2014, also claims the benefit of priority to U.S. Provisional Application No. 61/800,081, filed Mar. 15, 2013. This application also claims the benefit of priority to U.S. Provisional Application No. 62/173,958, filed Jun. 11, 2015. The disclosures of the above-referenced applications are hereby expressly incorporated by reference in their entireties. Any and all priority claims identified in the Application Data Sheet, or any correction thereto, are hereby incorporated by reference under 37 C.F.R. §1.57.

FIELD OF THE INVENTION

The present invention relates generally to systems, devices and methods for measuring analytes in breath, preferably endogenous analytes in human breath.

BACKGROUND OF THE INVENTION

There are many instances in which it is desirable to sense the presence and/or quantity or concentration of an analyte in a gas. "Analyte" as the term is used herein is used broadly to mean the chemical component or constituent that is sought to be sensed using devices and methods according to various aspects of the invention. An analyte may be or comprise an element, compound or other molecule, an ion or molecular fragment, or other substance that may be contained within a fluid. In some instances, embodiments and methods, there may be more than one analyte present, and an objective is to sense multiple analytes. "Gas" as the term is used herein also is used broadly and according to its common meaning to include not only pure gas phases but also vapors, non-liquid fluid phases, gaseous colloidal suspensions, solid phase particulate matter or liquid phase droplets entrained or suspended in gases or vapors, and the like. "Sense" and "sensing" as the terms are used herein are used broadly to mean detecting the presence of one or more analytes, or to measure the amount or concentration of the one or more analytes.

In many instances, there is a need or it is desirable to make the analysis for an analyte in the field, or otherwise to make such assessment without a requirement for expensive and cumbersome support equipment such as would be available in a hospital, laboratory or test facility. It is often desirable to do so in some cases with a largely self-contained device, preferably portable, and often preferably easy to use. It also is necessary or desirable in some instances to have the capability to sense the analyte in the fluid stream in real time or near real time. In addition, and as a general matter, it is highly desirable to accomplish such sensing accurately and reliably.

The background matrix of breath presents numerous challenges to sensing systems, which necessitate complex processing steps and which further preclude system integration into a form factor suitable for portable usage by layman end-users. For example, breath contains high levels of humidity and moisture, which may interfere with the sensor or cause condensation within the portable device, amongst other concerns. Also, the flow rate or pressure of breath as it is collected from a user typically varies quite considerably. Flow rate variations are known to impact, often significantly, the response of chemical sensors. Breath, especially when directly collected from a user, is typically at or near core body temperature, which may be considerably different than the ambient temperature. Additionally, body temperature may vary from user to user or from day to day, even for a single user. Devising a breath analyzer thus is a non-trivial task, made all the more difficult to extent one tries to design and portable and field-amenable device.

Notably, the measurement of endogenous analytes in breath presents different challenges and requires different techniques and devices than the measurement of exogenous analytes. Endogenous analytes are those that are produced by the body, excluding the lumen of the gastrointestinal tract, whereas exogenous analytes are those that are present in breath as a result of the outside influence or as a result of user consumption. However, many analytes are produced endogenously and can also be exogenously introduced. For example, ammonia is produced endogenously through the metabolism of amino acids, but can also be introduced exogenously from the environment such as ammonia-containing household cleaning supplies. The term "endogenous" is used according to its common meaning within the field. Endogenous analytes are produced by natural or unnatural means within the human body, its tissues or organs, typically excluding the lumen of the gastrointestinal tract.

There are a number of significant challenges to measuring endogenous analytes in breath. Endogenous analytes typically have significantly lower concentrations in the breath, often on the order of parts per million (ppm), parts per billion (ppb), or less. Additionally, measurement of endogenous analytes requires discrimination of the analyte in a complex matrix of background gases. Instead of typical atmospheric gas composition (e.g., primarily nitrogen), exhaled breath has high humidity content and larger carbon dioxide concentration. This leads to unique challenges in chemical sensitivity, selectivity and stability. For example, chemistries conducive for breath ammonia measurement are preferably sensitive to 50 ppb in the presence of 3 to 6% water vapor with 3 to 5% carbon dioxide.

Because of the historical difficulty in even detecting endogenous breath analytes, other challenges have not been extensively investigated. Examples of such challenges include: (a) correlating the analytes to health or disease states, (b) measuring these analytes given characteristics of human exhalation, e.g., flow rate and expiratory pressure, (c) measuring these analytes sensitively and selectively, and (d) doing all these in a portable, cost effective package that can be implemented in medical or home settings.

Colorimetric devices are one method for measuring a reaction involving a breath analyte. Colorimetric approaches to endogenous breath analysis have historically been plagued with lengthy response times, and expensive components. Often such analysis has to be performed in a laboratory. Thus there remains a need for a breath analyzer that can measure endogenous breath components present in relatively low concentrations, such as acetone, accurately and quickly, without a long wait period for results, in addition to being inexpensive and useable by the layperson. It is also preferable if the breath analyzer is capable of measuring multiple analytes.

SUMMARY OF THE INVENTION

In accordance with one aspect of the invention, a system is provided for sensing an analyte in breath of a user. The system comprises a base; a breath input operatively coupled to the base that receives the breath; a cartridge coupled to the base and in fluid communication with the breath input to receive the breath, wherein the cartridge comprises an interactant subsystem that is selected to undergo a reaction with the analyte when the analyte is present in the breath and to undergo an optical change corresponding to the reaction; and an optical subsystem coupled to the base and configured to sense the optical change, wherein the optical subsystem generates an output comprising information about the analyte in response to the optical detection.

The breath input optionally may comprise a mouthpiece and an attachment for attaching a non-human breath container in which the breath is contained. A preferred example of a non-human breath container would comprise a bag, such as a Tedlar bag. The cartridge preferably is detachably coupled to the base. The cartridge also optionally but preferably comprises a handle, and also preferably a light shielding device. More specifically, in some instances there is a concern that components of the cartridge, for example, such as chemical components, may be adversely affected by ambient light. Accordingly, in presently preferred embodiments and methods according to certain aspects of the invention, the base of the system comprises an exterior surface that forms an interior and shields the interior from ambient light, wherein the exterior surface comprises an aperture; and the cartridge comprises a shroud that substantially conforms to the aperture to shield ambient light from entering the aperture when the cartridge is coupled to the base.

In certain embodiments, the base is configured to accept breath from a plurality of breath inputs. The base may further be configured to accept variable volumes of breath and/or remove unneeded volume of breath.

In some instances, it is necessary or desirable to undertake a multiple-stage reaction system. Accordingly, in some presently preferred embodiments and methods, the interactant subsystem comprises a first interactant that is selected to undergo a first reaction with the analyte when the analyte is present in the breath and to generate a first intermediate; and a second interactant that is selected to undergo a second reaction with the first intermediate and to cause the optical change corresponding to the second reaction. In an illustrative but presently preferred example, the first interactant comprises a primary amine coupled to a first substrate a substantially in the absence of a tertiary amine; and the second interactant comprises the tertiary amine.

The optical subsystem can be configured to sense the optical change in a number of ways and according to a number of different criteria. It may be configured, for example, to sense the optical change at a predetermined time after the breath is inputted into the breath input. In some preferred embodiments, the system may further comprise a flow sensor that senses a characteristic of the breath as the breath moves in the system; and the optical subsystem is configured to sense the optical change in response to the flow sensor.

The system also may and preferably does comprise a processor that performs various roles in the system. One of those roles may comprise using process information, such as the identification of one or more specific analytes that the system is configured to sense, information relating to the analyte, such as expected concentration ranges, states, reactivities, temperature and/or pressure dependencies, partial pressure and other vapor state information, and the like, flow characteristics such as fluid temperature, pressure, humidity, mass or volume flow rate, etc., each measured statically or dynamically over time. The process information also may comprise information relating to the cartridge, for example, such as the type of cartridge, the analyte or analytes it is configured to sense, its capacity, its permeability or flow characteristics, its expected response times, at the like. The process information also may comprise information relating to the breath input, for example, such as the breath temperature, pressure, humidity, expected constituents, and the like. In such preferred systems and methods, the optical subsystem preferably is configured to sense the optical change in response to the processor, and in response to one more of such on the process-based information.

In some preferred system embodiments and methods, a flow facilitator also is provided, preferably coupled to the base. The flow facilitator facilitates the flow of the breath into the cartridge and into contact with the interactant subsystem.

In accordance with another aspect of the invention, a method is provided for sensing an analyte in breath of a user. The method comprises providing a cartridge comprising a cavity that comprises an interactant subsystem that is selected to undergo a reaction with the analyte when the analyte is present in the breath and to undergo an optical change corresponding to the reaction. The method also comprises providing a flow path for the breath that comprises a breath input and the cavity of a cartridge, and disposing an optical sensor in fixed relation relative to the cavity. In addition, the method comprises moving the breath through the flow path, causing the optical sensor to detect the optical change as the breath is moved through the flow path, and outputting an output that comprises information about the analyte in response to the optical detection.

In presently preferred implementations of this method, the providing of the flow path comprises providing a mouthpiece in the flow path; and the moving of the breath through the flow path comprises causing the user to exhale into the flow path through the mouthpiece. In addition or alternatively, the providing of the flow path also may comprise providing a non-human breath container in the flow path; and the moving of the breath through the flow path may comprise causing the breath to flow from the non-human breath container into the flow path.

In presently preferred implementations of the method, the cartridge is detachably coupled to the base. The method also optionally comprises shielding the interactant from ambient light as the breath is moved through the cavity.

In presently preferred implementations of the method wherein the interactant comprises a first interactant that is selected to undergo a first reaction with the analyte when the analyte is present in the breath and to generate a first intermediate; and a second interactant that is selected to undergo a second reaction with the first intermediate and to cause the optical change corresponding to the second reaction. In a presently preferred but merely illustrative implementation, the first interactant comprises a primary amine coupled to a first substrate a substantially in the absence of a tertiary amine; and the second interactant comprises the tertiary amine.

In presently preferred method implementations, the causing of the optical sensor to detect the optical change comprises sensing the optical change at a predetermined time after the breath is initially moved through the flow path. Alternatively or in addition, the method may comprise sensing a characteristic of the breath as the breath moves in the flow path; and the causing of the optical sensor to detect the optical change may comprise sensing the optical change in response to the sensing of the characteristic. The causing of the optical sensor to detect the optical change also may comprise sensing the optical change in response to process information, such as the process information summarized herein above.

In preferred implementations of the method, the moving of the breath through the flow path comprises facilitating the flow of the breath into the cavity and into contact with the interactant subsystem.

In accordance with another aspect of the invention, a system is provided for sensing an analyte in breath of a user. This system can be used, for example, where it is necessary or desirable to use multiple steps in processing the analyte or analytes, for example, to facilitate sensing. The system comprises a base; a breath input operatively coupled to the base that receives the breath; and a cartridge coupled to the base and in fluid communication with the breath input to receive the breath. The cartridge comprises a first interactant that is selected to undergo a first reaction with the analyte when the analyte is present in the breath to generate a first intermediate. The system further comprises a dispensing device coupled to the base that dispenses a second interactant that is selected to undergo a second reaction with the first intermediate wherein an optical change corresponding to the reaction is generated. The system further comprises an optical subsystem coupled to the base and configured to sense the optical change, wherein the optical subsystem generates an output comprising information about the analyte in response to the optical detection.

The breath input may comprise a mouthpiece, an attachment for attaching a non-human breath container in which the breath is contained, for example such as a bag, or both.

The cartridge is detachably coupled to the base. It preferably but optionally comprises a handle.

Particularly where internal system components such as the interactant are light-sensitive, the base may comprise an exterior surface that forms an interior and shields the interior from ambient light, wherein the exterior surface comprises an aperture; and the cartridge may comprises a shroud that substantially conforms to the aperture to shield ambient light from entering the aperture when the cartridge is coupled to the base.

The interactant subsystem preferably comprises a first interactant that is selected to undergo a first reaction with the analyte when the analyte is present in the breath and to generate a first intermediate; and a second interactant that is selected to undergo a second reaction with the first intermediate and to cause the optical change corresponding to the second reaction. As an illustrative but presently preferred example, the first interactant may comprise a primary amine coupled to a first substrate substantially in the absence of a tertiary amine; and the second interactant may comprise the tertiary amine.

The interactant subsystem may, in certain embodiments, comprise sodium nitroprus side, dinitrophenylhydrazine, sodium dichromate, pararosaniline, bromophenol blue, dischloroisocyanourate, sodium salicylate, sodium dichromate, crystal violet, benzyl mercaptan, or combinations thereof.

In preferred embodiments, the interactant subsystem is configured to measure endogenous levels of analytes in breath, where such levels may be 5 ppm or less.

As with embodiments and options described herein above, the dispensing device may be configured to dispense the second interactant at a predetermined time after the breath is inputted into the breath input. Alternatively or in addition, the system may comprise a flow sensor that senses a characteristic of the breath as the breath moves in the system; and the dispensing device may be configured to dispense the second interactant in response to the flow sensor.

Also as explained with respect to other embodiments and methods described herein above, the system may further comprise a processor that comprises process information, e.g., such as that described herein above; and the dispensing device may be configured to dispense the second interactant in response to the processor based on the process information.

The optical subsystem according to this aspect of the invention also may comprise the components and features as described herein above, and/or a flow facilitator as described more fully herein above.

In accordance with another aspect of the invention, a system is provided for sensing an analyte in breath of a user, wherein the system comprises a base; a breath input operatively coupled to the base that receives the breath; a cartridge detachably coupled to the base and in fluid communication with the breath input to receive the breath; and a sensing subsystem coupled to the base, wherein the base comprises an exterior surface that forms an interior and shields the interior from ambient light, and wherein the exterior surface comprises an aperture, and this aspect of the invention comprises the further improvement of a shroud coupled to the cartridge that substantially conforms to the aperture to shield ambient light from entering the aperture when the cartridge is coupled to the base.

In accordance with still another aspect of the invention, a system is provided for sensing a plurality of analytes in breath of a user. The system may comprise a base; a breath input operatively coupled to the base that receives the breath; a plurality of cartridges coupled to the base and in fluid communication with the breath input to receive the breath, wherein each of the cartridges comprises a corresponding interactant subsystem that is unique with regard to others of the cartridges and is selected to undergo a corresponding reaction with a corresponding one of the analytes when the corresponding analyte is present in the breath to form a corresponding product state; and a sensing subsystem coupled to the base and configured to sense the product states and to generate an output comprising information about the plurality of analytes.

In accordance with still another aspect of the invention, a method is provided for sensing a plurality of analytes in breath of a user. The method comprises providing a plurality of cartridges coupled to a base and in fluid communication with the breath input to receive the breath, wherein each of the cartridges comprises a corresponding interactant subsystem that is unique with regard to others of the cartridges and is selected to undergo a corresponding reaction with a corresponding one of the analytes when the corresponding analyte is present in the breath to form a corresponding product state; and causing a sensing subsystem coupled to the base and configured to sense the product states to sense the product states and to generate an output comprising information about the plurality of analytes.

In accordance with another aspect of the invention, a system is provided for sensing an analyte in breath of a patient. The system comprises a cartridge comprising a first container, a fluid container, and a reaction volume in fluid communication with the first container and the fluid container, the first container containing a first interactant and the fluid container containing a fluid, wherein the fluid container has an initial fluid level and a space above the initial fluid level. The system also comprises a base comprising a flow path for flow of the breath within the base, a breath input receiver in fluid communication with the flow path that receives the breath and directs the breath into the flow path, a cartridge housing that detachably receives the cartridge into the base so that the reaction volume is in fluid communication with the flow path, a dispensing device that creates a hole in the fluid container below the initial fluid level and that moderates pressure in the space above the initial fluid level so that the fluid flows out of the liquid container and into the reaction volume, thereby facilitating an optical change in the reaction volume in relation to at least one of a presence and a concentration of the analyte, and an optical subsystem that senses the optical change and generates an output comprising information about the analyte in response to the optical change. The dispenser preferably comprises an elongated member, for example, such as a needle, pin, rod and the like. It may comprise a solid member, or it may comprise a fluid channel.

In various aspects of the invention and preferred embodiments of them, the dispensing device and related function involves dispensing the liquid in the liquid container. To accomplish this, a hole is created in the liquid container below the initial level of the liquid, preferably well below this level and more preferably at the bottom of the liquid container or otherwise so that the maximum amount of liquid is obtained from the container. The dispensing function also involves moderating the pressure in the space above the initial fluid level as the fluid moves out of the liquid container so that the fluid moves out of the liquid container and into the reaction volume. This preferably is accomplished by piercing or otherwise creating an opening in the space above the liquid so that gas can enter the space to equalize the pressure, to avoid creating a negative pressure or vacuum in the space, and to thereby permit the liquid to flow or otherwise move out the hole in the liquid container below the initial liquid level. Thus, preferably the elongated member is outside the liquid container to a deployed position in which the elongated member has created the hole in the fluid container below the initial fluid level and has moderated the pressure in the space above the initial fluid level so that the fluid flows out of the liquid container and into the reaction volume. The elongated member may comprise, for example, a needle, pin, rod and the like.

In accordance with another aspect of the invention, a method is provided for sensing an analyte in breath of a patient. The method comprises providing a cartridge comprising a first container, a fluid container, and a reaction volume in fluid communication with the first container and the fluid container. The first container contains a first interactant and the fluid container contains a fluid. The fluid container has an initial fluid level and a space above the initial fluid level. The method also comprises providing a base comprising a flow path for flow of the breath within the base, a breath input receiver in fluid communication with the flow path, cartridge housing, a dispensing device, and an optical subsystem. The method further comprises inserting the cartridge into the cartridge housing of the base so that the reaction volume is in fluid communication with the flow path, and causing the breath to flow in the flow path and into the reaction volume. After the breath has flowed through the reaction volume, the method comprises using the dispensing device to create a hole in the fluid container below the initial fluid level and moderating pressure in the space above the initial fluid level so that the fluid flows out of the liquid container and into the reaction volume, thereby facilitating an optical change in the reaction volume in relation to at least one of a presence and a concentration of the analyte. In addition, the method comprises sensing the optical change and generating an output comprising information about the analyte in response to the optical change.

In accordance with still another aspect of the invention, a system is provided for sensing an analyte in breath of a patient. The system comprises a cartridge comprising a reaction volume and a shroud that is opaque to ambient light. It further comprises a base comprising a flow path for flow of the breath within the base, a breath input receiver in fluid communication with the flow path that receives the breath and directs the breath into the flow path and through the reaction volume, wherein flow of the breath through the reaction volume facilitates an optical change to the reaction volume in relation to at least one of a presence and a concentration of the analyte, a cartridge housing that detachably receives the cartridge into the base so that the reaction volume is in fluid communication with the flow path, wherein the shroud of the cartridge mates with the cartridge housing of the base to block ambient light from impinging on the reaction volume, and an optical subsystem that senses the optical change and generates an output comprising information about the analyte in response to the optical change.

In accordance with one aspect of the invention, a system is provided for sensing an analyte in a breath sample. The system comprises a breath bag, a cartridge and a base. The breath bag contains the breath sample comprising a mouthpiece fixedly disposed on the breath bag. The cartridge comprises an interactant that reacts with the analyte and generates a change in an optical characteristic relative to a reference. The base comprises a flow path, a breath bag receiver for detachably receiving and retaining the mouthpiece of the breath bag in fluid communication with the flow path and a cartridge receiver that detachably receives and retains the cartridge in the base, such that the base engages the cartridge so that the interactant is in fluid communication with the flow path. The base further comprises a flow handling system in fluid communication with the flow path, an optical subsystem for sensing the change in the optical characteristic, a processor operatively coupled to the flow handling system and the optical subsystem, and a user interface operatively coupled to the processor and comprising a start command. Upon user selection of the start command, the processor is configured to automatically regulate the flow handling system to move the breath sample in the flow path and to contact the breath sample and the interactant. Upon the occurrence of a predetermined process parameter, the processor is configured to perform the following actions: (a) to automatically regulate the optical subsystem to sense the change in the optical characteristic, (b) to correlate the sensing of the optical system with information about the analyte in the breath sample, and (c) to output the information about the analyte in the breath sample to the user interface.

In certain embodiments, the mouthpiece is fixedly disposed at a corner of the breath bag. The breath bag receiver preferably is configured to fluidically connect the breath bag with the flow handling system and is configured to retain the breath sample in the breath bag until the processor causes the flow handling system to move the breath sample through the flow path.

In certain embodiments, the optical subsystem comprises only a single optical sensor. A low cost system may also function without the use of light pipes and the single optical sensor may be positioned within 1" or preferably ¼" of the disposable cartridge.

In certain embodiments, the cartridge further comprises an optical sensing zone, and, wherein the optical subsystem comprises an optical detector that is fixedly positioned with regards to the optical sensing zone. The cartridge may further comprises a cartridge identifier, and further wherein the optical detector generates a signal with information about this cartridge identifier.

The optical subsystem is preferably designed so that it senses through the optical sensing zone of the cartridge, but the cartridge does not physically move. A stationary cartridge provides certain advantages for the flow handling system as well.

In certain configurations, the cartridge comprises beads with a mesh size smaller than 100. In other configurations, the cartridge comprises beads with a mesh size between 270 and 100. An application utilizing these beads is sensing acetone for certain purposes.

The cartridge may comprise a flow path. The flow path may be substantially linear.

In one embodiment, the interactant is specific for an endogenous analyte. Preferably, the interactant is useful over a physiological range of interest.

The cartridge may comprise at least one liquid reagent and at least one dry reagent.

The predetermined process parameter may be at least one of: (a) elapsed time from a start command, (b) elapsed time from pump initiation, (c) elapsed time from flow initiation, (d) elapsed time at a predetermined pressure, and (e) volume of the breath sample through the flow path is greater than 350 mL.

The optical subsystem may comprise a camera.

The processor may be configured to do at least one of: (a) activate an optical detector, (b) activate an illuminator, and (c) obtain an image from a camera and store the image in memory.

In certain embodiments, the base is configured to receive a plurality of cartridges, each having a different cartridge type, and, wherein the processor is configured to regulate the flow handling system and to regulate the optical subsystem according to different parameters, wherein these parameters vary depending on the cartridge type. The plurality of cartridges may comprise interactants that are specific for the analyte, but different ranges thereof. Also, the plurality of cartridges may comprise interactants that are specific for a plurality of analytes.

Certain embodiments of the cartridge comprise a cartridge identifier, and further wherein the base is configured to recognize the cartridge identifier. The cartridge identifier may be a standard barcode, but may also be the color of the liquid container or the color of the handle of the cartridge.

The base may be configured to recognize the cartridge identifier using at least one of (a) a barcode scanner, (b) a magnetic scanner, (c) a chip, (d) a pin set, and (e) a mirror configuration. Also, the cartridge identifier may comprise information about the interactant and wherein the processor uses this information to determine information about the analyte. The information is at least one of (a) batch lot, (b) expiration date, (c) chemical variability, (d) analyte identifier, and (e) serial number.

The interactant may generate an intended change in an optical characteristic and an unintended change in an optical characteristic, and further wherein the processor is configured to separate the intended change from the unintended change. The unintended change may be caused by at least one of (a) bubbles, (b) a second analyte in the breath sample, (c) packing anomalies, (d) particle size void space, (e) liquid reagent concentration changes, (f) cartridge recognition, (g) packing anomalies, (h) subsystem failure, and (i) device failure.

Certain cartridges contain an optical sensing zone. For these cartridges, the optical subsystem is able to sense a change in optical characteristic in two spatial dimensions within the optical sensing zone. The optical sensing zone may have an inlet and an outlet corresponding to the direction of the flow path. Here, the processor determines if the cartridge is saturated by comparing the change in the optical characteristic at the inlet and the outlet and determining that they are approximately the same. Another approach would be to measure the gradient of the optical characteristic along the axis of the flow path. In certain configurations, the change in optical characteristic has greater than three levels.

In certain embodiments, the breath bag further comprises an outlet. The full breath sample may be directed through the mouthpiece and a portion is directed from the outlet. The outlet may be configured to close when the breath sample is no longer being input through the mouthpiece. The outlet may also be configured to close when the breath bag depresses against a spring.

In one configuration, the breath bag receiver is on the top portion of the base. In another, the breath bag receiver is configured to accept the breath bag without moving the base. In yet another embodiment, the cartridge receiver is configured to accept the cartridge without moving the base. The cartridge may be designed such that a portion of it remains outside the base at all times during the sensing process.

In certain embodiments, the breath bag may attach to the breath bag receiver via a face seal flange with a spring loaded snap fit. The breath bag may mate with the interior of the base.

The cartridge may be comprised of an inlet aperture and an outlet aperture, wherein the base comprises a dispensing device, and further wherein the dispensing device delivers the breath sample through the inlet aperture using an elongated member.

In accordance with an aspect of the invention, a cartridge is provided for use with a breath analysis system comprising an optical subsystem for sensing an analyte in a breath sample. The cartridge comprises a housing, a flow path, an interactant, an optical sensing zone. The flow path may begin at an inlet aperture and end at an outlet aperture. The interactant region comprises interactant beads. The optical sensing zone is within view of the optical subsystem. The breath sample is delivered to the interactant region and generates a change in an optical characteristic that is sensed by the optical subsystem through the optical sensing zone.

In one cartridge embodiment, the housing is comprised essentially of plastic. The housing may also be manufactured from a single material and parts of that single material were extruded from it. The housing may not held together using mechanical parts.

The aspect ratio of the cross sectional area along the axis of flow of the breath sample through the interactant region may be between 1 and 10. The cross sectional area may be between 1 and 10 square millimeters. In certain embodiments, the length of the interactant region is less than 0.25".

In some embodiments, a cartridge may comprise a liquid container. The liquid container may be essentially opaque and the housing is not opaque. The liquid container, for certain applications, contains between 25 and 150 microliters of liquid reagent.

In systems described herein, the analyte may be acetone, ammonia or carbon dioxide.

The base may be configured to receive a plurality of cartridges, wherein the cartridges contain interactants for at least two of: acetone, ammonia and carbon dioxide.

In accordance with another aspect of the invention, a cartridge is provided for use with a breath analysis system comprising an optical subsystem for sensing an analyte in a breath sample. The cartridge comprises (a) a housing, (b) a flow path disposed in the housing for directing flow of the breath sample, the flow path comprising an inlet aperture and an outlet aperture, (c) an interactant region in fluid communication with the flow path that comprises interactant that, when contacted by the analyte in the breath sample, generate a change in an optical characteristic of the interactant region, and (d) an optical sensing zone in operative communication with the interactant region and the optical subsystem so that, when the breath sample is directed through the flow path and the analyte in the breath sample contacts that interactant and generates the change in the optical characteristic, the change in the optical characteristic is sensed by the optical subsystem at the optical sensing zone.

In accordance with another aspect of invention, a cartridge is provided for use with a breath analysis system for sensing an analyte in a breath sample. The cartridge comprises an interactant region that comprises an interactant that reacts with the analyte in the breath sample, an inverted cup, inverted with respect to local gravity, wherein the cup comprises a liquid and a bottom portion, a biasing device that biases the inverted cup so that the bottom portion creates a liquid seal to retain the liquid in the inverted cup, and an actuation receiver responsive to the breath analysis system so that the actuation receiver interacts with the biasing device to break the liquid seal and release the liquid from the inverted cup in response to the breath analysis system.

In accordance with another aspect of the invention, a breath analysis system is provided for a user to analyze an analyte in breath. The system comprises a cartridge comprising a liquid chamber comprising a liquid and a reactive bead chamber, and a base unit comprising an actuator, wherein the actuator is configured to release the liquid without interaction with the user.

In accordance with still another aspect of the invention, a breath analysis system is provided for use by a user to analyze an analyte in breath. The system comprises a base unit comprising a cartridge receiver and an actuator, and a cartridge detachably disposed in the cartridge receiver of the base unit. The cartridge comprises an interactant region that comprises an interactant, an inverted cup, inverted with respect to local gravity, wherein the cup comprises a liquid and a bottom portion, a biasing device that biases the inverted cup so that the bottom portion creates a liquid seal to retain the liquid in the inverted cup, an actuation receiver operatively coupled to the actuator so that, in response to the actuator, the actuation receiver interacts with the biasing device to break the liquid seal and release the liquid from the inverted cup. This breaking of the liquid seal is achieved without interaction with the user other than user activation of the breath analysis test.

In accordance with another aspect of the invention, a method is provided for producing a cartridge for use in sensing an analyte in a breath sample. The method comprises providing a housing that comprises a flow path comprising an upstream direction and a downstream direction. The housing comprises a first chamber, a second chamber positioned in the downstream direction relative to the first chamber, and a housing outlet positioned in the downstream direction relative to the second chamber. The method further comprises disposing an interactant in the first chamber, disposing a first porous barrier material between the first chamber and the second chamber, which first porous barrier material retains the interactant in the first chamber but allows passage of the breath sample, disposing a breath sample conditioning material in the second chamber, disposing a second porous barrier material at a downstream end of the second chamber; and immobilizing the second porous barrier material by disposing a plurality of notched protrusions in the housing at the second porous barrier material. The disposing of the plurality of the notched protrusions preferably comprises using heat to form the notched protrusions.

According to another aspect of the invention, a cartridge is provided for use with a breath analysis system comprising an optical subsystem for sensing an analyte in a breath sample. The cartridge comprises a housing comprising an exterior surface having an exterior surface dimension. It also comprises a first chamber disposed in the housing and comprising a first chamber surface having a first chamber dimension. The first chamber comprises an interactant that interacts with the analyte in the breath sample. The housing exterior surface dimension at the first chamber comprises a first housing exterior surface dimension. A first chamber wall thickness is defined by the first housing exterior surface dimension minus the first chamber dimension, and the first chamber wall thickness is uniform throughout the first chamber surface. The cartridge also comprises a second chamber disposed in the housing and comprising a second chamber surface having a second chamber dimension. The second chamber comprises a breath sample conditioner. The housing exterior surface dimension at the second chamber comprises a second housing exterior surface dimension. A second chamber wall thickness is defined by the second housing exterior surface dimension minus the second chamber dimension, and the second chamber wall thickness is uniform throughout the second chamber surface. The first housing exterior surface dimension differs from the second housing exterior surface dimension, and the first chamber wall thickness is the same as the second chamber wall thickness.

In accordance with another aspect of the invention, a breath analysis system is provided that comprises a disposable system component comprising at least one of a cartridge and a breath bag. The system also includes a base unit that comprises a disposable system component receiving port configured to detachably receive and affix the disposable system component to the base; and a gasket disposed between the disposable system component and the disposable receiving port to create an air-tight seal.

In addition, related methods for the foregoing inventions are also provided herein.

The present invention according to one aspect comprises a method of determining the concentration of an analyte of interest in breath. The method comprises the steps of obtaining a disposable cartridge comprising a reaction chamber, a liquid chamber, and a window to permit determination of a color intensity in the reaction chamber. The method also comprises directing a volume of breath into the cartridge, and initiating a sequence whereby liquid is released from the liquid container into the reaction chamber to cause a reaction which produces a change in the intensity of a color viewable through the window. The intensity of the color corresponds to the concentration of the analyte of interest. The reaction progresses through a kinetic phase and eventually reaching equilibrium. The sequence additionally comprises the step of measuring the intensity of the color at a point in the kinetic phase, to determine the concentration of the analyte of interest in breath.

In some presently preferred implementations of the method, the analyte comprises acetone. In others, it may comprise ammonia, isoprene or other endogenous analytes.

The reaction optionally but preferably is with an amine, more preferably wherein the amine is bound to a surface, a silica gel surface, the surface of a plurality of silica gel beads, or a combination of two or more of these. Where silica gel beads are employed, the silica gel beads have a size distribution between 270 and 100 mesh. In some implementations of the method, it is preferred that the silica gel beads have a volume of no more than about 1.0 ml.

The liquid released from the liquid container optionally but preferably comprises a nitroprusside solution. In some method implementations, prior to the release of liquid step, the reaction chamber comprises an alkaline environment. Optionally but preferably, no more than about 1 ml of liquid is released from the liquid container, and in some implementations of the method no more than about 0.5 ml of liquid is released from the liquid container.

The method optionally but preferably comprises a step of removing water vapor from the volume of breath.

The step of measuring the intensity of the color preferably is accomplished within six minutes following the initiating step, and more preferably within four minutes following the initiating step. The step of measuring the intensity of the color also preferably is accomplished using a camera. The method may comprise using the camera to view information carried by the cartridge in addition to the color intensity.

The method may comprise using the camera to view both color intensity as well as a bar code. Similarly, it may comprise using the camera to view both color intensity as well as an indication of expiration date.

The present invention according to one aspect comprises a disposable cartridge for indicating the concentration of an analyte of interest in breath. The disposable cartridge comprises a housing, having a side wall and a longitudinal axis, and a reaction chamber in the housing. The disposable cartridge also comprises an optically transparent window in the side wall for viewing contents of the reaction chamber, wherein the window has a height measured in the direction of the longitudinal axis. The disposable cartridge further comprises a liquid chamber in the housing. The cartridge is configured to display a color that extends along the entire height of the window following the transfer of liquid from the liquid chamber into the reaction chamber. The intensity of the color corresponds to a concentration of the analyte of interest in the reaction chamber.

The disposable cartridge may further comprise an actuator for opening the valve and releasing liquid from the liquid chamber into the reaction chamber. The cartridge also may comprise an opening in the side wall for providing access to the actuator, wherein the actuator may be laterally displaceable.

The liquid chamber may be defined within a container having an open end, and the cartridge may further comprise a cover on the open end, for enclosing liquid. In such method implementations, the open end and the cover optionally may separate to release liquid in response to displacement of the actuator.

The liquid optionally but preferably comprises a nitroprusside solution. The disposable cartridge in such method implementations may comprise a primary amine in the reaction chamber.

The window of the disposable cartridge optionally but preferably has a height of no more than about 7 mm, and more preferably a height of no more than about 4 mm.

The disposable cartridge also comprises particles in the reaction chamber. Such particles optionally but preferably have a size of no more than about 200 microns, and in some implementations a size of no more than about 120 microns.

The actuator optionally but preferably is isolated from contents of the liquid chamber throughout operation of the cartridge.

The particles in the reaction chamber in some implementations have a volume of no more than about 0.5 ml, and in some implementations their volume is no more than about 0.1 ml.

In some implementations, no more than about 0.2 ml of nitroprusside solution is disposed in the liquid chamber.

The disposable cartridge in preferably is configured to produce a color change corresponding to a concentration of the analyte of interest in no more than about 6 minutes.

In accordance with one aspect of the invention, an analyzer is provided for sensing an analyte in breath of a patient. The analyzer comprises a base, a breath input port on the base for removable coupling to a source of breath, a cartridge receiving cavity on the base for removably receiving a disposable cartridge having an optically transparent window and a reaction volume, and a flow path disposed in the base. The flow path is configured to place the breath input port into communication with the reaction volume when the cartridge is installed in the cartridge receiving cavity. The analyzer further comprises an optical subsystem in the base that senses an optical change in the reaction volume through the window. A pump is disposed in the base and configured to pump breath from the source of breath to the reaction volume during a measurement cycle when the source of breath is coupled to the breath input port, and to pump atmospheric air through the flow path during a flush cycle.

Optionally but preferably, the pump is programmed to deliver air through the flow path at a first flow rate during the measurement cycle, and at a second, different flow rate during the flush cycle. The second flow rate during the flush cycle preferably is greater than the first flow rate during the flush cycle, and more preferably the first flow rate during the measurement cycle is lower than the second flow rate during the flush cycle. The first flow rate during the measurement cycle preferably is within the range of from about 150 mL per minute to 750 mL per minute, but preferred ranges in various applications and embodiments, for example, also may extend at the upper end to 300 mL/min or 500 mL/min, and upwardly to 1 L/min, 2 L/min and 5 L/min. The first flow rate during the measurement cycle preferably is about 330 cc per minute, and the second flow rate during the flush cycle preferably is at least about 300 mL per minute, but these are not necessarily limiting. The second flow rate during the flush cycle, for example, may extend to about 1000 mL per minute, but in various applications and embodiments may be about 500 mL/min, 1.5 L/min, 2 L/min, 4 L/min, or 10 L/min.

Optionally but preferably, the pump is programmed to turn off after a predetermined flush cycle duration. That predetermined flush cycle duration preferably is at least about 30 seconds, but in various applications and embodiments, for example, may be at least about 5 sec, 15 sec, 30 sec, or and 60 sec.

The optical subsystem preferably comprises a camera oriented so that the optically transparent window is within a field of view of the camera when the cartridge is installed in the cartridge receiving cavity. The camera may be configured to capture an image of the contents of the reaction volume through the window and also capture an image of information on the cartridge adjacent the window when the cartridge is installed in the cartridge receiving cavity.

The analyzer preferably is configured to initiate the flush cycle following removal of the source of breath from the breath input port. It also preferably is configured to generate a baseline flow rate during the flush cycle, and to increase the flush cycle flow rate in response to a determination by the optical subsystem that the analyte is present in a concentration which is greater than a preset threshold.

In a presently preferred embodiment of the analyzer, the analyte is acetone and the preset threshold is about 40 ppm, although that threshold in variants of this embodiment may be about 20 ppm, 30 ppm, 60 ppm, or 100 ppm.

In accordance with one aspect of the invention, a method is provided for extending an effective working range of an analyzer for measuring an analyte in a breath sample. The method comprises initiating a reaction in the analyzer that produces an optically discernable reaction product having an optical property that is indicative of a concentration of the analyte in the breath sample. The method also comprises taking a first reading of the optical property at a first time, and comparing the first reading to a reference. If the comparison of the first reading to the reference has a first state, the method comprises determining the concentration using the first reading. If the comparison of the first reading to the reference has a second state different from the first state, the method comprises taking a second reading of the optical property at a second time and determining the concentration of the analyte using the second reading.

The determining of the concentration using the first reading may be conducted using a first calibration data set, a lookup table, a calibration curve, or a combination of these.

Similarly, the determining of the concentration using the second reading may be conducted using a second calibration data set, a lookup table, a calibration curve, or some combination of these.

The method preferably but optionally comprises displaying the concentration.

The optical property preferably comprises intensity, but this is not necessarily limiting.

The first calibration data set in a presently preferred embodiment calibrates the analyzer to measure the analyte over a working range of from about 0 to 10 ppm of the analyte, and the second calibration data set calibrates the analyzer to measure the analyte over a working range of from about 0 to 20 ppm of the analyte. These are not, however, necessarily limiting. In related embodiments, the first calibration data set calibrates the analyzer to measure the analyte over a working range of from about 0 to 20 ppm of the analyte. In similarly related embodiments, the first calibration data set calibrates the analyzer to measure the analyte over a working range of from about 0 to 120 ppm of the analyte. In other related embodiments, the first calibration data set calibrates the analyzer to measure the analyte over a first working range of less than about 20 ppm and the second calibration data set extends the first working range by at least about 100%. In certain embodiments, the analyzer has an effective working range equal to the sum of at least a first working range and a second working range, wherein the second working range is at least 100% of the first working range. In others, the second working range is at least 300% of the first working range.

In accordance with another aspect of the invention, a method is provided for measurement of an analyte in a breath sample using a breath analysis device. The method comprises initiating a reaction that produces an optically discernable reaction product having an optical property that is indicative of the concentration of the analyte in the breath sample, taking a first reading of the optical property at a first time, and comparing the first reading to a reference. If the comparison of the first reading to the reference has a first state, the method comprises determining the concentration using the first reading. If the comparison of the first reading to the reference has a second state, the method comprises adjusting a process parameter of the breath analysis device and taking a second reading of the optical property at a second time subsequent to the adjusting of the process parameter, and using the second reading to obtain the concentration of the analyte using a calibration process. The method also preferably comprises displaying the concentration of the analyte.

The adjusting of the process parameter may comprise changing a pump speed, adjusting a duration of pump operation, avoiding the process parameter to avoid saturation of the reaction, or some combination of these.

The optical property comprises intensity.

In a presently preferred implementation of the method, the taking of the second reading is commenced within about six minutes following the initiating of the reaction.

In certain preferred method implementations, the initiating of the reaction comprises releasing a nitroprusside solution into a reaction volume. In such implementations, for example, the displaying of the concentration of the analyte comprises displaying a concentration of acetone within a range of from about 0 ppm to about 120 ppm.

BRIEF DESCRIPTION OF DRAWINGS

The accompanying drawings, which are incorporated in and constitute a part of the specification, illustrate a presently preferred embodiments and methods of the invention and, together with the general description given above and the detailed description of the preferred embodiments and methods given below, serve to explain the principles of the invention. Of the drawings:

FIGS. 4A-4G show various perspective drawings of an embodiment of a cartridge. FIG. 4A shows the internal components for an embodiment of a cartridge. FIG. 4B shows an embodiment of a labeled cartridge. FIG. 4C shows an embodiment of a cartridge when viewed from behind. FIG. 4D shows an embodiment of a cartridge when viewed from the bottom. FIG. 4E shows an embodiment of a cartridge when viewed from the front. FIG. 4F shows an embodiment of a cartridge when viewed from the top. FIG. 4G shows an embodiment of a cartridge when viewed from the side.

FIG. 8A shows an exemplary image analysis sub-system of a breath analysis system. FIG. 8B shows the target area for the camera within the image analysis sub-system.

FIG. 16A shows an embodiment of a valve fitment used in a breath bag.

FIG. 16B shows the breath bag used in conjunction with the valve fitment embodiment. FIG. 16C shows a perspective drawing of a breath bag embodiment.

FIG. 18A shows an embodiment of another valve fitment used in another breath bag. FIG. 18B shows the breath bag used in conjunction with that valve fitment embodiment. FIG. 18C shows a perspective drawing of a breath bag embodiment.

FIG. 25A shows a cartridge embodiment before the liquid container has been pierced. FIG. 25B shows the cartridge embodiment in contact with the piercing mechanism.

FIG. 26A shows the ampoule embodiment with a specific lid. FIG. 26B shows the cartridge embodiment with a different lid.

FIG. 27A shows the cup embodiment when viewed from the bottom. FIG. 27B shows the cup embodiment when viewed from the side. FIG. 27C shows a cutaway view of the cup embodiment. FIG. 27D shows an additional perspective view of the cup embodiment. FIG. 27E shows the cup embodiment when viewed from the top.

FIG. 28A shows the cup embodiment when viewed from the top. FIG. 28B shows a perspective view of the cup embodiment with additional components. FIG. 28C shows another perspective view of the cup embodiment with additional components. FIG. 28D shows a cutaway view of the cup embodiment with additional components.

FIGS. 29A to 29G show an embodiment of an inverted cup with additional components. FIG. 29A shows a perspective drawing of the cup embodiment. FIG. 29B shows a perspective drawing of the cup embodiment. FIG. 29C shows various perspective drawings of the cup embodiment. FIG. 29D shows a cutaway view of the cup embodiment when joined with a compression disk. FIG. 29E shows a cutaway view of the cup embodiment when separated from a compression disk. FIG. 29F shows an additional cutaway view of the cup embodiment when coupled to a compression disk. FIG. 29G shows an additional cutaway view of the cup embodiment when not coupled to a compression disk.

FIG. 31A shows a perspective view of the ampoule embodiment and its components. FIG. 31B shows an additional perspective view of the ampoule embodiment and its components.

FIG. 32A shows the cartridge embodiment before contacting a piercing mechanism. FIG. 32B shows the cartridge embodiment after contacting a piercing mechanism.

FIG. 40A shows a particular embodiment a multi-purpose cartridge. FIG. 40B shows a separate embodiment of a multi-purpose cartridge.

FIG. 45A shows the internal components of the cartridge embodiment. FIG. 45B shows an expanded view of some liquid container subcomponents. FIG. 45C shows a perspective drawing of the cartridge embodiment. FIG. 45D shows another perspective drawing of the cartridge embodiment. FIG. 45E shows a cartridge embodiment when viewed from the top. FIG. 45F shows a cartridge embodiment when viewed from the bottom. FIG. 45G shows a perspective drawing of the cartridge embodiment. FIG. 45H shows another perspective drawing of the cartridge embodiment. FIG. 45I shows a cutaway view of the cartridge embodiment before activation. FIG. 45J shows a cutaway view of the cartridge embodiment after activation.

FIGS. 50A to 50E are different scenarios that may be generated within the optical sensing zone. FIG. 50A, FIG. 50B, FIG. 50C, FIG. 50D, and FIG. 50E each show a different image of the optical sensing zone.

FIG. 56A shows the embodiment of a cartridge before contacting the sliding mechanism. FIG. 56B shows the embodiment of a cartridge after contacting the sliding mechanism.

FIG. 60A shows the cartridge embodiment before being contacted by a piercing mechanism. FIG. 60B shows the movement of a liquid reagent within a cartridge embodiment after contacting the piercing mechanism.

FIG. 61A shows an embodiment of a cartridge containing two liquid reagents. FIG. 61B shows the movement of a first liquid inside the cartridge embodiment, after the first liquid container has been pierced. FIG. 61C shows the movement of a second liquid reagent inside an embodiment of a cartridge, after the second liquid container has been pierced.

FIGS. 62A to 62D show another embodiment of a cartridge utilizing a plunger-type mechanism. FIG. 62A shows an embodiment of a liquid container a plunger-type mechanism. FIG. 62B shows the cartridge embodiment after filling with liquid. FIG. 62C shows the cartridge embodiment after activating the plunger mechanism. FIG. 62D shows the movement of a liquid reagent through the cartridge embodiment, after the plunger mechanism has been implemented.

FIG. 63 illustrates another example of a multi-liquid cartridge.

FIG. 64A shows the cartridge embodiment before contacting a piercing mechanism. FIG. 64B shows the cartridge embodiment while being piercing by the mechanism. FIG. 64C shows the movement of liquid through the cartridge embodiment after being pierced.

FIG. 65A shows the cartridge embodiment before contacting a piercing mechanism. FIG. 65B shows the cartridge embodiment while being piercing by the mechanism. FIG. 65C shows the movement of liquid through the cartridge embodiment after being pierced.

FIG. 66A shows the cartridge embodiment before contacting a piercing mechanism. FIG. 66B shows the cartridge embodiment while being piercing by the mechanism. FIG. 66C shows the movement of liquid through the cartridge embodiment after being pierced.

FIG. 67A shows the cartridge embodiment before contacting a rupturing mechanism. FIG. 67B shows the movement of liquid through the cartridge embodiment after being ruptured.

FIG. 68A shows the cartridge embodiment before contacting a piercing mechanism. FIG. 68B shows the cartridge embodiment while being piercing by the mechanism. FIG. 68C shows the movement of liquid through the cartridge embodiment after being pierced.

FIG. 69A shows the cartridge embodiment before contacting a piercing mechanism. FIG. 69B shows the cartridge embodiment while being piercing by the mechanism. FIG. 69C shows the movement of liquid through the cartridge embodiment after being pierced.

FIG. 70A shows the cartridge embodiment before contacting a piercing mechanism. FIG. 70B shows the cartridge embodiment while being piercing by the mechanism. FIG. 70C shows the movement of liquid through the cartridge embodiment after being pierced.

FIGS. 82A, 82B, 82C, and 82D show four (4) different perspective drawings of the base unit described in FIG. 78.

Figure 1:
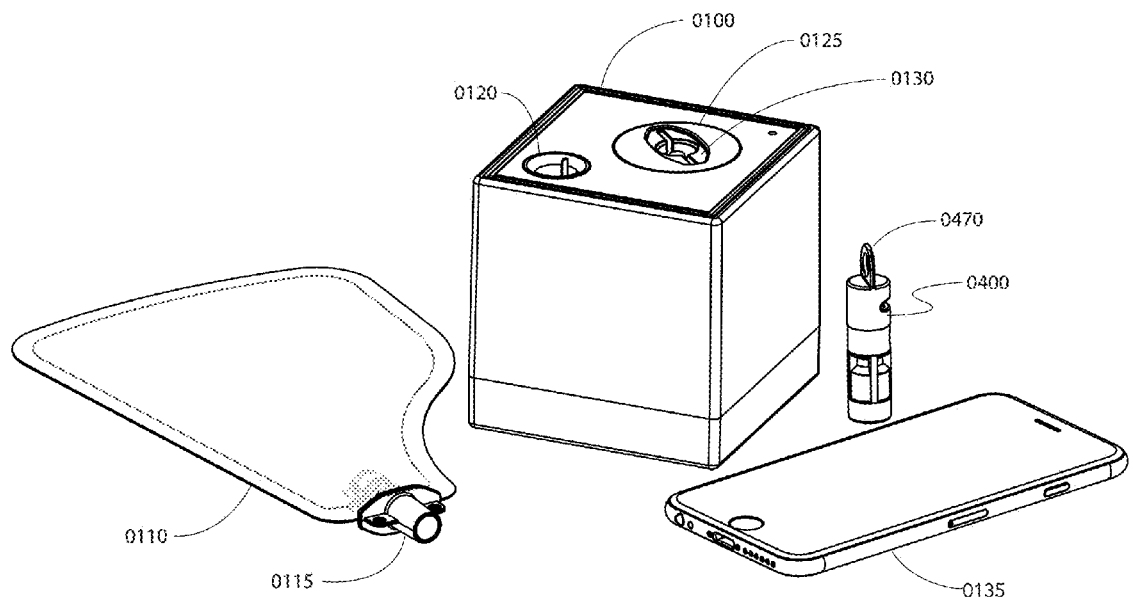
FIG. 1 shows an embodiment of a breath analysis system.

DETAILED DESCRIPTION OF THE PRESENTLY PREFERRED EMBODIMENTS AND METHODS OF THE INVENTION

Reference will now be made in detail to the presently preferred embodiments and methods of the invention as described herein below and as illustrated in the accompanying drawings, in which like reference characters designate like or corresponding parts throughout the drawings. It should be noted, however, that the invention in its broader aspects is not limited to the specific details, representative devices and methods, and illustrative examples shown and described in this section in connection with the preferred embodiments and methods. The invention according to its various aspects is particularly pointed out and distinctly claimed in the attached claims read in view of this specification, and appropriate equivalents.

The present invention relates to devices and methods for the sensing of analytes in breath, and preferably for the sensing of analytes that are endogenously produced in a breath sample. The devices and methods can and preferably do include cartridges that contain or comprise breath-reactive chemistries or interactants, i.e., chemical components that react with specific or desired chemical species or components in the breath. Preferably, these breath-reactive interactants are specific, even in the background of breath.

One area of particular interest involves breath analysis. Included among illustrative breath constituents, i.e., analytes, that have been correlated with disease states are those set forth in Table 1, below. As noted, there are perhaps 300 volatile organic compounds that have been identified in the breath, all of which are candidate analytes for analysis using such embodiments and methods. Additionally, in some instances combinations of constituents (analytes) in breath may serve as a superior disease marker relative to the presence of any single analyte.

TABLE 1

| Candidate Analyte | Illustrative Pathophysiology/Physical State |
|---|---|
| Acetone | Lipid metabolism (e.g., epilepsy management, nutritional monitoring, weight loss therapy, early warning of diabetic ketoacidosis), environmental monitoring, acetone toxicity, congestive heart failure, malnutrition, exercise, management of eating disorders |
| Ethanol | Alcohol toxicity, bacterial growth |
| Acetaldehyde | |
| Ammonia | Liver or renal failure, protein metabolism, dialysis monitoring, early detection of chronic kidney disease, acute kidney disease detection and management |
| Oxygen and Carbon Dioxide | Resting metabolic rate, respiratory quotient, oxygen uptake |
| Isoprene | Lung injury, cholesterol synthesis, smoking damage |
| Pentane | Lipid peroxidation (breast cancer, transplant rejection), oxidative tissue damage, asthma, smoking damage, COPD |
| Ethane | Smoking damage, lipid peroxidation, asthma, COPD |
| Alkanes | Lung disease, cancer metabolic markers |
| Benzene | Cancer metabolic monitors |
| Carbon-13 | *H. pylori* infection |
| Methanol | Ingestion, bacterial flora |
| Leukotrienes | Present in breath condensate, cancer markers |
| Hydrogen peroxide | Present in breath condensate |
| Isoprostane | Present in breath condensate, cancer markers |
| Peroxynitrite | Present in breath condensate |
| Cytokines | Present in breath condensate |
| Glycans | Glucose measurement, metabolic anomalies (e.g., collected from cellular debris) |
| Carbon monoxide | Inflammation in airway (asthma, bronchiesctasis), lung disease |
| Chloroform | |
| Dichlorobenzene | Compromised pulmonary function |
| Trimethyl amine | Uremia |
| Dimethyl amine | Uremia |
| Diethyl amine | Intestinal bacteria |
| Methanethiol | Intestinal bacteria |
| Methylethylketone | Lipid metabolism |
| O-toluidine | Cancer marker |
| Pentane sulfides | Lipid peroxidation |
| Hydrogen sulfide | Dental disease, ovulation |
| Sulfated hydrocarbon | Cirrhosis |
| Cannabis | Drug concentration |
| G-HBA | Drug testing |
| Nitric oxide | Inflammation, lung disease |
| Propane | Protein oxidation, lung disease |
| Butane | Protein oxidation, lung disease |
| Other Ketones (other than acetone) | Lipid metabolism |

TABLE 1-continued

| Candidate Analyte | Illustrative Pathophysiology/Physical State |
|---|---|
| Ethyl mercaptane | Cirrhosis |
| Dimethyl sulfide | Cirrhosis |
| Dimethyl disulfide | Cirrhosis |
| Carbon disulfide | Schizophrenia |
| 3-heptanone | Propionic acidaemia |
| 7-methyl tridecane | Lung cancer |
| Nonane | Breast cancer |
| 5-methyl tridecane | Breast cancer |
| 3-methyl undecane | Breast cancer |
| 6-methyl pentadecane | Breast cancer |
| 3-methyl propanone | Breast cancer |
| 3-methyl nonadecane | Breast cancer |
| 4-methyl dodecane | Breast cancer |
| 2-methyl octane | Breast cancer |
| Trichloroethane | |
| 2-butanone | |
| Ethyl benzene | |
| Xylene (M, P, O) | |
| Styrene | |
| Tetrachloroethene | |
| Toluene | |
| Ethylene | |
| Hydrogen | |

Examples of other analytes would include bromobenzene, bromochloromethane, bromodichloromethane, bromoform, bromomethane, 2-butanone, n-butylbenzene, sec-butylbenzene, tert-butylbenzene, carbon disulfide, carbon tetrachloride, chlorobenzene, chloroethane, chloroform, chloromethane, 2-chlorotoluene, 4-chlorotoluene, dibromochloromethane, 1,2-dibromo-3-chloropropane, 1,2-dibromoethane, dibromomethane, 1,2-dichlorobenzene, 1,3-dichlorobenzene, 1,4-dichlorobenzene, dichlorodifluoromethane, 1,1-dichloroethane, 1,2-dichloroethane, 1,1-dichloroethene, cis-1,2-dichloroethene, trans-1,2-dichloroethene, 1,2-dichloropropane, 1,3-dichloropropane, 2,2-dichloropropane, 1,1-dichloropropene, cis-1,3-dichloropropene, trans-1,3-dichloropropene, ethylbenzene, hexachlorobutadiene, 2-hexanone, isopropylbenzene, p-isopropyltoluene, methylene chloride, 4-methyl-2-pentanone, methyl-tert-butyl ether, naphthalene, n-propylbenzene, styrene, 1,1,1,2-tetrachloroethane, 1,1,2,2-tetrachloroethane, tetrachloroethene, toluene, 1,2,3-trichlorobenzene, 1,2,4-trichlorobenzene, 1,1,1-trichloroethane, 1,1,2-trichloroethane, trichloroethene, trichlorofluoromethane, 1,2,3-trichloropropane, 1,2,4-trimethylbenzene, 1,3,5-trimethylbenzene, vinyl acetate, vinyl chloride, xylenes, dibromofluoromethane, toluene-d8, 4-bromofluorobenzene.

For acetone measurement, ranges of physiological interest vary. In preferred embodiments for diet monitoring, a preferred measurement range is 0 to 2 ppm with a resolution of 0.5 ppm. For monitoring ketogenic diets, a preferred measurement range is 0 ppm to 20 ppm with a resolution of 2 ppm. For monitoring diabetic ketoacidocis, a preferred measurement range is 0 to 100 ppm with a resolution of 10 ppm. For screening potential type II diabetes, a preferred measurement range is 1 to 10 ppm with a resolution of 1 ppm. For screening prediabetic individuals at risk for diabetic retinopathy, the preferred measurement range is 1 to 10 ppm with a resolution of 0.1 ppm.

For ammonia sensing or measurement, ranges of physiological interest vary. In preferred embodiments for monitoring protein metabolism, a preferred measurement range is 0.05 to 2 ppm with a resolution of 0.01 ppm. For monitoring potential kidney failure in prediabetics, a preferred measurement range is 0.5 to 5 ppm with a resolution of 0.1 ppm. For monitoring dialysis patients, before, during or after dialysis, a preferred measurement range is 0.2 to 2 ppm with a resolution of 0.1 ppm. For monitoring for hepatic failure or related diseases such as hepatic encephalopathy, a preferred measurement range is 0.5 to 5 ppm with a resolution of 0.1 ppm. For screening for Reye syndrome, a preferred measurement range is 0.5 to 5 ppm with a resolution of 0.1 ppm. In screening infants and children for urea cycle disorders, a preferred measurement range is 0.5 to 5 ppm with a resolution of 0.1 ppm. For measuring environmental or work exposure, a preferred measurement range is 0.5 to 5 ppm with a resolution of 0.1 ppm.

In accordance with one aspect of the invention, as outlined herein above, a system is provided for sensing an analyte in a breath sample from a user. The system comprises a base; a breath input operatively coupled to the base that receives the breath; a cartridge coupled to the base and in fluid communication with the breath input to receive the breath, wherein the cartridge comprises an interactant subsystem that is selected to undergo a reaction with the analyte when the analyte is present in the breath and to undergo an optical change corresponding to the reaction; and an optical subsystem coupled to the base and configured to sense the optical change, wherein the optical subsystem generates an output comprising information about the analyte in response to the optical sensing.

In accordance with another aspect of the invention as noted herein above, a method is provided for sensing an analyte in a breath sample from a user. The method comprises providing a cartridge comprising a region that comprises an interactant subsystem that is selected to undergo a reaction with the analyte when the analyte is present in the breath sample and to undergo an optical change corresponding to the reaction. The method also comprises providing a flow path for the breath sample that comprises a breath input and a region of a cartridge, and disposing an optical subsystem in fixed relation relative to the region. In addition, the method comprises moving the breath sample through the flow path, causing the optical subsystem to detect the optical change as the breath sample is moved through the flow path, and outputting an output that comprises information about the analyte in response to the optical sensing.

To illustrate these aspects of the invention, a presently preferred embodiment will now be described with reference to FIG. 1 and others of the drawings, and a presently preferred method of implementation will be illustrated using that embodiment. It should be understood, however, that the invention according to these aspects is not necessarily limited to such specific and illustrative device and method.

Figures 3A, 3B:
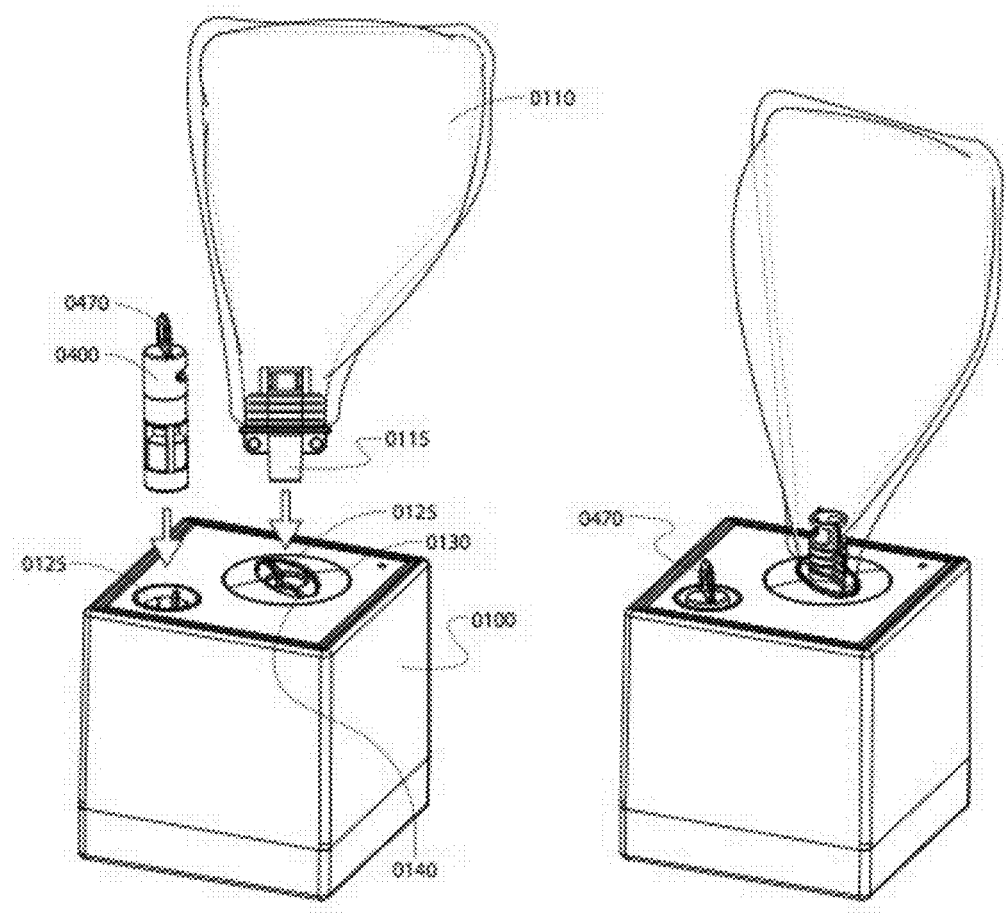
FIG. 3A shows the direction of component insertion for an embodiment of a breath analysis system.
FIG. 3B shows exemplary detachable components of a breath analysis system fully inserted into an embodiment of a base unit.

FIG. 1 is a presently preferred embodiment of a system according to certain aspects of the invention for measuring at least one analyte in breath. The overall breath analysis system of FIG. 1 has four sub-systems: (a) a flow handling subsystem, (b) an actuation subsystem, (c) a sensing subsystem, and (d) a processing subsystem. The system comprises a base unit (0100), a detachable cartridge (0400), and a breath input (0110), which may comprise a breath bag or other container or direct connection to a patient to receive exhaled air. The base (sometimes referred to "base unit" or "base device") optionally forms a housing or a connection point for the other components that make up the breath analysis system. The cartridge (0400) is coupled to the base unit via a first port (0120) and the breath input is coupled via a second port (0130). FIGS. 3A and 3B show the insertion of these two components into the base unit. Inserting either disposable may cause a "click" or other user feedback, such as via a partial button (0140) in line with the insertion path. The base unit communicates via wireless or wired connection with an interface such as a mobile device (0135).

Exemplary mobile applications and systems using mobile applications are described, for example, in U.S. patent application Ser. No. 14/690,756 entitled: "Ketone Measurement System and Related Method With Accuracy and Reporting Enhancement Features" and U.S. patent application Ser. No. 14/807,821 entitled: "Ketone Measurement System with User Interface for Efficient Categorization of Measurements", commonly owned by the Applicant, and which are hereby incorporated by reference in their entirety.

Figure 2A:
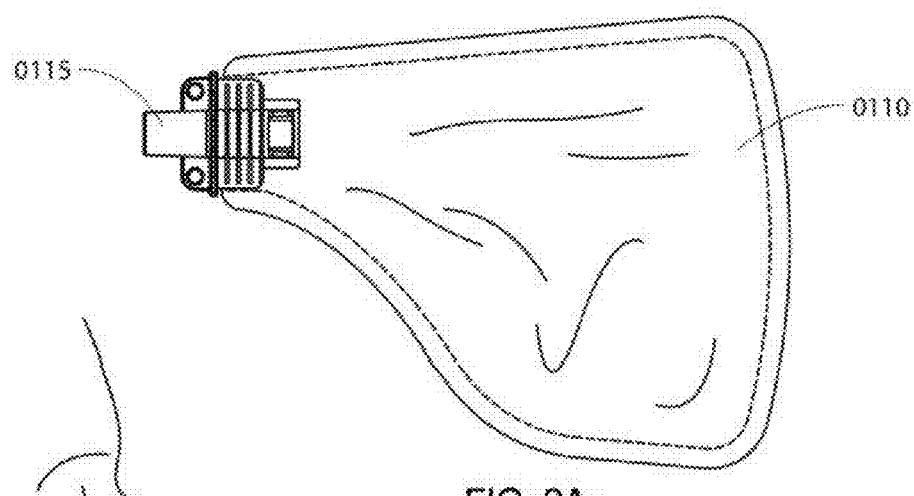
FIG. 2A shows an embodiment of a breath bag.
Figure 2B:
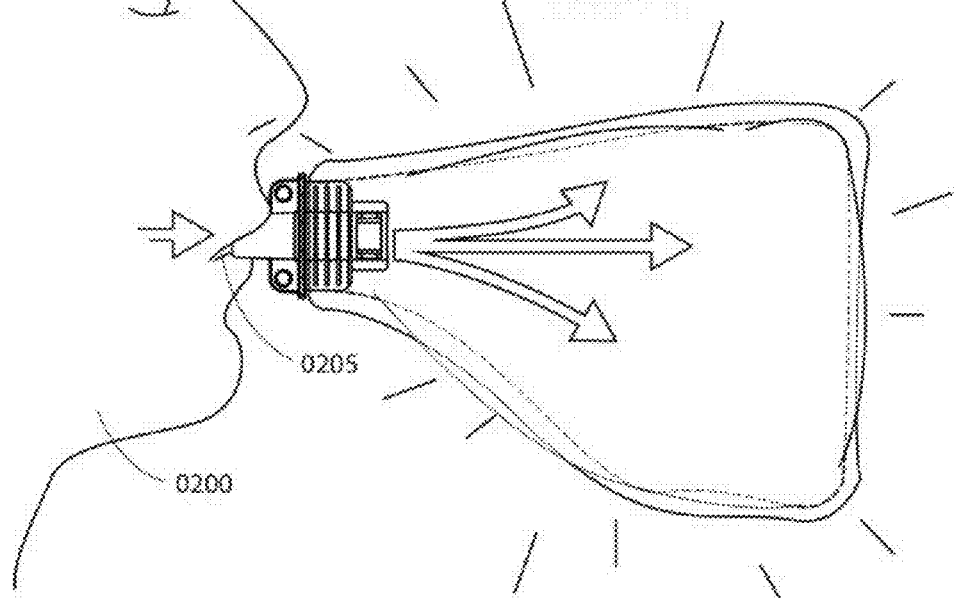
FIG. 2B shows a user exhaling into the embodiment of the breath bag shown in FIG. 2A.

Referring to FIGS. 2A and 2B, a user (0200) exhales into the breath input (0100), here a breath bag, via a mouthpiece (0115).

FIGS. 4A-G shows an exemplary cartridge that works in conjunction with the base unit shown in FIG. 1. The illustrated embodiment is configured to operate using, for example, the inverted cup wetting method, discussed in greater detail herein. In this embodiment, the cartridge (0400) is comprised of three plastic parts: (a) an upper body (0405), (b) a cup (0415) and (c) a lower body (0435). Other wetting configurations are discussed herein.

Referring to FIG. 4A, the lower body (0435) is preferably optically clear or contains an optically transparent window and comprises two chambers, one for the reactive beads (0430) and the second for the desiccant (0445). A porous disk (0440) separates the desiccant (0445) and the reactive beads (0430). Atop the reactive beads, a disk (0425) is disposed. Below the desiccant (0445), a final disk (0450) is disposed.

The upper body (0405) may be assembled upside down. Within the upper body (0405), there is a small perch (not shown) on which a ball (0410) rests. An inverted cup (0415) also contains a perch (0480) upon which the ball is placed. Liquid reagent (0455) is stored in the cup. The cup is preferably opaque to prevent light from interacting with this reagent, if it is light sensitive. Optionally, a spring (described in FIGS. 28A to 28D) also may be placed within the cup to assist with breaking the seal between the cup and the cog (0420) and to release liquid when the ball is displaced. A cog (0420) is placed on top of the cup. The lower body (0435) is then press fit atop the assembled upper body.

Side profiles of the cartridge (0400) are shown in FIGS. 4 C, G and E.

Modifications to the design can be made. One such modification is shown in FIGS. 4A to 4G in which the upper body (0405) has a key (0460) such as an axially extending ridge groove or flat, or radially extending post, that ensures that it is inserted in only one way into the base unit.

Figure 5:
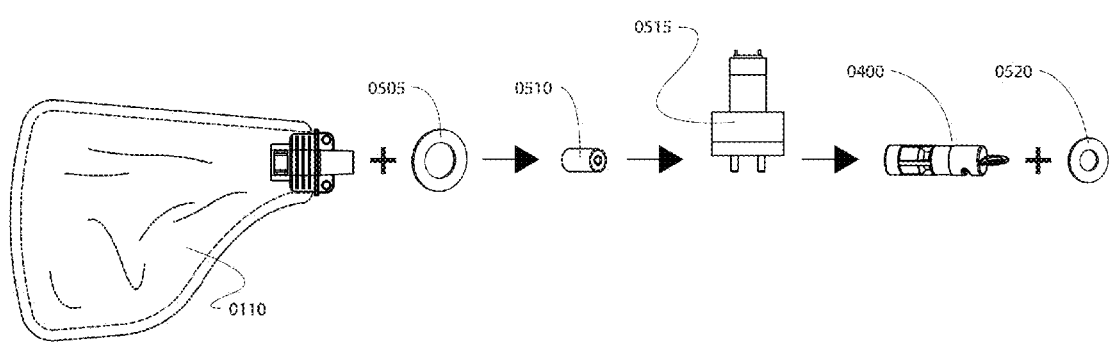
FIG. 5 shows an exemplary flow sub-system of a breath analysis system.

FIG. 5 shows basic components of one embodiment of a flow handling subsystem. The flow path starts with a breath input (0110), here a breath bag. The breath input, however, can be any apparatus that is capable of receiving a breath sample, whether rigid or flexible. In some embodiments, the breath input is integrated into the base unit. In others, it is detachable as shown in FIG. 1. The breath input (0110) is coupled to the base unit via some type of gasket (0505) or other mechanism to ensure an effectively gas-tight seal. The breath sample is optionally directed from the breath input (0110) through a flow restrictor (0510) or other means to reduce or regulate the flow. A pump (0515) or other mechanism such as a fan may be located anywhere along the flow path, such as directly upstream from the cartridge (0400) as illustrated, and directs the breath sample from the breath input (0110) and into the cartridge (0400). The cartridge (0400) is also in line with another gasket (0520) or other apparatus to ensure an effectively gas-tight seal. In preferred embodiments, the pump speed and pump time are controlled by a processor (not shown).

Figure 6A:
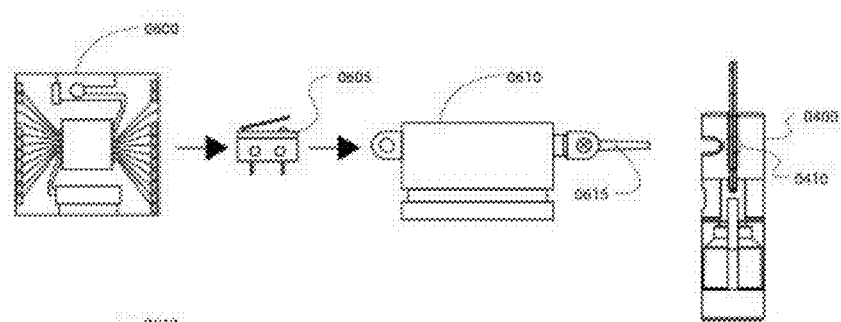
FIG. 6A shows an exemplary cartridge actuation sub-system of a breath analysis system before actuation of the cartridge embodiment.
Figure 6B:
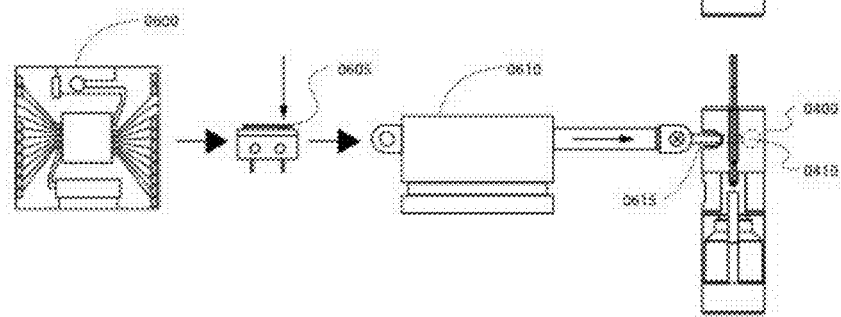
FIG. 6B shows an exemplary cartridge actuation sub-system of a breath analysis system after actuation of the cartridge embodiment.

FIGS. 6A and 6B show basic components of one embodiment of an actuation subsystem. A processor (0600) causes an actuator (0610) to release liquid from a liquid container in the cartridge. In the illustrated embodiment, the actuator (0610) extends a kicker or elongated member (0615) (compare FIG. 6A and FIG. 6B) at the appropriate time into the cartridge (0400). Optionally, this actuation step only occurs if a switch (0605) or other control mechanism indicates that the cartridge (0400) is in place so that the actuator does not extend if, for example, a user's finger is inside the cavity (0120) through which the cartridge is inserted.

Figures 7A, 7B:
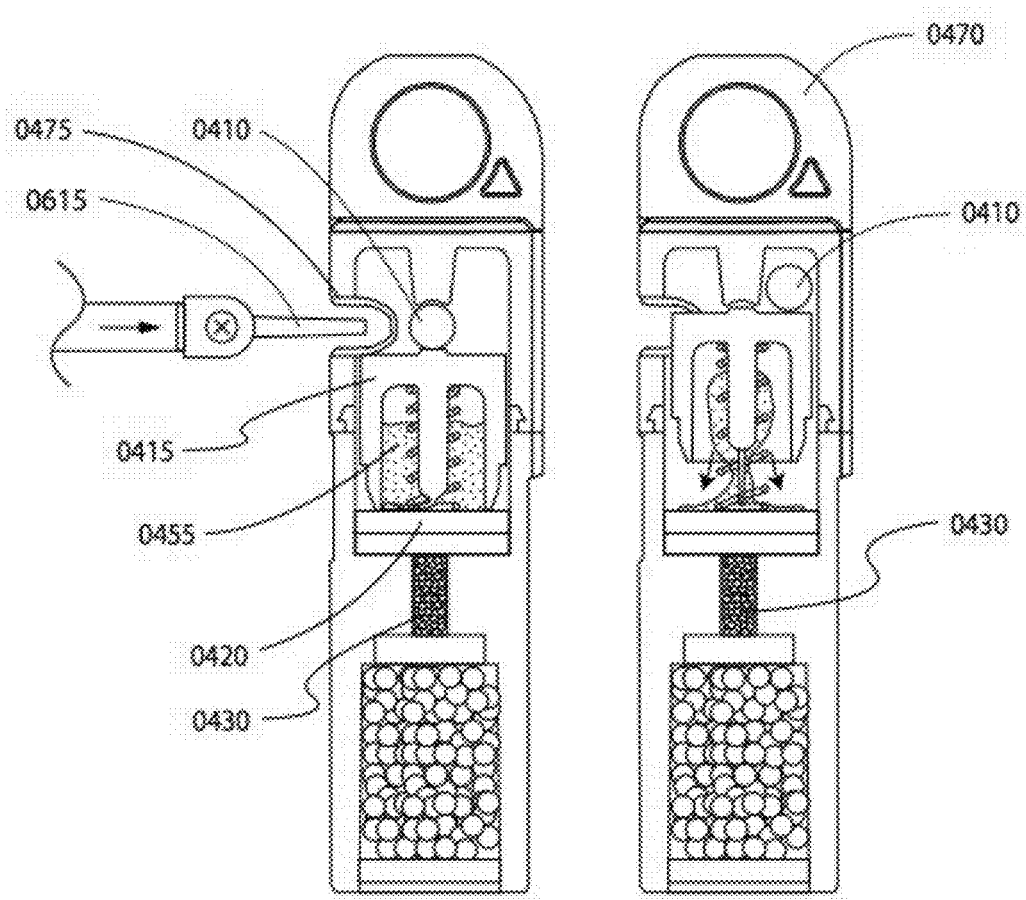
FIG. 7A shows another embodiment of a cartridge before actuation.
FIG. 7B shows the cartridge embodiment after actuation.

FIGS. 7A & 7B show the operation of the cartridge embodiment of FIGS. 4A to 4G. The cartridge (0400) comprises a window (0475) that allows a kicker (0615) to displace a restraint such as a ball (0410) from the position shown in FIG. 7A in which a liquid reservoir is in a closed configuration, to the position shown in FIG. 7B in which the restraint is displaced, enabling liquid to exit the liquid container. In the illustrated embodiment, this displacement of the ball (0410) causes or allows the inverted cup (0415) to move in an upward direction (compare position A to position B) such that liquid contained within the cup (0455) is released and is then able to move along a flow path such as through passageways of the cog (0420) and penetrate to the reactive beads (0430) in a reaction volume to engage in a reaction.

FIGS. 8A & 8B show basic components of one embodiment of a sensing subsystem. A processor (0600) is in communication with an image sensor (0815). An optical path from the image sensor (0815) extends through a lens (0825) carried by the lens mount (0820). In some embodiments, the lens (0825) is a finite conjugate lens such that it is able to focus better on nearby objects. The sensing subsystem may be configured to capture a first, narrow field of view which is focused through an optical window on the cartridge (0400) and into the reaction volume. The first field of view is used to monitor an optical characteristic such as color intensity in the reaction volume. Preferably, as shown in FIG. 8B, the sensing subsystem is configured to focus the lens to capture a second, wider field of view that includes both the portion of the cartridge that exposes the reaction volume, as well as some amount of adjacent surface of the cartridge, which may be provided with printed information about the cartridge. The second field of view may also include at least a portion of the upper and/or lower disk (as shown in the cutout) to enable optical (e.g. visual) inspection for potential defects. The processor may be powered via an AC or DC source. In this embodiment, it is powered by a battery (0805).

Figure 9:
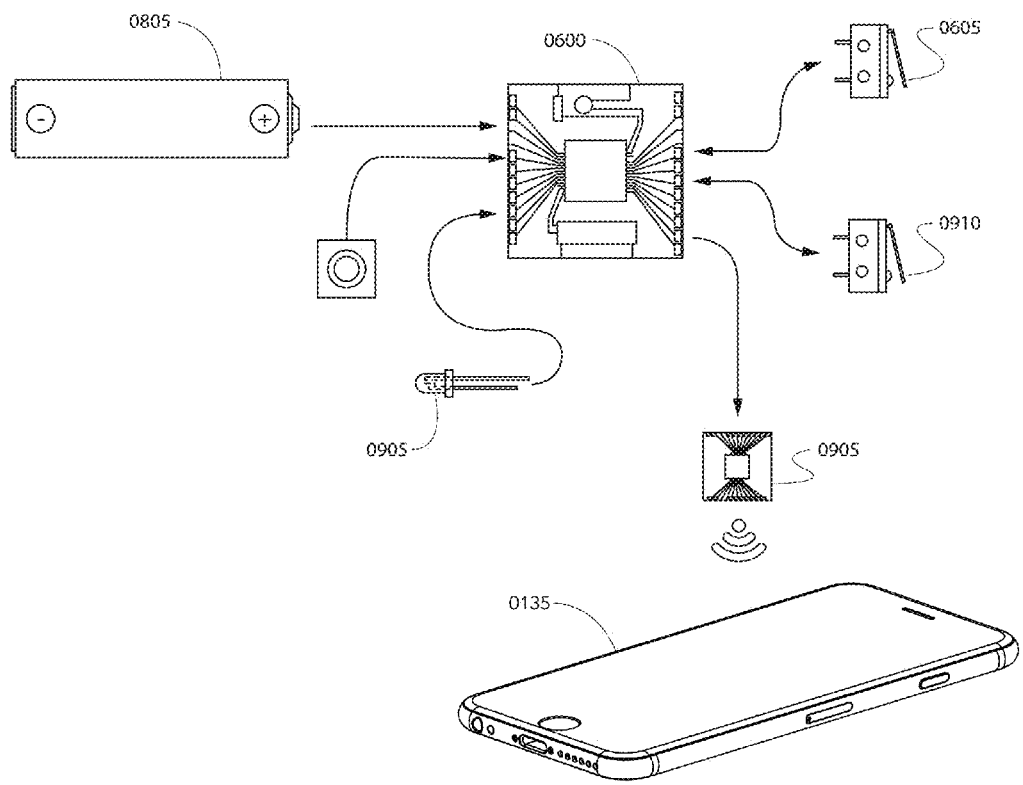
FIG. 9 shows an exemplary user experience sub-system of a breath analysis system.

FIG. 9 shows basic components of one embodiment of a user interface subsystem. The processor (0600) communicates with several components. A first presence sensor (0605) senses proper installation of an appropriate cartridge (0400). A second presence sensor (0910) senses proper installation of an appropriate breath input (0110). A transceiver (0905) and an indicator such as an LED (0905) are also provided. The color of the LED varies depending on the state of the system. For example, if the system is not paired with a mobile device, the LED is a first color, such as orange. If the system is paired and ready for a measurement, the LED is a second color, such as blue. The transceiver may be wired or wireless. Preferably, it is a BLE wireless module that communicates with a mobile device (0135) such as a cell phone.

Figure 10:
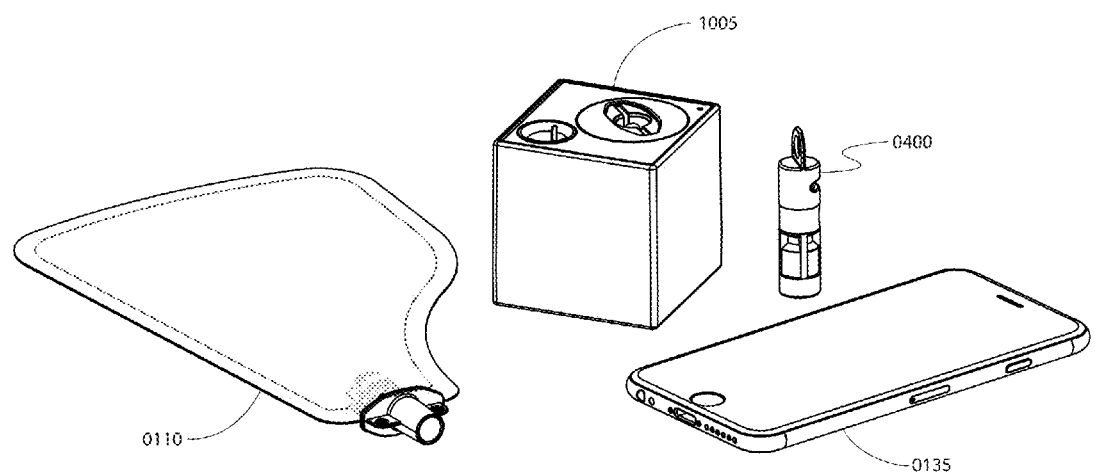
FIG. 10 shows another embodiment of a breath analysis system.

The form factor of the base unit is not intended to be limiting. FIG. 10 shows, for example, a base unit (1005) that is substantially smaller than the base unit (0100) shown in FIG. 1, but works with the same disposable components.

The base unit is preferably portable, such as less than about 250 cubic inches, often less than about 125 cubic inches (or 5 inches cubed). In preferred embodiments, the base unit is between 27 and 125 cubic inches. For example, in the embodiment shown in FIG. 1, the base unit is approximately 27 cubic inches (3 inches cubed). In other embodiments, the base unit is between 8 cubic inches and 27 cubic inches. For example, in the embodiment shown in FIG. 10, the base unit is approximately 8 cubic inches (2 inches cubed). In other yet embodiments, the base unit is less than 8 cubic inches. Of course, the cuboidal shape is not limiting.

The cartridge is preferably compact. In preferred embodiments, the cartridge is less than 8 cm in length. In other embodiments, the cartridge is less than 6 cm in length. The cartridge shown in FIGS. 4A to 4G, for example, is preferably 5.3 cm, including the length of the handle. In other embodiments, the cartridge is between 4 cm and 6 cm. In certain configurations, the cartridge is less than 4 cm. The width of the cartridge is typically no more than about 33% of the height, and often is no more than about 20 to 25% of the height.

The height of the reactive chamber of the cartridge is preferably short. In certain embodiments, it is less than 3 cm. In preferred embodiments, it is less than 2 cm. In certain embodiments, it is less than 1 cm. In other embodiments, it is less than 0.5 cm or between 0.25 cm and 0.5 cm. In other yet embodiments, it is less than 0.25 cm. The ratio of the height of the reactive column to the height of the column overall is often less than 25% and is preferably less than 10%.

In certain embodiments, the breath bag volume is preferably less than 1 L. In certain embodiments, it is between 500 mL and 1 L. In other embodiments, it is between 250 mL and 500 mL.

The overall breath analysis system may be packaged so that the base unit and disposable kits are provided separately. For example, a monthly disposable kit may be provided, comprising 30 disposable cartridges and 30 breath bags. Or, if the breath bag is designed for limited re-use, the monthly disposable kit may be 35 disposable cartridges and 5 breath bags (5 week "monthly plus extras" kit with 1 breath bag for each week). If the breath bag can be re-used for the month, a kit may be comprised of 30 disposable cartridges and a single breath bag. Alternatively, weekly disposable kits may be provided, including 7 cartridges and one or seven breath bags depending upon the intended reuse. The cartridges may be packaged in a sleeve, such as the one described in FIG. 37 described herein.

Figure 11A:
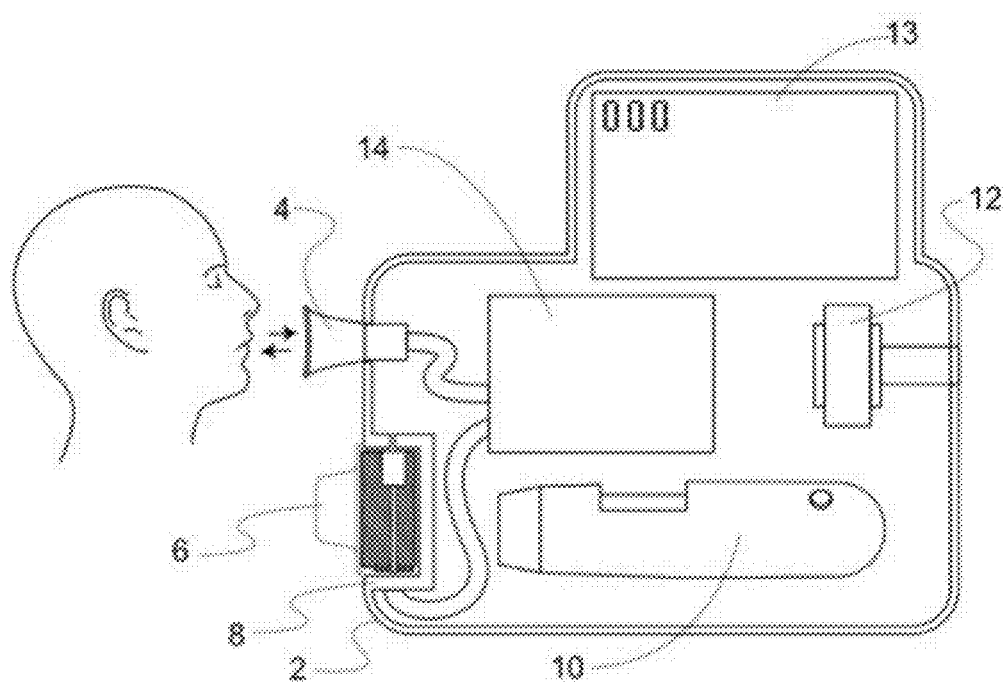
FIG. 11A shows a composite illustration of a device used in sensing changes of optical characteristics from reactions with breath analytes.
Figure 11B:
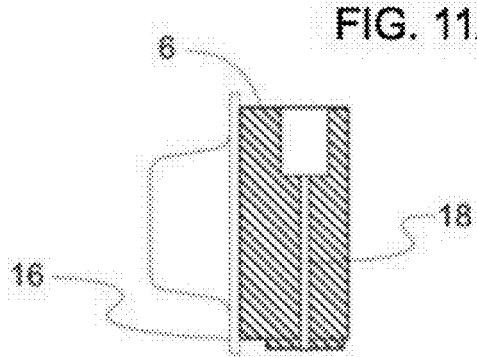
FIG. 11B shows an illustration of a cartridge embodiment used in conjunction with the above-mentioned device.

FIGS. 11A and 11B show another embodiment of a breath analysis system in the form of a base (2), a cartridge receiver (8), which preferably is connected to a dispensing device, an optical subsystem (10), a flow handling system, here specifically in the form of a pump (12) and a processor (14). The base (2) receives a breath sample from a user via a breath input (4). The insertion mechanism for a cartridge includes means for a cartridge to be inserted, where the cartridge contains an interactant capable of reacting with at least one analyte when present in the breath in concentrations typical of endogenous breath analytes, e.g., less than about 5 ppm, to generate an optical change. The optical subsystem (also referred to as "optical sensing subsystem", "sensing subsystem", "breath sample analysis subsystem", "optical detection subsystem", "optical setup" and "imaging system") senses an optical change. The term "optical change" is used interchangeably with a "change in an optical characteristic." The flow handling system (also referred to as pneumatic handler) is preferably included within the base unit, although this is not always the case. The flow handling system allows for the breath to interact with the interactant in the cartridge. The processor (also referred to as the "digitizer" or "control electronics") quantifies the optical change measured by the optical subsystem and outputs information regarding at least one analyte in the breath sample to the user interface.

The base can be any apparatus that receives a breath sample from a user. In certain embodiments, the base contains the flow handling system. In preferred embodiments, the base is portable and capable of individual patient use. The base may also be capable of withstanding (measuring and compensating for) temperature and humidity changes so as to improve the accuracy of the measurement process.

A method for sensing an analyte in breath of a patient according to another aspect of the invention will now be described using preferred breath analysis system and cartridge. It will be appreciated, however, that the method is not necessarily limited to these preferred apparatus, and that other apparatus and components may be employed to practice or implement the method.

According to this method, one first provides a cartridge comprising a first container, a liquid container, and a reaction zone in fluid communication with the first container and the liquid container, wherein the first container containing a first interactant and the fluid liquid containing a liquid, wherein the liquid container has an initial fluid level and a space above the initial fluid level. These aspects of the method are provided in this implementation by providing cartridge as described herein above.

The method also comprises providing a base comprising a flow path for flow of the breath sample within the base, a breath input receiver in fluid communication with the flow path, a cartridge housing, a dispensing device, and an optical subsystem. These aspects of the method are provided in this preferred implementation by providing base 440 of FIG. 48 as described herein above, including one of the dispensing device embodiments disclosed herein.

The method further comprises inserting the cartridge into the cartridge housing of the base so that the reaction zone is in fluid communication with the flow path. In the preferred implemented herein, this comprises inserting cartridge into cartridge housing of base unit.

The method then comprises causing the breath to flow in the flow path and into the reaction zone.

After the breath has flowed through the reaction zone, the method comprises using the dispensing device to create a hole in the fluid container below the initial fluid level and moderating pressure in the space above the initial fluid level as the fluid moves out of the liquid container so that the fluid moves out of the liquid container and into the reaction volume, thereby facilitating an optical change in the reaction zone in relation to at least one of a presence and a concentration of the analyte.

The method also comprises sensing the optical change and generating an output comprising information about the analyte in response to the optical change. This preferably is implemented by using an optical subsystem (including illuminator and camera), processor and outputs (user interface and/or communications output) of system.

A breath input can be anything capable of receiving a breath sample from a user, and optionally perform the function of breath metering. The breath input may optionally include the step of breath conditioning, but this may also be handled by the base itself. The breath input can also include breath sampling, which preferably utilizes a reservoir for containing the breath sample. The breath input can be rigid or flexible.

The breath input preferably holds a breath sample greater than 300 mL in volume, but this volume may vary depending on the application. Depending on the application, the volume may be greater than 450 mL, between 300 mL and 450 mL, between 200 mL and 300 mL, between 100 mL and 200 mL and under 100 mL.

In general, breath collection is a subset of "breath sampling." Breath sampling involves obtaining a breath sample from a user. Breath sampling may be direct or indirect. An example of direct breath sampling involves a user exhaling directly into the system or into the base. Such an example is shown in FIGS. 11A and 11B. Indirect breath sampling involves, for example, a user breathing into a collection vessel (e.g., a collection bag) where the vessel is connected to the system for evacuation. Unless noted otherwise, the following terms are used interchangeably: "breath bag", "breath collection bag", "breath sampling bag", "collection bag", "bag", "breath sample bag assembly", "bag unit", "breath sample bag", and "gas collection vessel." FIG. 14 demonstrates an example of an indirect breath sampling performed by a breath input. A three-way non-rebreathing valve (30) with an additional outlet tap (32) enables portions of numerous breaths to be sequentially deposited into a breath bag (34). A mouthpiece, with or without an integrated anti-bacterial/viral filter (35), protects a user from cross-contamination.

In one embodiment of the present invention, the collection of a breath sample is performed separately from the analysis of the breath sample. Separating the steps creates certain advantages that can be well suited for certain applications. For example, if the breathing resistance through the interactant is high (e.g., packed bed reactor), the user will experience more comfort breathing into a breath bag with little to no breathing resistance. The base itself can then deliver the breath sample or a portion thereof to the interactant for sensing purposes.

An example of a use case is provided. A user picks up a breath bag with a one-way valve assembly. The breath bag is either pre-assembled with the valve assembly or the user attaches a clean, disposable breath bag to the valve assembly. The breath bag can be comprised of various plastics, especially useful is a breath bag wall material of relatively thick (0.01" to 0.02") polyethylene. The user attaches a disposable mouthpiece over the end of the valve assembly if desired (if the base is shared with multiple users). The user then breathes into the breath bag. The user does not need to be concerned with flow rate, flow duration, flow pressure, or sample capture during the sampling procedure. The breath bag is filled until a small back-pressure is obtained, with a tenth of a psi, for example. The back-pressure causes the valve to close. A breath bag designed according to this approach can retain breath acetone for some period of time, such as overnight. Within this period of time, the user attaches the breath bag to the base. Only minimal force is required to engage the bag in an air-tight fashion with the breath bag receiver. Inputting the breath bag with the breath bag receiver opens the one-way valve, permitting the flow handling system of the base to have access to the contents of the breath bag. The flow handling system of the base in preferred embodiments contains components which serve to dramatically limit the leakage of the breath sample through the flow handling system components until the sample is ready to be analyzed by the base. Analysis does not need to be immediate. It can be delayed by several minutes without significant loss of sample. For immediate analysis, such as a typical consumer experience, the breath bag materials can be disposable and made of very thin, very inexpensive plastics such as nylon.

One way to collect the breath sample separately from analyzing the breath sample is by using a flow handling system with active components. Specifically, in the breath analysis system, the breath sample is directed to the interactant region or the reactive zone. Passive or active flow handling systems can be used for this purpose. Passive systems involve use of components such as flow restrictors, flow partitioning devices, and other mechanical means that do not require the input of energy (other than the pressure applied during exhalation). In contrast to these passive systems where the user forcibly exhales breath into the interactant region or reactive zone, active systems can be used to decouple user breathing from delivery of the breath sample to the interactant region or reactive zone. Sensor constraints such as controlled gas delivery flow rate, stable drive pressure, high pressure drop of flow over the reactive zone, etc. can be divorced from user breathing requirements. In particular, extended breaths through high pressure drop systems or a requirement that a user blow with a stable pressure or flow rate are eliminated. In addition, gas delivery parameters outside of a user's ability can be achieved. For example, the maximum pressure that an average healthy adult can produce via forcible exhalation is only approximately 0.3 psi, whereas active gas handling equipment does not bear that limitation. This enables a wide range of configurations for the flow handling system. As another example, a low flow rate of 50 ml per minute can be sustained for several minutes using an active flow handling system, which means there is no burden to the user of sustained breath output over that same period. (Comfortable human breath rates are on the order of 6 L per minute with negligible breathing resistance).

System (410) comprises a breath sampling subsystem (412) (sometimes referred to as a breath collection subsystem) and a breath analysis subsystem (414) (sometimes referred to as a breath sample analysis subsystem). Breath sampling subsystem (412) and breath analysis subsystem (414) in this preferred but merely illustrative embodiment are physically separate, attachable and detachable components, but this is not necessarily required or limiting. Alternative configurations, e.g., in which the breath sampling subsystem (412) and breath analysis subsystem (414) are contained in a single unit, are within the scope of the invention.

Although breath sampling subsystem (412) may comprise a direct flow-through conduit to the breath analysis subsystem (414), in this embodiment it provides a means to retain or store the breath sample until it is ready for use in the breath analysis subsystem (414). When called upon to do so, the breath sampling subsystem is fluidically connected to the breath analysis subsystem. The breath sampling subsystem (412) may comprise a variety of forms, provided it can perform the functions required of it as described herein.

For improved relevance of the sensing results made by the breath analysis system, breath sampling can be performed with attention to details such as: (a) total volume of breath collected; (b) source of collected breath (e.g., upper airways vs. alveolar air); (c) number of breaths collected; (d) physiological status of the subject prior to and during breath collection (e.g., rested state with normal breathing vs. active state with increased breath rate vs. hyperventilation, as examples); and (e) breathing effort of the sampling mechanism (e.g., does the subject need to breath through a high-resistance sampling apparatus at extended duration, or does the mechanism allow for normal breath exhalations?).

The breath sample may also be conditioned. Particular examples of breath conditioning include: (a) desiccation (e.g., removal of water); (b) filtering (sometimes referred to as "scrubbing") (e.g., removal of carbon dioxide or certain volatile organic compounds); and (c) heating or cooling of the gas stream (condensation prevention/instigation). As noted, breath conditioning, if performed, can be carried out by the breath input or a separate system.

As mentioned, the breath input can optionally meter the breath sample. Metering of the breath sample means measuring the volume of breath being sampled through the breath input. This can be accomplished in a number of ways by one of skill in the art, including actually measuring the amount of breath sampled (e.g., using a pneumotachometer, and recording the total volume of breath over a given amount of time), or by sample volume restriction, such as by having a user breathe into a fixed volume container.

In one aspect of the invention involving indirect breath sampling, the breath input can have integrated metering capacities, such as a breath bag with integrated flow measurement capabilities.

Figure 12:
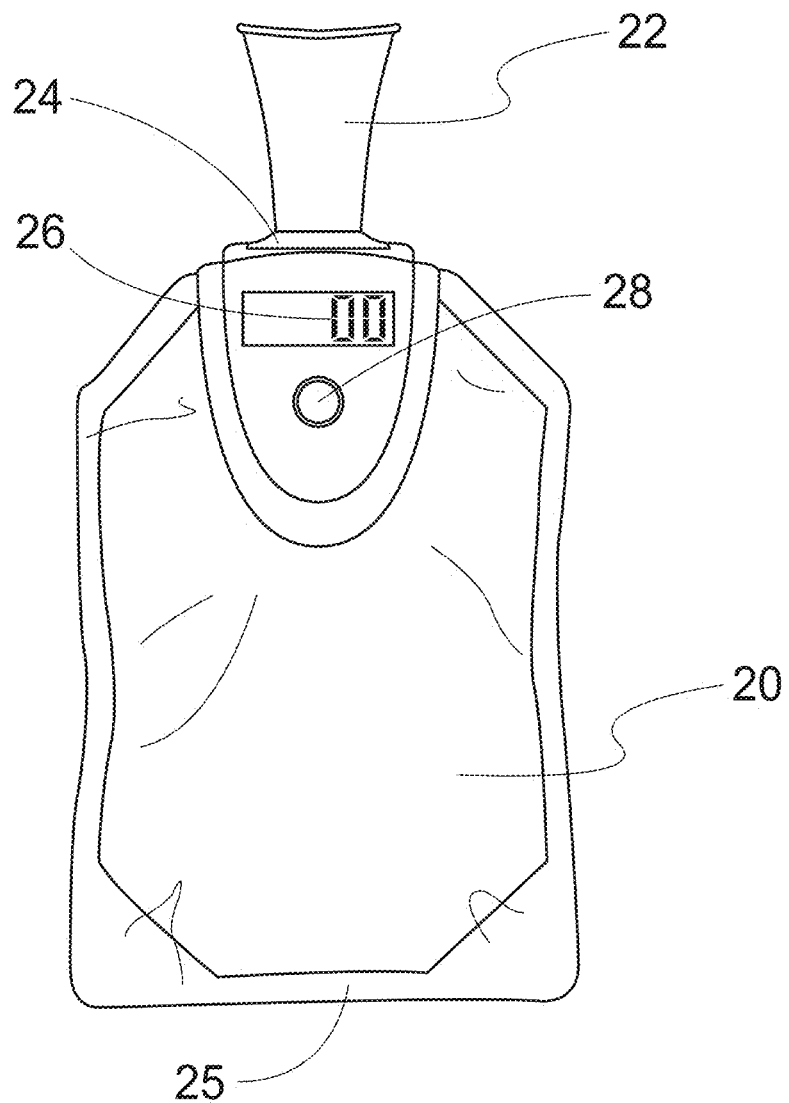
FIG. 12 shows an example of a breath bag with integrated flow measurement capabilities.

FIG. 12 shows an example of a breath bag with integrated flow measurement capabilities. A breath bag (20) comprised of wall materials impermeable to the analytes of interest and in some cases also their ambient interferents contains a breath sample inlet (24) fitted with a mouthpiece (22). An upper portion of the assembly houses electronics and/or mechanical devices useful in analyzing or conditioning breath samples, including in some cases a visual indicator (26). The electronics can consist of a variety of assets, including temperature probes, pressure transducers, timing circuits, humidity sensors, and others depending on the application. Mechanical devices can include one-way breathing valves, flow restrictors, scrubber or desiccant chambers, computer-controlled or automatic valves, manual valves, and others. In one embodiment, the breath sample inlet (24) comprises a one-way valve. The breath sample inlet (24) is designed to mate with a breath bag receiver on a base (not shown in FIG. 12) and the breath bag receiver (sometimes referred to as a "receiver port") is equipped with fingers or protrusions designed to open the one-way valve. This system enables a breath sample to be collected from a user and to be contained within the breath bag without user interaction. Attaching the breath bag to the base allows the fingers or protrusions to open the one-way valve (for example, a flapper valve) so that the contents of the breath bag can be removed by, for example, a pump (subcomponent of the flow handling system) of the base. No manual interaction with the one-way valve is required by the user. Also shown in FIG. 12 is a user interface button (28), exemplifying a possible interaction of the user with the electronics, such as to start a timer. A second end of the breath bag (25) can be fitted with similar facilities. For example, the lower portion of the bag (25) can be fit with a second one-way valve, such that the user breathes into the breath sample inlet with the first one-way valve (24) and out through the second end with the second one-way valve (25) so that the last exhaled portion of breath is captured in the breath bag. This can be used to sample, for example, the deep alveolar airspace whereas without the second one-way valve the breath collected is the first portion blown into the bag. The bag may likewise be fitted at other points, for example on the sides or front/back faces.

Although it is desirable to obtain a representative breath sample, it is not necessarily advantageous or necessary for the entire sample volume to be analyzed. Rather, in some embodiments, a representative sample may be analyzed. One reason why it may not be desirable to analyze the full volume of breath is gelling of a desiccant (the terms "desiccant material" and "desiccant" are used interchangeably). As mentioned, the breath input may optionally include breath metering, which preferably uses a sample reservoir. For example, the sample reservoir may be a one-milliliter syringe that extracts a representative portion from, for instance, a breath bag. In this configuration, the user breathes into a breath bag, which contains some number of exhaled breaths. The breath bag may, and preferably does, contain metering capabilities to determine sample volume and/or sample volume per unit time as the user is inflating the breath bag. Once the breath bag is inflated, a metering mechanism is triggered which extracts some smaller volume of the exhaled breath sample and stores this in the sample reservoir. The metering mechanism may be an active pump, but it may also be a passive tool such as a syringe that requires the user to exert force to meter the sample. The breath bag may then be deflated. The user then is left with a metered breath sample (of lower total volume) in a sample reservoir. This sample reservoir may be used to "inject" a breath sample into the base.

Figure 13:
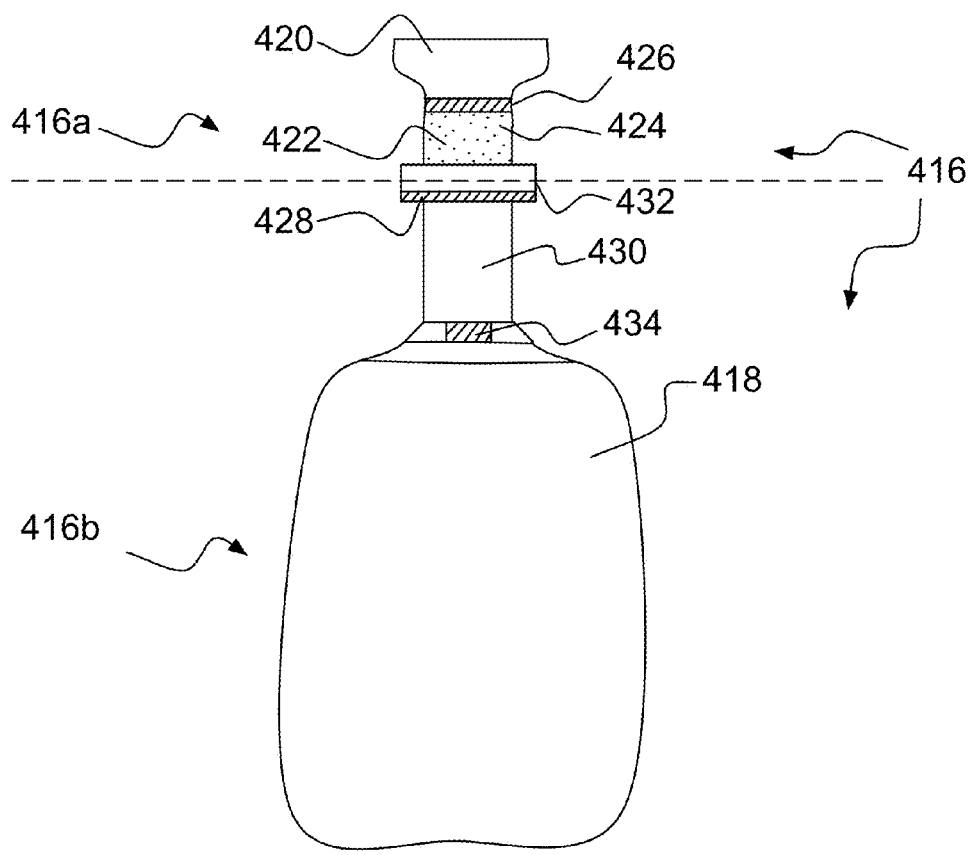
FIG. 13 is a perspective drawing of a breath bag for collecting and storing a breath sample, and for inputting the breath sample to the breath analysis system of FIG. 48 and FIG. 49.

In another embodiment, breath sampling subsystem (412) comprises a breath sample bag assembly (416) for retention of a breath sample, and for delivery of the breath sample to the breath analysis subsystem as further described herein below. Breath sample bag assembly (416) according to this embodiment, shown separately and enlarged in FIG. 13, comprises a detachable breath sample input unit (416a) and a bag unit (416b), the latter comprising a breath reservoir (418).

The breath sample input unit (416a) provides a means for inputting the breath sample into the bag unit (416b) in a manner so that contamination or otherwise unwanted external gases or substances (external to the breath sample itself) are not allowed to infiltrate into the breath reservoir (418). Although a variety of breath sample inputs are possible, in presently preferred breath sampling subsystem (412) the breath sample input unit (416a) comprises a mouthpiece (420). Examples of alternative breath sample inputs would include tubular or conduit-based inputs, inputs that segregate the breath sample into components or segments, and the like.

Breath reservoir (418) comprises a flexible, air-tight container that has insubstantial or no permeability for breath samples of the type for which this system is used. The permeability of analyte or analytes of interest out of or through the container under storage or retention conditions should be zero or as close to zero as possible over anticipated or desired retention times, and certainly below the lower range of detectability for the overall device so that such leakage does not affect the sensing results. Examples of containers generally suitable for present uses include Tedlar and mylar foil bags. Breath sample bag assembly (416) according to this embodiment comprises mylar foil, which is generally preferred based on its relatively low permeability for ammonia. For applications such as transient use, the container may be made of other materials such as polyethylene.

The breath sampling subsystem, and more specifically the breath sample input unit (416a) in this embodiment, also includes a breath conditioning device that conditions the original breath sample so that it has a desired level or range of water, or relatively humidity. In the presently preferred embodiment, the breath conditioning device comprises a pre-filter (422) in fluid communication with breath reservoir (418) between the container itself and the mouthpiece (420) so that a breath sample inputted into the mouthpiece (420) passes through pre-filter (422) and into the interior of the breath reservoir (418).

Pre-filter (422) comprises a granular desiccant (424). The grain size (including the grain size distribution) of desiccant (424) preferably is selected so that it is effective but the risk of inadvertent inhalation or ingestion of the desiccant by the patient or other user is minimized. This balancing must take into account the fact that larger particle sizes generally decrease the total surface area available for interaction with and removal of the water. This latter potential impact in some instances can be mitigated, for example, by increasing the porosity or tortuosity of the grains themselves. In view of these criteria, the granular desiccant (424) preferably has a mesh size of at least 1, and more preferably has a mesh size of between about 1 and about 100. Given the relative importance of accurate and reliable removal of the water to the desired levels, the desired mesh size preferably is at the lower end of the broader range, e.g., between about 5 and about 80, and more preferably between about 10 and about 30-40.

The material of the desiccant preferably is selected so that it does not extract the analyte or analytes of interest ammonia from the breath sample, or does so only minimally. By this is meant that the desiccant (424) either does not extract any of the available analytes to be sensed, or that to the extent some is extracted, the amount is well below the sensing or measurement threshold so that the measurement of the analyte or analytes in the breath analysis device is not adversely affected within its sensitivity and margin of error. Given the granular nature of the desiccant and the potential for ingestion risk, screens (426) are disposed at each flow end of pre-filter (422).

The breath sample input unit (416a), and more specifically the mouthpiece (420), comes into direct contact with the patient, and therefore cannot be re-used unless thoroughly disinfected. In addition, the pre-filter (422) traps or contains certain components of the breath sample, including water and potentially water-borne microorganisms or other contaminants, and similarly cannot be re-used without thorough disinfection. Accordingly, in presently preferred embodiments, the detachable breath sample input unit (416a) comprising the mouthpiece (420) and pre-filter (422) is detachable and disposable.

The bag unit (416b) in this embodiment is configured to receive and retain the breath sample during a "sampling" mode, during which breath sample input unit (416a) is attached, and to provide that breath sample to the breath analysis subsystem (414) while bag unit (416b) is detached from breath sample input unit (416a). A ferrule (430) is fixedly coupled to the end of breath reservoir (418) adjacent to pre-filter (422). Bag unit (416b), and more specifically ferrule (430), is detachably coupled to the breath sample input unit (416a), and more specifically to pre-filter (422), using a coupler (432). These components are conjoined in air-tight fashion so that, when a patient blows breath into mouthpiece (420), the breath sample travels through pre-filter (422) and ferrule (430) and into the interior of breath reservoir (418) without leakage. A one-way valve (434), in this embodiment a simple flapper valve, is disposed at the interface between ferrule (430) and the top interior of breath reservoir (418) so that breath blown into mouthpiece (420) and passing into breath reservoir (418) via pre-filter (422) and ferrule (430) is trapped in the reservoir interior and is not allowed to escape.

To reiterate and clarify, breath sampling subsystem (412) comprises two primary and detachable components, i.e., breath sample input unit (416a) and bag unit (416b). Input unit (416a) comprises mouthpiece (420) and pre-filter (422) fixedly coupled to one another. Bag unit (416b) comprises breath reservoir (418) with fixedly-coupled ferrule (430). These two components (416a) and (416b) are detachably coupled to one another by coupler (432). When detached, bag unit (416b) can be used with the breath analysis subsystem (414) as described herein below. The input unit (416a), having been directly contacted by the patient, is disposable and can be discarded.

Figure 14A:
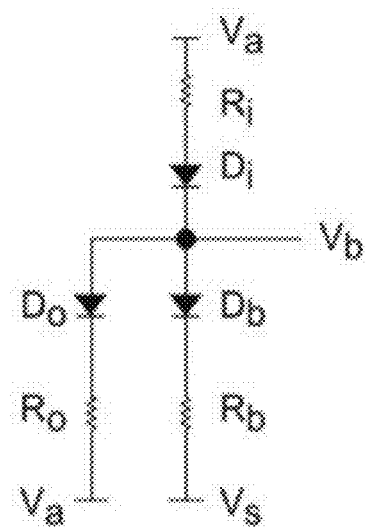
FIGS. 14A and 14B demonstrate an example of an indirect breath collection performed by a breath input.
Figure 14B:
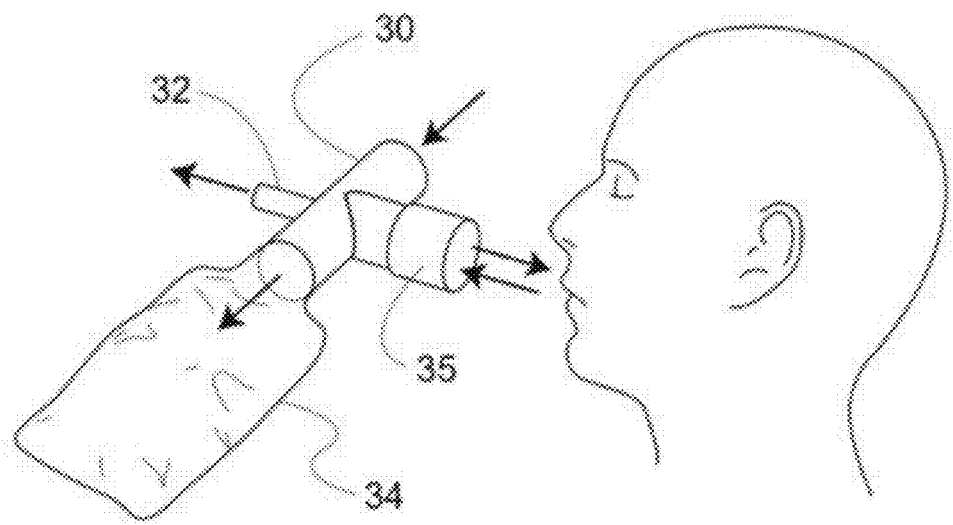

In FIGS. 14A and 14B, a three-way non-rebreathing valve (30) with an outlet tap (32) enables portions of numerous breath samples to be sequentially deposited into a breath bag (34). A mouthpiece, with or without integrated anti-bacterial/viral filter (35), protects a user from cross-contamination. The user first inhales, opening a first one-way valve in the non-rebreathing valve allowing ambient air to fill the lungs. Upon exhalation, the second one-way valve opens (the first closes), allowing the breath sample to pass into the breath bag (34) and out the outlet tap (32). The proportion of the breath sample filling the breath bag with each breath can be adjusted by adjusting the ratio of entrance resistances of the breath bag and the outlet tap. Also displayed in FIGS. 14A and 14B, is a flow circuit example, where Va and Vb represent the ambient pressure (a) and bag pressure (b); Ri, Ro, and Rb represent the inlet resistance (i), outlet resistance (o), and bag entrance resistance (b); Di, Db and Do represent the inlet (i), bag outlet (b), and ambient outlet one-way valves. The dead-volume of the housing of the three-way non-rebreathing valve should be minimized to reduce the amount of ambient air that is blown into the breath bag. An alternative embodiment is based on sensing of the breath flow direction (such as with embedded pressure transducers)

and active control of the one-way valves to virtually eliminate dilution of the breath sample by leaked ambient air due to dead-volume crossover.

In an analogy to a circuit, voltages represent gas pressures and currents represent gas flows. The user controls voltage at the diode junction while exhaling (positive with respect to Va) and inhaling (negative with respect to Vb). When a small portion of exhaled breath is collected, and the resistance ratios are known, then the total volume of gas exhaled by the user over a set time is proportional to the sample in the breath bag. Knowing the total amount of exhaled breath over a set time is valuable for estimating the moles of analyte expired by an individual over a certain time. This information can be useful in interpreting the physiological significance of breath analyte concentrations. Note that the resistance divider performs reliably without measuring the pressure in the sample (Vs) as long as the breath bag does not begin to inflate substantially such that the walls of the breath bag are pushed out against the pressure of the breath bag. A timing unit, similar to that described for FIG. 12, can be used to record the time spent in breath sampling and to optionally control the one-way valves. An alternative use of the device in FIGS. 14A and 14B is to allow breath averaging. Instead of filling a breath bag with a single exhalation, a user can breathe multiple exhalations and have a portion of each mixed with the others in the breath bag. Such averaged sampling can be used to increase repeatability between breath samples.

Figure 15:
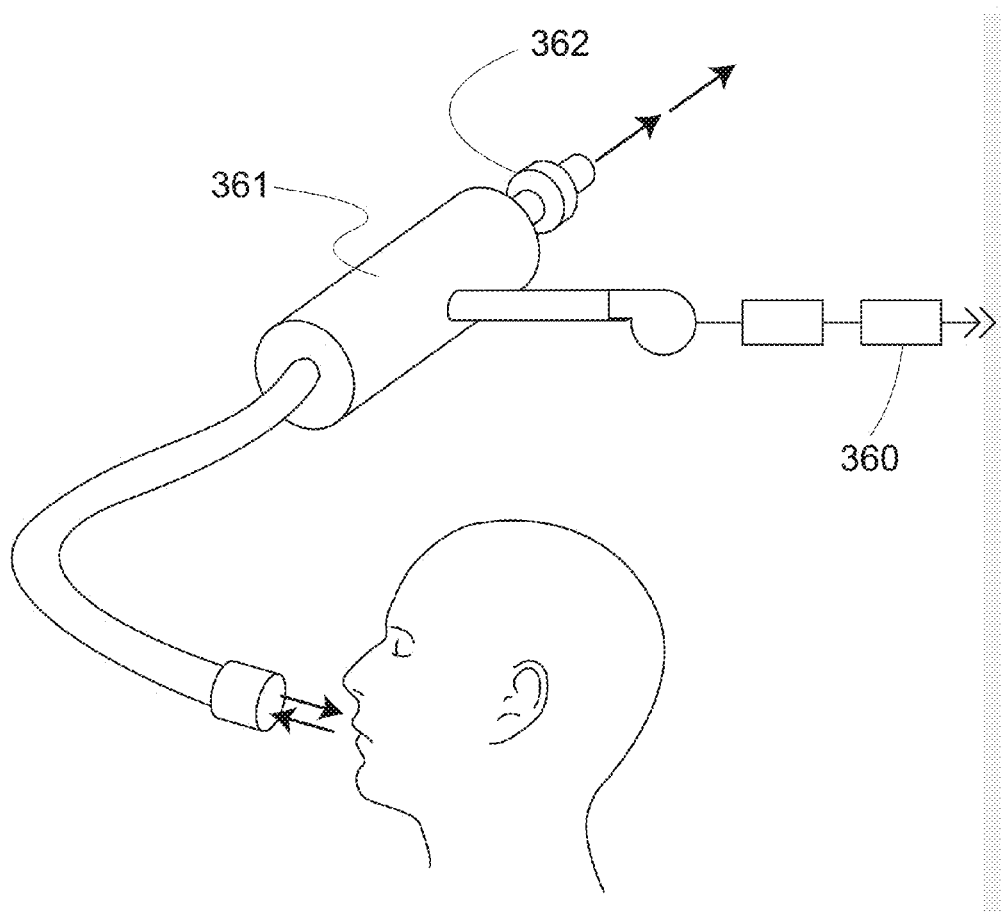
FIG. 15 shows an embodiment of a breath-sampling loop based on multiple breath exhalations into a base.

A breath sample can be input into the device using direct means. FIG. 15 illustrates how this can be done. A user blows into the end of a hose fitted with a three-way non-rebreathing valve and optional bacterial/viral filter which attaches to an inner containment vessel (361). As the user continuously exhales into the inner containment vessel, the air is pushed out through a breath flow measurement device (362), such as a pneumotachometer or turbine flowmeter. Other means of flow measurement are known to those skilled in the art and can be used here as well. A sensor sampling loop (360) uses a pump to withdraw the breath sample from the inner containment vessel at a controlled rate using methods as described earlier. The breath sample is then passed into the cartridge or sensing area for analysis. This method of using a breath flow measurement device enables the gathering of analyte rate of production information, which can have greater utility than simple concentration measurements.

FIGS. 16A to 16C show three perspective views of another embodiment of a breath input.

The breath input (1610) is comprised of a cutout bag (1605) and a fitment (1645). In this example, the cutout bag (1605) is comprised of a plastic that preferably prevents loss (via diffusion and such) of the selected analyte into the ambient air. The bag preferably contains between 500 mL to 750 mL of a breath sample.

Figure 17A:
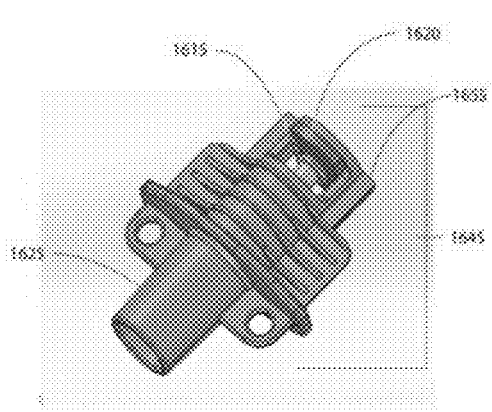
FIG. 17A shows an embodiment of a fitment that works in conjunction with the breath bag of FIGS. 16B and 16C.
Figure 17B:
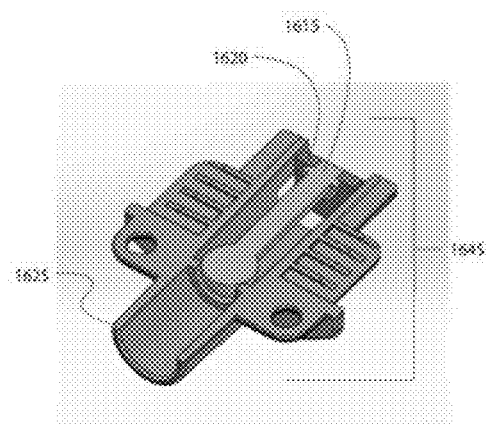
FIG. 17B shows a cutaway view of that valve fitment embodiment.

The fitment (1645) is comprised of three main components: a plastic housing (1625), a valve (1615), and a diaphragm (1620). The plastic housing (1625) comprises the mouthpiece into which the user exhales and which is further configured to be attached to the bag insertion port (e.g., 0130 of FIG. 1) of the base unit. The plastic housing is preferably comprised of a strong plastic, such as high density polyethylene. The plastic housing optionally further comprises a snap end (1655) that "snaps closed" so that the ball and the valve (or other internal components) do not fall out. The snap end preferably has openings to allow airflow. The valve (1615) is shaped like a shaft coupled to a ball. The valve is configured to snap into the plastic housing. The valve is snap-fit or otherwise tightly coupled with the diaphragm (1620). The valve is preferably comprised of a strong plastic, such as high density polyethyelene. The diaphragm (1620) is a disk that is preferably comprised of a resilient material, such as resounding memory foam rubber. FIGS. 17A and 17B show the fitment at an additional perspective view (B) and a cutaway view (A).

When the breath bag (1610) is not in use, it is in an essentially sealed state. As a user exhales into the bag, the air flow from the breath generates enough force to push the valve (1615) up against the rubber diaphragm (1620), opening the seal and enabling the breath sample to fill the cutout bag (1605). When the user is done exhaling and the air flow stops, the diaphragm (1620) has the rebounding capabilities to push the valve (1615) back into place, thus resealing the bag (1610) and preventing the breath sample from leaving the bag.

On the device-end, the base unit comprises an insertion port (e.g., 0130 from FIG. 1). Within this port, there is a single prong. Once the user attaches the bag (1610) to the base unit, the fitment (1645) interacts with the prong, pushing up the valve (1615) by about some amount, e.g., 1/16" to 1/8", against the diaphragm (1620), and thereby breaking the seal. The bag is thus capable of releasing the breath sample into the base unit for the duration of the test. The breath sample is maintained within the system through the use of a gasket (or similar mechanism) within the base unit. At the end of the test, when the user removes the breath bag (1610) from the device, the diaphragm (1620) pushes back against the valve (1615), thereby pushing it back into its initial position within the fitment (1645), and creating a seal.

The prong may be any apparatus that allows the breath sample to flow from the breath input bag or container into the base unit. In one configuration, the prong is coupled to the base unit. Here, the user exhales into the breath input (bag or container) easily and a valve, such as a one-way valve, prevents the sample from leaving the bag. When the bag is coupled to the base unit, the prong penetrates the bag, creating fluidic connectivity, and allows the breath sample to flow into the base unit. Alternatively, however, the prong may be coupled to the bag or container in the form of a shut-off valve that allows the user to exhale into the bag. Then, once the bag is coupled, the valve may be opened (by the user or the device) so that the breath sample can flow into the base unit. These embodiments can be modified in the event that the user exhales directly into the base unit.

Breath bags and breath containers described herein may be and preferably are reusable. In certain embodiments, this is facilitated by the coupling mechanism that allows the breath input to be coupled and decoupled on a plurality of occasions. Additionally or alternatively, the contents of the breath input may be purged either by running the pump longer than needed (to fully evacuate the bag), by pre-flushing or post-flushing the unit, or by heating the bag to facilitate removal of any residual acetone. Finally, in certain embodiments, if reusability is desired, the material of the bag or bag pouch may be thin or semi-permeable (over time) to acetone or the analyte of interest. This is desirable so that any residual acetone (or analyte) slowly diffuses from the bag if left on a countertop or other location by the user between measurements.

FIGS. 18A to 18C show three perspective views of another embodiment of a breath input.

The breath input (1810) is comprised of a cutout bag (1805) and a fitment (1855).

Figures 19A, 19B:
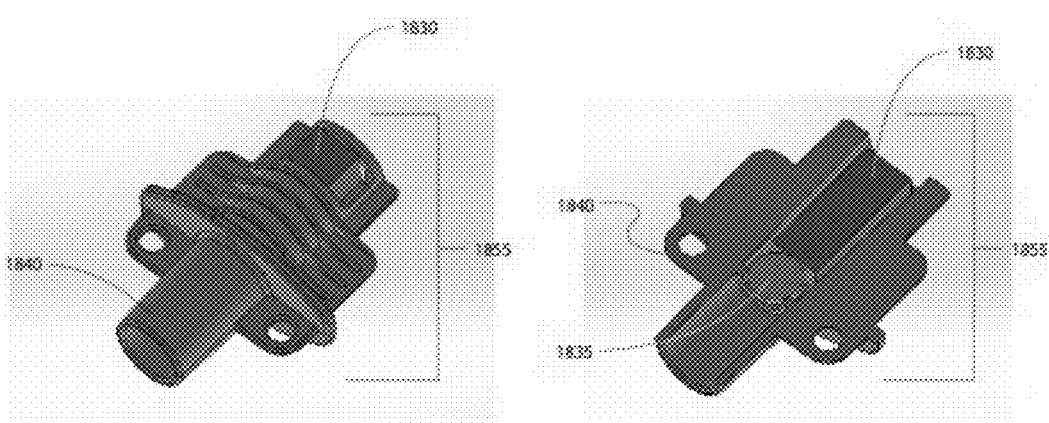
FIG. 19A shows another embodiment of a fitment that works in conjunction with the breath bag of FIG. 18.
FIG. 19B shows a cutaway view of that valve fitment embodiment.
Figure 20A:
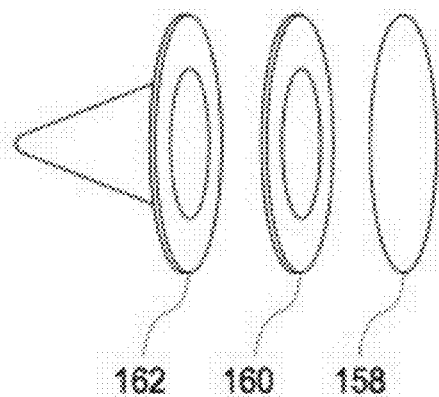
FIG. 20A shows an embodiment of a piercable foil ampoule.
Figure 20B:
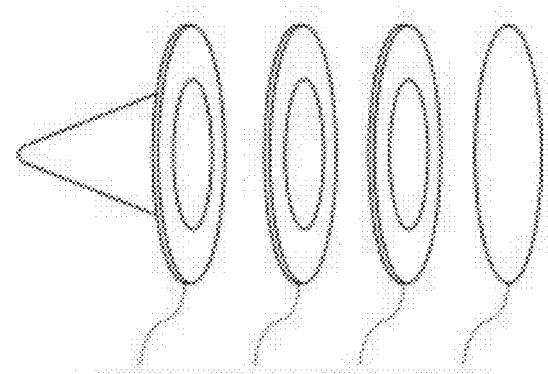
FIG. 20B shows another embodiment of a piercable foil ampoule.
Figure 20C:
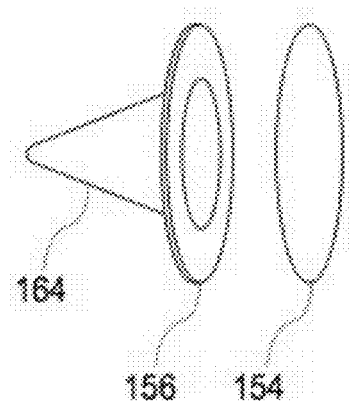
FIG. 20C shows another embodiment of a piercable foil ampoule.
Figure 20D:
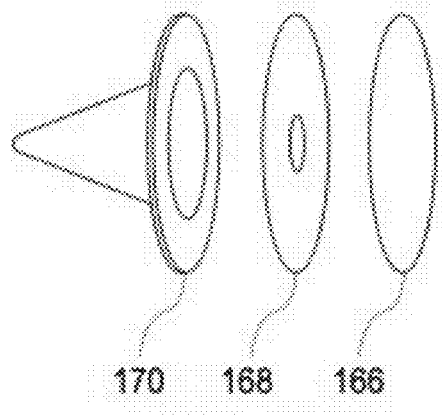
FIG. 20D shows another embodiment of a piercable foil ampoule.

The fitment (1855) is comprised of three main components: a plastic housing (1840), a ball (1835), and a foam block (1830). The plastic housing (1840) comprises the mouthpiece into which the user exhales and which is further configured to be attached to the bag insertion port (e.g., 0130 of FIG. 1) of the base unit. The plastic housing is preferably comprised of a strong plastic, such as high density polyethylene. The ball (1835) is preferably in the shape of a sphere but operatively needs to move away from its original position as gas flows into the housing and return after the gas flow has ceased. The ball mates with the foam block at the appropriate time. The foam block (1830) is preferably comprised of a resilient material, such as resounding memory foam rubber. FIGS. 19A and 19B show the fitment at an additional perspective view (B) and a cutaway view (A).

When the breath bag (1810) is not in use, it is in an essentially sealed state. As a user exhales into the bag, the air flow from the breath generates enough force to push the ball (1835) up against the foam block (1830), opening the seal and enabling the breath sample to fill up the bag. When the user is done exhaling and the air flow stops, the foam block (1830) has the rebounding capabilities to push the ball (1835) back into place, thus resealing the bag and preventing the breath sample from leaving the bag.

Cartridges comprise another aspect of the invention. Cartridges comprise interactants capable of reacting with at least one breath analyte, and preferably at least one endogenous breath analyte. There are a variety of cartridge configurations that can work with systems according to the invention for measuring at least one analyte, preferably an endogenous analyte, in breath.

In one embodiment, cartridges comprise a housing with a flow path for a breath sample that is further coupled to an automated dispensing device or reaction initiator that allows the developer to contact the interactant. Cartridges preferably contain a barrier, preferably porous, located adjacent to the interactant. The cartridge may contain a single interactant or a plurality of interactants.

In another embodiment, cartridges contain a pneumatic loader that transports developer through the cartridge.

In yet another embodiment and aspect of the invention, cartridges block ambient light when inserted into the base and preferably comprises a handle. As noted herein above, where internal system components such as the interactants, intermediate products, etc. are light-sensitive, the base may comprise an exterior surface that forms an interior and shields the interior from ambient light, wherein the exterior surface comprises an aperture; and the cartridge may comprises a shroud that substantially conforms to the aperture to shield ambient light from entering the aperture when the cartridge is coupled to the base.

Cartridges can be designed into various shapes and sizes to facilitate different applications. In one embodiment, the cartridge is comprised of: (a) interactant, (b) a first region containing a first developer, and (c) a second region containing a second developer. The first and second developer can be the same or different. In another embodiment, the cartridge is comprised of: (a) interactant, (b) a region containing a developer, and either (c) mechanism for coupling the cartridge to a dispensing device, or (d) mechanism for coupling to a reaction initiator. In a preferred embodiment, the cartridge requires no external liquid flow to the cartridge.

Liquid reagents can be contained directly in regions of the cartridge housing, using the cartridge housing as "side walls" with foil or other membrane barriers adhered to the cartridge housing. For aggressive solvents, for example dimethylsulfoxide or methanol, such embodiments may be temporary due to solvent attack of the adhesives. One embodiment of the present invention uses a separate container to contain liquid reagents. The material compatibility between the cartridge housing and solvent is no longer a direct concern. Various liquid containers (sometimes referred to as liquid cans) can be configured, and these containers can be placed into a pocket of the cartridge housing. Preferably a liquid container, such as an ampoule, is completely inert to the retained liquid reagent. FIGS. 20A to 20D show four embodiments of a piercable foil ampoule, described in the following paragraphs.

Liquid containers that are breakable or piercable (e.g., piercable solvent ampoules) can be manufactured by a variety of methods. For example, in one case described in FIGS. 20A to 20D, a flanged conical foil base (152) is welded or otherwise adhered to a weldable or heat-sealable intermediate material (150) to form the bottom half of an ampoule. The weldable or heat-sealable intermediate material may be a low thermal conductivity thermoplastic. A top foil layer (146) is likewise attached to a weldable or heat-sealable intermediate material (148) to form the top half of the ampoule. The bottom half is then filled with a liquid reagent and the top half ultrasonically welded or heat sealed to the bottom half. The liquid reagent is contained within four barriers: (a) the foil base (forming the major contact surface), (b) the intermediate material, (c) the weld joint between the foil base and the intermediate material (adhesive), and (d) the weld joint between the two intermediate materials. This configuration is useful because (a) it allows an adhesive time to cure independent of solvent presence (the adhesives can be fully cured before filling of the solvent), thus enabling a wide range of adhesives to be employed; (b) conductive heating caused by ultrasonic welding is shielded by low thermal conductivity thermoplastic, eliminating or controlling the amount of fill solvent lost to evaporation during ultrasonic welding.

A piercable solvent ampoule can also be manufactured using a thermal barrier material. A second case ultrasonically welds the two foil components to one another and uses a thermal barrier. Specifically, a top foil layer (154) is attached to a bottom foil layer (156) by direct ultrasonic welding of the metal foil. The solvent is pre-loaded for welding, thermally protected by a thermal barrier, such as a wax cone (164) that is hollowed. The thermal barrier must protect the solvent from conductive heating caused during ultrasonic welding, but it must also be easily pierced. Other materials, such as thin plastics, rubber, or spray-on silicone adhesives may also be suitable.

An adaptation of the thermal barrier method is to perform ultrasonic welding in the presence of appropriate heat sinking. The ultrasonic weld jig contains an annular clamp made of highly conductive metal. The clamp engages the top and bottom metal foil layers inward from the outer locations of ultrasonic welding such that any heat conducting away from the weld joint sinks into the conductive clamp. Alternative methods of heat sinking, such as blowing the bottom foil with cold air may also be suitable, depending on the solvent in use.

A third method for developing a piercable solvent ampoule uses a crimp seal between a top foil layer (158) and a flanged conical foil base (162). A wax gasket or gasket comprised of solvent-resistant material (160) is included between the layers to increase the retention time of the liquid into the ampoule. The gasket material must be chosen with the appropriate resilience and barrier properties to the solvent of interest.

Figure 21A:
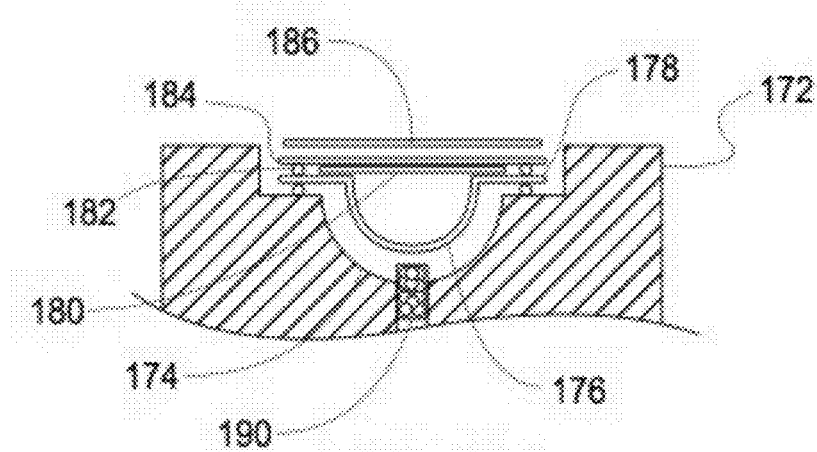
FIG. 21A shows an embodiment of a piercable ampoule inside a base carrier.
Figure 21B:
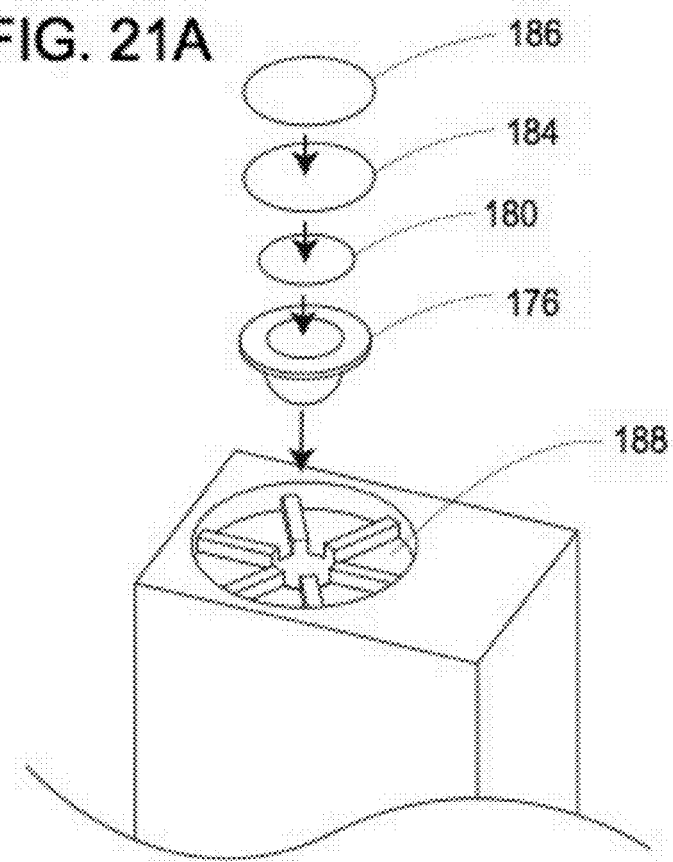
FIG. 21B shows a perspective drawing of the same piercable ampoule embodiment.

FIGS. 21A and 21B show certain embodiments of a piercable ampoule. In this embodiment, a cold-formed foil (176), or other formed, piercable barrier, is attached into the head portion of a base plastic carrier (172) using points of adhesive. These points may make contact with a series of bosses (188) and are intended to adhere the floor of the ampoule to the base plastic carrier in a non-airtight fashion. The floor of the ampoule (176) is filled with solution, and a temporary barrier (180) may be affixed to seal the liquid. The temporary barrier can be affixed through pressure sensitive adhesives, thermally set adhesives, or any other convenient method. The adhesive for the temporary barrier does not need to resist and retain the solution beyond the time required to complete the sealing process. A circular bead of adhesive (182) is next applied. This adhesive forms a permanent barrier for the entrapped solution, but a temporary barrier (180) allows the permanent barrier material (182) to cure independent of solution activity. The liquid is capped with a disc of barrier material (184). A separate material (186), such as a rubber septum, is optionally placed to prevent temporary passage of liquid after the barriers have been broken.

This method can be used to retain particles in a packed state. That is, by positioning a compressible, porous material (190) directly beneath the bottom floor (176), particles can be immobilized.

Figure 22A:
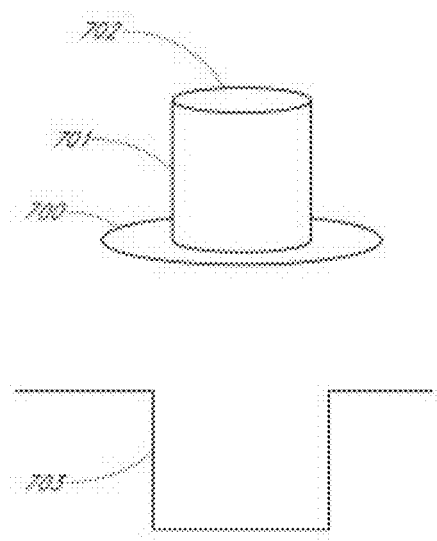
FIG. 22A shows an embodiment of a liquid container before being placed into a base.
Figure 22B:
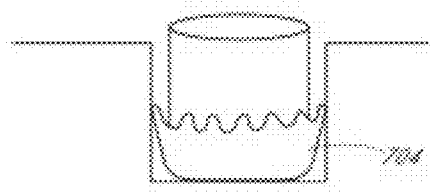
FIG. 22B shows the liquid container embodiment after being placed into a base.

FIGS. 22A and 22B show an embodiment of a liquid container. This embodiment is useful to prevent the liquid container from being pulled out of a region in a housing. In some embodiments, a needle is used to pierce a liquid container. In those situations, sometimes the drag of the needle against the piercable barrier lifts the liquid container causing impediments to liquid dispersion. One approach to retain the liquid container in a region in a housing utilizes an oversized bottom barrier (700). This barrier can be comprised of a plastic and foil laminate which can be heat-sealed to a cylindrical liquid container (701) which is otherwise open on both ends. A barrier on the other side of the liquid container (702) is sized to match the diameter of the liquid container. The liquid container is then pressed into a region of the housing (703), which has been sized so that insertion of the liquid container, as illustrated in FIG. 22B, causes the oversized barrier to deform (704) in a manner such that the removal of the liquid container from the region of the housing is impeded sufficiently to resist the pull of the needle retraction or to otherwise keep the liquid container in place.

Figure 23A:
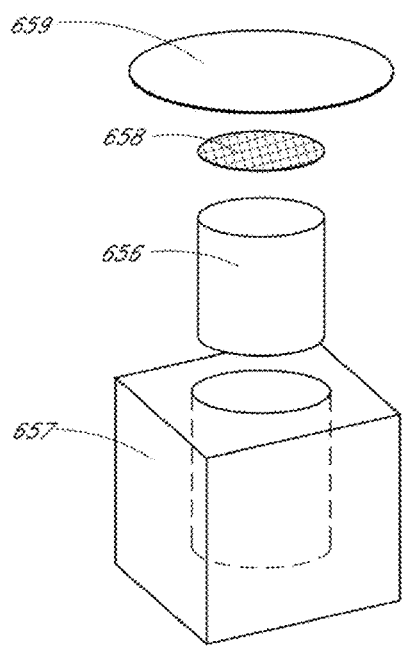
FIG. 23A shows certain components of a cartridge embodiment and its liquid container sub-components.
Figure 23B:
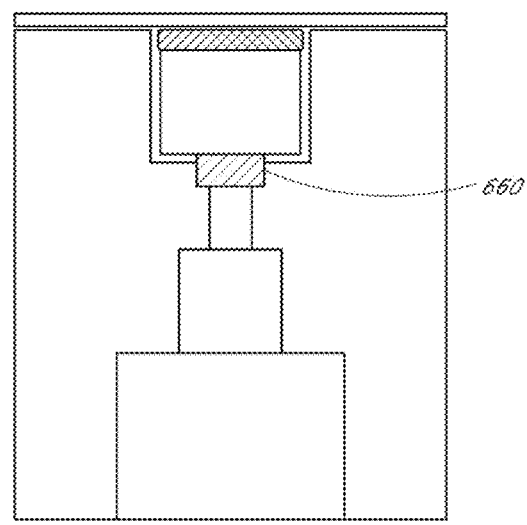
FIG. 23B is another embodiment of a cartridge, showing placement of the liquid container into housing.

FIGS. 23A and 23B illustrate an example of a means for keeping a piercable ampoule fixed in position so that it is not lifted up when a needle retracts. In this example, a piercable ampoule (656) is placed into a pocket of a cartridge (657). A disk of fibrous plastic such as fibrous polyethylene (658) is placed on top of the ampoule. The fibrous plastic is spongy and acts as a spring to compress against the top of the ampoule. A barrier (659), such as a plastic/foil laminate, is placed on top and heat sealed (or adhesive fixed) to the cartridge (657). Thus, when a needle retracts upwardly after piercing the ampoule, as described elsewhere, the ampoule is restricted in its upward motion and will stay fixed in position, tightly coupled to a wicking material (660) such as porous polyethylene to promote liquid dispensing. FIG. 23A shows an isometric view of these components, and FIG. 23B shows these components in a side view.

Figure 24:
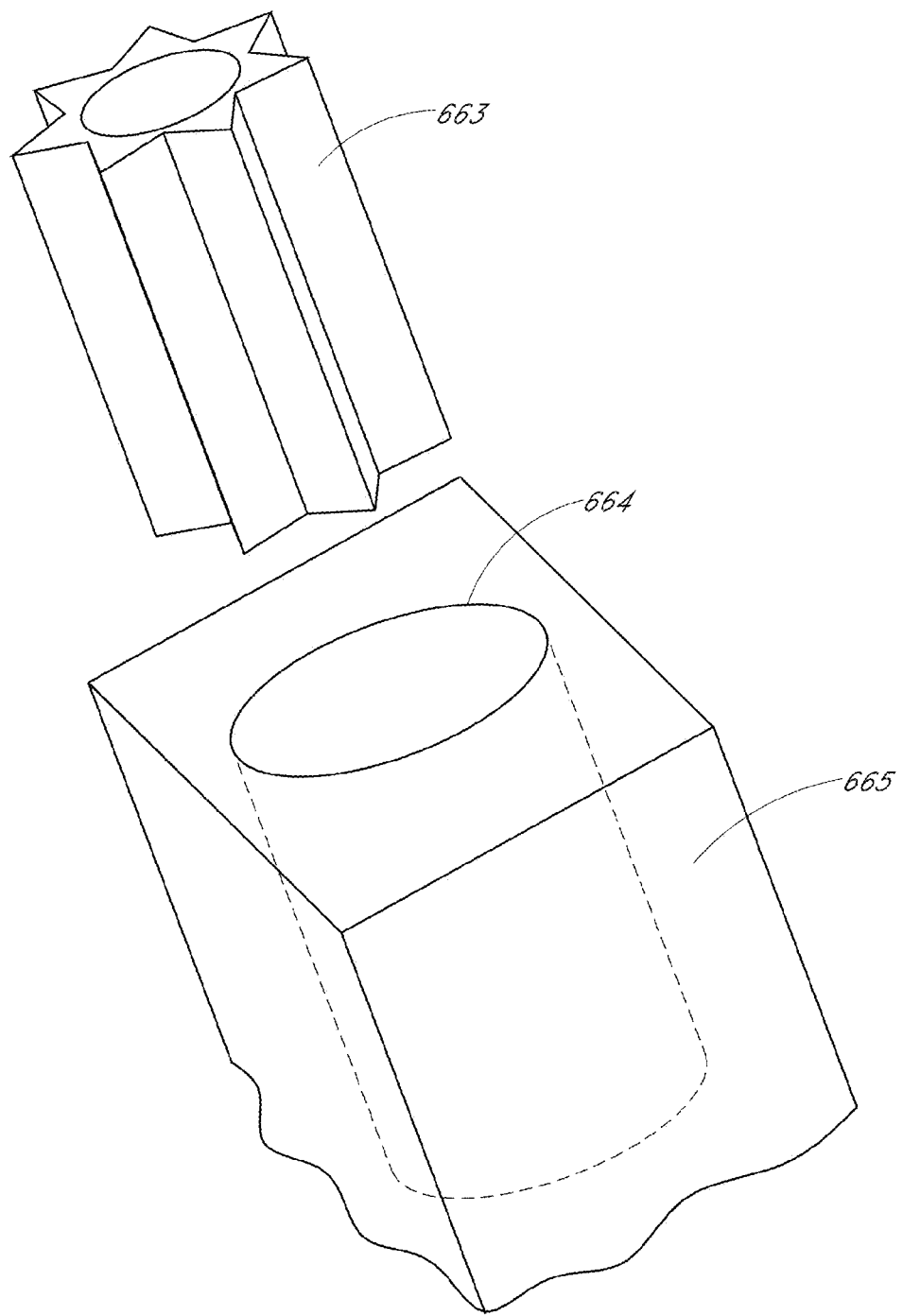
FIG. 24 is another embodiment of a cartridge, showing placement of the ampoule into housing.

FIG. 24 shows an example of a means to keep a piercable ampoule in place after piercing with a needle as described elsewhere. In this example, an ampoule (663) is fashioned like the piercable can (FIGS. 31A and 31B) with a top and bottom piercable membrane. In this example, however, the body of the can is comprised of a star-shaped extrusion. This ampoule can be press-fit into a circular hole (664) in a cartridge (665) such that the ampoule is fixed in position and will not be drawn up during needle retraction. Gaps between the ampoule and the circular hole walls create air vents which facilitate liquid dispensing from the ampoule. The extrusion profile of the ampoule need not be star-shaped; any profile that provides contact points with the cartridge receiving pocket enabling a press-fit but that also preserves sufficient gaps to promote venting as the ampoule drains can be used.

Figure 25A:
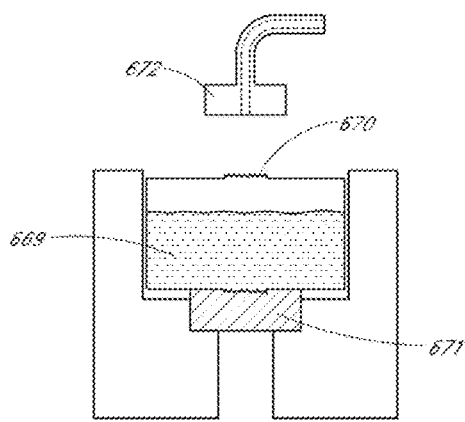
FIGS. 25A and 25B show another example of an ampoule piercing mechanism.
Figure 25B:
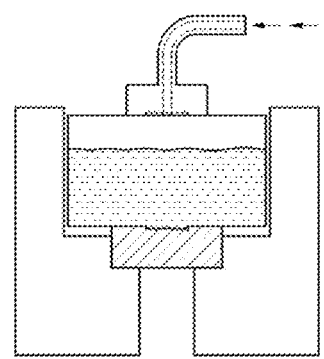

FIGS. 25A and 25B show an example of an ampoule that can be pierced with pressure alone. An ampoule (669) is manufactured with two pressure relief valves (670) and (671). A pressure nozzle with sealing gasket (672) is brought down to contact the ampoule as shown in FIG. 25B. Flow into the nozzle causes the rupture first of the top pressure relief valve (670), followed by the rupture of the bottom pressure relief valve (671). The rupture of the bottom pressure relief valve (671) causes a hole below the ampoule's liquid fill line; the incoming gas (through the pressure nozzle with sealing gasket (672) mediates the vacuum that might form in the ampoule to impede flow. Alternatively, after rupturing the pressure relief valves, the pressure nozzle with sealing gasket (672) may be retracted, leaving the holes in the ampoule to facilitate liquid evacuation from the ampoule.

Figures 31A, 31B:
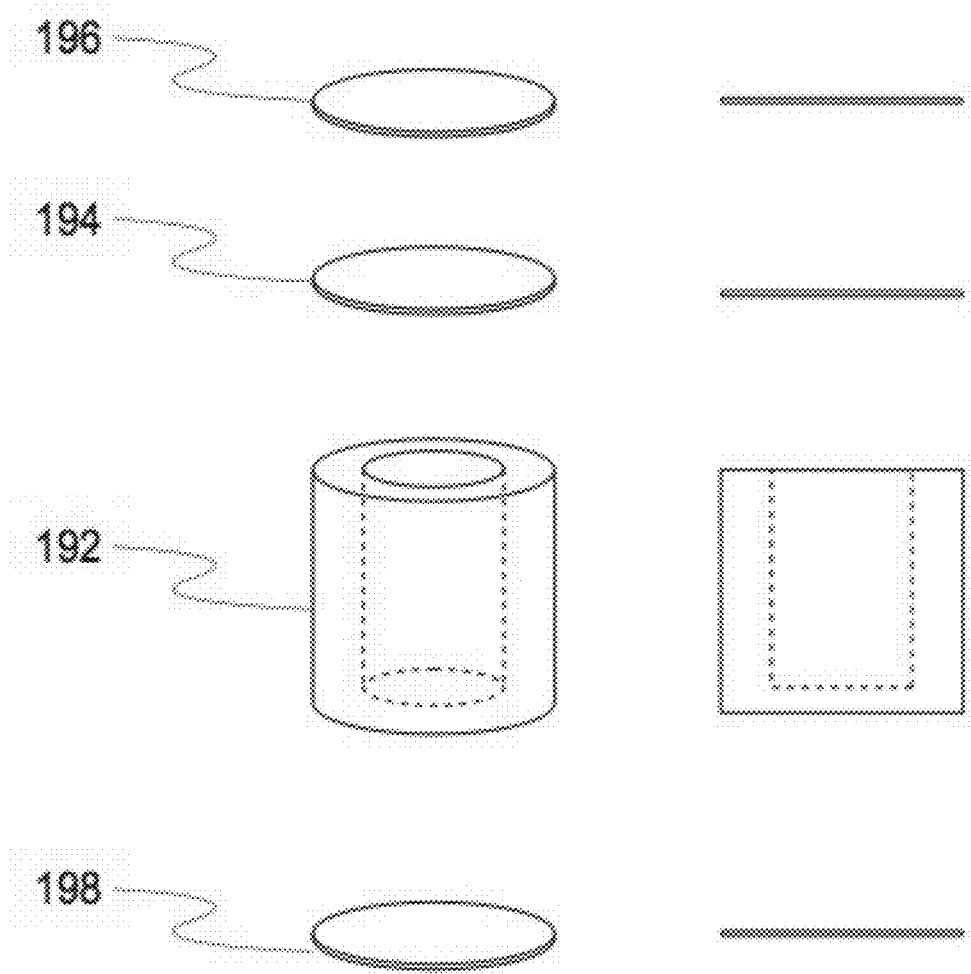
FIGS. 31A and 31B show embodiments of a piercable ampoule of a cylindrical design for containing liquid.

FIGS. 31A and 31B show embodiments of a piercable ampoule, in the shape of a cylindrical "can". In this example, a thin-bottomed can (192) is cast of a thermoplastic material. After filling with the desired liquid, a thin barrier (194) (a laminated foil with a thermoplastic layer, for example) can be attached via an appropriate method, such as ultrasonic welding or heat-sealing. As necessary, more extensive barriers (196, 198) can be affixed after the can is filled with liquid. Optionally, depending on the material requirements of the liquid to be contained, barrier materials (196, 198) can be attached directly to the can through pressure sensitive adhesives, thermally set adhesives, or other methods (note that the can does not need to be constructed of thermoplastic materials). A variation on this design uses a thick-walled plastic cylinder as the body of the ampoule and is sealed on both ends with piercable barriers.

Ampoules can also be blow-molded from numerous materials including glasses and plastics. These single-material ampoules are constructed of thin walls to enable ampoule piercing, but sufficiently thick walls to obtain the necessary barrier properties.

Figures 26A, 26B, 26C:
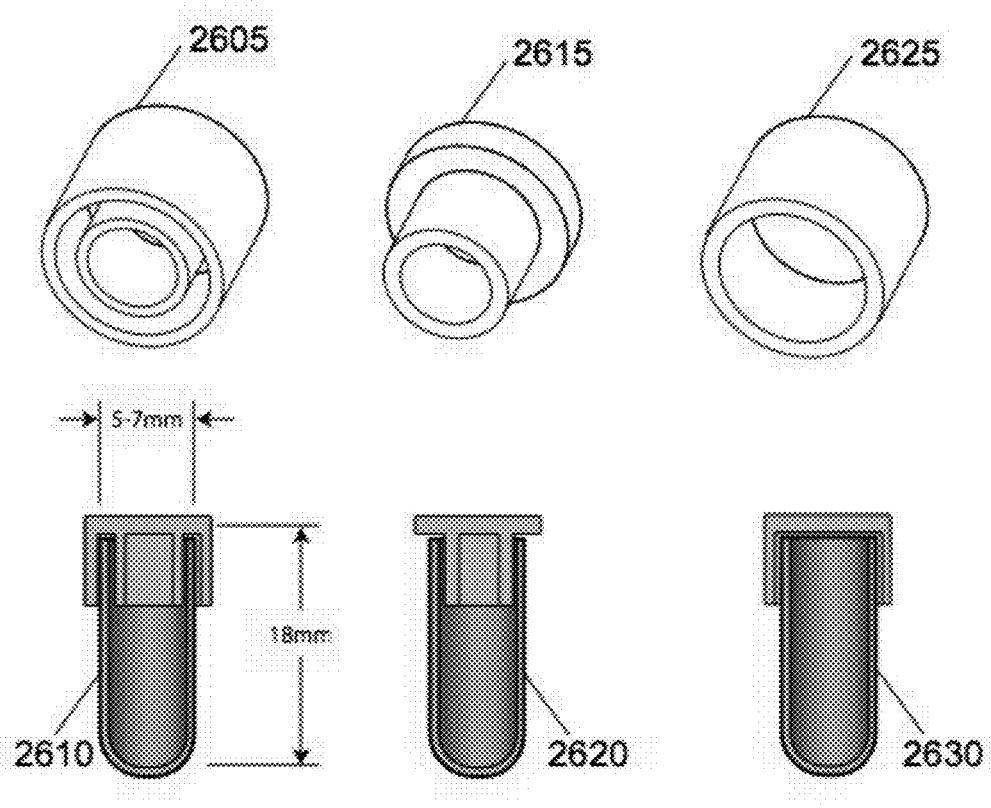
FIGS. 26A and 26B show an embodiment of a crushable ampoule.
FIG. 26C shows the cartridge embodiment with a different lid.
Figure 27A:
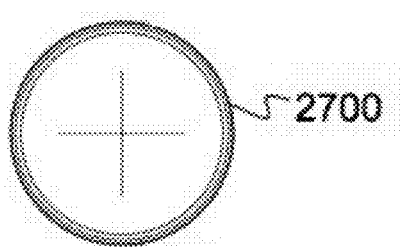
FIGS. 27A to 27E show a further embodiment of an inverted cup.
Figure 27B:
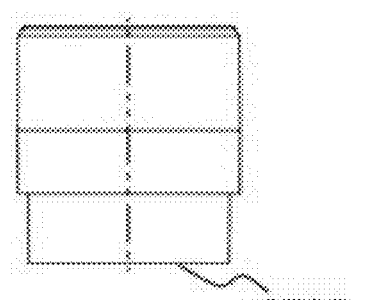
Figure 27C:
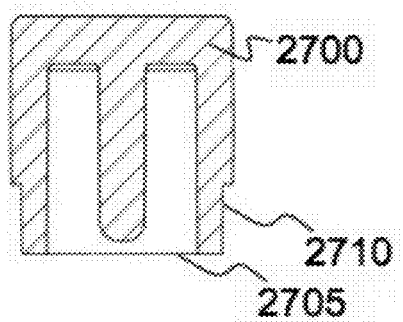
Figure 27D:
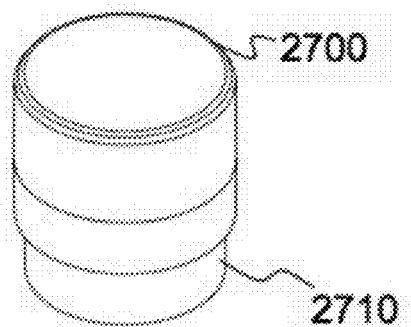
Figure 27E:
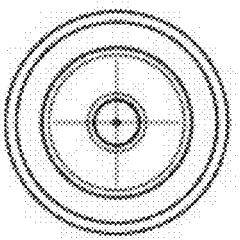
Figure 28A:
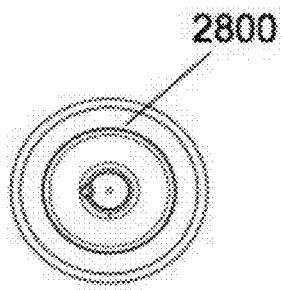
FIGS. 28A to 28D show various view of an embodiment of an inverted cup with certain additional components.
Figure 28B:
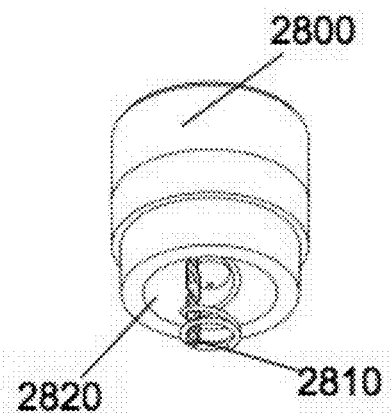
Figure 28C:
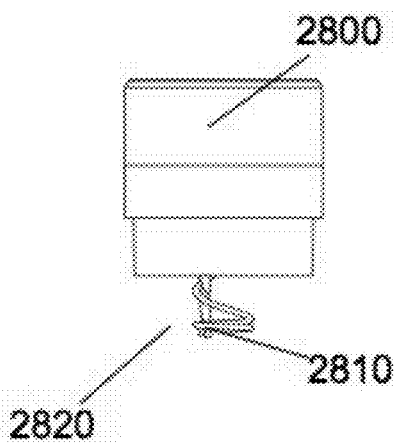
Figure 28D:
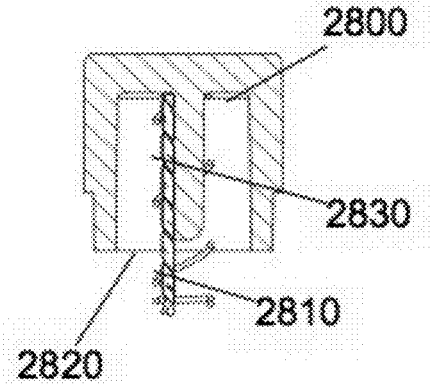

As shown in FIGS. 26A to 26C, liquid may be contained within a crushable ampoule (e.g., 2610, 2620, or 2630). Different ampoule designs may be used, including those shown in FIGS. 26A to 26C. In each embodiment, the ampoule (e.g., 2610, 2620 or 2630) is capped with a plastic stop (e.g., 2605, 2615, or 2625) that preferably makes a strong seal when coupled to the glass ampoule. For these designs, an actuator (not shown, but described elsewhere in this disclosure) would press down on the plastic stop to cause the glass to fracture, thereby causing liquid to be released. Alternatively, an actuator could pinch the sides of the glass ampoule and cause liquid to be released.

Metals are excellent as barrier materials and can be sealed in gas-tight fashion through crimping (such as a beverage can). Miniature ampoules made of aluminum and other metals can be manufactured and dropped into the select regions of disposable cartridges.

Ampoules can be fully enclosed or they can provide a partial container that is further sealed by either the cartridge housing or other components, such as a cog or rubber material. FIGS. 27A to 29G (described later herein) provide examples of a partial container that is useful in certain embodiments of cartridges.

With regards to the laminates, foils and numerous other plastics are also available with adhesive backing. Polyimide top layers can be preferable to foil layers in some attachment methods since foil layers can have a greater tendency to separate from their adhesive backing during certain heat pressing processes, especially where the contact surface area is large. Polyimide may be preferable to other plastics due to its potentially high heat transfer and resistance to heat damage, especially when thermal grade polyimides are used.

Various embodiments of the cartridge described herein comprise internal components such as, for example, desiccant, reactive beads, and porous disks. It is desirable for these components to remain in the same physical location and experience limited displacement. This is particularly important to ensure that the cartridges remain intact during shipping and handling or during use by a lay user. Certain methods are useful to ensure limited displacement of such cartridge components.

To illustrate the positioning of a compressible, porous material (disk) beneath the component disposed in the "bottom-most" location within the cartridge, and with reference to FIGS. 32A and 32B, a disk (516) is disposed below the desiccant (518) to hold the desiccant in place. Preferably, this disk is larger than the diameter of the desiccant chamber such that force is required to press fit this disk into place (compressing the edges of the compressible, porous disk). This prevents the disk from dislodging.

In certain situations, the "vertical" force to press fit the disk is not sufficient to ensure that the disk does not move. In such situations, one may use notches with protrusions that extend from the housing onto the disk to immobilize it. A method that utilizes this approach comprises providing a housing that includes a flow path comprising an upstream direction and a downstream direction. The housing comprises a first chamber, a second chamber positioned in the downstream direction relative to the first chamber, and a housing outlet positioned in the downstream direction relative to the second chamber. The method also includes disposing an interactant in the first chamber. The interactant, as described herein, is a chemical or material that reacts with the analyte in the breath sample. The method also includes disposing a first porous barrier material between the first chamber and the second chamber. The first porous barrier material retains the interactant in the first chamber but allows passage of the breath sample. The method also includes disposing a breath sample conditioning material, e.g., such as a desiccant material, in the second chamber. The method further includes disposing a second porous barrier material at a downstream end of the second chamber, and immobilizing the second porous barrier material by disposing a plurality of notches in the housing at the second porous barrier material. A preferred method for disposing of the plurality of the notches comprises using heat to form the notches.

Figure 30:
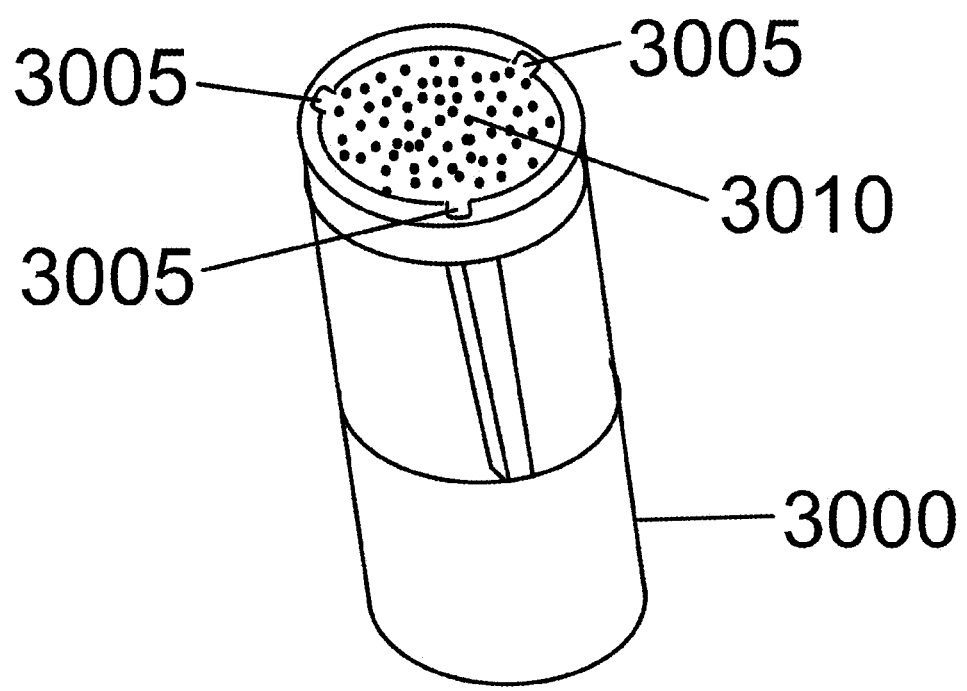
FIG. 30 shows another embodiment of a cartridge.

To illustrate, the cartridge housing (3000) may be modified as shown in FIG. 30. FIG. 30 shows the cartridge upside down, with the desiccant (3010) facing up. Here, the edges of the cartridge housing are exposed to a hot surface to create protrusions (3005) which result from inward melting of the cartridge housing. As shown in FIG. 30, it is desirable for a single cartridge housing to comprise a plurality of protrusion (three are shown in the figure).

The plastic protrusions shown in FIG. 30 can be created by a hot surface, such as an impulse sealer that is coupled to a soldering iron. Alternatively, these protrusions can be created by chemical means, such as by dispensing a drop of methylene chloride in select locations in a flow chamber that allows the methylene chloride to react, melt the cartridge housing, and then be directed (by flow) laterally so that it does not diffuse into the cartridge body. An advantage of this approach is that the protrusions can be created after all cartridge components are assembled, lending the assembly process to a press-fit assembly process.

Single analyte cartridges can be configured in numerous ways to facilitate various interactions. Interactant regions with sequentially packed dry reagents can be packed into the flow path (where shifting of particles is not a concern) or into partitioned pockets within the cartridge. Some examples are shown in FIG. 33 and FIG. 34.

Figure 33:
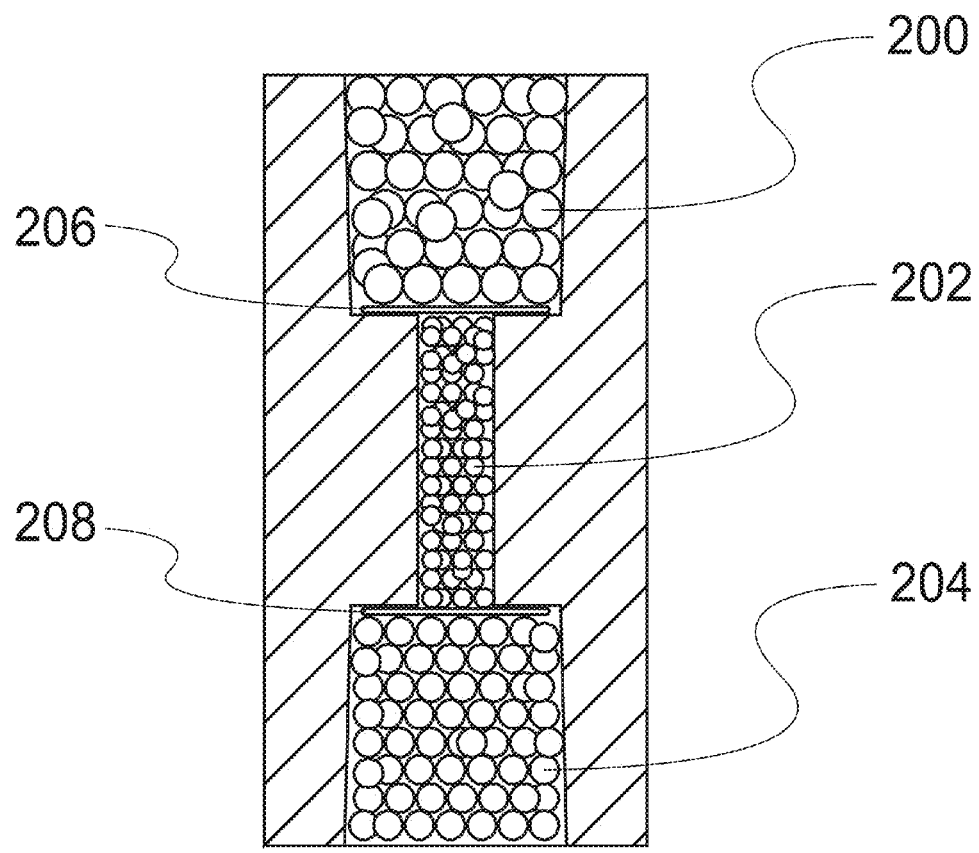
FIG. 33 shows different dry reagents packed into a single cartridge.

In FIG. 33, three distinct dry interactant beads (200, 202, 204) are packed into a single flow path that is cylindrical in nature. Porous barriers (206) and (208) are in place to retain the interactant beads. Interactant beads can be of dissimilar size when barriers are in place. Additional interactant beads can be packed by creative design of the cartridge housing, such that it contains regions of increasing diameter. In this way, flat ledges are created whereupon barriers can be affixed.

Figure 34:
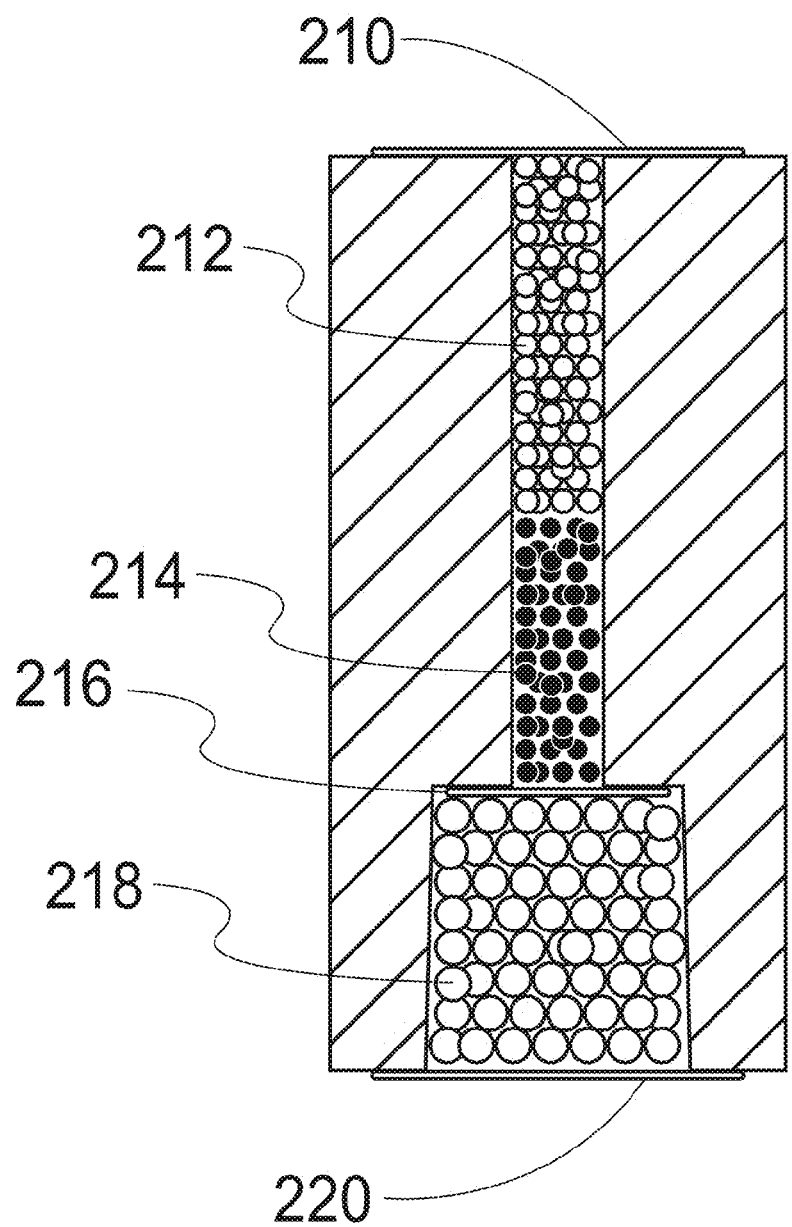
FIG. 34 shows another set of stacked dry reagents packed into a single cartridge.
Figure 35:
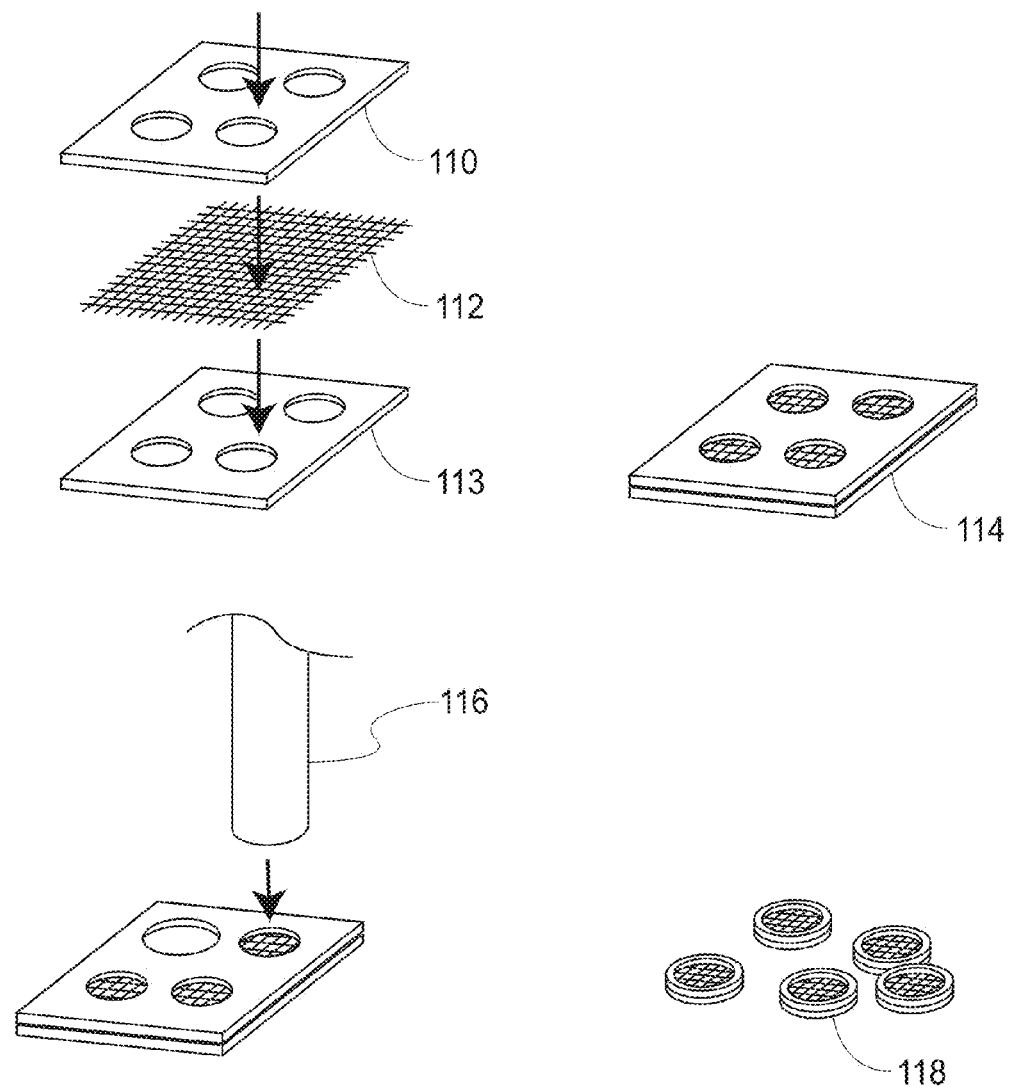
FIG. 35 displays an example of a substrate sheet that can be pressed into retention disks.
Figure 36:
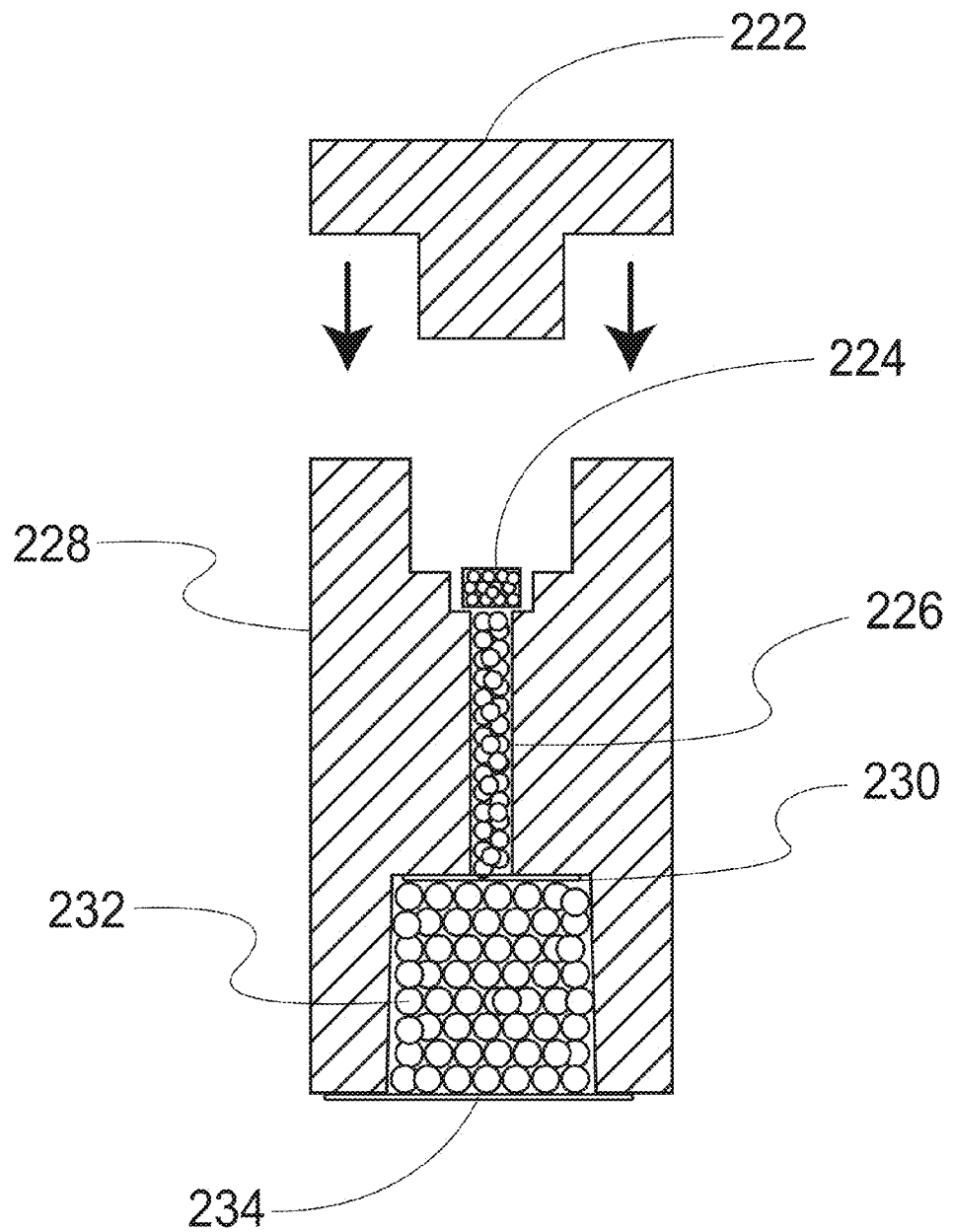
FIG. 36 illustrates interactants being held in place using compressible, porous barriers.

In FIG. 34, the stacking of interactant beads is shown. When distinct interactant beads of similar size (212 and 214) need to be packed, they can be packed into a single flow path, here in the form of a cylindrical column, as shown. Larger interactant beads (218) will need a barrier (216) for separation and retention. One method of separation makes use of thin disks of porous material, such as nylon mesh as described in FIG. 35, but porous plastics or other porous media can be used in additional embodiments. The outer ends of the cartridge housing (e.g., the inlet aperture and the outlet aperture) can be sealed using retention membranes (210) and (220). It is often desirable to pack columns with interactants in such a manner that the interactants are not free to move. In this case, materials can be held using compressible, porous barriers. FIG. 36 illustrates such a configuration. In this embodiment, a cartridge is comprised of two housing pieces, a top housing (222) and a bottom housing (228). A first dry reagent (232) is packed into the lowermost region of the bottom housing, retained by two porous barriers (230 and 234). A second dry reagent (226) is packed into the central region (e.g., a cylindrical column) of the cartridge. At the topmost end of the bottom housing, a wider diameter is molded to accommodate slight overfilling of the second dry reagent (to relax filling tolerances) and to facilitate compression of the reagents with a porous, compressible material. This material, when compressed by the top housing (222), still allows fluidic communication through the top housing and bottom housing while compressing the second dry reagents (226) to keep them immobile.

Internal components of a cartridge can be positioned relative to one another, e.g., a disk is "locked in" by a certain volume of desiccant, etc. However, the components can also be positioned based on separate sub-assemblies as shown, for example, in FIGS. 45A to 45J (described elsewhere herein).

In accordance with an aspect of the invention, a cartridge will now be described for use with a breath analysis system comprising an optical subsystem for sensing an analyte in a breath sample. The cartridge comprises a housing comprising an exterior surface having an exterior surface dimension. A first chamber is disposed in the housing and comprises a first chamber surface having a first chamber dimension. The first chamber includes an interactant that interacts with the analyte in the breath sample, such as those described herein. The housing exterior surface dimension at the first chamber comprises a first housing exterior surface dimension. A first chamber wall thickness is defined by the first housing exterior surface dimension minus the first chamber dimension. The first chamber wall thickness is uniform throughout the first chamber surface.

The cartridge further includes a second chamber disposed in the housing and comprising a second chamber surface having a second chamber dimension. The second chamber comprises a breath sample conditioner, such as a desiccant material. The housing exterior surface dimension at the second chamber comprises a second housing exterior surface dimension. A second chamber wall thickness is defined by the second housing exterior surface dimension minus the second chamber dimension. This second chamber wall thickness is uniform throughout the second chamber surface.

In this cartridge, the first housing exterior surface dimension may and typically does differ from the second housing exterior surface dimension. The first chamber wall thickness, however, is the same as the second chamber wall thickness.

To illustrate this aspect of the invention, the wall thicknesses of the lower body (0435) in the cartridge of FIGS. 4A to 4G have been normalized (or made uniform) such that plastic warping during manufacturing is minimized. This is particularly useful to ensure that the optical region of interest (0465) is consistent from batch to batch.

FIGS. 4A to 4G also show that the upper body (0405) itself is opaque, which provides an additional optical barrier to minimize light to the light sensitive reagents contained within the inverted cup (0415).

Figure 37:
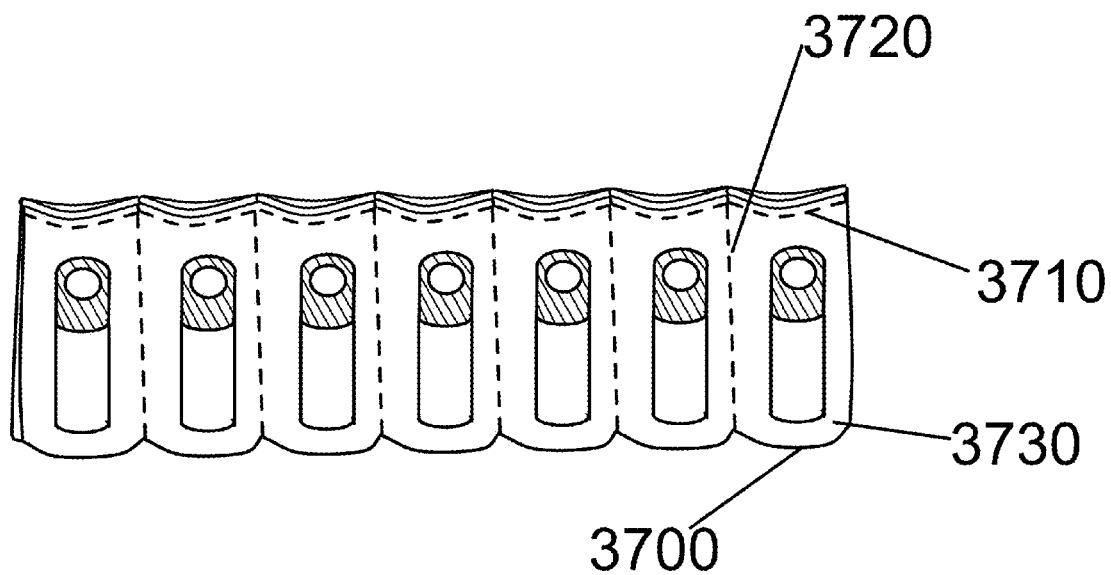
FIG. 37 shows an example of packaging for a plurality of cartridges.

A preferred packaging approach for the cartridges is shown in FIG. 37. A plurality of cartridges is disposed in a plastic sleeve (3700). Between each cartridge, the plastic sleeve is perforated along a seam (3720) such that each cartridge is in its own individual cartridge area (3730) that can be removed from the rest of the sleeve (3700). The top of each individual cartridge area (3730) is perforated (3710). In this embodiment, the cartridges are assembled in a weekly package with seven (7) cartridges, but of course different numbers of cartridges may be used in similar packaging. A technical benefit of this design is that the material of the sleeve may be optically opaque, such as metallized mylar.

Figure 38:
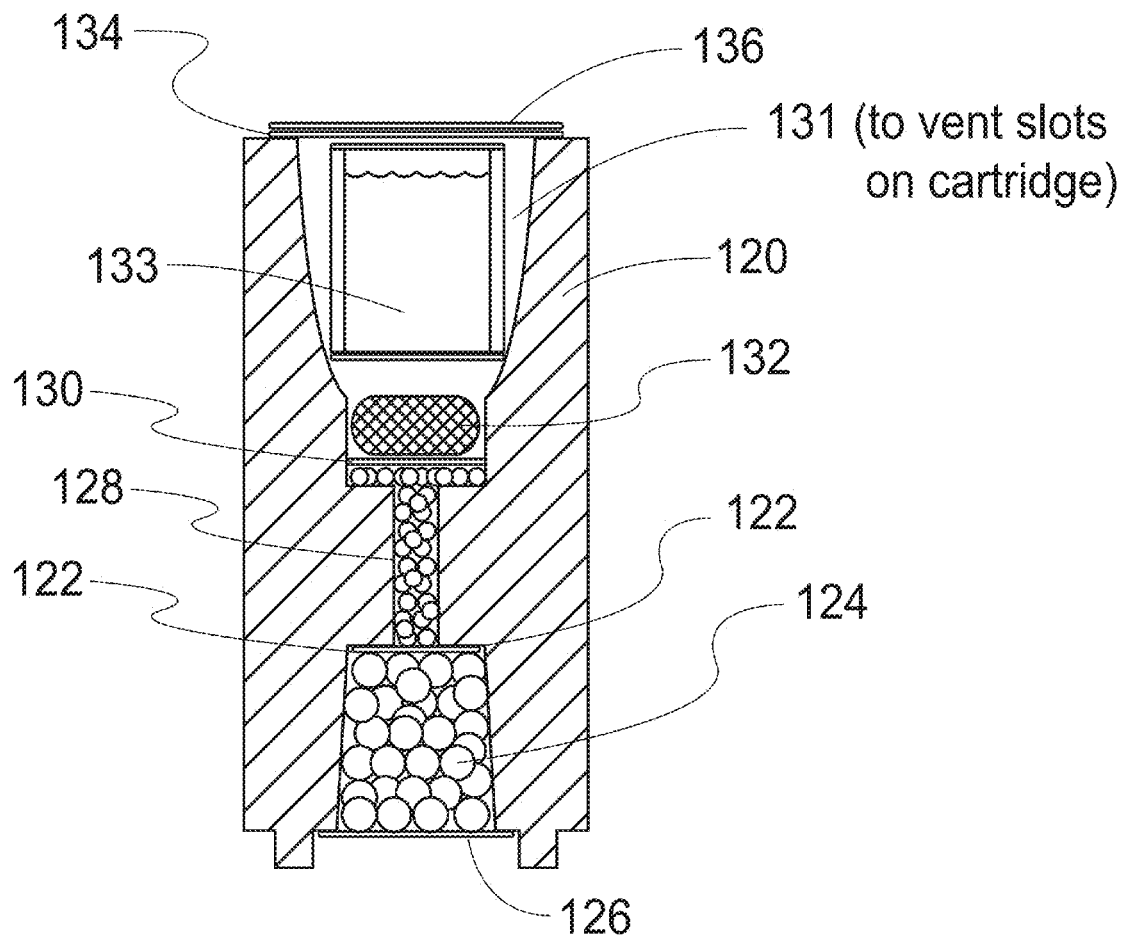
FIG. 38 shows an exemplary general schematic of cartridge design.

An exemplary general schematic of cartridge is shown in FIG. 38. This cartridge is preferably used for optical sensing, and preferably includes interactants that can be used to sense endogenously produced analytes in human breath. Here, the interactant (128) is contained within a cartridge housing (120) consisting of a single piece. Preferably, but not necessarily, the housing is comprised of material that is optically clear. There is a barrier (122) that separates the interactant from a filter (124) or more broadly a breath conditioner. In this embodiment, the filter (124) is a desiccant, but this may also be a scrubber or pre-concentrator. The desiccant is kept tightly packed by a porous membrane (126). In some embodiments, a peelable or piercable barrier can be affixed to the underside of the cartridge housing to enhance storage of the interactants and breath conditioners, such as desiccants. On the other side of the interactant is a second barrier (130). The barrier serves to keep the interactant tightly packed. This barrier can be molded compression fittings, on-cartridge gaskets, o-rings, etc. Atop this barrier is a wicking material (132). The wicking material is designed to allow liquid reagents (133), such as a developer or solvent, to flow towards the interactant. In an alternative embodiment, components (130) and (132) are replaced by a single component that can be both compressive fit into the pocket of the cartridge housing and preferably is porous. Hydrophilic, porous polyethylene disks are useful for this purpose. A developer (133) is contained within a liquid container, in this case a piercable ampoule, that sits within a region (131) in the upper portion of the cartridge housing, which is formed with vertical channels to facilitate venting of the breath sample when the developer flows down into the reaction zone that contains the interactant (128). The ampoule-containing region (131) is sealed with a piercable membrane (134). Once the cartridge is inserted in the base, the piercable membrane (134) and the piercable liquid container are pierced by the reaction initiator and/or dispensing device of the base so that liquid flows to the interactant. To ensure that residual liquid does not leak out post-use of the cartridge, in this embodiment, there is a rubber septum (136) that seals the cartridge. The cartridge preferably is designed such that the developer is "absorbed" by the interactant and/or breath conditioner (e.g., desiccant) such that it does not leak through the inlet aperture (or gravitational bottom) of the cartridge. One optional addition is coupling to a pump (not shown). This pump pulls/pushes the developer through the cartridge. Thus, while the cartridge can be oriented such that the liquid interacts with the interactant due to gravitational pull or wicking, it can also be designed to allow for automated, active interaction via a pump.

Figure 39:
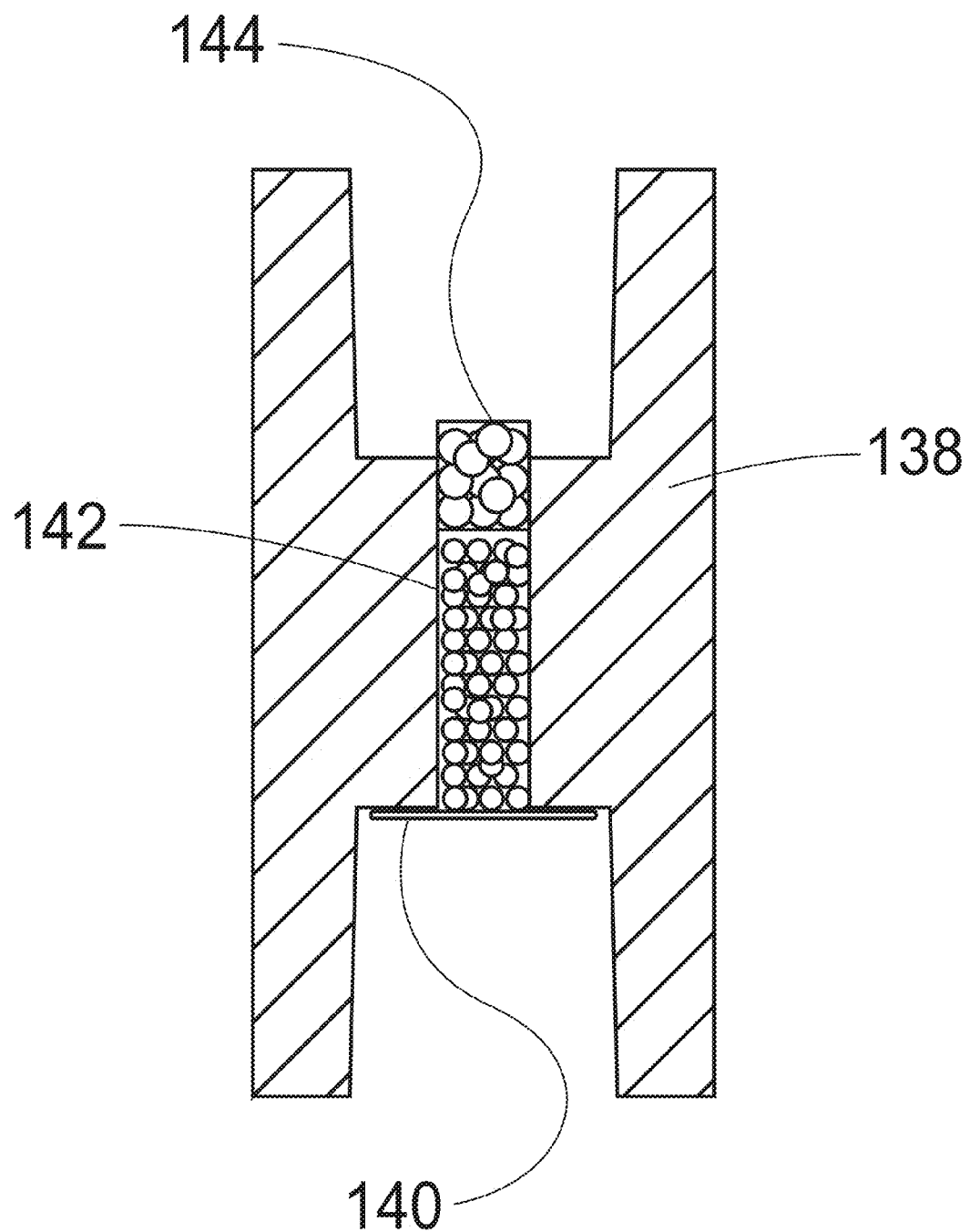
FIG. 39 shows one alternative to the barrier (130) of FIG. 38 for containing interactant beads.

FIG. 39 shows one alternative to the barrier (130) of FIG. 38. A cartridge housing (138) manufactured in plastic comprises an interactant region that is a packed bed of interactant beads (142). A porous membrane (140) is affixed to the cartridge housing on the gravitational bottom. A porous barrier (144) is compression fit into the flow path. This porous barrier may be plastic, metal, ceramic, or fibers such as glass or metal wool. It is The pressed tightly against the interactant beads (142) to prevent shifting during usage or transportation.

The wicking material (132) exemplified in FIG. 38 preferably has the following properties: fine pore (able to retain small beads, for example 75 micron beads), high open area (low pressure drop, low resistance to flow), inert to analyte of interest, easy to manufacture (e.g., "pick and place" automation), able to adhere sufficiently to the cartridge housing. Materials in sheet form are often amenable to mass production. Sheets of various materials are easily pressed into barriers. A sheet that is porous to begin with may be processed into barriers for use in the cartridge, such as retention disks. FIG. 35 displays an example of a porous sheet that can ultimately be used to form laminated disks. A porous sheet is punched so that the sheet now contains an array of holes (110, 113). Such a sheet may be thin polyimide (0.001"-0.003") with adhesive backing, such as Devinall SP200 Polyimide film with FastelFilm 15066 adhesive backing. Additionally, a sheet of fine woven mesh (112), such as 307×307 nylon mesh, 9318T48 from McMaster-Carr, is pressed with two of the punched polyimide sheets (110, 113) to form a laminate. The laminate (114) is then punched with a larger diameter tool (116) to create laminated disks with a porous center (118). The laminated disk (118)

contains a topside (and bottomside) annulus of polyimide. Such disks are easily picked up by vacuum means to be positioned easily, even into deep regions of a cartridge housing. These disks are adhered to receiving surfaces using heat pressing tools. The particular adhesive melts at 66 C, well below the melting points of numerous plastics suitable as cartridge housing. Disks can be fashioned by this method using commercial rotary cutters and other common production tools. These disks are especially well-suited to retaining interactants in deep wells, for example (324) in FIG. 41, discussed infra.

To illustrate, a cartridge embodiment will first be reviewed and then its operation described. FIGS. 4A to 4G show a cartridge embodiment that is configured to operate using the inverted cup wetting method. In this embodiment, the cartridge (0400) is comprised of three plastic parts: (a) an upper body (0405), (b) a cup (0415) and (c) a lower body (0435).

Referring to FIG. 4A, the lower body (0435) is preferably optically clear and comprises two chambers, one for the reactive beads and the second for the desiccant. A porous disk (0440) separates the desiccant (0445) and the reactive beads (0430). Atop the reactive beads, a disk (0425) is disposed. Below the desiccant (0445), a final disk (0450) is disposed.

The upper body (0405) is assembled upside down. Within the upper body (0405), there is a small perch (not shown) on which a ball (0410) rests. An inverted cup (0415) also contains a perch (0480) upon which the ball is placed. Liquid reagent (0455) is stored in the cup. The cup is preferably opaque to prevent light from interacting with this reagent, if it is light sensitive. Optionally, a spring (described in FIGS. 28A to 28D) also may be placed within the cup to assist with breaking the seal between the cup and the cog and to release of liquid when the ball is displaced. A cog (0420) is placed on top of the cup. The lower body is then press fit atop the assembled upper body.

Side profiles of the cartridge (0400) are shown in FIGS. 4C, 4G, and 4E.

The operation of the cartridge embodiment of FIGS. 4A to 4G is described in FIGS. 7A and 7B. The cartridge (0400) comprises a window (0475) that allows a kicker (0615) to displace the ball (0410) from the position shown in FIG. 7A to the position shown in FIG. 7B. This movement of the ball causes the inverted cup (0415) to move in an upward direction (compare position A to position B) such that the liquid contained within the cup (0455) is released and is then able to move through the spindles of the cog (0420) and penetrate to the reactive beads (0430) to engage in a reaction.

Modifications to the design can be made. One such modification is shown in FIGS. 4A to 4G in which the upper body (0405) has a key (0460) that ensures that it is inserted in only one way into the base unit.

FIGS. 27A to 27E show different views of a preferred embodiment of an inverted cup (2700). The lip (2705) of the open end is blunt to create a strong seal with the rubber, cog-shaped disk it presses up against and to help keep it centered inside the cartridge. The step (2710) on the side of the cup is near the lip of the cup. This ensures that the cup is centered in the cartridge and ultimately prevents leaks during storage of the cartridge. The inverted cup is preferably black. The bottom side of the cup contains a small perch (2700) to meet with the ball and keep the ball centered with respect to the cup.

FIGS. 28A to 28D show an embodiment of an inverted cup that utilizes a spring and wick. Here, the inverted cup (2800) has a central post (2830). A spring (2810) is centered around this post. A wick (2820) is pushed through the spring, leaving only a small amount (1-2 mm or preferably none) protruding from the cup. The wick is preferably an adsorbent material, such as cotton thread, but non-reactive with the liquid reagent. Alternatively, the wick may be something non-adsorbent that still promotes the movement of the liquid, such as nylon or some other monofilament. The spring may be any spring that is capable of assisting in displacing the cup. In this embodiment, the spring (2810) is comprised of stainless steel and has five (5) coils. The spring coil is flattened on one end, which is pressed against the cog and prevents tearing of said cog/compression disk.

FIGS. 29A to 29G show a further embodiment of an inverted cup. The inverted cup (2900) has a perch (2905) on which the ball (described earlier) or other displaceable object may rest. Like the previous embodiment, the cup has a central post (2920). However, this post has an extension (2915) that is preferably flexible, either by virtue of the material composition or by the geometry. Preferably, the extension is made of the same material as the post and is simply "tacked on" plastic added during the molding process. When liquid is added to the inverted cup and the lip (2910) is compressed against the cog (2935), the extension (2915) lays flat (see FIG. 29F). However, when the ball is displaced, causing loss of compression between the lip and the cog, the extension (2915) protrudes outward, serving as a channel or guide for the liquid (2930) to leave the inverted cup and proceed to the chamber of the cartridge with the reactive beads (see FIG. 29G).

Although chemical reagents may be consumed with each reaction, cartridges of the present invention need not be limited to single-use. Multiple use devices can be comprised of strips or carousel wheels of devices in a single substrate. This same form factor can be used to allow multiple analytes to be measured in a single breath sample, either with sequential or parallel processing.

Figure 40A:
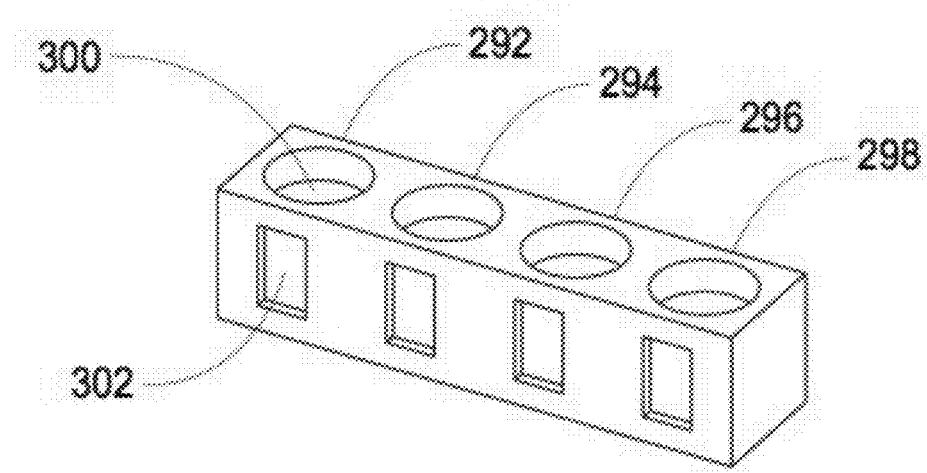
FIGS. 40A and 40B show some cartridges that enable multi-use applications.
Figure 40B:
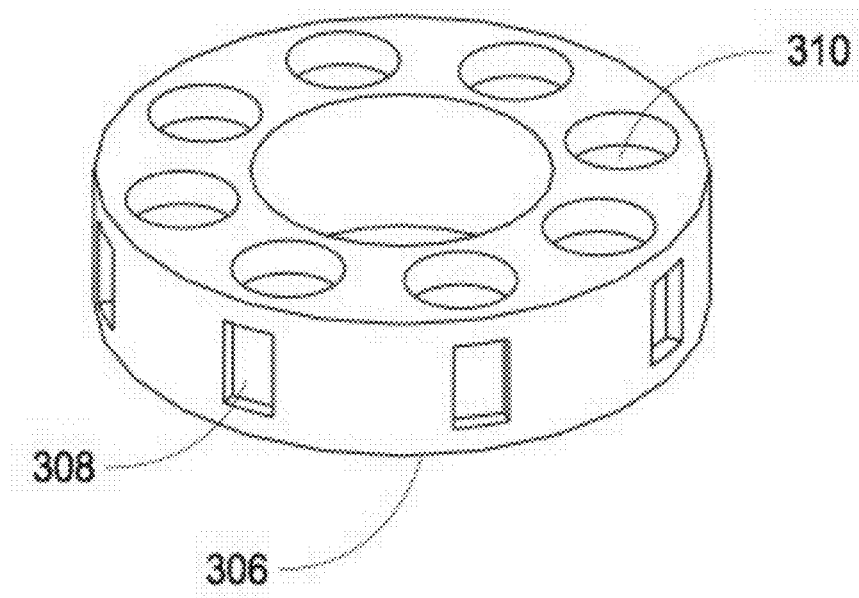

FIGS. 40A and 40B show some cartridge designs to enable these applications. Displayed on the left side of the top rectangular diagram is a strip or blister pack of interactant regions. Each of the four channels (292, 294, 296, 298) depicted can be filled with identical or different interactants, depending on whether the application is to measure, as examples, acetone on four occasions, acetone and ammonia each on two occasions, or to measure 4 separate analytes from a single breath sample. Each interactant region can be sealed with a separate barrier (300), such as a foil barrier, or with a single barrier, such as a foil strip placed over the entire top portion. These barriers may be piercable or peelable. Windows to reduce material volume and wall thickness for optical clarity can be fashioned next to each packed interactant region. The base must contain four fixed flow paths or moving parts (to move either actuators or the table containing the multi-channel cartridge). Also shown in FIGS. 40A and 40B, multiple channels are incorporated into a carousel-shaped cartridge (306) which rotates to align each interactant region with a fixed-position seal breaking/fluid driving head.

Figure 41:
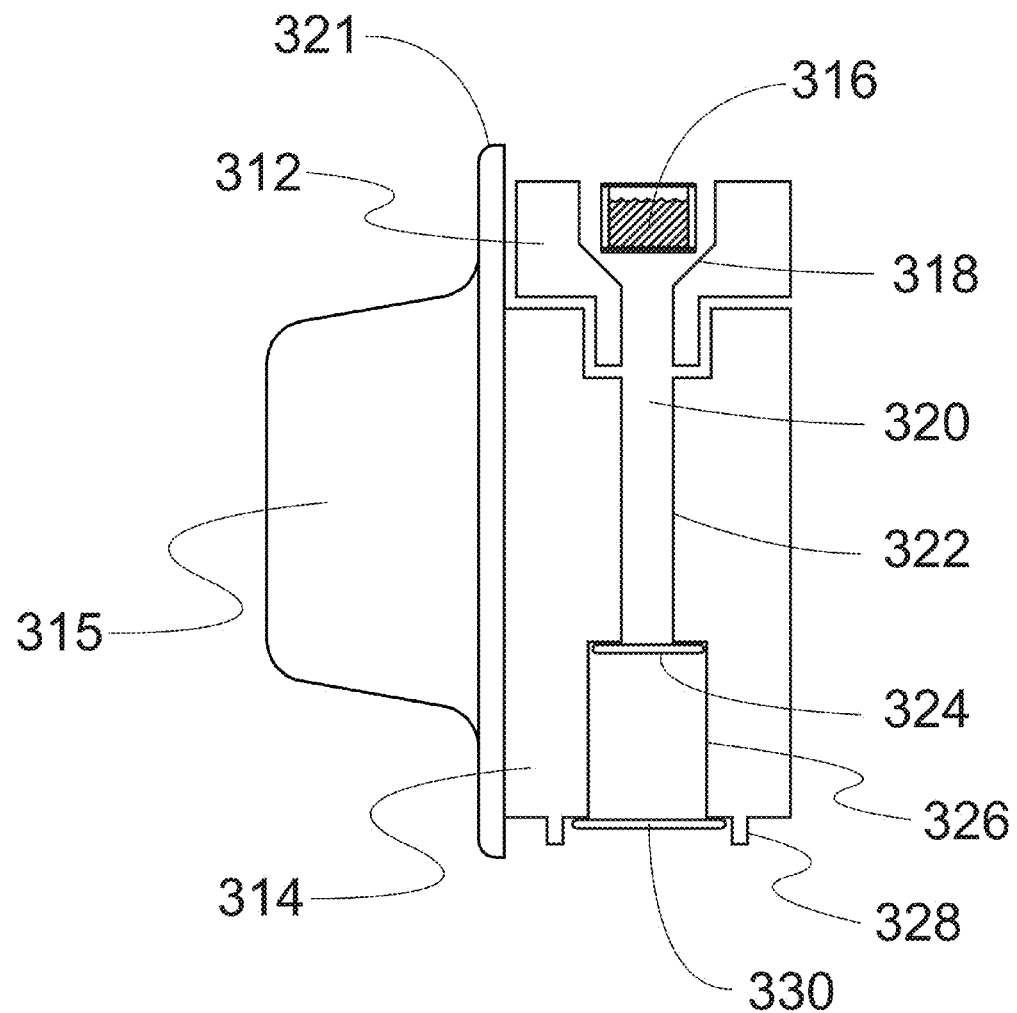
FIG. 41 shows an embodiment of a cartridge.

FIG. 41 shows an embodiment of a cartridge that facilitates or accomplishes the following tasks: (a) sample desiccation, (b) sample concentration, (c) sample reaction, (d) built-in fluid direction control (via one non-reversible one-way valve, schematically similar to three one-way valves), (e) two-phase reagent containment (dry reagent, liquid reagent), (f) inexpensive barriers (retention means), (g) easy receiving into the base, and (h) low reagent volume.

The exemplary cartridge in FIG. 41, in connection with appropriate reagents, is appropriate to measure acetone in human breath. The cartridge is comprised of two housing pieces that are mechanically fastened together, for example with snap fits. A top housing (312) attaches to a bottom housing (314). The top housing and bottom housing, by design, do not form an air-tight seal. Liquid reagent is contained in a liquid container (316) placed in a region of the top housing. One embodiment consists of a developer contained in a liquid ampoule between two foil seals, one on the top plane of the ampoule and a second on the bottom plane. Beneath the bottom foil seal, a conical housing pocket (318) is fashioned to facilitate liquid reagent dropping without intermittent air bubble entrapment. The interactant is packed into an interactant region (322) running through the center of the bottom housing. To ease tolerances on the packing of the interactant, the top-most portion of the interactant region is widened. A porous, compressible material is deposited in the top-most, widened region of the conical housing pocket such that when the top housing (312) is sealed against the bottom housing (314), the interactant loaded into the interactant region (322) is packed tightly. In general, open cell foams, both foam-in-place and pre-formed and cut, are well-suited as porous, compressible retention barriers as long as the chemistry is compatible with the system. Columns that are not packed tightly are subject to material shifting, a situation which hampers reproducibility and increases measurement errors. Desiccants are packed into a lower, wider region of the cartridge housing (326). A porous seal (324) is attached to the ceiling of the desiccant region (326) to provide a gas-permissive barrier for the interactant. In one embodiment, the barrier is comprised of woven nylon, which incurs negligible resistance to gas flow. A similar barrier (330) seals the cartridge housing on the bottom, or at the base of the desiccant region (326). The bottom region of the cartridge is formed to facilitate compression against a trapped gasket in the base to enable leak-free communication with the fluid handling system. Regions have been fashioned into the cartridge housing to enhance optical sensing. The region depth is selected to minimize housing thickness while simultaneously preserving the mechanical integrity of the cartridge, especially in relation to the wider bores required for the pockets that contain accessory reagents. The angle of the housing internal walls, with respect to the four relatively square sides of the cartridge, can be adjusted to promote effective illumination and to attenuate harsh reflections of excitation light in particular.

FIG. 38 shows a preferred method for single-analyte cartridge construction. A single piece of molded clear plastic (120) such as acrylic forms the cartridge housing. A particle retention barrier (122), as previously described, is attached to the bottom of the flow path but is comprised preferentially of thermal adhesive-backed (Fastel 15066, 3 mil thick) polyimide (Devinall, 2 mil thickness) with woven nylon center (198×198 mesh, 0.0031" opening, 49% open). Desiccant (30-60 mesh anhydrous calcium chloride) fills a desiccant region (124). A particle retention barrier (126) similar to (122) is placed on the bottom portion of the housing to retain a desiccant. The interactant beads (128) (100-140 mesh aminated and nitroprus side-attached beads in a 2:1 ratio) are placed in the flow path, and the top portion of the flow path opens to facilitate low-tolerance filling. A porous barrier (130) such as glass wool, stainless steel mesh, or porous hydrophilic polyethylene plastic (preferentially) is placed over the interactant beads. In some embodiments, the interactant beads (128) and porous barrier (130) may need additional means to be compressed tightly against the beads. An o-ring, external toothed push-on ring, or deformable retainer ring may be suitable for this purpose, but porous plastic can make its own compression fit without the need of these means. A piercable liquid ampoule that contains a liquid reagent (133), comprised preferentially of a thermoplastic, heat-sealed with pierceable barriers on top and bottom, is placed into the cartridge housing in a manner that does not occlude airflow. The top portion of the cartridge is sealed with a piercable foil (134) and a liquid barrier septum layer (136), such that liquid cannot leak through the lid after the cartridge has been used.

Figure 42:
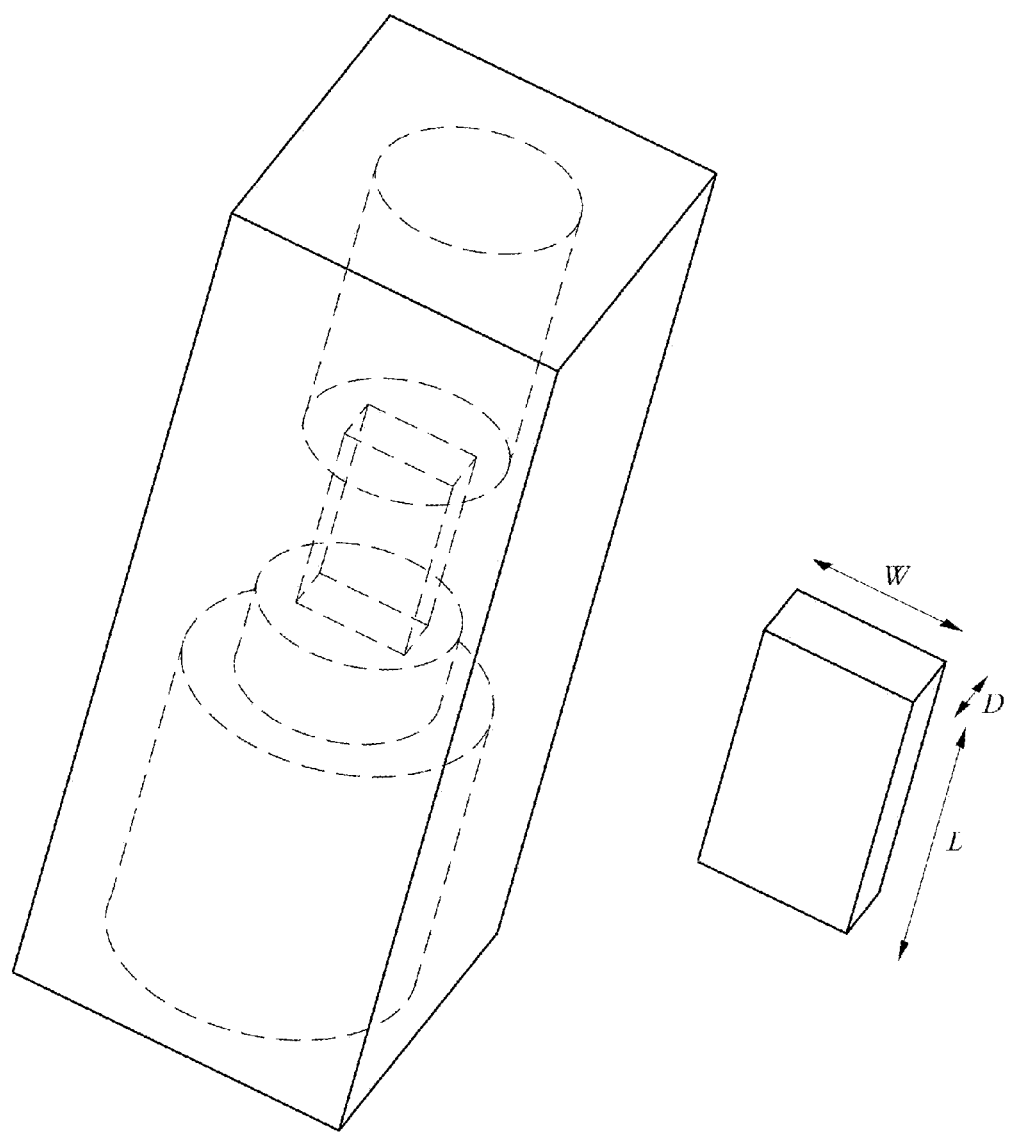
FIG. 42 is a cartridge housing with a cuboidal interactant region.

FIG. 42 shows a housing with a cuboidal interactant region. A housing for dry reagents useful for breath sensing can be made with an interactant region of cuboidal geometry. For clarity, the geometry of the interactant region is illustrated separately at right.

Figure 43:
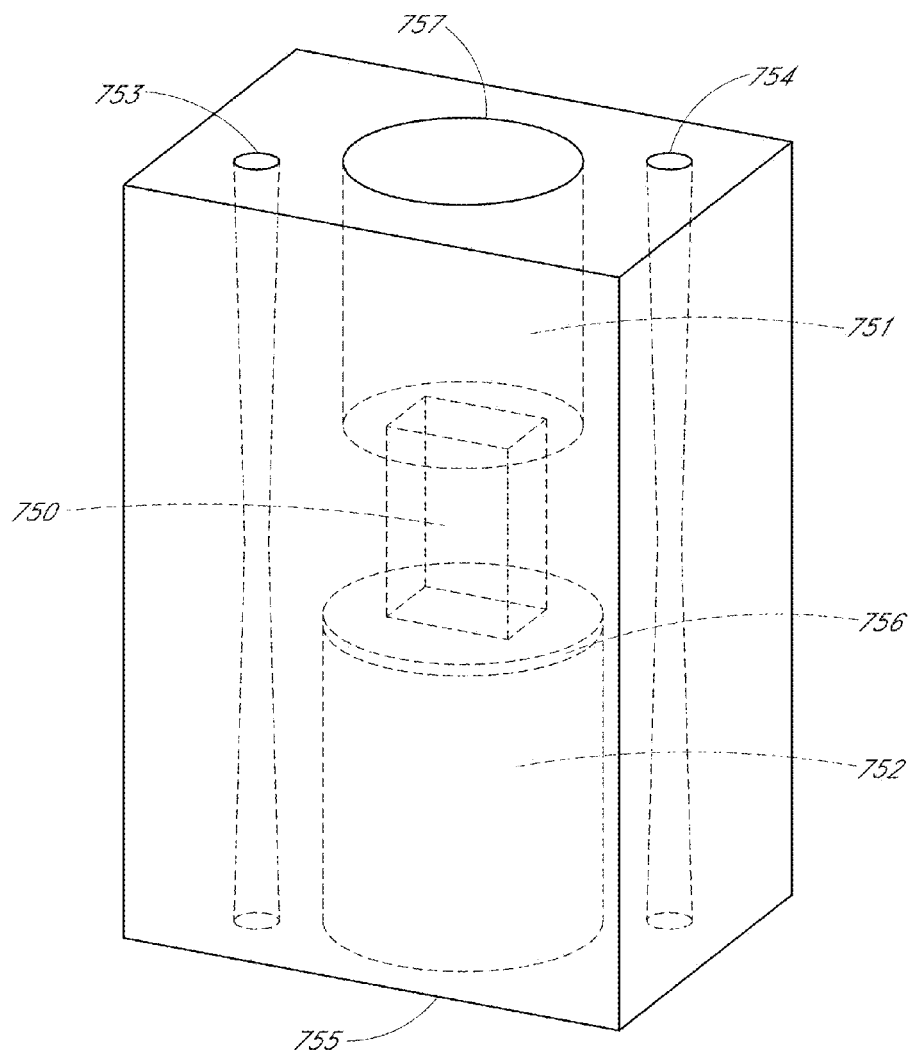
FIG. 43 is an alternative cartridge embodiment.

FIG. 43 shows an alternative cartridge embodiment. This embodiment is useful for sensing analytes in a breath sample using a wet chemical system. An interactant region (750) with an appropriate geometry is designed to contain a liquid reagent with responsivity to an analyte of interest. Two regions (751) and (752) are provided for packing components and to interface with the flow handling system. Two flow throttles (753) and (754) are disposed within the housing (757). The housing is comprised of a clear, inert plastic. This housing is designed such that a breath sample is introduced at an inlet side (755) of the housing. Flow of the breath sample through the interactant region (750) is prohibited via a barrier material (756) disposed on the "inlet side" of the interactant region (750). Rather, the flow of the breath sample passes through the flow throttles producing a back pressure in the inlet region (752). Mass transfer through the barrier occurs due to the selective permeability of the barrier material to the analyte of interest. The transferred mass reacts with the wet chemicals in the interactant region (750) to produce a color change which is measured by an optical sensor.

Figure 44:
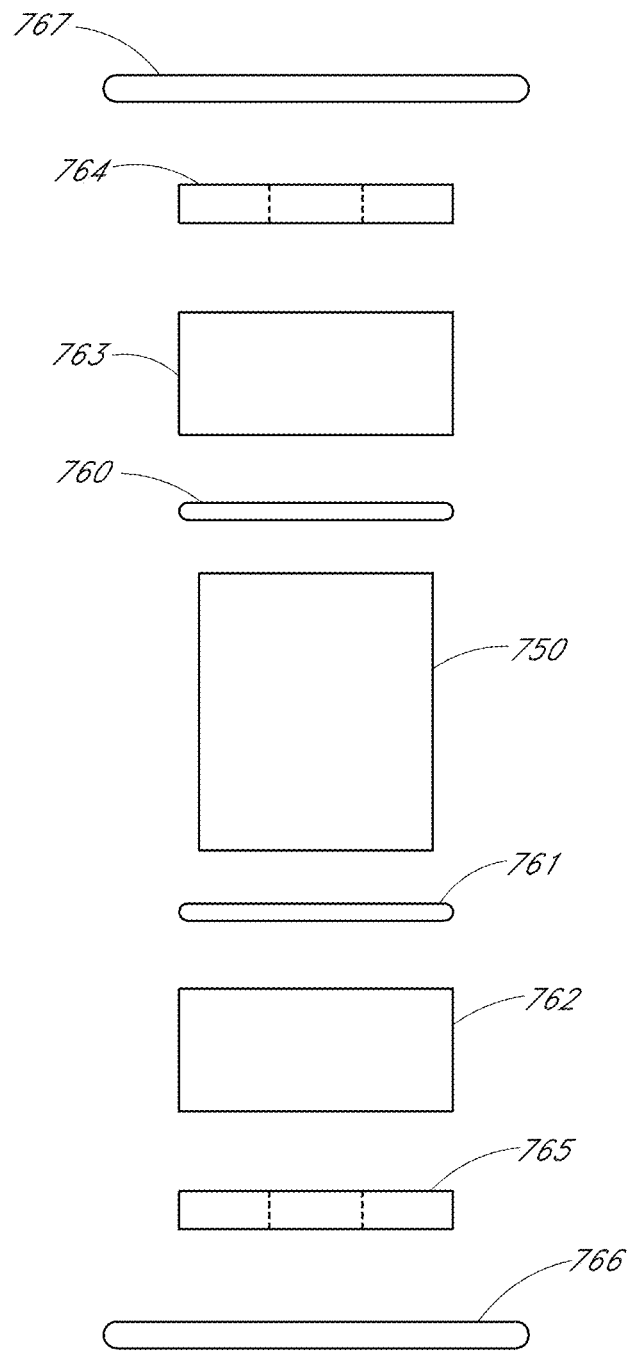
FIG. 44 shows components for an embodiment of a cartridge.
Figure 45:
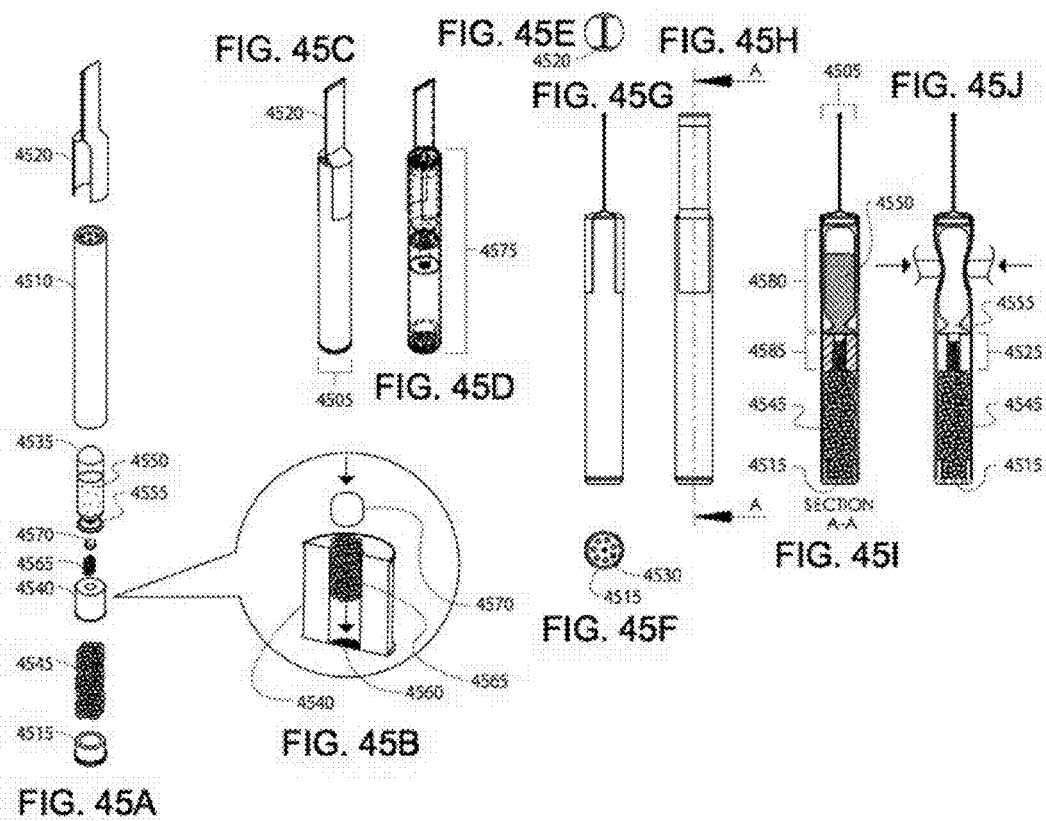
FIGS. 45A to 45J show another embodiment of a cartridge.

FIG. 44 shows an example of the manufacturing approach that can be used to fabricate the cartridge illustrated in FIG. 43. First, selectively permeable barriers (760, 761) are placed on opposite ends of an interactant region (750). Next, compressible porous barriers (762, 763) are fitted into the housing (755 of FIG. 43). These compressible porous barriers (762, 763) place pressure on the selectively permeable barriers (760, 761) sufficient to create a liquid-tight seal. Then, moisture-impregnated papers (764, 765) are introduced. The moisture impregnated papers (764, 765) maintain the appropriate humidity levels inside the housing to prevent evaporation of the liquid reagents disposed in the interactant region (750). Finally, gas impermeable, piercable heat seal membranes (766, 767) are fixed in position.

Carbon dioxide in a breath sample can be sensed when the components described in FIG. 44 are loaded into a housing described in FIG. 43 as follows. First, a selectively permeable barrier (760) of FIG. 44, comprised of a $CO_2$-permeable material such as silicone membrane with a thickness of 0.01," is press-fit into the outlet side (751 of FIG. 43) using a compressible porous barrier (763) comprised of hydrophilic porous polyethylene with a pore size of 90 microns and material thickness of 1/8". Next, a moisture impregnated paper (764) comprised of cellulose with a thickness of 0.1" previously equilibrated with a headspace water concentration equivalent to 100% saturation at 25 C is loaded. Next, a $CO_2$-responsive solution comprised of an appropriate phenol red and pH buffer solution in water (where the buffer and indicator concentration are chosen to suite the measurement range of interest) are loaded into the interactant region (750 of FIG. 43). After loading, the same components just described above are loaded in similar fashion into the housing to close off the interactant region (750 of FIG. 43). Finally, gas-impermeable barrier materials (766, 767), such as mylar/foil laminates are heat-sealed onto the inlet and outlet sides respectively on the housing.

Figure 32A:
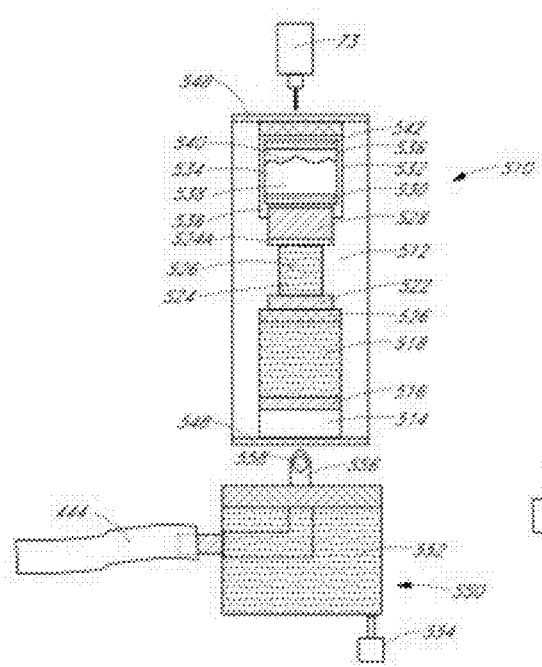
FIGS. 32A and 32B show a schematic diagram of a presently preferred embodiment of a cartridge.
Figure 32B:
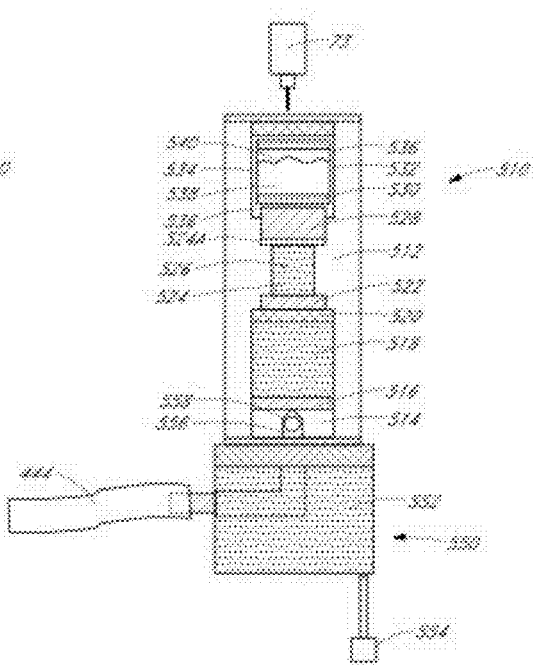

A cartridge (510) according to another presently preferred embodiment of the invention is shown in FIGS. 32A and 32B. This cartridge preferably would be used in a breath analysis system, for example, as shown in and described in connection with FIG. 48 and FIG. 49. Cartridge (510) comprises a body or housing (512), which in this embodiment comprises a solid plastic cylindrical component. Housing (512) has an inlet (514), wherein the breath sample is inputted into cartridge (510). The breath sample travels upwardly through the flow path, here a substantially cylindrical flow channel centered, about the longitudinal axis of the cartridge (510). Note that the direction from the inlet of cartridge (514) toward its output (upwardly in FIGS. 32A and 32B) is referred to herein as the "downstream direction," (given that the gas (breath sample) flows in this downstream direction), and the opposite direction, i.e., downwardly in the drawing figure toward inlet (514), is referred to herein as the "upstream" direction.

Cartridge (510) at its input comprises a porous polyethylene disk (516). Immediately downstream from disk (516) is a conditioner (518) that comprises a desiccant. A fibrous polyethylene disk (520) is disposed immediately downstream from and contacting the desiccant conditioner (518). A porous polyethylene disk (522) is disposed immediately downstream from disk (520). Disk (520) forms a lower boundary of a container or region (524) for one or more interactants (526) disposed within container (524). In this embodiment, the interactant or interactants (526) comprise solid-phase material, for example, such as those described herein. A porous polyethylene disk (528) is disposed at the downstream end of container or region (524) and forms its upper or downstream boundary. Container (524) in this embodiment comprises a slightly enlarged neck portion (524a) that includes overfill of the solid-phase material. A foil laminate (530) comprising a layer of foil sandwiched between two layers of thermoplastic material is disposed immediately downstream from disk (528). Cartridge housing (512) includes a well (532) that is open at its lower end (as shown in FIGS. 32A and 32B) to reaction volume via disk (528). Foil laminate (530) is disposed in the bottom of this well.

A liquid container (534) is disposed in well (532). Liquid container (534) has a diameter that is slightly smaller than the diameter of well (532), so that an annular channel or vent (536) is provided in fluid communication with reaction zone (524) via disk (528). Liquid container (534) contains a liquid (538) that comprises an interactant, a developer, a catalyst, a solvent, or the like. In its initial state, i.e., prior to use, the liquid (538) has an initial liquid level (540) in container (534). The bottom portion of liquid container (534) comprises foil laminate (530). Liquid container (534) also has a top, which in this embodiment comprise a foil laminate (542), preferably similar to or identical to foil laminate layer (530). Immediately above foil laminate layer (542), however, is a layer of material, in this embodiment a fibrous polyethylene, that provides a resilient seal for container (534), and which also absorbs liquid (538). The sides of container (534) may comprise a rigid and relatively brittle material, such as glass, polycarbonate, and acrylic resin or the like. At each end of cartridge (510), a foil laminate layer (548), preferably as described above, encloses and seals the contents of the cartridge. They preferably are heat-sealed to the ends of the housing (512). The top, bottom and sides of container (534) of course should be inert with respect to the liquid (538) to avoid structural deterioration, fouling or poisoning of the liquid, and the like.

The layer which, in this embodiment comprises foil laminate (530), functions to seal the bottom of ampoule or can so that leakage of liquid is prevented. It also serves as a boundary for the flow of the breath sample emanating from reaction zone (524) as it flows downstream. The gas (breath sample) in channel (536) incidentally vents through the top layers (542) and (548) after the hole or holes have been created in them by the dispensing device. The dispensing device may and in this instance preferably is used at the initial stage of the analysis, as the breath sample travels through and out column (524), but prior to dispensing of the liquid (538), to provide this exhaust route for the gas. The foil laminate top and bottom of liquid container (530 and 542) also are sufficiently resilient, are sufficiently tough (non-brittle), so that the dispensing device, such as dispensing device (73), can create one or more holes in each such foil laminate of sufficient size to achieve their desired functions without breakage.

As in other embodiments described herein above, cartridge (510) is configured to operate in conjunction with a dispensing device, such as the elongated members (e.g., a needle, pin, rod, and the like). For illustrative purposes, dispensing device (73) is shown in FIGS. 32A and 32B.

In many preferred embodiments or applications, it is desirable that the liquid container, or at least the hole or holes in it through which the liquid is dispensed, be in close proximity to, and more preferably immediately adjacent to, the reaction zone. In such embodiments and applications, it is preferred, and in some instances even necessary, that a medium be provided at the exit hole or holes in liquid container to facilitate movement or flow of the liquid out of and away from the liquid container and toward the reaction zone, through wicking or capillary action. More preferably, the bottom of the liquid container and the top of the reaction zone should abut one another, but be separated only by this wicking material. It is also preferred that there be no air gaps or other spacing between those two surfaces, except the wicking material. This is provided in cartridge (510) by porous polyethylene disk (528), which is contiguous with foil layer (530) at the bottom of liquid container (534) and which is contiguous with and open to interactant region and reaction zone (524).

When a breath sample analysis begins, input seal (548) at inlet (514) is pierced by a seal piercing assembly (550). Assembly (550) comprises a block (552) that is coupled to a moveable actuator (554). Assembly (550) also comprises a needle (556) that includes a fluid channel (558) fluidically coupled to the breath sample, e.g., from the flow path (444) of base (440) in FIG. 49. In its normal state prior to analysis, block (552) is spaced from the cartridge (510). When the breath sample analysis begins, actuator (554) moves block (552) to the inlet (514) of cartridge (510), and needle (556) is inserted through layer (548) so that the breath sample flows through flow path (444 of FIG. 49) and into the cartridge inlet (514).

As can be seen, for example, in FIGS. 32A and 32B, cartridge (510) has a flow path that extends from its inlet (514), through conditioner (518) and container-reaction volume (524), and out around ampoule (534). Cartridge (510), when inserted into the cartridge housing of the base (440 of FIG. 48), is configured as described herein regarding the insertion mechanisms so that this flow path within cartridge (510) aligns with and becomes part of flow path (434), as described herein above with respect to FIG. 49.

FIGS. 45A to 45J show another embodiment of a cartridge.

The cartridge (4505) is comprised of three major components: a packed plastic cylinder (4510), a bottom plug (4515), and a pull tab or handle (4520).

The unpacked cylinder (4510) is made of a flexible material, preferably a plastic. This cylinder (4510) is optically clear in order to properly view the post-packing reaction zone (4525). The cylinder (4510) has no bottom and contains a top with holes (4530) that are, for example, drilled into it. Once the cartridge is fully assembled, these holes act as an air channel, allowing the breath sample to move through the cartridge (4505).

The unpacked cylinder (4510) is packed by inserting materials from the open bottom up into the cylinder body. A full cylinder (4575) is comprised of a first ampoule subassembly (4580), a second ampoule subassembly (4585), a desiccant (4545) and closed off with a plug (4515). The first ampoule subassembly (4580) is essentially a highly pliable, preferably plastic, container (4535) that is filled with a liquid reagent (4550) and which further comprises a breakable bottom portion (4555). An example of a first ampoule subassembly is a polyethylene blister pack (such as that found in a disposable pipette) with a fluted bottom.

Following the first ampoule subassembly (4580), a second ampoule subassembly (4585) is inserted into the cylinder (4510). The second ampoule subassembly (4585) contains a housing that is optically clear (4540), which is essentially a cylindrical spacer that is open on the top and which has a bottom with microholes. The microholes (4560) allow the breath sample to flow through the cartridge and also prevent the beads contained within the subassembly from moving out of this container. This second ampoule subassembly is basically filled with reactive beads (4565). To the presently open top of the second ampoule subassembly, a wicking material (4570) is packed. This wicking material (4570) allows the liquid reagent (4550) to contact the reactive beads, including within the viewable reaction zone (4525). With the wadding side up, the second ampoule subassembly (4585) is packed into the cylinder (4510) against the first ampoule subassembly (4580).

After the first two subassemblies are packed into the open cylinder, the cylinder is now loaded with a desiccant (4545). Then, a small plug (4515) is inserted into the bottom of the cylinder (4510) to keep all packed materials in place. The bottom plug (4515) is also made of a plastic material that contains holes (4530) to allow the flow of air.

The cylinder (4510) is placed facing up with the ampoule (4535) at the top. A handle (4520) is attached to the top of the cylinder. The handle is preferably comprised of a vinyl decal material that can be folded into a pull-tab.

Sensors (sometimes referred to as detectors) are well developed for numerous applications and can be applied to breath analysis. Suitable sensing modalities for a given application are dependent upon the nature of the chemical interaction that is being harnessed to sense a given analyte.

The optical subsystem can be any detector or other sensor that is capable of sensing an optical characteristic, or more commonly changes in optical characteristics. This may be a direct measurement of an optical characteristic. It may also be an indirect measurement of an optical characteristic (e.g., transduction through other energy states). The optical characteristic may involve any of the following, alone or in combination, without limitation: reflectance, absorbance, fluorescence, chemiluminescence, bioluminescence, polarization changes, phase changes, divergences, scattering properties, evanescent wave and surface plasmon resonance approaches, or any other optical characteristics known to those skilled in the art.

The optical subsystem may be contained within the base or it may be a separate module that is plugged into the base. The optical subsystem may be single use or it may be used multiple times. The optical subsystem may also comprise an array of optical sensors that work in tandem to measure the optical change.

System senses the analyte or analytes of interest using colorimetric principles. The term "colorimetric principles" is used as a subset of optical principles. More specifically, the breath analysis subsystem according to this aspect of the invention comprises an interactant region that receives the conditioned breath sample and causes it to interact with an interactant. The interactant interacts with the analyte or analytes in the conditioned sample and causes a change in an optical characteristic of the interactant region in relation to the amount of the analyte or analytes in the breath sample. As the analyte reacts with the interactant, in other words, contents of the reaction zone undergo an optical change relative to the initial optical conditions. The system is designed so that the desired information about the analyte, e.g., its presence and concentration, is embodied in the optical change.

Optical characteristics that can be used in connection with this aspect of the invention comprise any optical measurement that is subject to change in relation to a change in the presence of the analyte, or in relation to the concentration of the analyte. Examples include the color, colors or spectral composition of the reaction vessel, the intensity of the radiation at a particular frequency, frequency band, range of frequencies, reflectance, absorbance, fluorescence, and others.

Each of these modalities can be employed with spot interrogations or with scanning mechanisms. A scanning system can be useful in breath analysis systems, especially where analyte concentration varies along an axis and where that variation is indicative of analyte concentration in the breath sample.

In a preferred embodiment utilizing any of reflectance, absorbance and fluorescence, an illuminator supplies excitation light to the breath analysis system and changes in that light are tracked in relation to changes in the state of the interactant subsystem. It is preferred to minimize the amount of unmodulated light that enters the optical subsystem and to measure only the light that is being changed by the interactant subsystem. For example, an interactant subsystem that produces a maximum absorbance change at 400 nm may be implemented with excitation light at 400 nm as opposed to unfiltered broadband light sources such as incandescent lamps. However, if a base is intended to sense numerous interactants that cause various spectral characteristics, broadband excitation sources may be preferable.

Illuminators (sometimes referred to as excitation sources) include, but are not limited to, incandescent lamps, such as tungsten filaments and halogen lamps; arc-lamps, such as xenon, sodium, mercury; light-emitting diodes, and lasers. Excitation light may benefit from optical conditioning efforts, such as filtering, polarization, diffusion or any of the other methods known by those skilled in the art. For example, allowing only light of the wavelength that matches the wavelength of the interactant's peak optical response is useful in increasing the signal to noise ratio of the optical subsystem.

Figure 46:
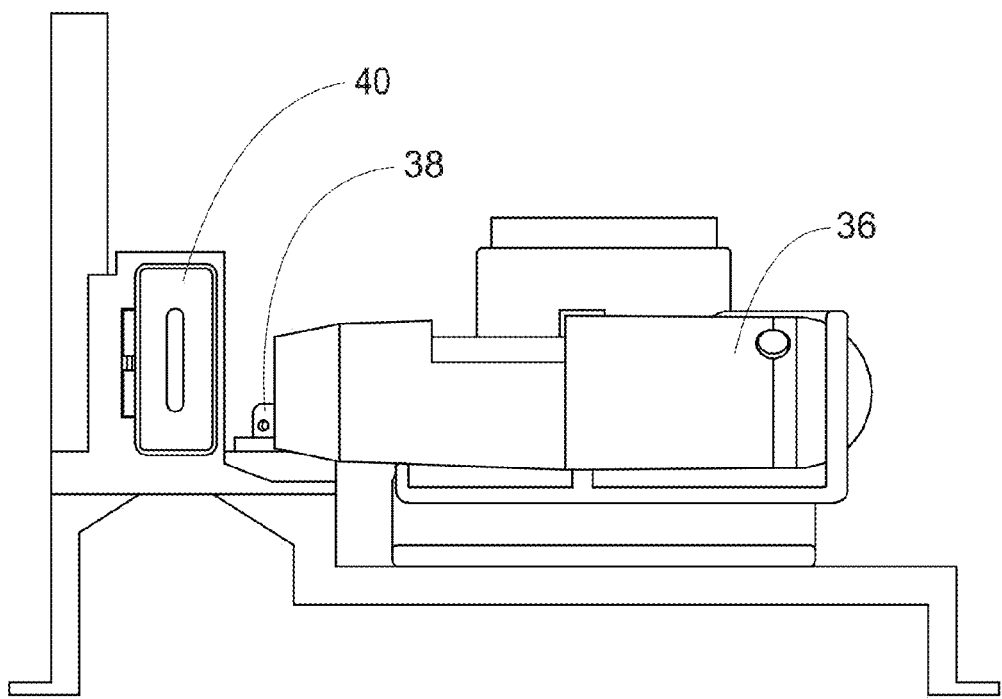
FIG. 46 depicts a general layout for an optical subsystem configuration.
Figure 47:
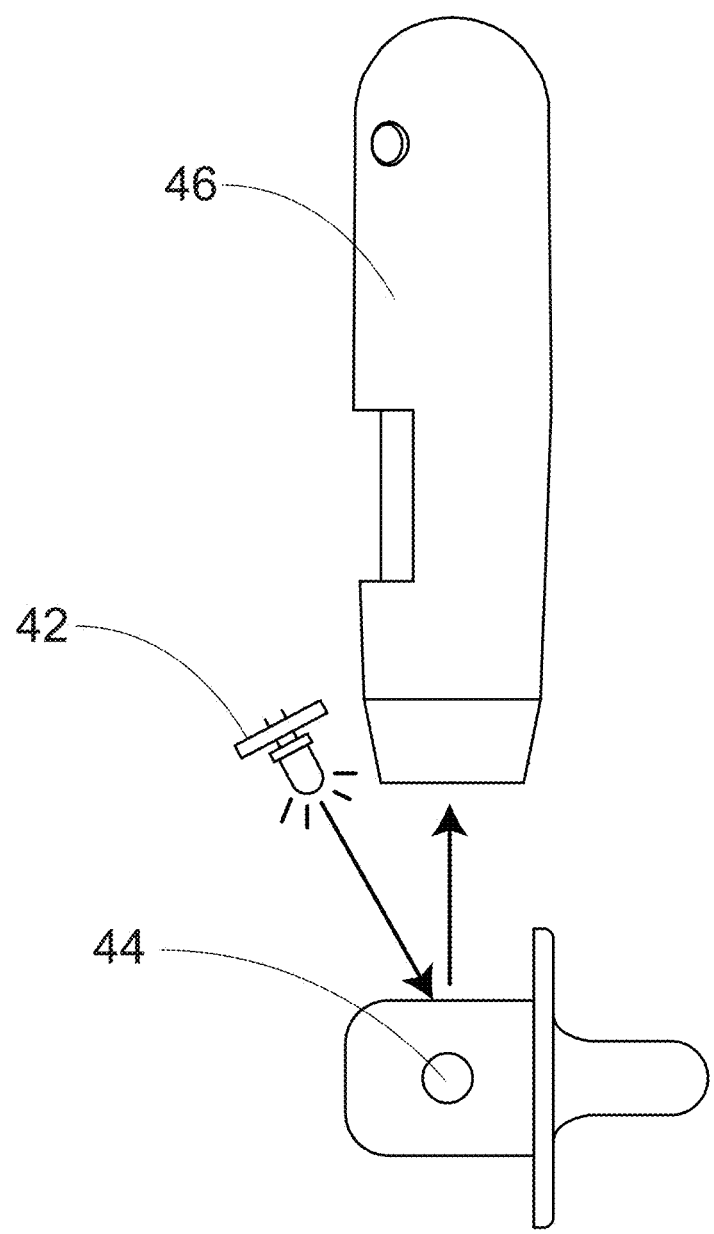
FIG. 47 depicts a general layout for an optical subsystem configuration from a top-view.

FIG. 46 and FIG. 47 depict embodiments of the optical subsystem that are useful for endogenous breath sensing. FIG. 46 depicts a general layout for an optical subsystem comprising a camera (36) in relation to a light source (38) and cartridge (40). FIG. 47 depicts similar components from a top-view, illustrating the relative angle of the illuminator (42) to the incident plane of the cartridge (44) and to the focal plane of the camera (46). Such an embodiment reduces glare from the illuminator and is suitable for capturing high-quality outputs comprising information (in this case, images) of the interactant. The images can be processed to derive or to interpolate from correlations of breath analyte concentrations and developed color. A camera is especially well-suited to systems where multiple interactants are to be sensed due to the additional power afforded by both a wide spectral range, a degree of spectral sensitivity (images are captured onto red, green, and blue pixels), and a high degree of spatial resolution. In particular, spatial resolution allows very simple instrumentation setups to be used for a wide range of applications, for example quality assurance. Other embodiments such as semiconductor photodetectors can provide low processor overhead and compact size.

Figure 48:
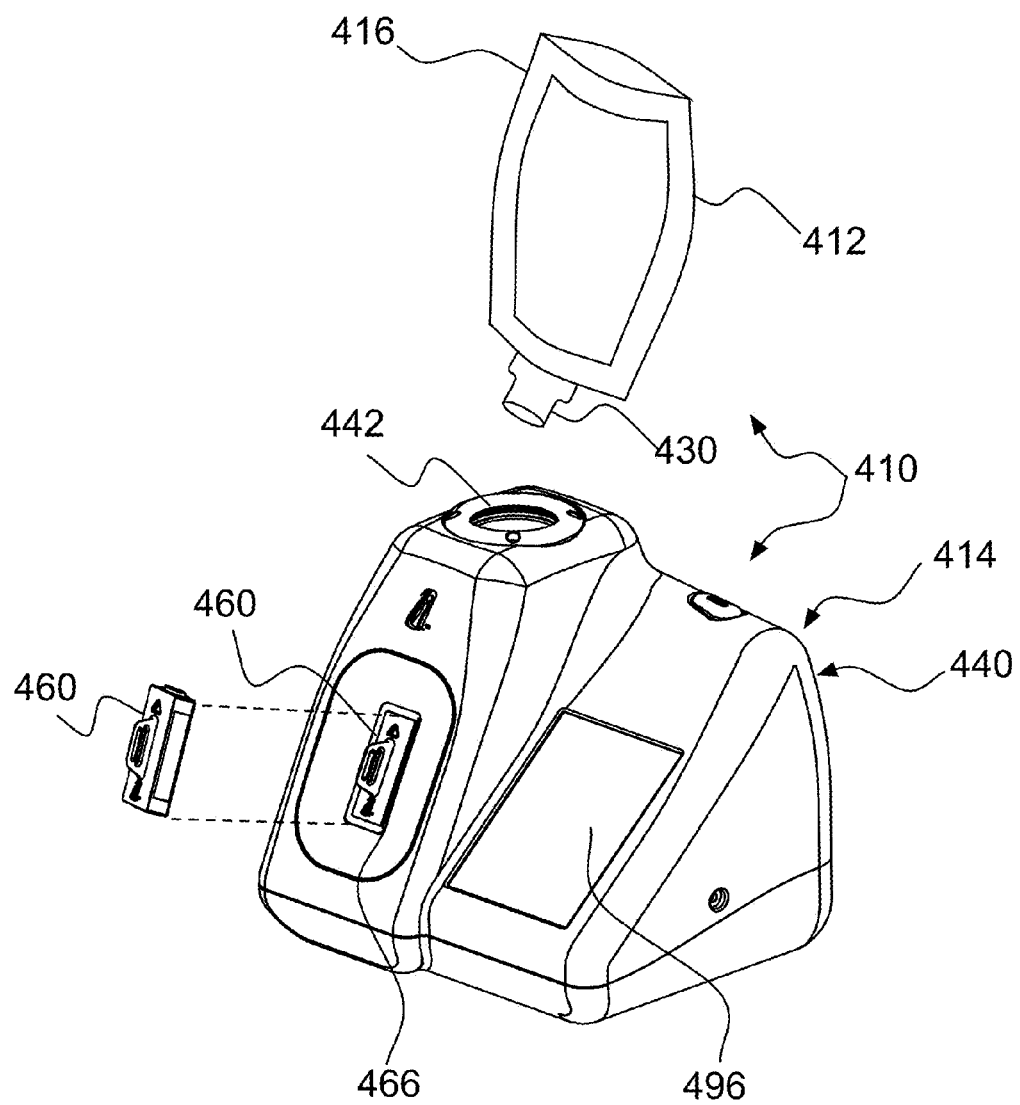
FIG. 48 shows a breath analysis system according to another presently preferred embodiment of the invention.
Figure 49:
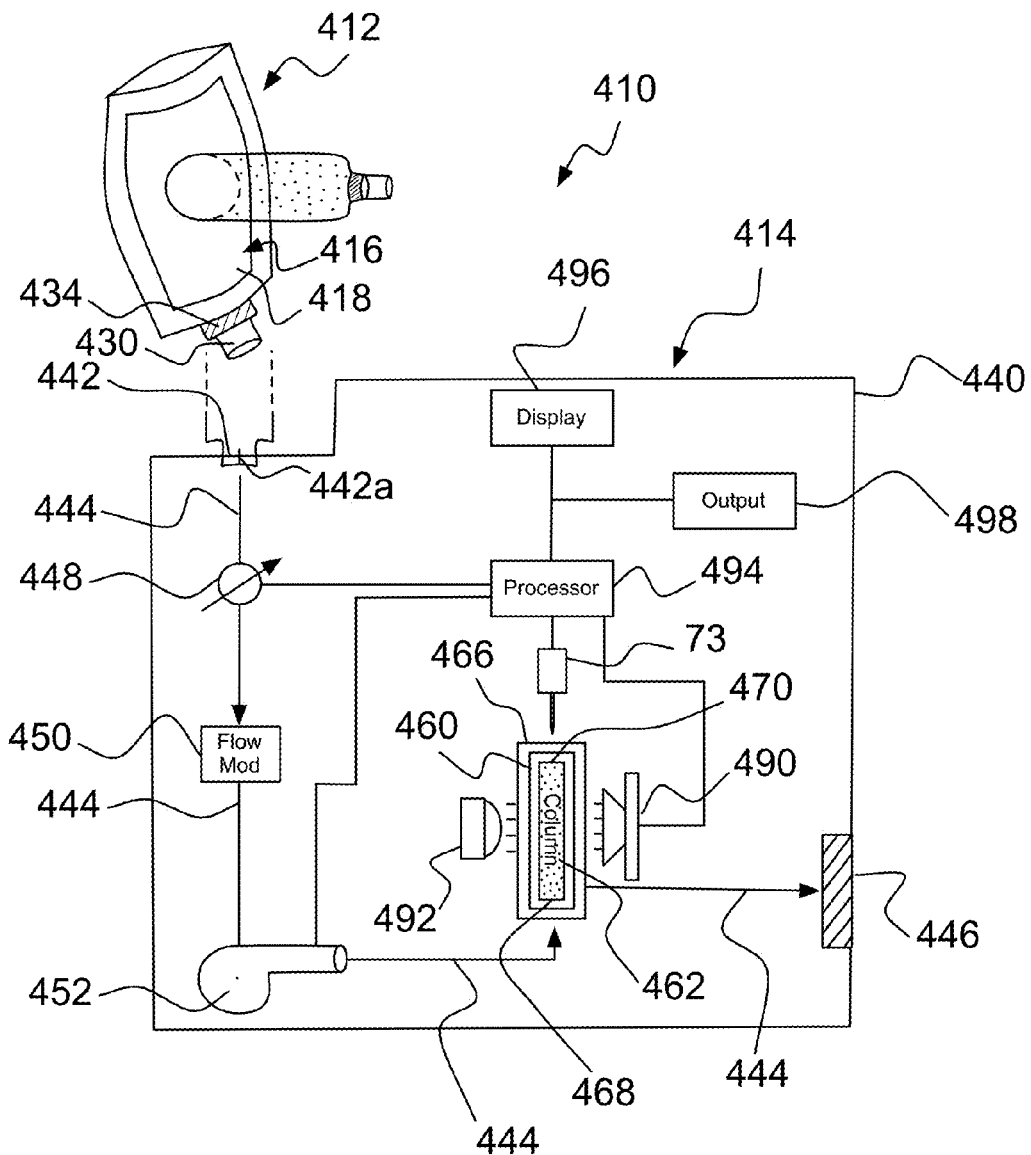
FIG. 49 is a hardware block diagram of the system shown in FIG. 48.

As embodied in system shown in FIGS. 48 and 49 (410), the breath analysis subsystem (414) comprises a detachable cartridge (460) that includes a cylindrical region, in this case comprising a reaction zone (462) containing an interactant. As shown, for example, in FIG. 48, the front exterior surface of base (440) has a cartridge receiver in the form of rectangular aperture (466). Cartridge (460) is sized and configured to mate with this cartridge receiver (466) in substantially light-tight or light-sealing form. The cartridge (460) comprises a tubular or cylindrical space that comprises reaction zone (462), with an inlet aperture (468) and an outlet aperture (470) at respective ends.

The interactant is configured to interact with the analyte or analytes of interest in the breath sample to yield a "product" (e.g., a reaction product or resultant composition) and to cause a change in an optical characteristic between the interactant and the product in relation to the amount of the analyte that interacts with the interactant. The interactant may comprise a solid-state component, such as a plurality of beads or other substrates with selectively active surfaces or surface active agents, for example, in a packed bed configuration. Interactant also may comprise other forms, for example, such as liquid-phase, slurries, etc. Note that the term "react" as used herein is used in its broad sense, and can include not only chemical reactions involving covalent or ionic bonding, but also other forms of interaction, e.g., such as complexing, chelation, physical interactions such as Van der Wals bonding, and the like.

In presently preferred embodiments and method implementations of the present invention, it is desirable to use a small disposable cartridge such as cartridge (460) for personal, regular (e.g., daily) use in a clinical or home. Large consumables (namely the interactant) are inconvenient and relatively more expensive. To reduce the size of the consumable and that of the overall device required to analyze the analyte or analytes of interest, a smaller particle size for the interactant generally is preferred.

Further in accordance with this aspect of the invention, the system comprises a sensor that senses the change in the optical characteristic and generates output comprising information about the change in the optical characteristic. As embodied in system (410), and with reference to FIG. 49, the sensor comprises an optical subsystem that comprises a camera (490), preferably a digital camera, with associated an illuminator (492), that can obtain optical characteristics, and changes in optical characteristics, of reaction zone (462). Illuminator (492) is disposed to provide light or an appropriate electromagnetic radiation at or through the interactant in a manner so that the radiation interacts with the contents of the reaction vessel and is then directed to camera (490). The light or electromagnetic radiation may comprise essentially a single frequency (a single, narrow band), a set of such single frequencies, on or more frequency ranges, or the like. In presently preferred system (410), illuminator (492) provides white or broad-band light at a fixed level of intensity. (See arrows in FIG. 49 at illuminator (492))

Digital camera (490) generates a signal that embodies the information on the optical characteristic or characteristics of interest. Signal generation can be accomplished using a wide variety of known transduction techniques. Commercially-available digital cameras, for example, typically provide automatic download of digital images as they are obtained, or transmit timed or framed video signals.

Embodiments of the optical subsystem described herein have particular utility in breath analysis applications. In such applications, the optical change may be complex, confounded by physiological variations between users, interfering substances or other breath-specific challenges.

FIGS. 50A to 50E show different scenarios that may be generated within the optical sensing zone.

Embodiments that utilize an optical sensor with spatial (two dimensional or 2D) and spectral (at least red-green and blue or RGB) selectivity can sense both errant and normal functioning of changes in optical characteristics. Such performance has particular utility in a multi-analyte breath analysis system.

A preferred optical subsystem is capable of employing algorithms which can identify abnormalities and normalize them through such means as pattern recognition, multi-axis differential analysis, rate of color formation change, blemish rejection, interpolation, extrapolation, etc.

Additionally, for certain applications, it is advantageous to utilize an optical sensor with an aspect ratio that matches the aspect ratio of the interactant region. In this configuration, the absolute size of the interactant region permits close coupling of a sensor array within a suitable working distance in a way that completely captures the region of interest without expensive optical components.

In FIG. 50A, a color bar penetration profile indicative of channeling or otherwise irregular mass deposition and reaction is presented. In FIG. 50B, a bubble is shown which results in a high intensity reflection of illumination light; such light contains wavelengths that are of interest and those that are not. An algorithm that recognizes the bubble and completely eliminates it from the analysis may be used in conjunction with the optical sensor. In FIG. 50C, a diffuse color bar formation is shown such as might be indicative of multi-chemistry competition for adsorption onto available sites. Content in the optical sensing zone can be used to recognize the more diffuse collection of analyte into the interactant region and may be useful in extrapolating the total color change based on the pattern in the interactant region; thus, the color formation lost due to column breakthrough can be estimated. In FIG. 50D, an optical image is illustrated where the particles used to pack the interactant region are sufficiently large and irregular so as to cause high variability of the exposed surface area. A 2D scanner with RGB and temporal resolution enables numerous algorithms to calculate the resultant color changes based on the amount of total possible color change available due to reaction sites. In FIG. 50E, an example of an optical sensing zone that is seen in breath analysis systems utilizing a liquid reagent is shown. Here, the color change in the liquid phase is used to assess the extent of analyte interaction. Irregular settling of the liquid can be identified and processed appropriately. This can be especially advantageous, for instance, if the amount of liquid in the sample is known to leak at a certain rate and that the starting or ending color of the liquid can be indicative of its starting or ending reactivity. Alternatively, the change in area can be used to calculate the expected starting or ending reactivity in like manner.

Given the nature of the interactions between breath analytes and interactants contemplated and presented herein, for certain situations, discerning complex changes in optical characteristics is desirable. Certain specific examples were provided in FIGS. 50A to 50E. However, there are others, e.g., such as: changes in refractive index before and after a breath sample has been delivered to the interactant region, malfunction of housing (for example, the beads break free due to a failure in the retention mechanisms), rejection of a colored developer solution from the color of product formation, etc. In all of these scenarios, for certain applications, the ability of an optical system to scan the field regarding RGB characteristics can result in an optical subsystem with superior performance to those based on 1-D scanners or bulk "spot" measurements.

In various presently preferred embodiments and method implementations of the invention, the base contains a flow handling system, which preferably includes a pump (sometimes referred to as a flow facilitator or a sample pump) to deliver the breath sample through the flow path of the base. The flow handling system may comprise any apparatus that causes or allows the breath sample to interact with the interactant in the cartridge. For example, the flow handling system may comprise a series of specialized tubing that does not allow for condensation of endogenous breath analytes. The flow handling system may also comprise a pneumotachometer for differential pressure measurement. In presently preferred embodiments, the flow handling system is coupled to, and preferably contained within, the base and further the base ensures that the flow path is continuous between the flow handling system and the cartridge after the cartridge is inserted into the base. The flow handling system can be used to receive breath samples from various sources, including breath bags, mixing chambers, and ambient air.

To further illustrate various aspects of the invention, a system for sensing ammonia in a breath sample according to another presently preferred embodiment of the invention will now be described. FIG. 48 shows a perspective view of the system, and FIG. 49 provides a hardware block diagram of it. In this preferred embodiment, the system (410) is a portable device suitable for field use, or in the home of a patient or subject, and thus is not confined to use in a laboratory or hospital setting.

Turning to the breath analysis subsystem (414), and with reference to FIG. 49, it comprises a base (440) (also shown in FIG. 48) that houses its various components as described more fully below. An input port (442), which preferably is a breath bag receiver, is provided at the top of base (440) for receiving the distal end of ferrule (430) and thereby forming an air-tight seal and flow path between the interior of breath reservoir (418) and an interior flow path (444) of base (440). A post or stanchion (442a) is disposed in port (442) to interact with and open one-way valve (434) in bag unit (416b) so that the breath sample in breath reservoir (418) is allowed to flow in to flow path (444). The flow path (444) begins at input port (442) and extends through base (440), as described more fully herein below, to and outwardly from an exhaust port (446). For directional reference, flow or movement along the flow path (444) in the direction from the breath reservoir (418) and toward exhaust port (446) is referred to herein as "downstream," and flow in the opposite direction, from exhaust port (446) toward input port (442) is referred to herein as "upstream."

It is useful and in most cases important to quantitatively measure certain flow characteristics of the conditioned breath sample within flow path (444). Examples of such flow characteristics include flow velocity, flow rate (mass or volumetric), and the like. Accordingly, in this embodiment a flow meter (448) is positioned in flow path (444) downstream from input port (442). Flow meter (448) measures flow velocity and flow volume of the breath sample at that location.

Breath analysis subsystem (414) further includes a flow modulator in the form of a flow restrictor (450) downstream from flow meter (448), and a pump (452) downstream from flow restrictor (450). Pump (452) is appropriately sized and powered so that it is suitable for drawing the conditioned breath sample from breath reservoir (418) and causing the breath sample to flow through the flow path (444) and out exhaust port (446), taking into account the full system configuration as described herein. Flow restrictor (450) functions to absorb and smooth perturbations created by pump (452).

Breath analysis unit (414) further comprises a sensor or sensing unit that analyzes the conditioned breath sample and detects the presence and, preferably, the concentration, of ammonia in the sample.

Figure 51:
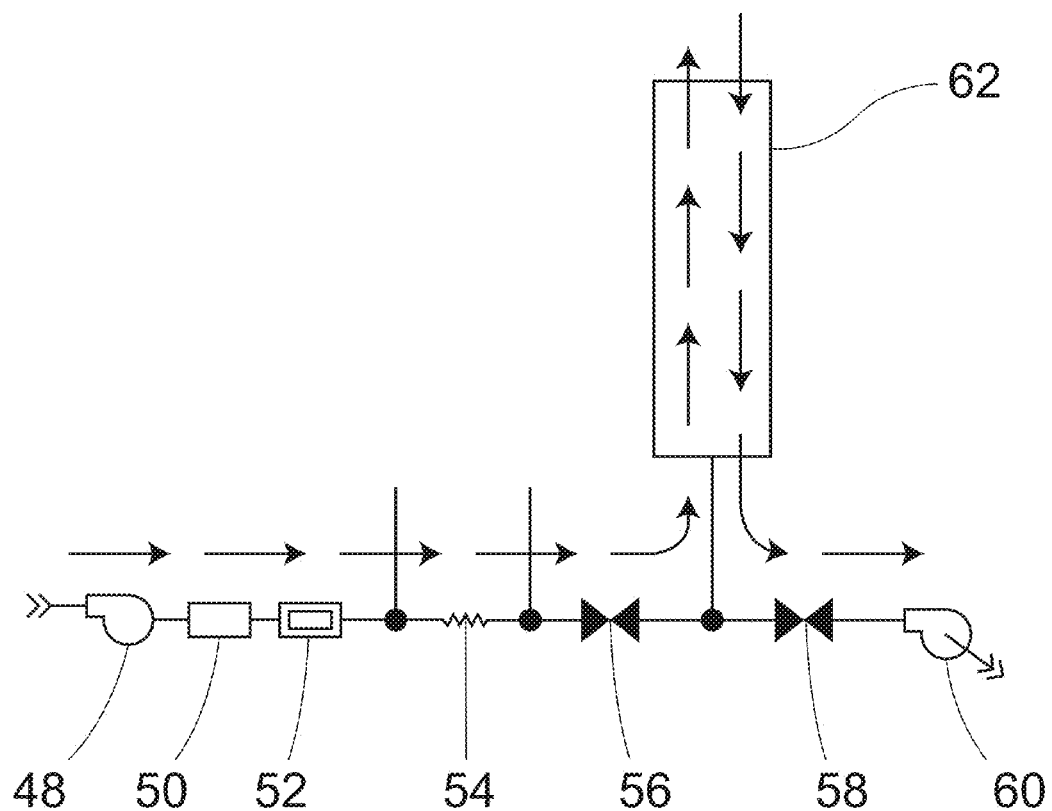
FIG. 51 depicts one flow handling system suitable for high quality breath sample measurements.

FIG. 51 depicts a flow handling system that utilizes a pump suitable for high quality breath analysis. A breath sample is connected to a pump configured to withdraw (48). The breath sample is then pushed through a pulse dampener (50) and then into a flow laminarization element (52). Pulseless, laminarized flow is then easily measured with a pressure transducer over a flow restrictor (54). The pressure drop over the known restriction of the flow restrictor can be used to quantify the amount of breath flowing through the flow restrictor, especially where viscosity of the breath sample can be accurately estimated.

Viscosity estimation has been well characterized, and the procedure makes use of gas constituency estimations/knowledge as well as temperature and pressure measurements of the gas itself. Such a configuration of components with appropriate algorithms can be used to accurately measure the amount of gas that flows through the flow path (sometimes referred to as channel), in terms of moles of gas per unit time. With the downstream valve (58) in the closed position in FIG. 51, the pump pushes the breath sample through the cartridge (62). Depending on the components selected, the flow rate and achievable drive pressure can be selected appropriate to the application. The user force of exhalation is decoupled from the pressure required to exposure the cartridge to the breath sample, greatly increasing the range of applications that can be successfully implemented. Also, the duration of breath sample delivery to the optical sensing zone of the cartridge can be easily controlled and can exceed comfort level or ability of a user-controlled, passive flow handling system. Flow through the cartridge can be reversed by closing the upstream valve (56) and activating a second pump (60) configured to withdraw.

Figure 52A:
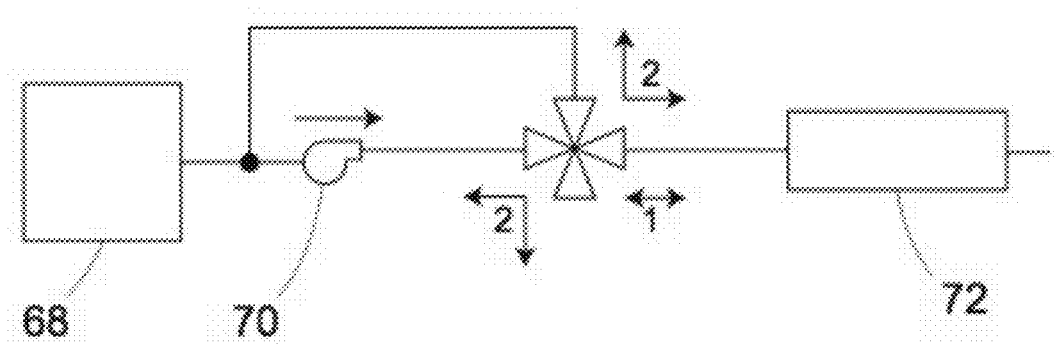
FIG. 52A shows one approach to component reduction using a specialized ball valve.
Figures 52B, 52C:
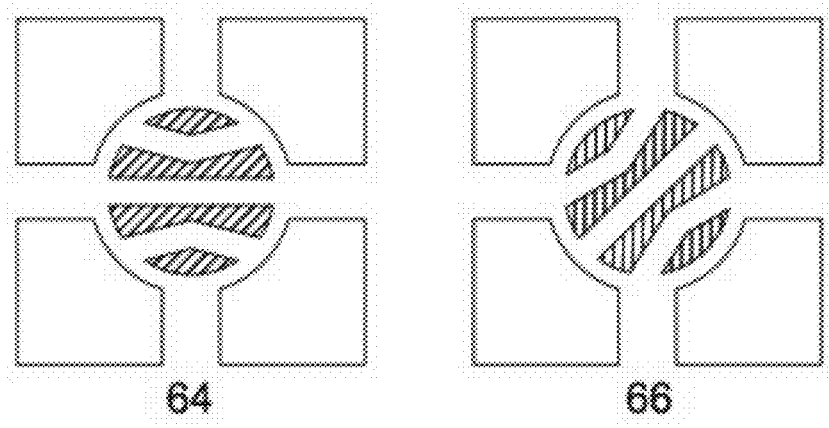
FIG. 52B is an embodiment of the first flow position for the ball valve.
FIG. 52C is an embodiment of the second flow position for the ball valve.

The flow handling system can and preferably is compact. Certain configurations facilitate this. Other pump and valve configurations may be preferable, particularly systems based on reversible, stopped-flow, and metering pumps. In the case of a pump that allows gas flow to be reversed without switching plumbing inlets, components (58) and (60) can be eliminated from the configuration and pump (48) can be used to both push and pull the breath sample through the cartridge. Also, pumps that stop back-flow when not being actuated can obviate the need for valves (56) and (58). Furthermore, pulse dampeners (50) and flow laminarization elements (52) may be combined into a single component, Also, a single component may accomplish the function of the pulse dampener (50), flow laminarization element (52), and pressure transducers over flow restrictors (54). Pumps with built-in metering capabilities, such as piston pumps with set stroke volumes, can also be used to obviate some of the components described here. Another approach to component reduction makes use of a specialized ball valve, as shown in FIGS. 52A to 52C. The specialized valve has two flow positions, (64) and (66). In the first flow position (64), the pump (70) can withdraw from a breath bag (68) and push the breath sample through a cartridge (72), more specifically through the flow path of a cartridge. In the second flow position (66), the same pump (70) with the same plumbing connections can withdraw the breath sample from the cartridge (72), or more specifically its flow path, and exhaust it to the atmosphere (assuming that the breath bag (68) has been completely evacuated). This is one example where the flow handling system is capable of accepting variable volumes of a breath sample and removing unneeded volume.

Figure 53:
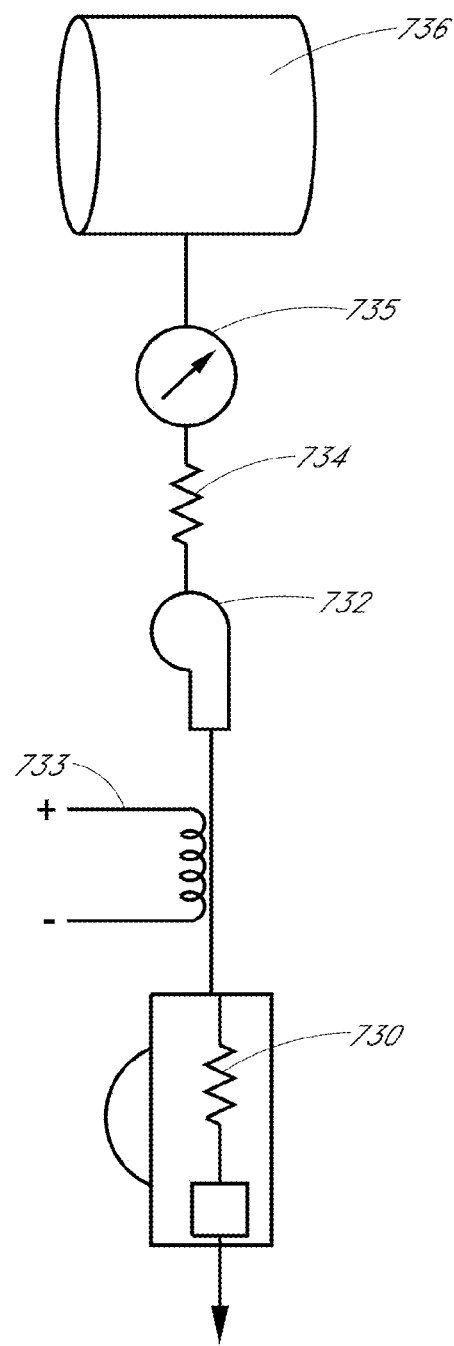
FIG. 53 is a flow handling system with a foreline heater.

FIG. 53 shows an optional foreline heater. In certain embodiments, increased inlet pressure on the interactant region of a housing (730) may cause condensation of analyte or breath water or both into the line between the pump (732) and the housing (730). In this case, a heater (733) can be used to prevent condensation and preserve sample integrity. The heater may utilize resistance or infrared principles. For reference, a flow restrictor or laminarization element (734), mass flow sensor or differential pressure sensor (735), and breath bag (736) are shown.

Figure 54:
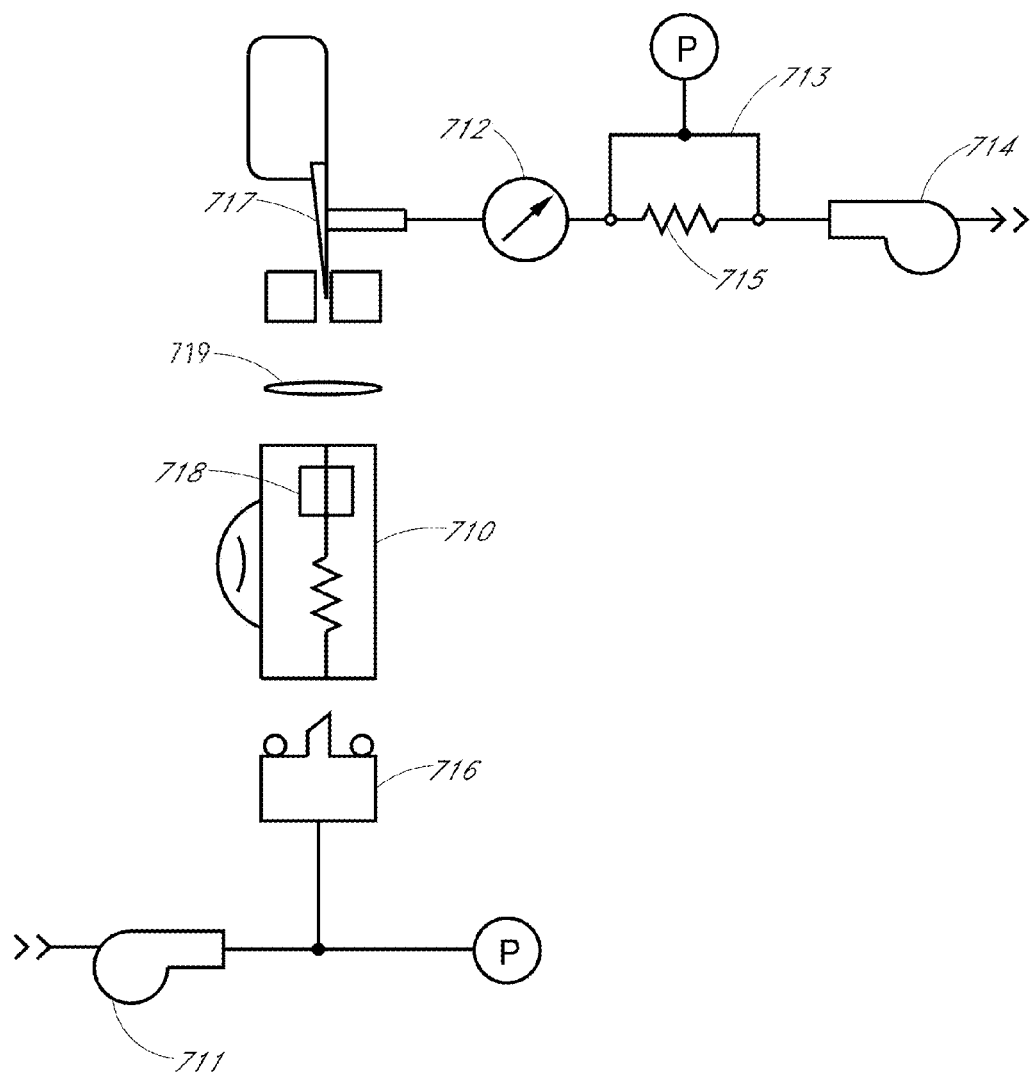
FIG. 54 is a flow handling system based on a housing with a septum.

FIG. 54 shows a flow handling system based on a housing (710) with a septum (719). Building a septum into the housing enables a set of flow handling systems that contain reduced components with respect to other flow handling systems. In one example, a pressure drive system is described wherein flow sensing can take place without the need for an external flow restrictor or pulse dampener; rather, the packed housing with its sufficiently high resistance to flow in its interactant region allows pressure pulses from an air pump to be flattened upstream of flow detection equipment. In this case, the pump (711) and mass flow sensor (712) or differential pressure sensor over a calibrated restrictor (713) are used. In an alternate configuration, a pump is configured for vacuum withdrawal. In this scenario, the pump (714) is connected to an upstream flow restrictor (715) which dampens pressure pulsations which enable either the use of a mass flow sensor (712) or differential pressure using the pressure drop of the interactant region of the housing for flow rate assessment. In either scenario, the liquid handling is as follows. First, the housing is engaged with a seal on one end (716). Next, the septum (719) is pierced with a 90 degree hollow needle (717). In this arrangement, the breath sample can be caused to flow over the interactant region in either vacuum or positive pressure. Once a set flow volume has been sampled, the 90 degree hollow needle (717) breaks an optional liquid container, causing its contents to wet the interactant region with a flow direction that is counter to the flow direction of the delivery of the breath sample.

Another aspect of preferred embodiments is ensuring the gas flow path is essentially leak-free. The coupling of disposable components into the flow path is thus important.

The cartridge receiver (sometimes referred to as "insertion mechanism" for the cartridge) can take a variety of forms. Receiving the cartridge into the base unit may comprise, for example: (a) spring-loaded insertion, (b) linear actuated insertion, (c) annular gasket, o-ring insertion, (d) taper compression fit, and (e) snap-in fit. The receiving mechanism for the cartridge may comprise control mechanisms for such parameters as humidity, temperature, pH, and optical phenomenon such as light. For example, the receiving mechanism for the cartridge may include light blocking apparatuses. Preferably, the receiving mechanism enables the cartridge to be inserted at an angle in the base with respect to the floor. This angle improves user comfort during the cartridge insertion step but should not be too reclined to diminish gravitational forces which are helpful in dispersal of liquid reagents. The angle is preferably in the range of 0-45 degrees with respect to a vertical line normal to the floor.

In a spring-loaded receiving approach, a sliding head under spring force can be used to compress the cartridge against a gasket on the base. The pressure of the cartridge housing against the gasket forms a tight fluidic face seal, sufficient for the moderate pressures (for example up to 5 psi) that may be required to drive breath samples through the interactant in the cartridge. To insert a cartridge, the user slides the cartridge into the sliding carrier of the cartridge receiver and pushes against the spring until the cartridge can be seated against the gasket, similar to the insertion of cylindrical batteries into common consumer devices. A lever can be used to provide an alternative means to pushing against the spring.

Figure 55:
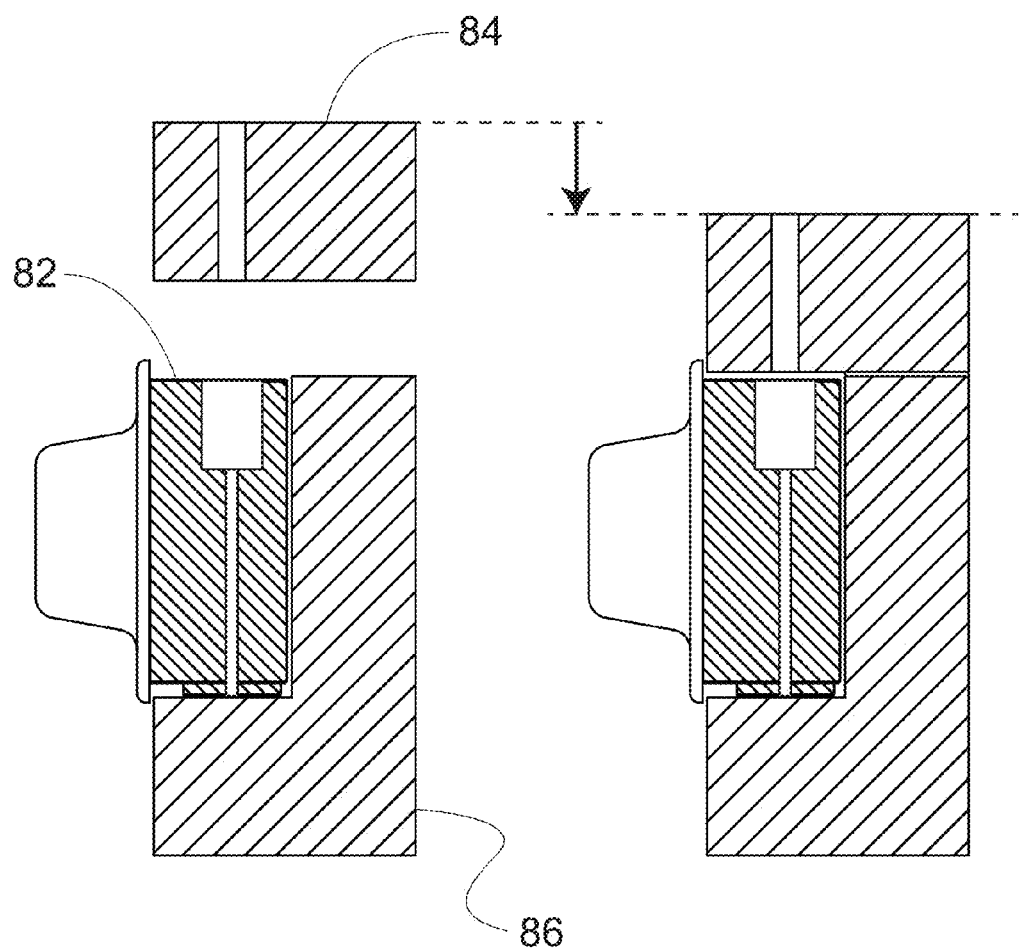
FIG. 55 shows a cartridge insertion into a base that makes use of a linear actuator.

Another approach to cartridge receiving into a base makes use of a linear actuator. As shown in FIG. 55, in such an example the cartridge (82) is compressed between a top (84) and bottom (86) surface. In this example, the sliding mechanism of the spring-loaded receiving approach described above is used in conjunction with a linear actuator instead of with a spring. In preferred embodiments, the top surface will be moveable and the bottom surface will be fixed, and the leak-free junction and inlet plumbing will attach to the bottom surface, which is fixed.

Figure 56A:
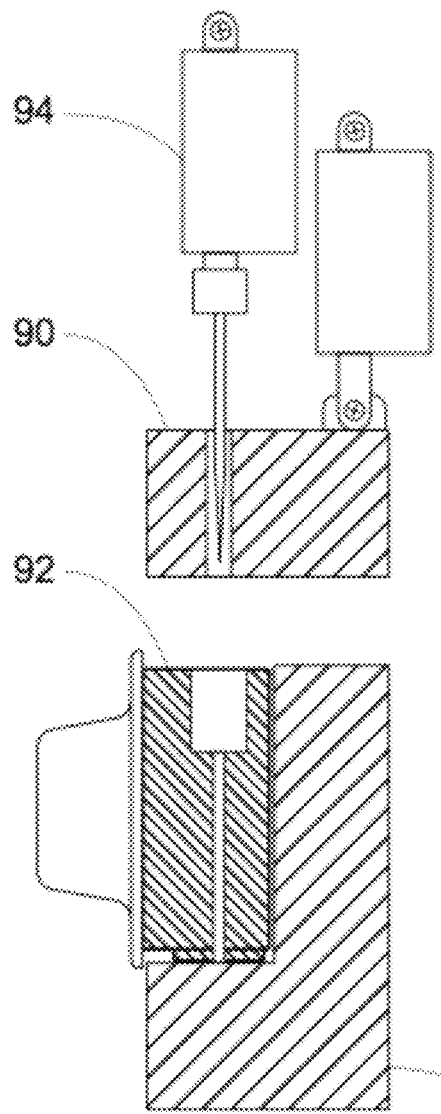
FIGS. 56A and 56B show the details of an embodiment of a sliding mechanism in relation to a cartridge.
Figure 56B:
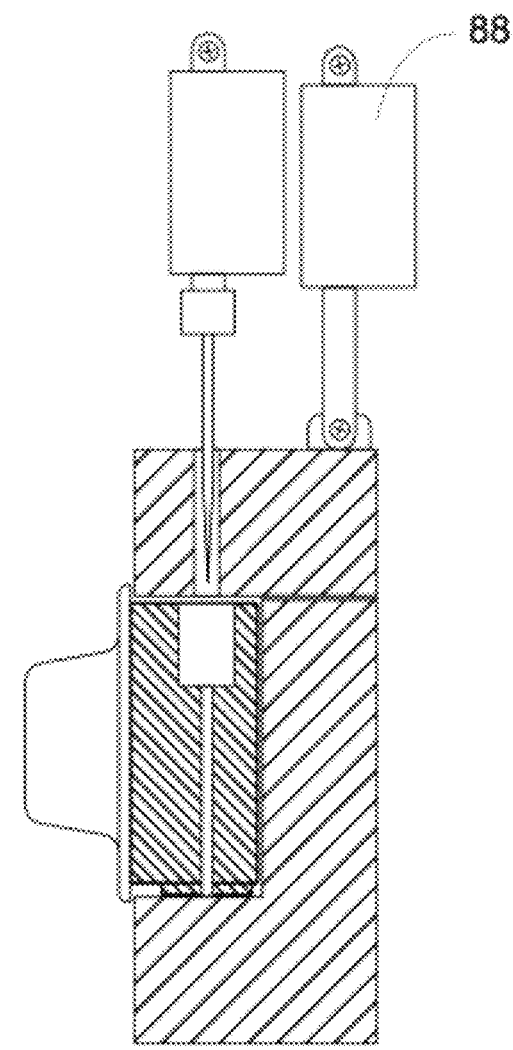

FIGS. 56A and 56B the details of an embodiment of a sliding mechanism in relation to a cartridge. In FIGS. 56A and 56B, a linear actuator (88) pushes a sliding platform (90) up and down to engage and disengage with the cartridge (92). The sliding platform can contain other elements, for example a separate linear actuator (94) useful in piercing operations. In this configuration, the tubing (component of flow handling system) that interacts with the cartridge is in the bottom surface (96) of the clamping mechanism, which remains fixed in order to reduce functional requirements of the flow handling system. In this case, prior to cartridge receiving, the actuator is positioned into a retracted state that lifts the clamping head (part of the clamping mechanism) away from the top surface of the cartridge. Sufficient distance is created to allow unobstructed receiving of the cartridge into the cartridge receiver. Once the cartridge is positioned in the cartridge receiver, a user presses a button to indicate to the processor that the cartridge is loosely positioned, after which the linear actuator extends until a desired force is perceived to be acting against further extension (as estimated using the force/current curve of the particular actuator) or until a specified position is attained.

Another embodiment of cartridge receiving is an annular gasket or o-ring. In such an embodiment, an o-ring fitted over a cartridge housing that includes a cylindrical base of the cartridge can be used to provide necessary sealing. In this case, an o-ring groove retains the o-ring as the bottom region of the cartridge housing is inserted into a round-shaped cartridge receiver. The walls of the cartridge receiver are sized appropriately to seal against the o-ring. Alternatively, the o-ring can be captive in the walls of the cartridge receiver of the base. Insertion force can be provided using a spring, linear actuator, or user force.

A tapered compression fit can also be used as cartridge receiving. In this embodiment, the cartridge housing has a tapered bottom portion that can be used to form a leak-free fluidic connection without an o-ring or gasket. In this case, the tapered bottom portion is compression fit into a slightly dissimilar tapered cartridge receiver. User force is used to insert and remove the cartridge. Alternatively, a linear actuator and pin engagement scheme can be used to push the cartridge into the cartridge receiver and to pull it out subsequent to measurement conclusion.

Another example of cartridge receiving based on user force input is a snap-in design. In this design, snap receptacles are fashioned into the bottom region of the cartridge housing. When the cartridge is compressed tightly against a soft gasket in the base (of the system), the snap receptacles engage with mating snaps in the base (of the system). To release the cartridge, the spring-loaded snaps in the base are retracted.

There are many reactions that can be used to sense the various analytes that may be of interest. In some of those reactions, a relatively simple one-step reaction can be used, e.g., wherein the breath sample is contacted with the interactant, whereupon the change in the optical characteristic is manifested. In others, however, it is necessary to carry out multiple process steps. An illustrative but important example would be reactions in which the breath sample must be contacted with a first interactant, and then subsequently be contacted with another interactant, such as a second reactant, solvent, enzyme, or the like. The devices of the present invention, for example, can also optionally comprise a reaction initiator or dispensing device. A reaction initiator or dispensing device may be any apparatus (and may also be the same apparatus) that allows the developer solution or the like to contact the interactant. (The reaction initiator or dispensing device may comprise a needle that pierces a canister of developer solution such that the solution passively contacts the interactant, as described more fully herein below.) In some breath analysis applications, it may be necessary or desirable to have three, four or more separate materials (interactants, solvents, developers, etc.) that are introduced at various times, e.g., simultaneously, sequentially, and so on, but which materials require separate storage prior to use. Such situations can be particularly demand when the material is in liquid phase (including but not limited to liquids, liquid suspensions, and the like).

To address such needs and circumstances, the invention according to various aspects comprises the use of a separate liquid container, or a plurality of such liquid containers (subcontainers), and a dispensing device that dispenses those liquids when and as needed for the particular application at hand.

Another optionally included component of the devices of the present invention is a kinetic enhancer. In a preferred embodiment, the kinetic enhancer is contained within the base. The kinetic enhancer increases the reactivity between the analyte and the reactive chemistry. One example is shaking the reaction vessel to allow for increased mixing. Temperature control can also be used to increase reactivity or otherwise improve sensor system performance. Temperature control can be accomplished in numerous fashions, including IR heating and conduction heating using resistive heaters. In IR heating, IR emitting lamps are targeted to regions of interest, and illumination causes non-contact heating. Resistive elements in contact with thermal conductors built into the cartridge, for example foil seals surrounding a developer solution, can be used to increase the temperature of reaction and thus the reaction speed.

Temperature control, including cooling, can also be useful for controlling adsorption and desorption from adsorptive resins, for example Tenax TA or silica gel. Conductive cooling via Peltier elements can be helpful in increasing the adsorption capacity of resins.

Figures 57A, 57B, 57C:
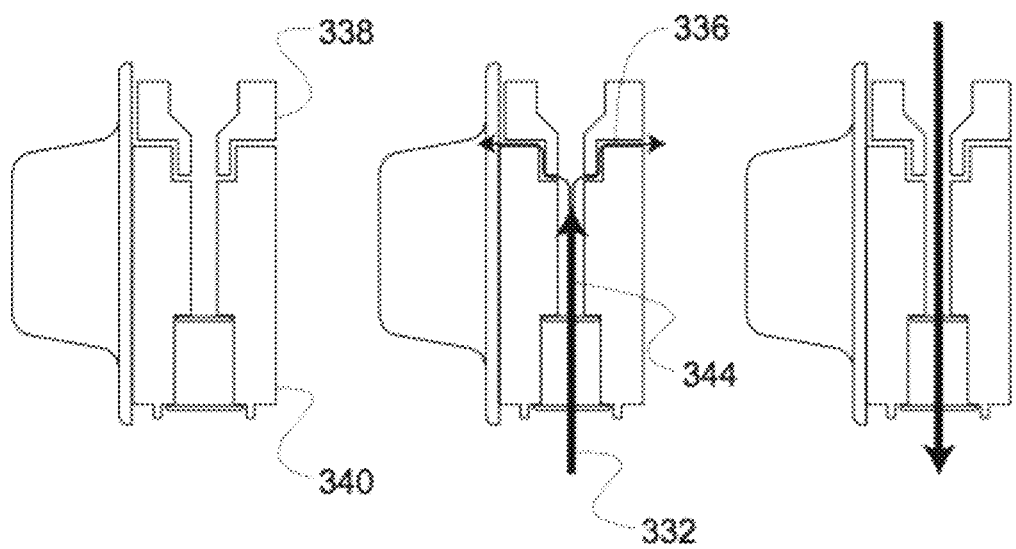
FIG. 57A shows an embodiment of a cartridge.
FIG. 57B shows a depiction of the flow path before the cartridge seals have been broken.
FIG. 57C shows a depiction of the flow path after the seals have been broken and a liquid seal is formed.

One preferred example of how a cartridge interacts with a base is in the following manner. First, the user opens a door through the wall of the base and places the cartridge into a cartridge receiver. No significant force is required of the user to make the insertion, and insertion orientation is restricted by mechanical stops. Either of two (of the four) sides of the cartridge must be oriented toward components of the optical subsystem. A cartridge receiver that receives the cartridge at an angle (whereby the top housing of the cartridge is inclined away from the user with respect to the bottom portion) increases user accessibility and comfort during cartridge insertion. Once the cartridge is loosely placed within the base, mechanical means are provided whereby the top housing of the cartridge is compressed against a captive gasket in the base. See FIG. 55 and FIGS. 56A to 56B. This compression forms a face seal between the gasket and the bottom housing of the cartridge, providing a leak-free fluidic connection capable of withstanding the driving pressure required to move breath samples and developer through the cartridge and its various housing regions. Once the cartridge is in position, a breath sample is collected through various means, for example a breath bag or sidestream sampling. Once a breath sample is ready for measurement, a flow handling system is activated which withdraws breath sample from the breath bag and pumps it first through the desiccant region, next through the intereactant region, and out through the cartridge outlet aperture. See FIGS. 57A to 57C. The cartridge is designed to be open to the flow of a breath sample at both ends. The bottom housing (desiccant region) is open through a woven mesh barrier, the top housing is open through the non air-tight sealing of the top housing (338) to the bottom housing (340). Thus, when breath samples are pushed through the bottom housing of the cartridge, they can vent through the top housing although the seals of the liquid container have not been broken. After the proper volume of breath sample has been pushed through the flow path of the cartridge at the selected rate of flow, the developer container is ruptured. See FIGS. 59A to 59C. An elongated member (236), in this case a pin, is driven through the top housing of the cartridge such that it breaks the top piercable membrane (252) of the liquid container first, then the bottom piercable membrane. Slower drive speeds of the pin and appropriate contained volumes of developer are preferred to prevent developer spillage during rupture. Also preferred is the ability of the liquid container to withstand deformation during rupture when such deformations result in spilled developer solution. Once the developer is released, it fills the conical cutout of the housing (250). The conical cutout assists in creating a liquid seal, such that when fluid is pulled through the interactant region, here in the shape of a column, there is a continuous pull of developer into the interactant region. The amount of developer pulled through the flow path of the cartridge can be controlled (open-loop) by adjusting the duration of the pulling pump's "on" cycle, or a closed-loop flow system can be employed. An optical subsystem (see FIG. 46 and FIG. 47) is used to record changes in optical characteristics which result from analyte reaction with the interactant beads in the interactant region or, in this case, reactive bed and developer. Developer can be largely contained in the desiccant region. Optional top septa and bottom septa can be built into the cartridge when potential user exposure to especially deleterious solvents should be prevented.

Figure 58:
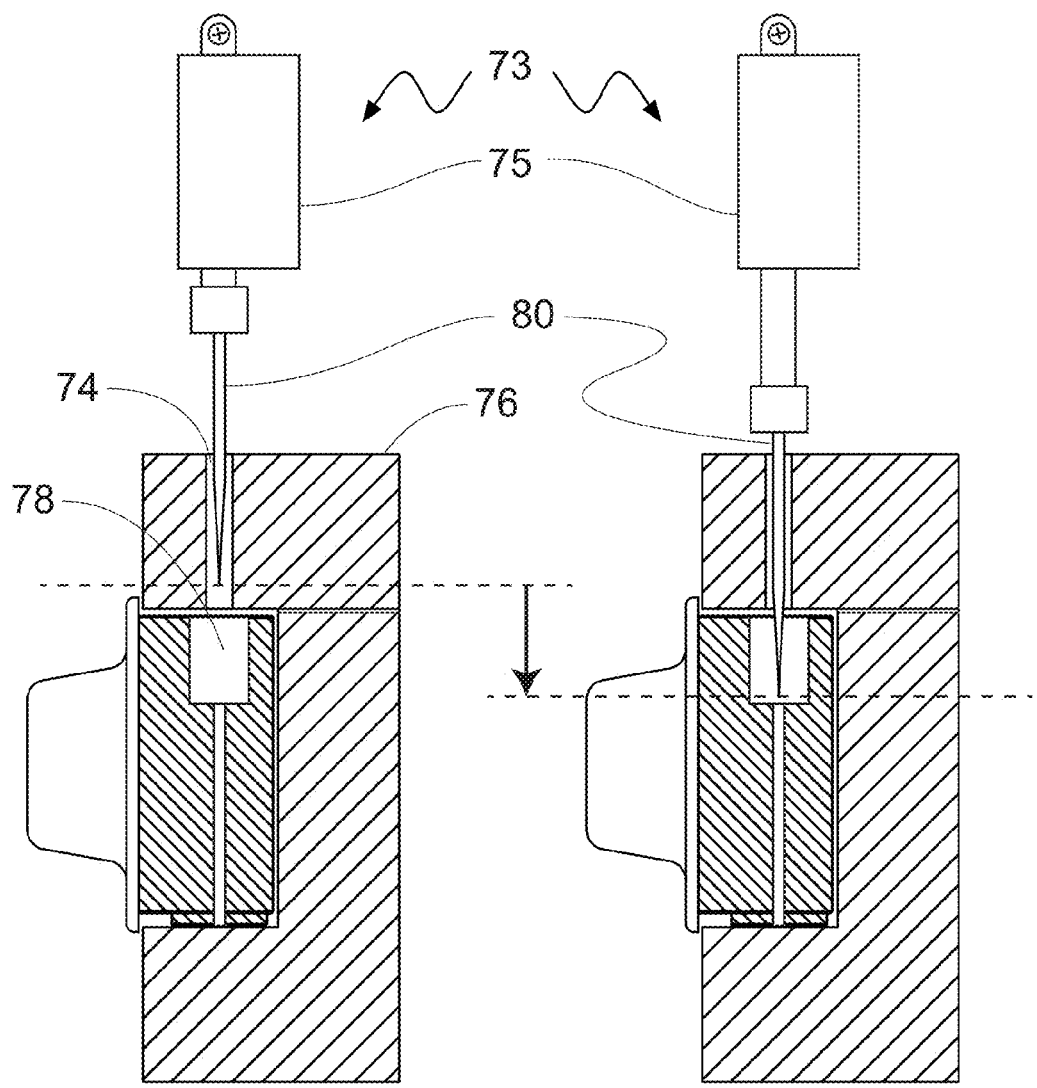
FIG. 58 shows an exemplary reaction initiator based on a needle.

To illustrate this aspect of the invention, FIG. 58 shows an exemplary dispensing device or reaction initiator (73) based on an elongated member (80), in this case a needle. In this example, an actuator (75), more specifically a linear actuator, with an attached needle is housed in the top region (74) of a cartridge-positioning clamp (76). To release liquid contained within a container (78), here a piercable liquid container, the linear actuator (75) drives the needle (80) through first the top seal and then the bottom seal. Once the seals are broken, the liquid is released to either be pumped by external pumps as described elsewhere or to wick through the reaction zone.

Figures 59A, 59B, 59C:
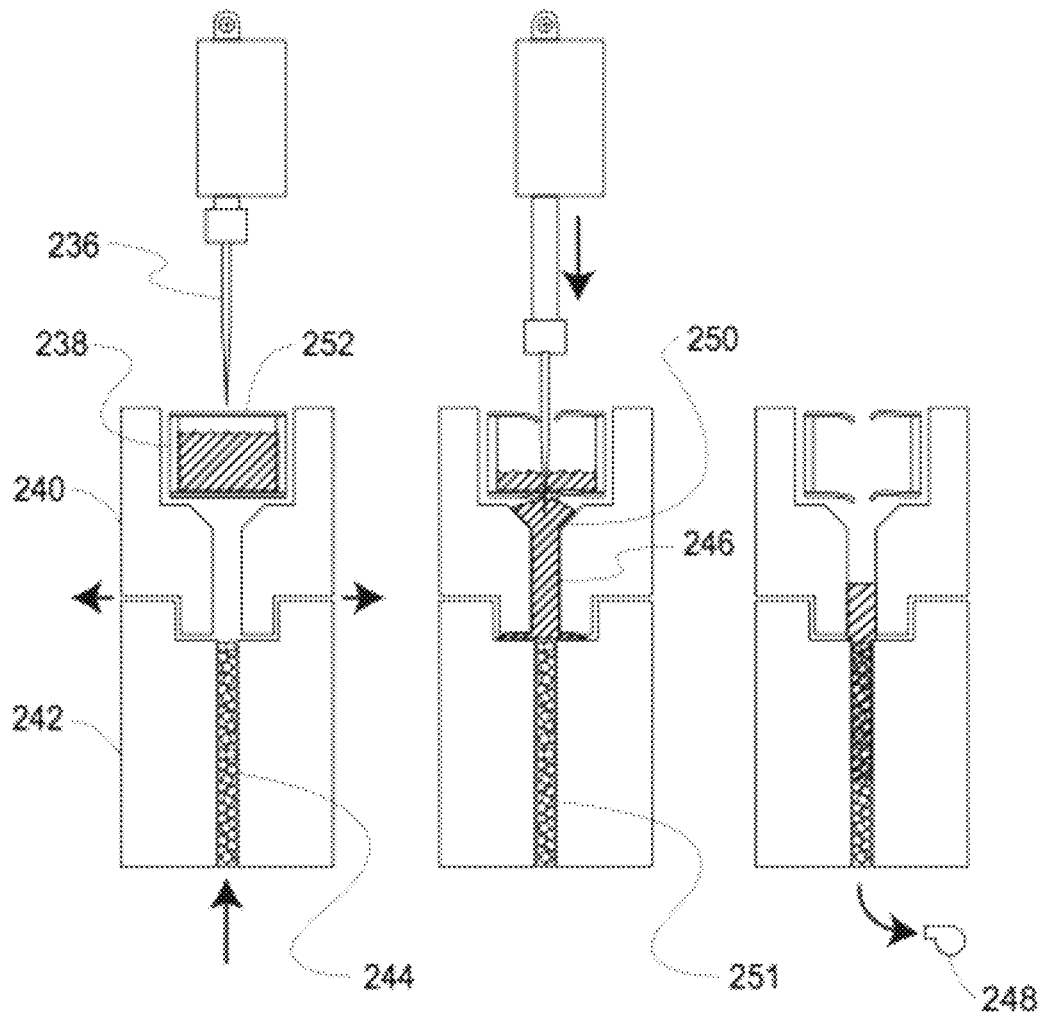
FIG. 59A shows an example of how a liquid reagent is housed within a cartridge.
FIG. 59B shows the release of a liquid reagent from a liquid container by a piercing mechanism.
FIG. 59C shows the movement of a liquid reagent at the time of reaction.

Liquid reagents can be packed into cartridges to facilitate numerous chemical interactions useful in breath analysis. FIGS. 59A to 59C show an example of how a liquid reagent can be contained within a cartridge and how it can be released at the time of a desired interaction. In a top housing (240), a liquid container (238) is provided for the liquid reagent. This can be a distinct component (238) that is dropped into a region in the top housing (240) or it can be integrated with the top housing. In any case, this liquid container (238) can contain a liquid reagent between two piercable membranes (252) that are impermeable or otherwise compatible to the reagent of interest. An elongated member (236), here a needle, solid or hollow, is pressed through the piercable membrane at the required time, causing the liquid reagent to flow through a conical cutout (250) in the cartridge housing and through a downcoming channel (246) toward the interactant region (244). In this configuration, the seal between the top housing (240) and bottom housing (242) is not airtight (to allow gas flow from the bottom of the interactant region (244) through to the top and out the sides). Thus, the liquid reagent is preferably of low viscosity and appropriate surface tension such that the liquid drops all the way to the top of the interactant region and is drawn into the reactive bed of the interactant region when a pump (248), here a suction pump, is activated.

Figures 60A, 60B:
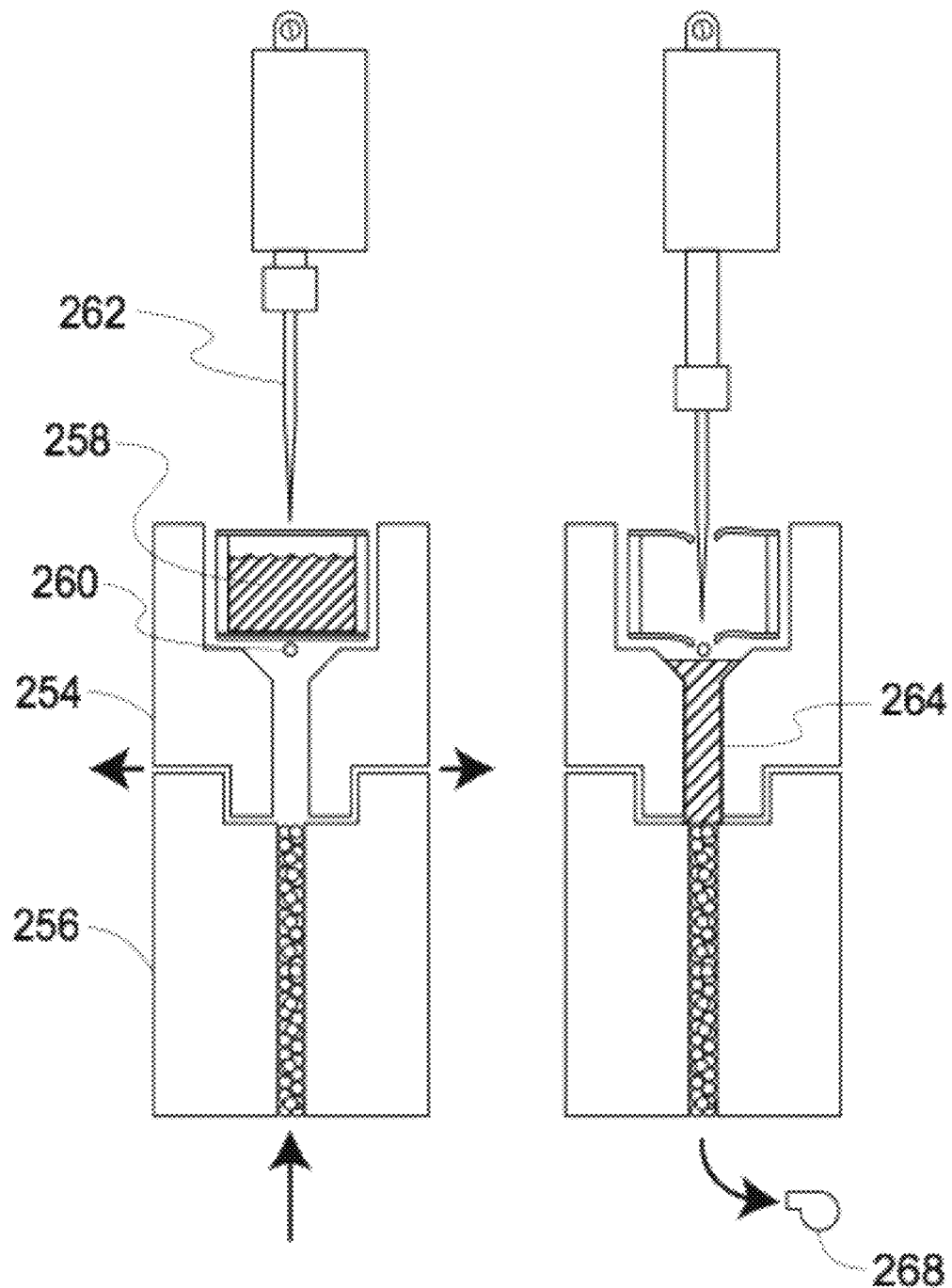
FIGS. 60A and 60B demonstrate another embodiment of how a liquid reagent can be housed within a cartridge and how it can be released at the time of reaction.

FIGS. 60A and 60B provide another embodiment. In this alternate configuration, a hole (260) is cut into the top housing so as to provide a gas exit port when the top housing (254) and the bottom housing (256) are fastened with an airtight seal. In this case, a breath sample is flown over the interactant region and out the exit port (260). Next, an elongated member (262), here a pin or needle, is pressed through a top piercable barrier and then a bottom piercable barrier to free the contained liquid and to create a hole to allow the breath sample to fill the vacated space. The liquid reagent fills a downcoming channel (264), blocking the exit port and creating a liquid seal so that a pump (268), here a suction pump, can pull the liquid reagent through the channel and through the interactant region, here a packed bed.

Figures 61A, 61B, 61C:
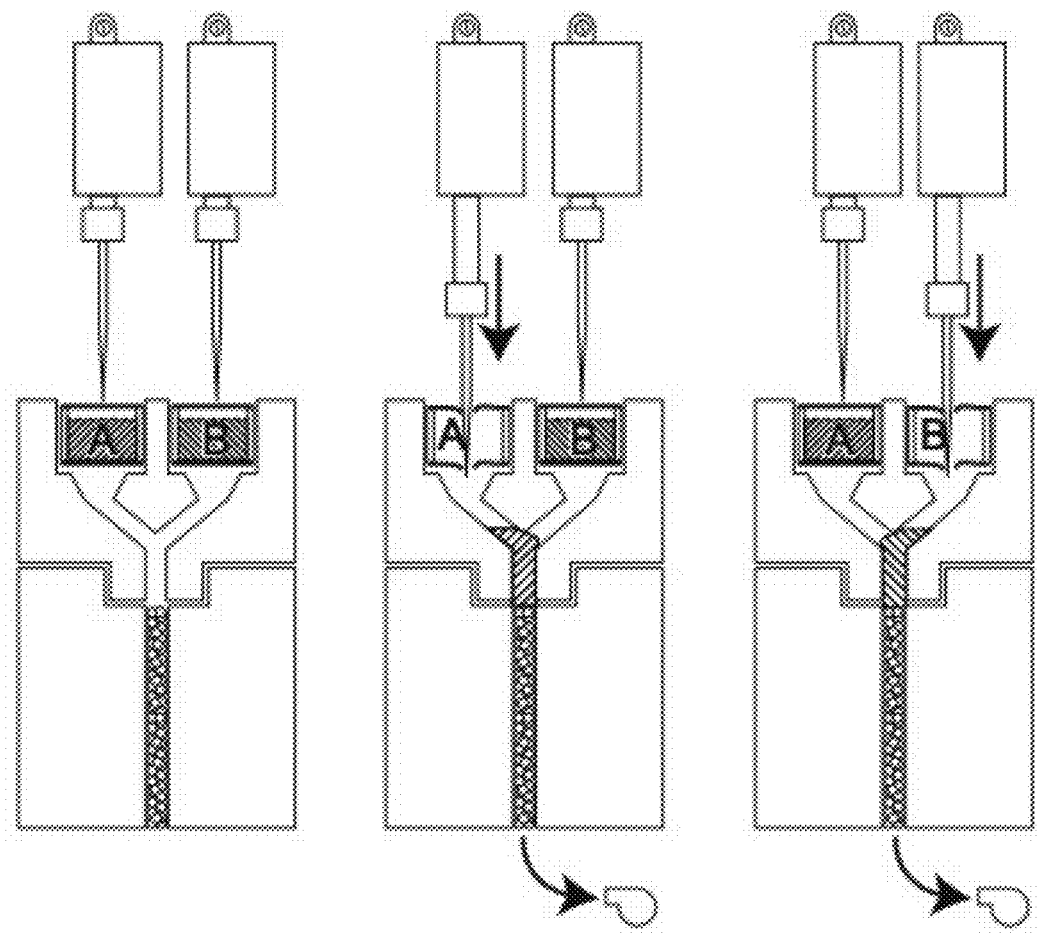
FIGS. 61A to 61C illustrate an example of a multi-liquid cartridge.

An extension of the liquid containment/release mechanism as described above allows multiple liquid reagents to be integrated into a single cartridge. FIGS. 61A to 62D illustrate examples of a multi-liquid cartridge. In FIGS. 61A to 61C, there are two liquid containers, A and B, that contain two liquid reagents (or one liquid reagent, if desired) between piercable seals as discussed. The downcoming channels are merged into a single path. When the first set of seals are broken, the liquid reagent from liquid container A fills the downcoming channel as before, where it is then suctioned away by a pump in fluidic connection with the flow path. Next, the second set of seals from liquid container B are broken, and the same procedure is followed. FIGS. 62A to 62D show a top housing that contains four such liquid containers. This method allows very sophisticated fluidic handling to be done with liquid reagents that are located on a single disposable piece.

The liquid containment/release mechanism described above is only one of several solutions that can be utilized with cartridges described in this disclosure. An objective of such a mechanism is to release the liquid reagent such that it contacts the reactive beads without involving the user.

In another approach, instead of sealing the liquid reagent within a pierceable ampoule, one may use an unsealed inverted cup, such as those described in FIGS. 27A to 29G. Here, a cartridge comprises a cup. The cup is filled upside down (so that it can hold the liquid reagent during assembly). Atop the inverted cup, an airtight seal is created with a compressible material, such as rubber. Preferably the rubber contains "holes" or "gaps" around the periphery. Some additional material or possibly the housing of the cartridge is used to clamp or otherwise secure the cup and the compressible material in place. The cartridge further comprises a window so that the cup is accessible from the outside of the housing. When in use, the cup is displaced by an external actuator such that the seal between the cup and the compressible material is broken. Liquid is then released from the cup into the reactive chamber of the cartridge.

A breath analysis system that utilizes this approach comprises a base unit and a cartridge. The base unit includes a cartridge receiver and an actuator. The cartridge, which is detachably disposed in the cartridge receiver of the base unit, and includes an interactant region that comprises an interactant, an inverted cup, inverted with respect to local gravity, wherein the cup comprises a liquid and a bottom portion, a biasing device that biases the inverted cup so that the bottom portion creates a liquid seal to retain the liquid in the inverted cup, an actuation receiver. The actuation receiver is operatively coupled to the actuator so that, in response to the actuator, the actuation receiver interacts with the biasing device to break the liquid seal and release the liquid from the inverted cup. This is done in the preferred embodiments without interaction with the user, other than user activation of the breath analysis test.

Another cartridge design to allow the liquid reactant to interact with the reactive beads is shown in FIGS. 62A to 62C and makes use of the ampoule shown in FIGS. 26A and 26B.

In this design, a rigid ampoule (6235) with an open top and bottom is used. A septum (6215) is used. Liquid reactant (6210) is added to the ampoule from a delivery system (6205) while the ampoule and septum are engaged as shown in FIG. 62A. When the liquid is fully added, the ampoule appears as shown in FIG. 62B. The septum (6215) is then locked into place as shown in FIG. 62C.

The outside walls (6229) of the rigid ampoule (6235) are housed within an overall cartridge (6255). As shown in FIG. 62D, when an actuator (6250) presses down on the top portion (6230) of the septum (6215), the base of the septum (6240) moves below the walls of the ampoule (6235) such that the liquid is released into the cartridge body (6260).

Figure 64A:
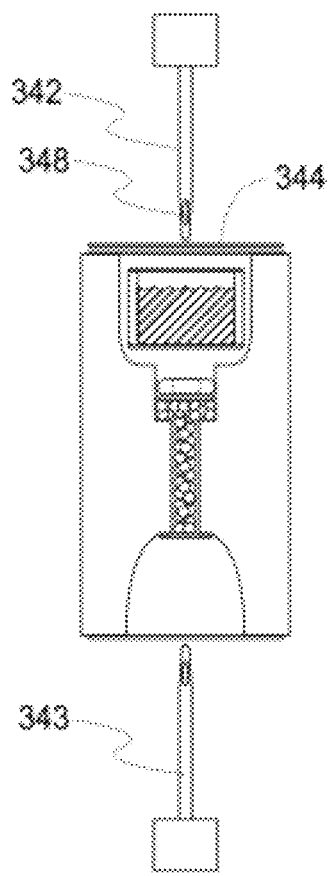
FIGS. 64A to 64C show an embodiment of a cartridge with a developer.
Figure 64B:
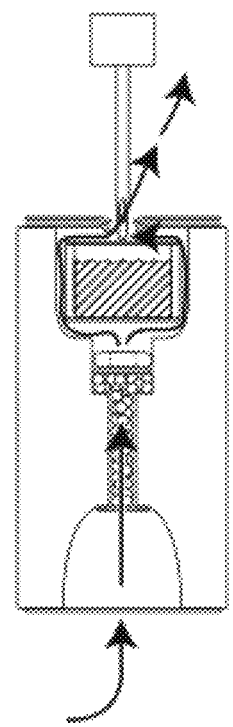
Figure 64C:
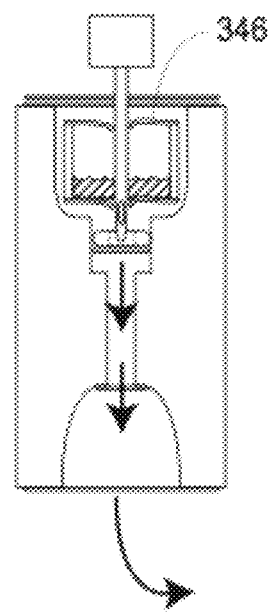

FIGS. 64A to 64C show a preferred method for using the cartridge discussed in FIG. 38. With the elongated member (342), here a needle, in the fully retracted position (FIG. 64A), the piercable barriers (344) have not been breached and the flow of the breath sample through the cartridge is not possible. With the needle in a first extended position (FIG. 64B), the top piercable barriers are breached such that the breath sample can flow as follows in the flow path: from the inlet aperture (at the bottom of the cartridge as shown in FIGS. 64A to 64C) through the various porous barriers, interactant region, around the liquid ampoule, and through the hole in the piercing needle (348). In a second extended position (FIG. 64C), liquid is released from the ampoule (346) and is pulled by suction force of a pump or by wicking downward through the interactant region, here where the full reaction zone is in the form of a packed bed. A needle in the base (343) can be used to pierce a piercable barrier on the bottom of the cartridge housing to allow the flow of the breath sample into the cartridge. This method allows the cartridge to be sealed for storage and shipping and to be automatically pierced upon usage without extra user steps. Also, the rubber septum on top and extra barrier on bottom can be used to contain the liquid inside the cartridge after use. Note that the barrier to contain desiccant or other conditioning materials is not shown in FIGS. 64A to 64C.

Figures 65A, 65B, 65C:
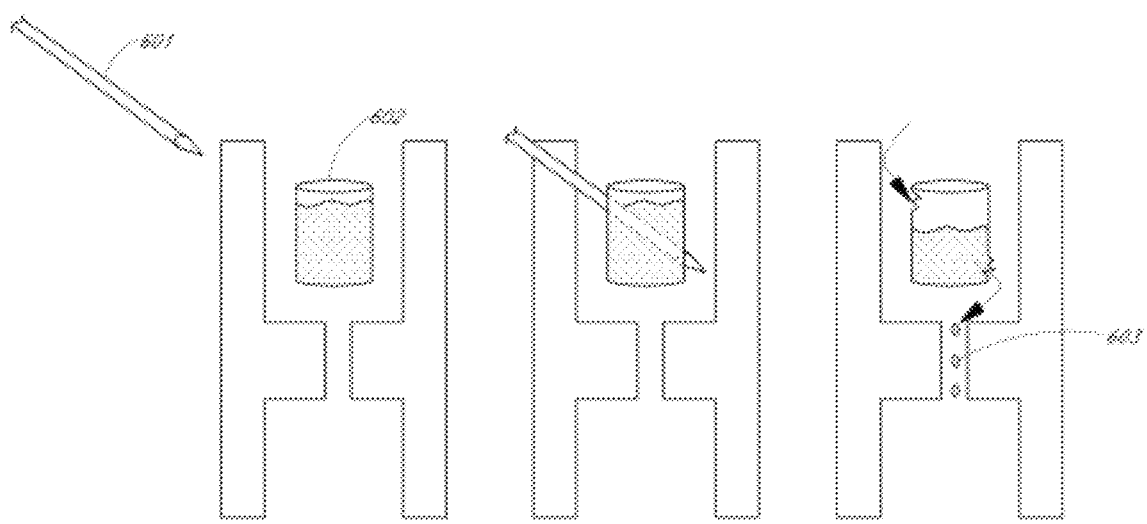
FIGS. 65A to 65C show an embodiment of an ampoule piercing mechanism.

FIGS. 65A to 65C show an alternate means of piercing the liquid container described previously as a piercable can (FIG. 39). In this drawing, a needle (601) inclined at an angle to the can illustrates that a needle need not pierce the can from the top through the bottom in order to both pierce the can below the liquid line and to also control the pressure in the container to facilitate liquid flow. The needle (601) is first held in a reserve position as shown in FIG. 65A. To pierce the ampoule (602), the needle is driven through the ampoule at two locations, one above the liquid line and one below as shown in FIG. 65B. With one hole below the liquid line and another above the liquid line, the liquid is free to flow out of the ampoule into the reactive zone (603) as shown in FIG. 65C.

Figure 66A:
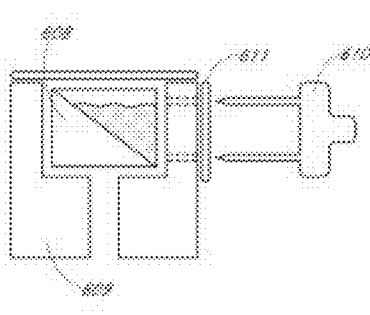
FIGS. 66A to 66C show another embodiment of an ampoule piercing mechanism.
Figure 66B:
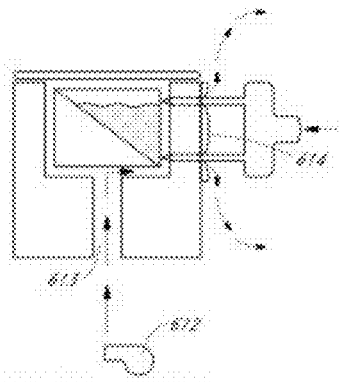
Figure 66C:
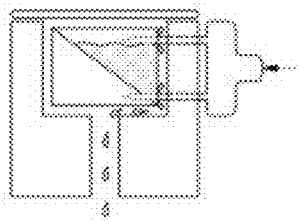

FIGS. 66A to 66C show how two needles in a single action can be used to create a hole in a piercable ampoule below the liquid line and one above the liquid line to moderate intra-ampoule pressure and facilitate liquid flow. In this case, an ampoule (608) constructed as a piercable can (FIG. 39) is laid on its side inside the cartridge housing (609). A needle carrier (610), which may be part of a dispensing device, is positioned to actuate through the side of the cartridge to interact with the ampoule. The ampoule (608) may or may not consist of a partially filled flooring; as shown here, the floor of the ampoule is inclined ("filled") so that very little fluid is left in the ampoule after rupture. Using this hardware for breath sensing would consist broadly in the following steps: first, as shown in FIG. 66A, a needle carrier (610) is poised to break a piercable barrier (611). With the barrier broken, as in FIG. 66B, the gas sample is able to flow upwards from the pump (612) or breath sample source, through the reactive zone (613), around the ampoule (608) and through the pierced barrier (614), venting to the atmosphere or wherever exhaust gas may be intended. FIG. 66C illustrates that a further progression of the needle carrier (610) leftward results in piercing the ampoule (608) at two points: one below the liquid line, and one above. The hole above the liquid line mediates the pressure (vacuum) formation in the ampoule, while the hole below allows the liquid to drain into the reactive zone (613).

Figure 67A:
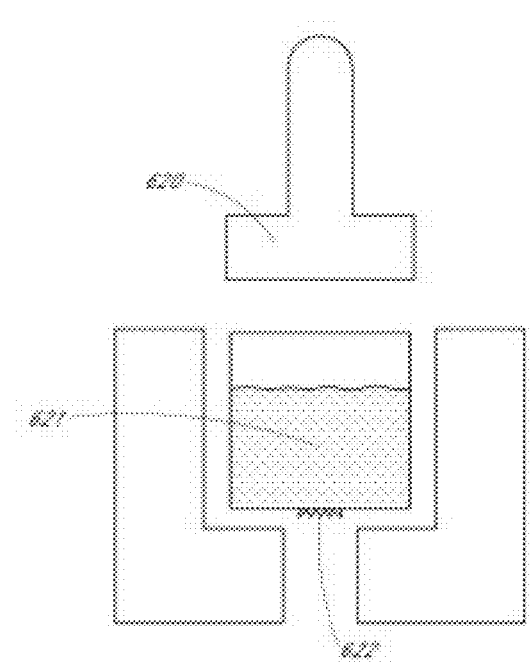
FIGS. 67A and 67B show an embodiment of an ampoule rupturing mechanism.
Figure 67B:
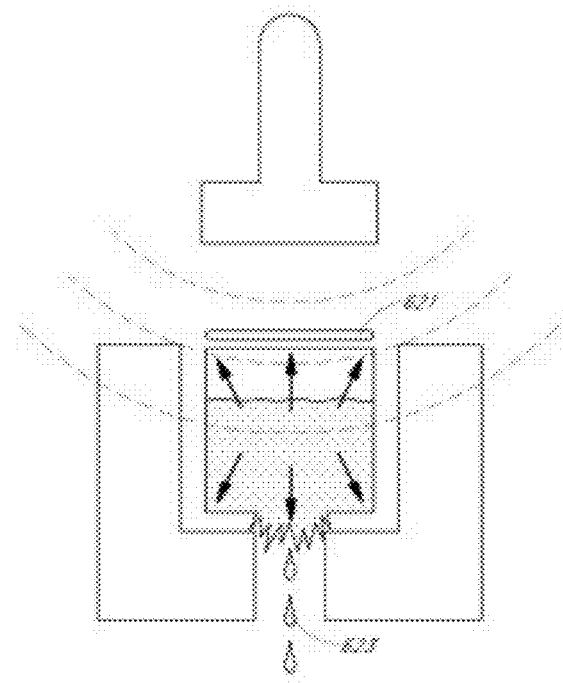

FIGS. 67A and 67B show one example of how a hole can be generated in an ampoule below the liquid line without a needle, and how the pressure within the ampoule can be moderated to facilitate liquid flow without creating a hole in the ampoule above the liquid line. In this example, an ultrasonic horn, IR heater, or contact heater head (620) is used to generate heat within an ampoule (621) which has been fashioned to create a pressure relief valve (622) below the liquid line. This can be done, for example, using blow-fill-seal technologies using plastic container materials, where the seal joint is designed to fracture when the pressure within the ampoule is sufficiently high. To free the liquid from the ampoule, as shown in FIG. 67B, the ultrasonic horn, IR heater, or contact heater head (620) couples heating energy to the ampoule fill contents or to a foil laminate barrier material (621) on the top-side of the ampoule. The elevated temperature increases the pressure within the sealed ampoule, causing the ampoule to rupture at the pressure relief valve (622) and then to facilitate the emptying of the ampoule into the reactive zone (623).

Figures 68A, 68B, 68C:
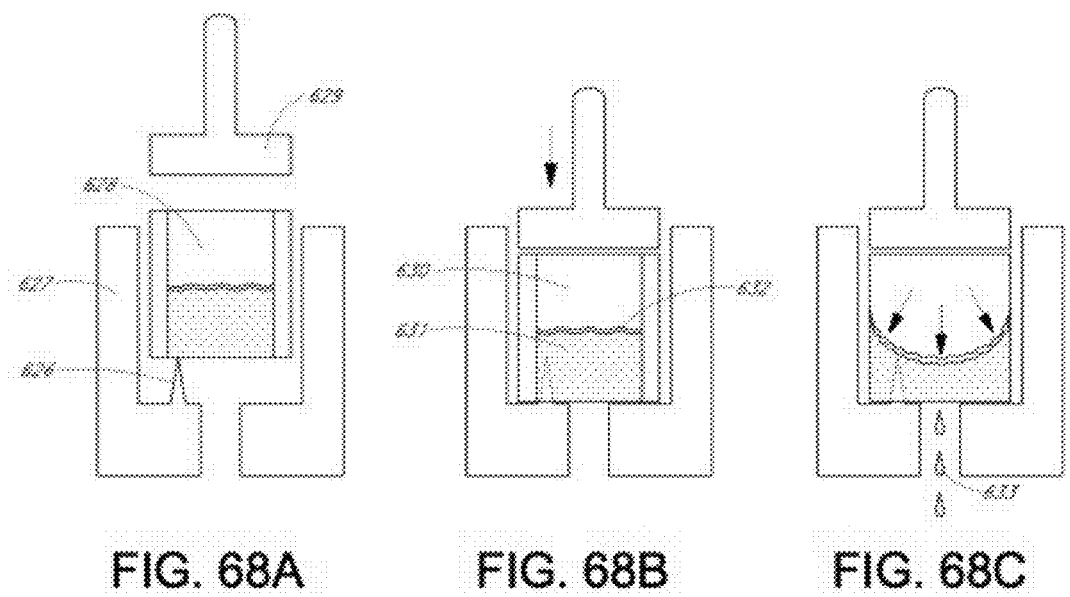
FIGS. 68A to 68C show another example of an ampoule piercing mechanism.

FIGS. 68A to 68C show how liquid can be released from an ampoule that has been filled at higher than ambient pressures. In this example, a piercing member (626) is positioned in a receiving pocket of a cartridge (627). The piercing member can be integral to the cartridge material or can be a drop-in component. A piercable ampoule (628) is placed over the piercing member, but without sufficient weight to cause piercing by the piercing member. To release the liquid from the ampoule (628), an elongated member (629), here a pressing member, is brought down upon the ampoule as in FIG. 66B. Pressing down on the ampoule with sufficient force causes the piercing member (626) to rupture the floor of the piercable ampoule (628) creating a hole below the liquid line. In this case, the ampoule is comprised of two interior regions (630 and 631). The lower space (631) is filled with liquid reagent. The upper space (630) is filled with a pressurized medium. Separating the two spaces is a distensible membrane or material interfacial region (632) which keeps the two interior spaces (630 and 631) (and their contained media) distinct and unmixed. When the pressing member (629) causes the piercing member (626) to pierce the bottom of the ampoule (628), the increased pressure in the top interior region (630) causes the membrane or material interfacial region (632) to extend and to thus remove any vacuum in the lower interior region (631) that would otherwise impede flow; liquid is dispensed into the reactive zone (633).

Figures 69A, 69B, 69C:
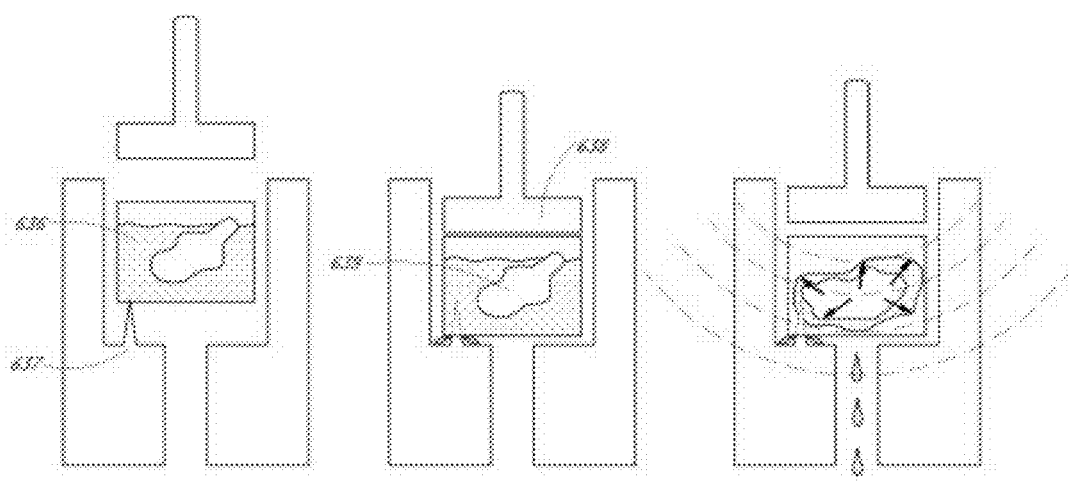
FIGS. 69A to 69C show another example of an ampoule piercing mechanism.

FIGS. 69A to 69C illustrate an example of how the pressure within an ampoule can be moderated after an ampoule is broken to facilitate liquid flow out of the ampoule, without creating a hole in the top portion of the ampoule. In this example, an ampoule (636) with a piercable barrier on the bottom of the housing can be pushed into a piercing member (637) as described earlier to cause the formation of a hole below the liquid fill line. To moderate against the vacuum that would form in the ampoule after rupture which would impede liquid evacuation of the ampoule, an ultrasonic horn, IR heater, or conductive contact heater head (638) couples heat to an expandable balloon material (639) filled with a substance that readily contracts when heated. Thus, after the ampoule is pierced as in FIG. 69B, the heater head (638) is activated as in FIG. 69C in order to expand the filled balloon material (639), resulting in the removal of the vacuum inside the ampoule which would otherwise impede liquid dispensing.

Figures 70A, 70B, 70C:
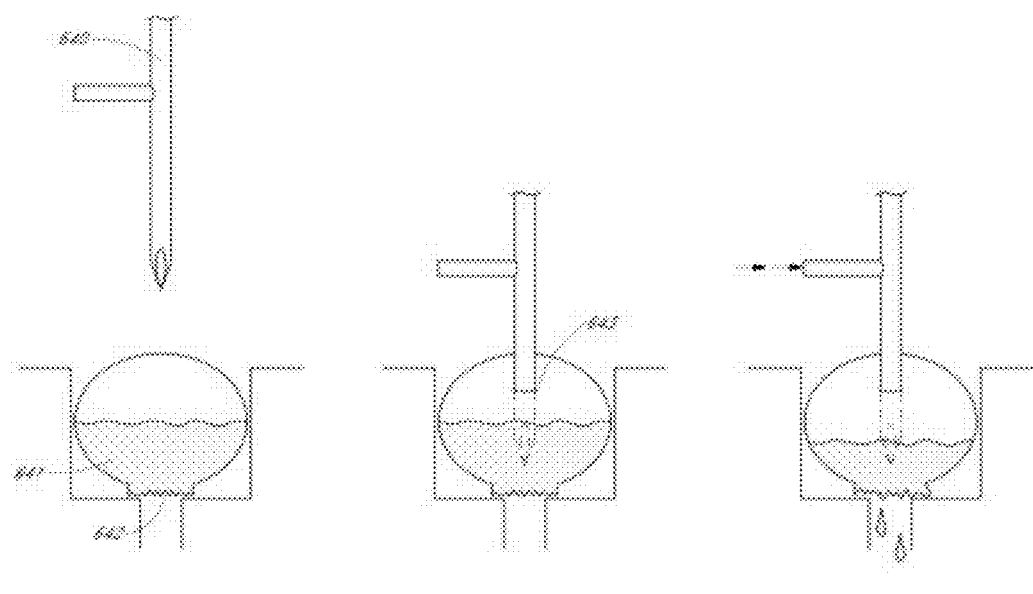
FIGS. 70A to 70C show another example of an ampoule piercing mechanism.

FIGS. 70A to 70C show how a hole can form in an ampoule below the liquid line and the vacuum can be moderated using injected air. In this example, a needle with an internal flow path (640) is brought down into an ampoule (641) with a pressure relief valve (642) as shown in panels FIGS. 70A and 70B. The top piercable portion of the ampoule (643), most preferably a piercable can (contrary to the depiction) is comprised of a rubber or septum material, such that piercing by the needle creates an air-tight mating of the needle walls and the top piercable portion of the ampoule. Injection of air as shown in FIG. 70C, for example by a pump, creates a pressurized internal region of the ampoule causing both the rupture of the pressure relief valve (642) and the mitigation of vacuum that would otherwise develop in the ampoule in response to the vacating fluid.

Figure 71:
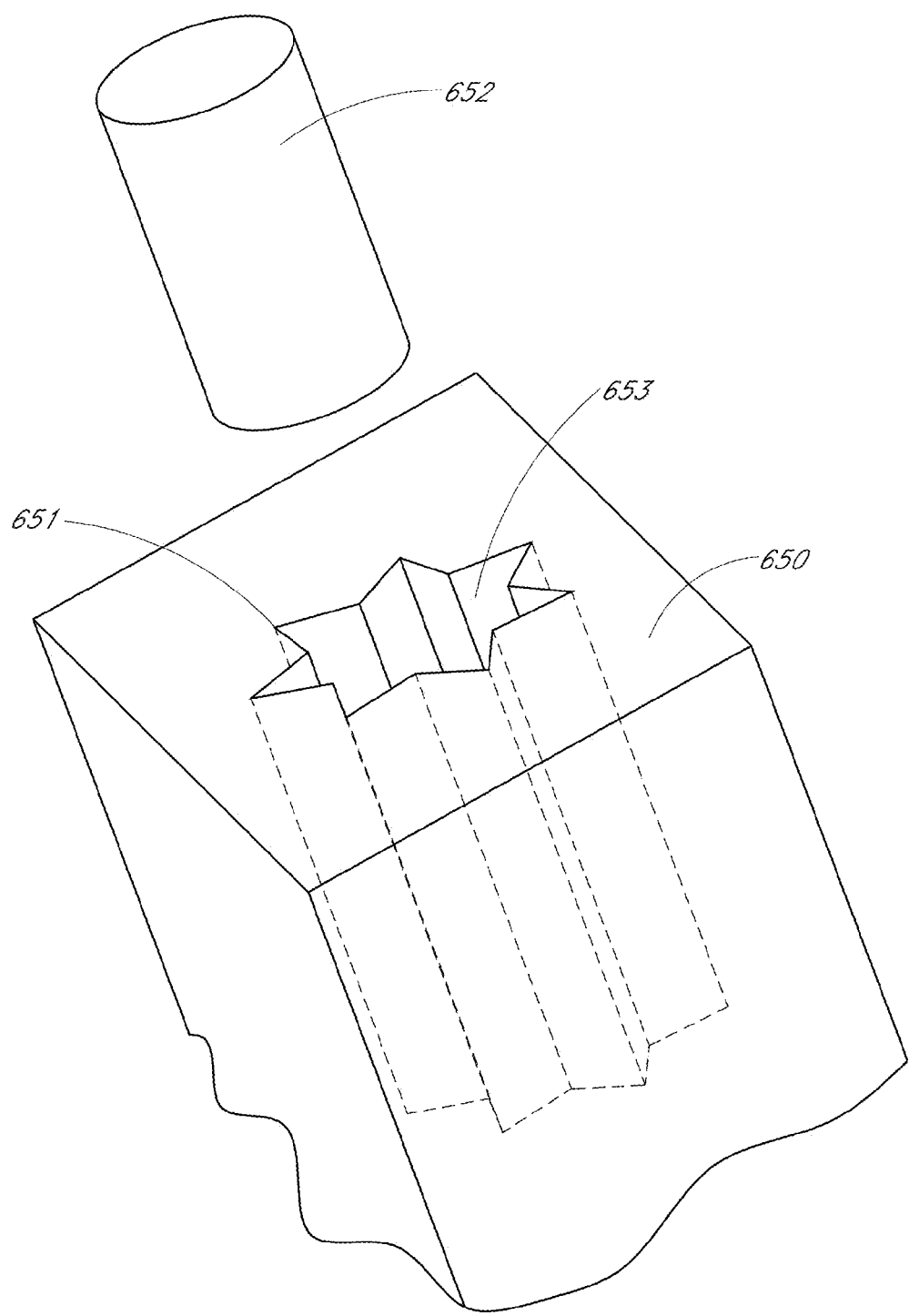
FIG. 71 is an embodiment of a cartridge, showing placement of the ampoule into housing.

FIG. 71 illustrates a means to keep a pierced ampoule fixed in position in order to facilitate liquid flow during ampoule piercing. A cartridge (650) is manufactured with a star-shaped pocket (651). A piercable ampoule (652) is press-fit into the pocket. The star configuration, or other non-circular geometry, is designed to provide contact points whereby the ampoule can be press fit into the pocket while preserving air vents (653) which promote liquid dispensing. Press fit as such, a retracting piercing needle will not carry the ampoule upwards with it which can in many instances impede fluid flow downward into reaction zones as described elsewhere.

The operation of the cartridge described in FIGS. 45A to 45J is as follows. An actuator squeezes the top portion of the packed cartridge (4505) to essentially "squeeze" the first ampoule subassembly (4580). Compare FIG. 45E and FIG. 45F. The force from the actuator has two effects: (1) it induces a flow path from the liquid in the first ampoule subassembly into the beads of the second ampoule subassembly by, for example, breaking the fluted bottom (4555) and (2) it forces a displacement volume of the liquid from the first ampoule subassembly to travel to the beads of the second ampoule subassembly. Preferably, the residual volume (the volume not displaced) is low, such as less than 20% of the total volume of the liquid. In effect, step (2) can be an adjunct or a replacement for simple gravitational pull of the liquid, thereby forcibly overcoming surface tension and other capillary forces.

Referring to FIG. 48, system (410) further comprises a processor (494) disposed within the interior of base (440) and operatively coupled to digital camera (490) to receive the signal from it. Processor (494) in this embodiment comprises a commercially available general-purpose microprocessor or microcontroller appropriately configured and programmed to carry out the functions as described herein, in addition to standard housekeeping, testing and other functions known to those in the art. A power supply (not shown) is disposed in base unit (440) and is operatively coupled to processor (494) and the sensor components to provide necessary power to those devices.

System (410) may output the information gleaned from the breath analysis using any one or combination of output forms or formats. In this specific embodiment shown in FIG. 48, system (410) comprises a user interface (496), in this case a touch screen display, disposed at the exterior of base (440) and operatively coupled to processor (494). Processor (494) is configured and programmed to present options, commands, instructions and the like on user interface (496), and to read and respond to touch commands received on it as they are received from the user. Processor (494) also outputs the sensed information to the user, e.g., in the form of a concentration of the analyte in the breath sample. This is not, however, limiting. The output also, or otherwise, may comprise a wired or, more preferably, a wireless data link or communications subsystem (498) with another device, such as a centralized database from which a care giver, such as a physician, family member, watch service or the like can monitor the output.

The timing of the test sequence is important and can be controlled by a processor. In one embodiment, the processor sends or receives signals from the following components: (a) a first presence sensor, (b) a second presence sensor, (c) an LED, (d) a camera, (e) a pump, (f) an actuator, and (g) a transceiver.

At the outset of the test, the processor optionally determines if the first and second presence sensors have been activated. This activation is an optional condition to test initiation.

Next, the pump turns on for a period of time referred to as the "measurement pump duration." The pump speed may also be controlled by the processor. The measurement pump duration may be 5 to 6 minutes. In other embodiments, the pump duration is between 3 minutes and 5 minutes. In preferred embodiments, the pump duration is between 1 minute and 3 minutes. In certain embodiments, the pump duration is less than 1 minute. The flow generated by the pump (or other flow initiator) may deflate the breath bag or breath container at an effective flow rate. The effective flow rate is preferably between 300 to 750 mL per minute. However, the effective flow rate may be in the following ranges: 150 mL per minute to 750 mL per minute, less than 150 mL per minute, less than 300 mL per minute, between 300 mL per minute and 500 mL per minute, between 750 mL per minute and 1 L per minute, or greater than 1 L per minute.

After the pump time has concluded, the actuator causes a reaction within the cartridge at the "actuation time." In certain embodiments, the actuation time is between 3 minutes and 5 minutes after test initation; in other embodiments, it is between 2 minutes and 3 minutes, 1 minute and 2 minutes, 30 seconds and 1 minute or less than 30 seconds.

The time period from the actuation time until the chemistry has developed to a satisfactory end point is referred to as a development period. In certain embodiments, the development time is between 3 minutes and 5 minutes after test initation; in other embodiments, it is between 2 minutes and 3 minutes, 1 minute and 2 minutes, 30 seconds and 1 minute or less than 30 seconds.

During the development time, the LED is turned on and the camera takes an image, which is analyzed to generate a result.

The result is transmitted via a transceiver to a user's mobile device or to a display at the "display time."

The total test time is essentially the sum of the flow period and the development period. The total test time is preferably less than ten minutes. In one embodiment, the total test time is between 6 minutes and 10 minutes. In another embodiment, the total test time is between 4 minutes and 6 minutes. In another embodiment, the total test time is between 3 minutes and 4 minutes. In another embodiment, the total test time is between 2 minutes and 3 minutes. In another embodiment, the total test time is between 1 minute and 2 minutes. In another embodiment, the total test time is less than 1 minute.

Following the test, the base unit may flush itself, preferably using ambient air. In a preferred embodiment, the detachment of the breath input or the completion of the test initiates a post-flush cycle. This post-flush cycle is characterized by a post-flush pump duration and a post-flush pump speed. The pump speed may be and preferably is higher than the measurement pump speed so as to "push" any residual air out of the unit. The pump speed may be higher if the last measurement result was higher than a threshold, such as a threshold known to cause carry-over effects. In certain embodiments, the post-flush duration is between 3 minutes and 5 minutes after test initation; in other embodiments, it is between 2 minutes and 3 minutes, 1 minute and 2 minutes, 30 seconds and 1 minute or less than 30 seconds.

The total set of parameters that the processor can control are referred to herein as "processing parameters." An exemplary set of parameters is provided in the following table.

TABLE 2

| Hardware Utilized | Parameter |
| --- | --- |
| Pump | Measurement (test) pump duration |
| Pump | Measurement (test) pump speed |
| Pump | Post-flush pump duration |
| Pump | Post-flush pump speed |
| Actuator | Actuation time |
| Camera | Capture time (after the development time has passed) |

For measurement of breath acetone, the performance characteristics necessary to achieve clinically meaningful results vary with different applications. For example, when an individual is beginning a diet, he or she may generate between 0 and 7 ppm of acetone. When an individual is adherent to a diet and in moderate ketosis, he or she may generate 0 to 20 ppm of acetone. When an individual is exercising or in a high level of ketosis, he or she may generate between 0 and 60 ppm of acetone. For an individual on a fat fast or utilizing intermittent fasting, he or she may generate between 0 and 120 ppm of acetone.

For most sensors, whether nanoparticle, enzyme or colorimetric, the sensor has a native measurement range and there is often a tradeoff between precision and the range. Sometimes the measurement range is referred to as the "linearity range", but this is not meant to suggest that the following approaches do not apply to non-linear relationships.

A unique feature of certain embodiments of breath analysis systems described herein is the ability to address disparate clinical needs with different precision and range requirements.

One approach is for the base unit to work in conjunction with different cartridge types. Each cartridge type has a characteristic internal geometry and a characteristic chemistry that is designed to achieve the desired performance characteristics. The cartridge has a label or other identified that contains information about the cartridge type. The base unit determines this information and sets the processing parameters accordingly.

A second approach involves using different cartridge types. However, each cartridge type has substantially the same internal geometry and chemistry. But, it has a different label or identifer associating it with a different application. The cartridge has a label or other identified that contains information about the cartridge type. The base unit determines this information and sets the processing parameters accordingly. For example, there may be two identical cartridges, but one is labeled "High Range" and the other labeled "Low Range." For the High Range cartridge, the pump time is reduced and the pump speed is increased.

Figure 72A:
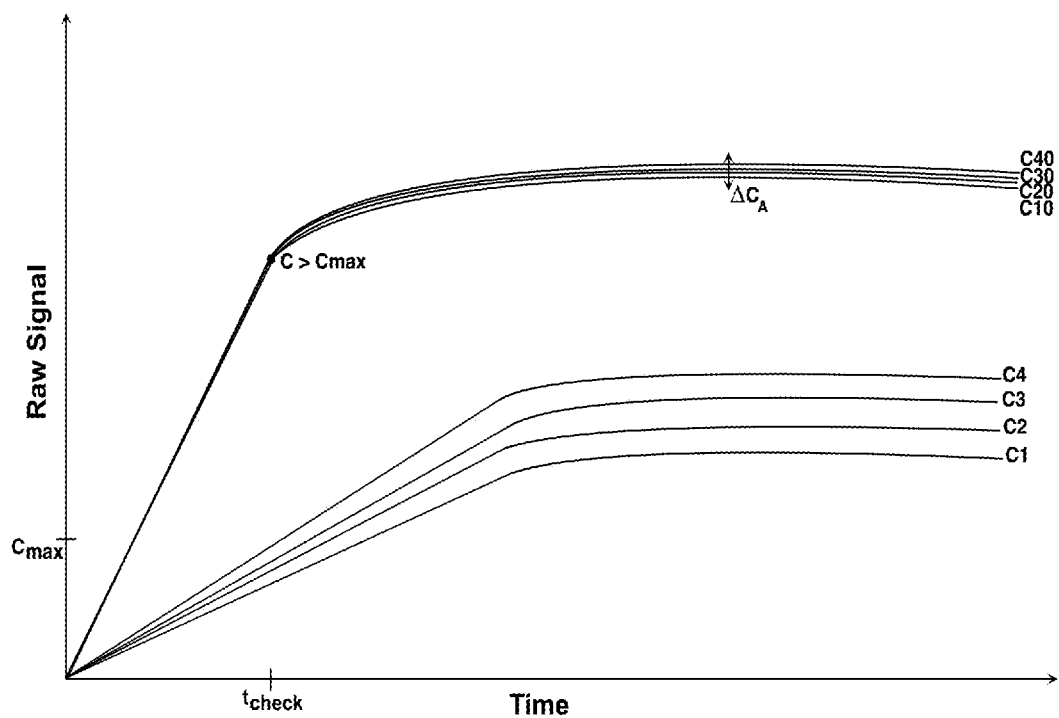
FIG. 72A depicts steps of a signal processing algorithm.
Figure 72B:
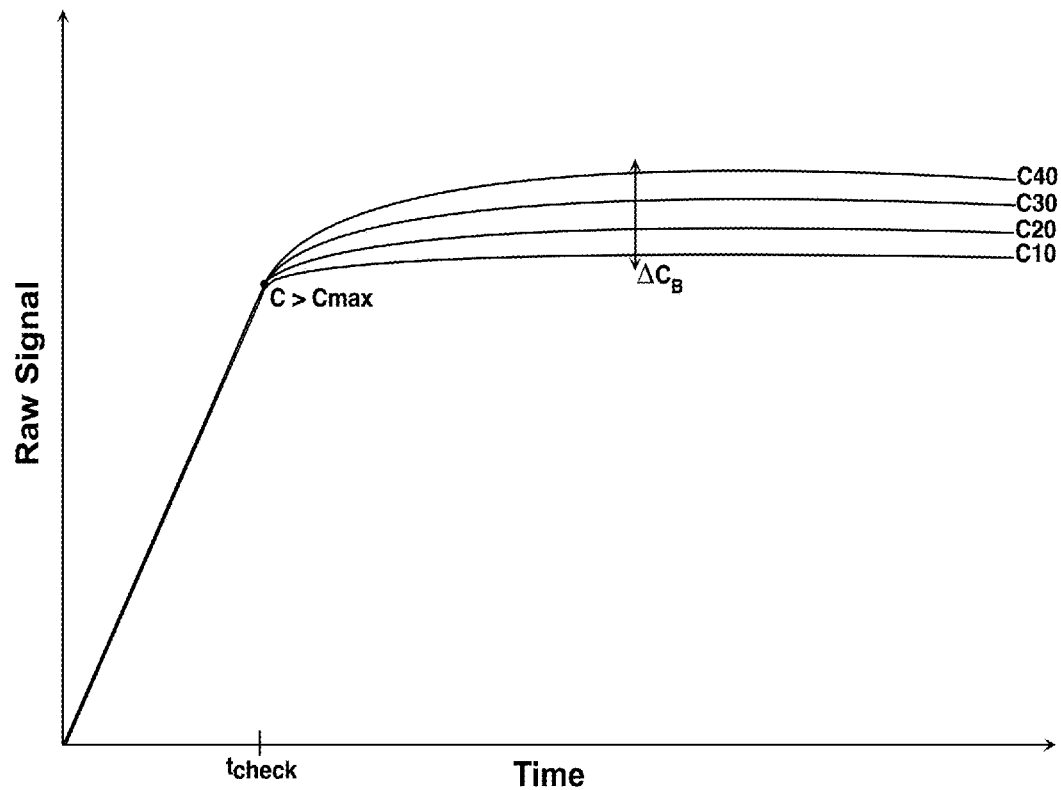
FIG. 72B shows an additional implementation of a signal processing algorithm.

A third approach utilizes a single cartridge type, but dynamically changes the processing parameters based on data taken at a given point. FIGS. 72A and 72B pictorially explain this algorithm. FIG. 72A depicts the raw signal as a function of time. The raw signal for an acetone concentration of 1 is depicted by C1, the raw signal for a concentration of 20 is depicted by C20 and so on. In this situation, the sensor is not able to resolve C10, C20, C30 and C40 as the differential between these concentrations, $\Delta CA$, is below the sensor resolution. As such, at a point in time, here tcheck, the processor determines if the raw signal is greater than the response for a concentration above some concentration that is close to or slightly exceeding the measurement range, Cmax. If so, the processing parameters are changed (e.g., the pump speed is increased or the pump duration is decreased), to avoid saturation. Because of this change, as shown in Graph B, the system is now able to resolve C10, C20, C30 and C40 as the differential between these concentrations, $\Delta CB$, is within the sensor resolution.

Figure 73:
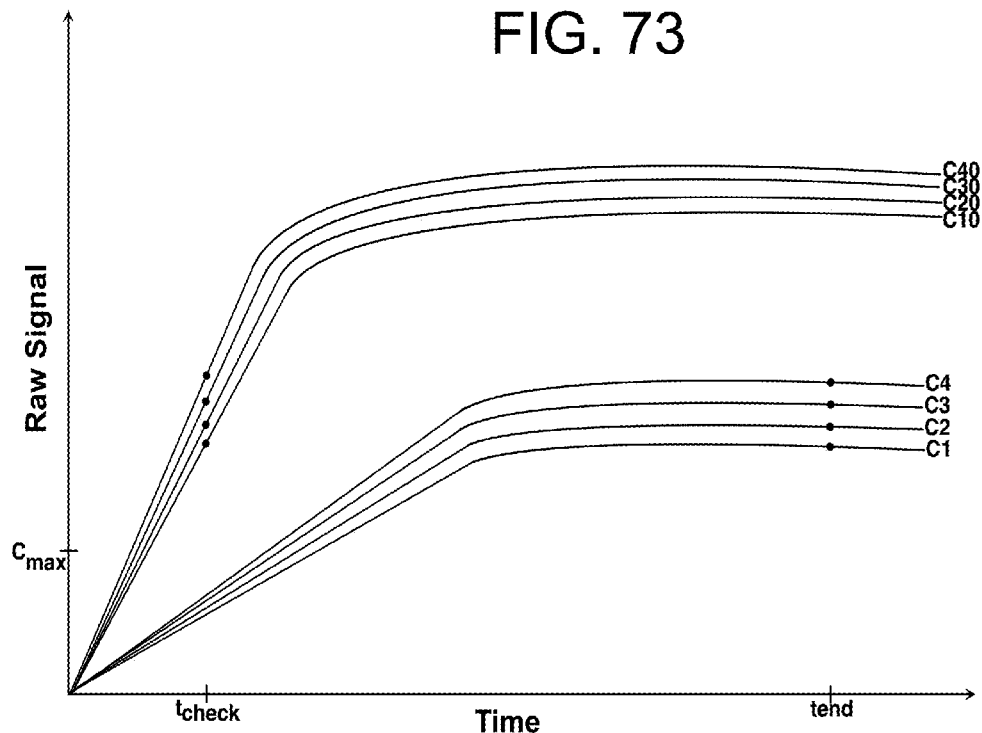
FIGS. 73, 73A, and 73B depict steps of a signal processing algorithm.
Figure 73A:
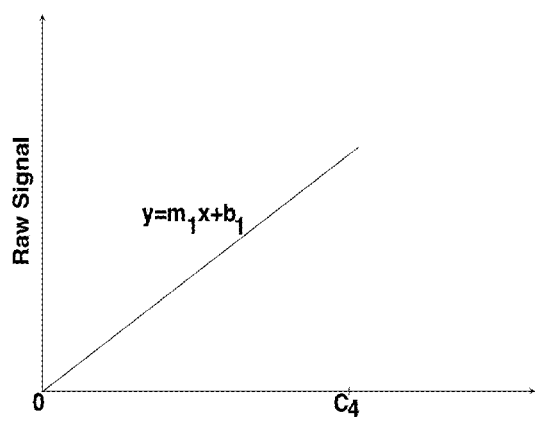
Figure 73B:
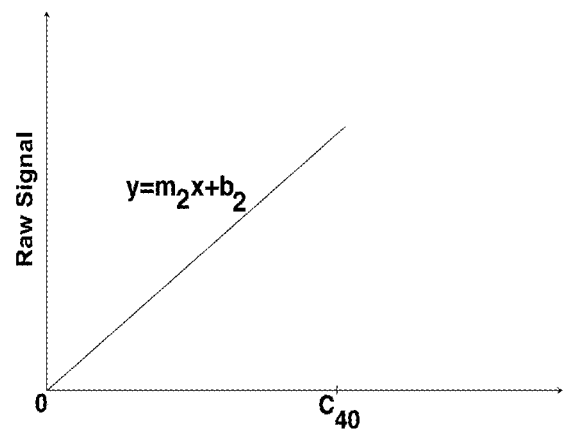

A fourth approach utilizes a single cartridge type and a plurality of measurements are performed during the test (see FIG. 73). Two measurements are taken: the first at tcheck and the second at tend. Similar to the third approach described above, the raw signal for an acetone concentration of 1 is depicted by C1, the raw signal for a concentration of 20 is depicted by C20 and so on. In this algorithm, the processor has access to two calibration curves (whether in the form of look-up tables or actual curves, etc.). The first, FIG. 73A, has the calibration curve for lower concentrations (C1, C2, C3, and C4) and the second, FIG. 73B, has the calibration curve for higher concentrations (C10, C20, C30, and C-40). As such, at a point in time, here tcheck, the processor determines if the raw signal is greater than some concentration, Cmax. If it is above Cmax, the Table B calibration curve is utilized. If it is below Cmax, the Table A calibration curve is utilized.

An unconditioned (raw) breath sample may be unsuitable for direct interaction with interactants. Problems due to humidity, oxygen, or carbon dioxide are particularly problematic when a desired chemical system is adversely impacted by the presence of these chemicals. Breath conditioning apparatuses and methods can be optionally used by the devices of the present invention. Breath conditioning can potentially include any or all of: moisture removal, carbon dioxide scrubbing, oxygen removal, removal of interfering breath-born volatile organic compounds, heating of gas samples, cooling of gas samples, reacting gas samples with derivatizing agents, compression or decompression of gas samples, and other methods of preparing the breath for analysis.

In one embodiment utilizing breath conditioning, desiccants can be used for removal of moisture. In general, a given desiccant has varied affinity for a number of chemicals. For example, anhydrous calcium chloride is known in general to preferentially bind water in the presence of acetone, and thus calcium chloride in the proper amount can be used to strip breath of water content while leaving acetone concentrations intact. Examples of other desiccants are well-known, including $CaSO_4$ (calcium sulfate), molecular sieve 4A, and activated carbon. Each of these examples can be used to remove water but care must be taken to ensure that the analyte of interest is not also being removed from the breath sample.

Desiccants may be contained within a desiccant region of a cartridge. This region may be between $\frac{1}{4}$" to $\frac{3}{8}$" in diameter. Ascarite II and sodium hydroxide with particle sizes between 10 to 60 mesh may be deposited in this region.

In certain applications, the desiccant region may be comprised of multiple desiccant containment regions separated by a porous barrier wherein the desiccant beads are of different sizes. The first sub-containment region, for example, may house beads with 20-30 mesh size and the second with 35-60 mesh size.

For aqueous interactants where varied pH may be a contributor to assay success, it may be desirable to remove $CO_2$ from the breath samples. Soda lime is routinely used as a scrubber of CO2 from exhaled breath in re-breathing circuits but may also be very valuable as a component to a breath analysis system. Numerous other adsorbent materials are known, for example Tenax TA, activated carbon, and Ascarite.

Many adsorbents may be useful as pre-concentration elements. Silica gel can be used to capture acetone such that large volumes are captured into microliter volumes. For example, the acetone from a 450 mL breath sample can be collected and packed onto silica beads occupying a volume of approximately 35 microliters, a more than 10,000-fold concentration. Pre-concentration may be used to gather sufficient analyte to cause a detectable reaction and may also be useful in speeding the rate of reaction and thus lowering the response time of the breath analysis subsystem. In some cases, the adsorbed analytes can be reacted in situ. In other cases, elution of the analyte off the adsorbent may be beneficial. One preferred reagent in this regard is Tenax TA. Acetone adsorbs strongly to the Tenax reagent in comparison to water such that humid breath samples can be passed over beds of Tenax particles to trap acetone and retain very little water. The breakthrough volume for water at 20° C. is as small as 65 ml per gram of Tenax TA, meaning that the water can be removed from the Tenax column with small volumes of gas. The breakthrough volume is even smaller at elevated temperatures. In contrast, the breakthrough volume for acetone is about 6 liters per gram.

Figure 74:
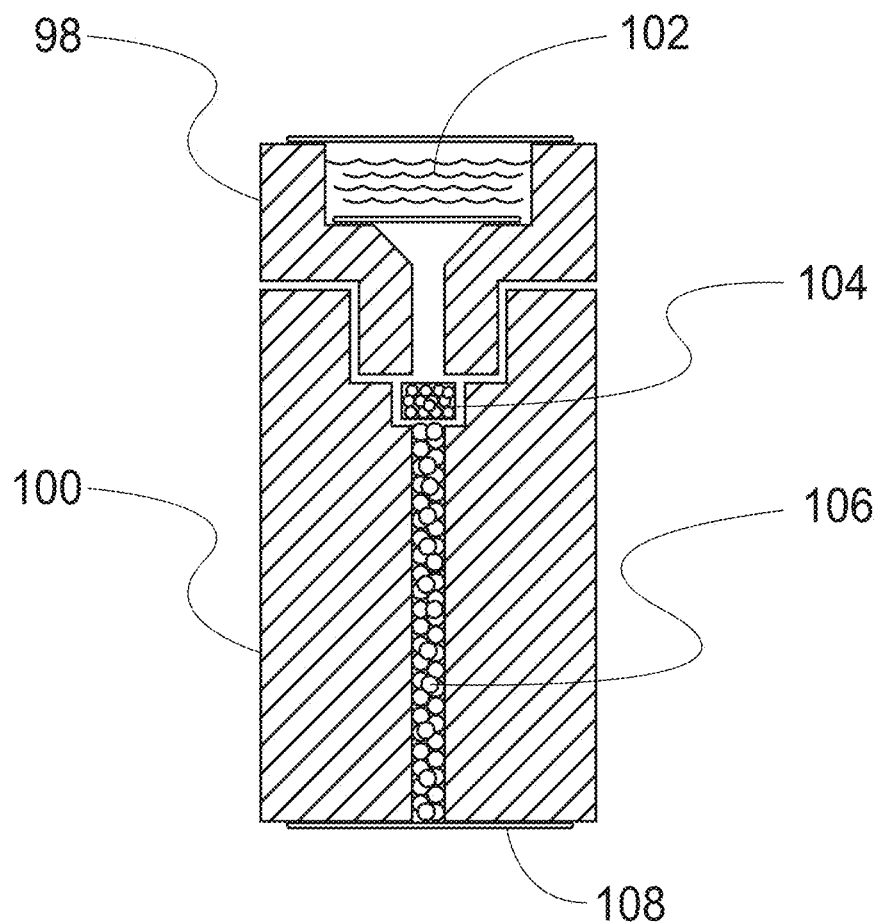
FIG. 74 shows an example of a cartridge using Tenax TA.

An example of a cartridge that uses Tenax TA is shown in FIG. 74. In this figure, the cartridge housing has two pieces: a top housing piece (98) and a bottom housing piece (100) that are snap-fit together. A liquid container (102), in this case containing a developer, is positioned in the top housing piece (98) with foil barriers, as described previously. A porous barrier (104), which may be a porous, open-cell foam plug, is positioned to compress a cylindrical region of Tenax TA beads (106) against a woven mesh barrier (108). Alternatively, components (104) and (108) can be replaced by a single component, such as porous polyethylene, that is porous and rigid enough to be compression fit into a region of the housing referred to as a "pocket" and characterized by different geometric properties than other regions. A humid breath sample is passed over the interactant from the inlet aperture (which is in the bottom housing piece of the cartridge shown in FIG. 74), exhausting through the non air-tight interface between the top housing piece (98) and bottom housing piece (100) of the cartridge. Next, the foil barriers (not shown) are broken and a developer is exposed to the Tenax particles with the trapped acetone. The developer interacts with the acetone and other bound reagents to produce an optical change, here a colored product. In this configuration, dedicated desiccants may no longer be necessary even if the interactant subsystem is sensitive to the presence of water.

Tenax TA and other adsorptive resins may also be useful in trap and release systems. In these approaches, the analyte of interest is captured and concentrated onto the resin while interferent materials, in particular water, freely pass without being retained. The captured analyte is later released via thermal desorption or elution to be reacted elsewhere. Such schemes are useful in controlling the interactants in light of interfering substances that cannot be selectively removed through other means, or in conducting the optical sensing in a location more amenable to optical readout.

The "interactant" or "interactant subsystem" can interact with the analyte by any of a variety of ways, including but not limited to chemical reaction, catalysis, adsorption, absorption, binding effect, aptamer interaction, physical entrapment, a phase change, or any combination thereof. Biochemical reactions such as DNA and RNA hybridization, protein interaction, antibody-antigen reactions also can be used as mechanisms for the interaction in this system. Examples of "interaction" regimes might comprise, for example, physical or chemical absorption or adsorption, physical or chemical reaction, Van der Waals interactions, transitions that absorb or release thermal energy, transitions that cause an optical change, and the like. As used herein, "interactant" and "reactive chemistry" are used interchangeably. Sometimes the term "chemically reactive element" is also used.

Reactive chemistries are preferably interactive even in the background typical of exhaled breath (e.g., large moisture concentrations, CO2, etc.) Reactive chemistries should further respond to endogenous levels of analytes in breath. Some examples of reactive chemistries useable in embodiments of the present invention and the analytes they are used to detect are found in the Table 3.

TABLE 3

| Breath Species | Reactive Chemistry | Method of Attaching Chemistry to Surface |
| --- | --- | --- |
| Acetone | Sodium Nitroprusside | Anion exchange |
| Acetone | Dinitrophenylhydrazide | Reverse phase |
| Alcohol | Sodium Dichromate | Anion exchange |
| Aldehydes | Pararosaniline | Cation exchange and/or reverse phase |
| Ammonia | Bromophenol blue | Anion exchange and/or reverse phase |
| Ammonia | Dichloroisocyanourate, Sodium salicylate | Anion exchange and/or reverse phase |
| Carbon dioxide | Sodium dichromate and crystal violet | Anion exchange (dichromate); Cation exchange and/or reverse phase (crystal violet) |
| Carbon disulfide | Benzyl mercaptan | Reverse phase |

In one embodiment of the present invention, the reactive species are attached to a surface. Surfaces can be of varied geometry and also of varied composition. For example, a surface can be a set of beads comprised of silica. Or, a surface can be a set of nanotubes comprised of quartz. In a preferred embodiment, the surface comprises a set of beads. Preferably the beads have diameters between about 40 and about 100 microns. Different materials can be used to compose the surface. Types of surfaces include metals, ceramics, polymers and many others. Some specific examples of materials that can be used with silane coupling agents include, but are not limited to, silica, quartz, glass, aluminum oxide, alumino-silicates (e.g., clays), silicon, copper, tin oxide, talc, inorganic oxides and many others known to those skilled in the art. Examples of materials that can be used with amino coupling agents include all types of polymers with epoxide, aldehyde or ketone functional chemistries, among others. Examples of materials that can be coupled with free radical forming coupling agents include acrylates, methacrylates and numerous polymers with aromatic bonds, double carbon bonds or single carbon bonds, and many others known to those skilled in the art.

In some embodiments, the reactive chemistry is coupled to the surface by using a coupling agent. "Coupling agents" are broadly defined as chemicals, molecules or substances that are capable of coupling (see definition for "react") a desired chemical functionality to a surface. Preferred coupling agents either have branched chemical functionalities or are capable of branching during coupling with the surface. "Branched chemical functionalities" or "branching" refers to having more than one chemically reactive moiety per binding site to the surface. Branching may be contained within a single coupling agent or may be achieved through the reaction of several coupling agents with each other. For example, tetraethyl orthosilicate may be mixed with aminopropyl trimethoxysilane for enhanced branching during the reaction.

There are numerous coupling agents known to those skilled in the art. In the class of silanes, there are literally thousands of functional chemistries attached to a silane. Silanes can be coupled to dozens of surfaces, with a preference for silica surfaces and metal oxides, and are capable of de novo surface formation. Examples of common functional silanes include aminopropyl trimethoxysilane, glydoxypropyl triethoxysilane, diethylaminopropyl trimethoxysilane and numerous others.

Coupling agents possessing a free amine are readily coupled to surfaces with epoxides, aldehydes and ketones, among other chemical moieties. Coupling agents with epoxides, aldehydes and ketones can also be used with surfaces containing a moderate to strong nucleophile, such as amines, thiols, hydroxyl groups and many others.

Some coupling agents are attached to the surface through a free radical reaction, such as acrylates and methacrylates among others.

Some coupling agents do not directly react with the breath analyte. Rather, they are intermediate agents. An "intermediate agent" is a coupling agent whose chemical functionality is to react with yet another coupling agent. For example, diethylaminopropyl trimethoxysilane is an intermediate agent in the reaction with acetone. It does not directly react with acetone, but reacts with sodium nitroprusside, which in turn reacts with acetone. Another example of an intermediate agent would be the use of glycidoxypropyl triethoxysilane, whose epoxide functional group could be reacted with a host of other molecules to achieve a desired functionality. Numerous intermediate agents are known to those skilled in the art.

The breath analysis system has great application in the field of endogenous breath analysis. Several technical hurdles had to be addressed to overcome breath-specific challenges. Some background in the physics useful in designing the system for breath analysis is helpful.

There have been several attempts through the years to develop beads that react with gases to form color. Few if any, however, are directed towards or address the challenges with endogenous breath analytes. To sense analytes in a breath sample and also to address physiological limitations of the user (e.g., expiratory pressure), the breath analysis system described herein preferably utilizes an interactant subsystem that comprises beads that are coupled to reactive species.

The beads in the interactant subsystem usually have certain varied properties, where the properties vary according to a distribution. Most distributions are designed such that there is a majority fraction that share same a similar property.

One of the key properties is the size of the beads. Bead size can be determined according to many different methods. One method relies on separating beads using sieves with given mesh opening sizes. Use of the term "diameter" or other similar terms, incidentally, is not intended to limit the beads to a spherical geometry.

A method that is used to determine bead size is described. In a room with relative humidity in the range of 15 to 30% and at temperatures of 74° to 79° F., sieving takes place manually. A sample of beads is placed into a set of sieves, that are manufactured according to ASTM E-11 specifications. Sieve assemblies are shaken by hand, rotated, and repeatedly struck against the palm of the hand for some period of time, for example 5 to 15 minutes, or until no significant sieving appears to be ongoing. Weight or volume fractions are assessed. The major fraction is the fraction with the greatest volume or weight of material collected. Minor fractions are those with approximately less than 10% of the weight of the total sample. Moderate fractions are in between. Sieve sizes used in these fractionations may include: 35, 40, 50, 60, 70, 100, 120, 140, 170, and 200.

In certain embodiments and for certain applications, the bead size is important. For these applications, beads in the range of 270-100 mesh have particular utility, especially in conjunction with the cartridges described herein. (For reference, please note that the mesh scale is counterintuitive. 50 mesh is larger than 100 mesh.)

A preferred cartridge embodiment involves packing beads in an interactant region so as to form a "packed" bed. Although packed beds have been studied for decades in other fields, the beads sizes used by others for colorimetrically sensing analytes in gas streams are considerably larger than 100 mesh. Utilization of beads in the range of 270-100 mesh represents a fundamental shift in the direction taken by others.

The following are examples of bead sizes used in packed beds that have been reported. Kundu used beads with diameter of 40 to 60 mesh (0.25 to 0.45 mm) (U.S. Pat. No. 5,174,959). Garbutt used beads with diameter of 35 to 70 mesh (0.2 to 0.5 mm) (U.S. Patent 2011/0098590). McAllister's 1941 air testing device disclosed beads with diameter of 20 to 40 mesh (U.S. Pat. No. 2,234,499). Shepherd's 1949 colorimetric gas detection system disclosed beads with diameter of 20 to 65 mesh (U.S. Pat. No. 2,487,077). Kretschmer's detector tube disclosed beads in the broad range of 0.1 to 0.5 mm (35 to 140 mesh), but a preferred range of 0.3 to 0.5 mm (30 to 50 mesh). (U.S. Pat. No. 4,022,578). Importantly, these detectors were not configured for rapid detection of endogenous breath analytes—which is an important reason why so many in the industry are using a fundamentally different approach to the design of their packed beds.

For certain applications, it is preferred that cartridges be designed to maximize three interconnected and often competing phenomenon: (1) extraction of the endogenous analyte, (2) generating a change in an optical characteristic within the optical sensing zone, and (3) maintaining the pressure drop within limitations of the fluid handling system. The optical sensing zone is the portion of the reaction zone that is within the view of the optical sensor.

To clarify the balance between extraction efficiency and generation of a change in an optical characteristic within the optical sensing zone, consider the case of a relatively large diameter packed bed, which efficiently extracts all of the analyte to generate an optical change. Such a packed bed may not be designed such that the optical change is discernible by an optical sensor, such as a camera. Some, if not most, of the optical change may exist "inside" the bed, hidden from the optical subsystem. In general, as the particle sizes of the beads of the packed bed become smaller relative to the geometry of the packed bed, the layers become more opaque and more color change, and therefore sample volume, is lost due to inefficiencies in optical sampling.

A related, but separate, issue with optical sensing from a given detection plane concerns channeling. Sometimes, irregular break-through patterns may result, e.g., due to inconsistencies in bed packing or geometry. Large-diameter or otherwise "optically thick" beds, which may tend to retard channeling propensity, are nevertheless more susceptible to optical readout errors when channeling occurs.

To restrict optical changes to areas within the view of the optical subsystem, it is helpful to create packed bed geometries with relatively shallow depths. This can be done with increasingly smaller tube diameters, however this generally causes a corresponding increase in pressure required to maintain a given flow rate. This also can have the tendency to increase gas velocity through the bed. To maintain cross-sectional area and therefore to keep the required pressure from increasing beyond what is acceptable for a given application, creating shallower packed beds requires wider aspect ratio packed beds, such as oblong or shallow cuboidal cross-sections. An added advantage to the shallow cuboidal packed bed geometry is the possibility of reducing the gas velocity (and thus improving mass transfer) but also reducing the required pressure drop. Incidentally, the term "column" as used herein does not imply a cylindrical or columnar geometry. Interactant regions that are cuboidal, including those with shallow rectangular profiles, are disclosed herein, as are cylindrical geometries.

In general, the pressure required to drive the analyte extraction onto the "column" (or interactant region) must be suitable for the intended application. Low-power or battery powered devices generally will not make use of high pressure delivery of the breath sample. Also, the propensity for analyte condensation (or dissolution into other condensates) must be balanced against the desired pressure drive.

In interactant regions designed as a "packed bed," the depth of the bed should be considered. Optical changes occurring outside the optical sensing zone are not directly useful to sense the analyte in the breath sample.

FIG. 42 shows a cartridge where the geometry of the interactant region is cuboidal. Here, the "depth" of the interactant region, d, is 1 mm. The cross-sectional area of the interactant region (W×D in FIGS. 45A to 45J) that is within the optical sensing zone is 5 um^2. Importantly, cuboidal geometries, especially those where the depth aspect (relative to the optical system's interrogation plane), allow deposition of particles in a manner most conducive to optical analysis for a few separate reasons.

First, unwanted glare and reflections are more readily mitigated. Second, optical alignment is facilitated (usually with wider aspect ratio geometries). A further advantage of the cuboidal geometry is the possibility to vary the cross-sectional area without compromising the optics. Relatively high cross-sectional areas can be achieved while maintaining the depth aspect suitable for optical sensing. Altering the cross-sectional area effectively reduces the velocity of the breath sample through the packed bed and therefore facilitates increased mass transport and sample concentration.

To better understand the principles behind extracting the endogenous analyte, some discussion regarding the physics behind extraction efficiency is useful.

Analyte extraction is variable depending on various considerations such as the adsorption capacity of the material (here, the material composition of the "bead") as well as the temperature and pressure. Such phenomenon can be described using an adsorption isotherm.

A rudimentary but nevertheless useful model is the linear driving force model. The model reflects mass transfer due to a concentration difference between an analyte in a gas stream (q) and that analyte's maximum adsorption capacity (q*) under given conditions.

$$\frac{\partial q}{\partial t} = k(q^* - q)$$

In this model, the time of contact between the analyte in the gas stream with the adsorbent surface determines the overall mass transfer, as well as a reaction-specific rate constant k.

Operating conditions that increase the maximum equilibrium concentration of analyte adsorption onto the beads increases mass transfer to the beads. This enables such things as: (1) increasing the allowable flow rate through the packed bed to achieve a given limit of detection, (2) increasing the concentration factor of the analyte in the bed to enable lower detection limits with a given sample volume, (3) extending the dynamic range of the packed bed (e.g., raising the saturation ceiling), and (4) decreasing the length of the packed bed required to sense a given concentration of analyte.

Figure 75:
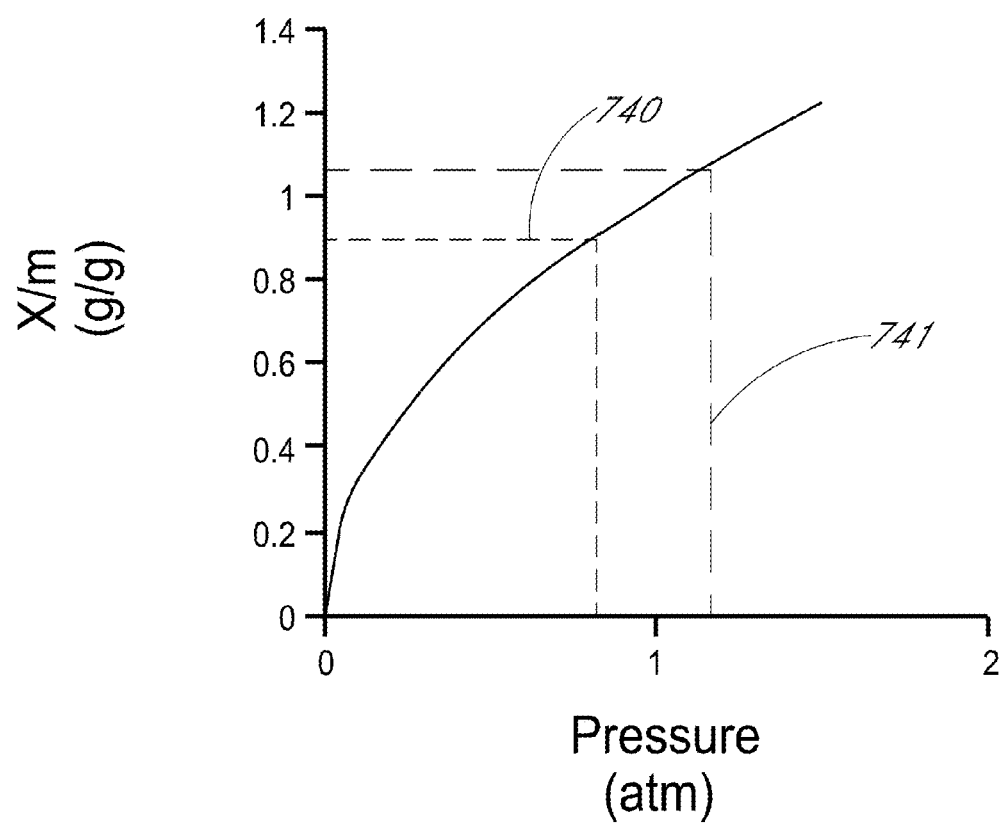
FIG. 75 is a generalized adsorption isotherm.

A second mathematical model is presented governing the relationship between the total mass of adsorbate per gram absorbent (X/m), system pressure (P), and system temperature (T). A plot of X/m vs. P for a given temperature is known as an adsorption isotherm. FIG. 75 is an example of such an adsorption isotherm.

A study of the aforementioned model and the design considerations that underlie breath analysis applications lend insight into the design space. As the pressure of the system increases to a particular saturation pressure, the total adsorption per unit adsorbent increases.

Referring to FIG. 75, two operating curves are shown. The first (740) is a finely broken line, which denotes an X/m value associated with a pressure drive system of less than 1 atm. This is representative of a vacuum drive system as is typical with gas collection tubes. The second (741) is a coarsely broken line, which denotes an X/m value associated with a drive pressure in excess of 1 atmosphere. This is representative of a positive pressure pump located upstream of the packed bed, more preferentially located directly upstream of the packed bed.

Fluid handling systems that make use of positive pressure gains an advantage over a flow handling system that uses vacuum to draw the sample since the adsorptive capacity of the packed bed is shifted to a higher region. This is advantageous for certain embodiments because the mass transfer is enhanced when the saturation pressure of the adsorbent bed increases. In such situations, the flow handling system preferably utilizes a pump that flows the breath sample through the packed bed using positive pressure in excess of ambient. Vacuum drive systems will only be able to operate at the ambient pressure on the adsorbent's isotherm.

Generally speaking, in such embodiments, the pump will be located directly upstream of the packed bed. The increased pressure effectively acts as a gas concentrator. Pulsating pumps such as diaphragm pumps may be especially useful at generating elevated pressures, as the average pressure generated is actually lower than the instantaneous pressures generated during pump strokes.

FIGS. 50A to 50E show five cases whereby a shallow cuboidal packed bed in conjunction with a camera can be helpful. The cuboidal packed bed is also used conveniently for "optics-free" optical detectors such as closely coupled LEDs and photodetectors, but has particular utility in conjunction with a camera or other optical sensor capable of x-y scanning.

In FIG. 50A, an example of channeling is depicted. A system that utilizes a camera is capable of identifying the occurrence of channeling optically and applying corrective algorithms.

In FIG. 50B, an illustration of an optical defect is shown. This is common in systems with bubbles but may also manifest when optical aberrations appear, for example, due to an optical window malformed during manufacturing. A system employing a camera is suited to both identify and potentially correct for the deformity.

In FIG. 50C, a complex adsorbance band is shown. In this example, a system employing a camera is capable of identifying the complex adsorbance pattern, for example due to competing adherence from different chemical species onto available adsorbent sites. The camera can apply corrective algorithms. Also illustrated in FIG. 50C is an example of a corrective algorithm based on pattern extrapolation. In this case, although the color bar has run off the end of the column, a reasonable extrapolation can be made due to pattern recognition and extrapolation.

These principles are useful in designing systems for sensing endogenously produced breath analytes.

Example 1

Reactive chemistry for acetone is described.

Two sets of silica beads (130 mesh to 140 mesh) are coupled with either DEAPMOS or aminopropyltriethoxysilane (APTES). 3 g of silica beads are placed in a mixture of 8.1 mL 2-propanol, 1.2 mL 0.02N HCl, and 2.7 mL APTES or alternatively, 1.5 g of beads are placed in a mixture of 4.05 mL 2-propanol, 0.6 mL 0.02N HCl, and 1.35 mL DEAPMOS. Beads are vortexed for a few seconds and then allowed to rock for 10 min at room temperature. Then the beads are centrifuged briefly to pellet the beads at the bottom of the tube. The excess solution is decanted off, leaving the beads with enough DEAPMOS or APTES mixture to just cover them. Then the beads are incubated at 90° C. for 1 to 2 hrs, until they are completely dry. The DEAPMOS beads are further coupled to sodium nitroprusside (SNP). 3.75 mL of SNP solution (10% SNP, 4% MgSO4 in diH2O) are added to 1.5 g of DEAPMOS coupled beads, which is then rocked for 5 min at room temperature. The fluid is then pulled off by vacuum filtration. Then the beads are dried under vacuum at room temperature for 2 hours.

1.5 g of SNP reacted beads are added to 3.0 g of APTES coupled beads and shaken until evenly mixed. Approximately 0.025 g of mixed beads are placed in a glass capillary (0.25" long with a 2.7 mm inner diameter). 450 mL of breath sample in a tedlar bag is pumped across a CaCl2 pretreatment section (0.35" long, 0.25" id) and then the beads at 150 mL/min. A developer solution (0.5% ethanolamine in 25% dimethylsulfoxide in methanol) is added to the beads. After a period of 1 to 3 minutes, a blue color bar appears if acetone is present at levels above 0.1 ppm. The length of the color bar increases with increasing concentrations of acetone.

Example 2

Reactive chemistry for acetone is described.

A concentrated solution of DNPH is made by dissolving 20 mg of DNPH in 40 uL of concentrated sulfuric acid at 90 C for 5 to 10 min. 8 uL of this solution is added to 200 uL of propanol. 0.1 g of 130 to 140 mesh silica beads are added to the solution and after briefly vortexing, are incubated at 90 C for 1 hr until the beads are dry and free flowing.

Prepared beads are placed in a glass capillary (0.25" long with a 2.7 mm inner diameter). 450 mL of breath sample in a tedlar bag is pumped across a CaCl2 pretreatment section (0.35" long, 0.25" id) and then the beads at 150 mL/min. A dark yellow stain, whose length is concentration dependent, indicates the presence of acetone.

Example 3

Reactive chemistry for ammonia is described.

A concentrated bromophenol blue mixture is made by adding 0.1 g of bromophenol blue to 10 mL of propanol. After rocking for 1 hr, the mixture is ready for use. Not all the bromophenol blue will go into solution. From this stock solution, a 1:10 dilution is made in propanol. 200 uL of 0.1 N HCl are added to 4 mL of the 1:10 dilution and mixed. 1.8 g of 35 to 60 mesh silica beads with a 60 angstrom pore size are added to the mixture, vortexed and incubated at room temperature for 10 minutes. Then the beads are incubated at 80 C for 25 min. The liquid should have evaporated, but the beads should still stick together. At this point, the beads are placed under vacuum for 1 hour to finish drying. Aliquots (about 0.05 g/aliquot) are made and stored in a freezer or under vacuum.

Prepared beads are placed in a glass capillary (0.25" to 1" long with a 1.2 mm inner diameter). 900 mL of breath sample in a tedlar bag is pumped across an Ascarite II pretreatment section (0.7" long, 0.25" id) and then the beads at 225 mL/min. A navy blue stain, whose length and kinetics of reaction are concentration dependent, indicates the presence of ammonia. The detection limit is less than 50 ppb.

Example 4

Reactive chemistry for oxygen is described.

Under dry nitrogen, 0.1 g of titanium trichloride are dissolved in 10 mL of acetone or acetonitrile. 200 uL of this solution is added to 0.1 g of 130 to 140 mesh silica beads. The mixture is dried at 90 C for 1 hr.

Under dry nitrogen, a 0.25" long glass capillary with a 2.7 mm id is filled with the prepared beads and sealed air tight. During analysis, the seal is removed or pierced and 150 mL of breath sample in a tedlar bag is passed across the beads at 150 mL/min for 30 seconds. A length dependent color change from dark purple to colorless is observed based on the concentration of oxygen present. A silica gel bed at the end of the capillary should be used to trap released HCl.

Example 5

Reactive chemistry for carbon dioxide is described.

0.1 g of crystal violet are dissolved in 10 mL of propanol. A 1:10 dilution is made in propanol. 10 uL 1M NaOH is added to 200 uL of this solution. Then 0.1 g of 130 to 140 mesh silica beads are added and mixed. The mixture is dried at 90 C for 1 hr.

A 0.25" long glass capillary with a 2.7 mm id is filled with the prepared beads and sealed air tight. During analysis, the seal is removed or pierced and 150 mL of breath sample in a tedlar bag is passed across the beads at 150 mL/min for 30 seconds. A length dependent color change from colorless to blue is observed based on the concentration of carbon dioxide present.

Example 6

Reactive chemistry for aldehydes is described.

A set of silica beads (100 mesh to 140 mesh) may be coupled with DEAPMOS. 1.5 g of beads are placed in a mixture of 4.05 mL 2-propanol, 0.6 mL 0.02N HCl, and 1.35 mL DEAPMOS. The acid in the solution during coupling creates a positive charge on the tertiary amine in addition to catalyzing the reaction. Beads are vortexed for a few seconds and then allowed to rock for 10 min. Then the beads are centrifuged briefly to pellet the beads at the bottom of the tube. The excess solution is decanted off, leaving the beads with enough DEAPMOS mixture to just cover them. Then the beads are incubated at 90° C. for 1 to 2 hrs, until they are completely dry. The DEAPMOS beads are further coupled to either fuschin or pararosanilin. 3.75 mL of solution (0.2% fuschin or pararosanlin in diH2O) is added to 1.5 g of DEAPMOS coupled beads, which is then rocked for 5 min. The fluid is then pulled off by a vacuum filter. Then the beads are dried under vacuum at room temperature for 2 hours.

Approximately 0.1 g beads are placed in a glass capillary (1" long with a 2.7 mm inner diameter). 450 mL of breath sample in a tedlar bag is pumped across the beads at 150 mL/min. A developer solution (0.2 M sulfuric acid) is added to the beads to catalyze the reaction. After a few minutes, a magenta color bar appears if aldehyde is present. The length and intensity of the color bar increases with increasing concentrations of aldehyde.

Example 7

One embodiment of the system is useful for measuring multiple analytes via distinct analyte cartridges in conjunction with a single base. For example, if the user is interested in measuring acetone, then an acetone cartridge is inserted into the base. If carbon dioxide is of interest, then a carbon dioxide cartridge is inserted into the base. Any of the chemistries described herein can be measured this way when: 1) all reactive chemistries are contained in cartridges that are closely matched in size so that the optical subsystem of the base can sample the reactive beds properly, 2) the base can adjust sample volume, 3) the base can adjust sample flowrate, 3) the height of the cartridge receiver is adjustable to accommodate cartridges of variable heights, as necessary, and 4) the base is capable of delivering excitation light of suitable and possibly variable spectrum.

A system designed to measure acetone and ammonia through distinct cartridges but a single base will now be described. This system can be used with a range of reactive chemistries. A base is comprised of an automated sliding clamp mechanism, as described earlier, whereby the means used to end the stroke to clamp the cartridge is done using either: a) knowledge of the required cartridge clamp height either acquired using visual cues in the cartridge itself, as discerned automatically using the camera or software, or entered manually into the software of base, b) setting the clamping force, such that the clamping stroke ends when a particular force is required to advance it further. Measuring the current through a linear actuator is a means whereby the applied force can be ascertained and used to end the stroke advancement. The base is capable of adjusting sample volume by using a volumetric flow measurement apparatus (as a part of the flow handling system) comprised of a differential pressure transducer, an ambient temperature sensor, an ambient pressure sensor, and appropriate algorithms to transform the raw output data into mass flow data. The volumetric flow rate can be adjusted in the base by using the mass flow data to provide feedback to the pump, resulting in steady delivery at various flowrates despite potential variations in cartridge packing and resultant resistance to gas flow. The base contains lighting that is based on surface mount LEDs with white emission spectra. The LEDs may or may not be under computer control and their intensity variable. An acetone cartridge is comprised of an interactant region of 0.25" long with a diameter of 2.7 mm, with SNP beads as detailed in Example 1. A pretreatment region of the cartridge is upstream of the reactive bed and is comprised of anhydrous calcium chloride contained within a 0.35" long by 0.25" diameter region of the cartridge. Gases are delivered to the column at 150 standard cubic centimeters for approximately 3 minutes. Developer is contained in a breakable liquid container, like a canister, above the reactive zone such that breaking of the canister results in wicking of the developer into the reactive zone, producing a color which is easily evaluated by the optical subsystem comprised of white LEDs, a miniature CMOS camera, and simple algorithms as discussed previously. The same base is also capable of evaluating color produced in an ammonia cartridge which is based on the ammonia chemistry detailed in Example 3. The reactive bed is 0.25" to 1" long with a 1.2 mm diameter. A gas pretreatment column is comprised of Ascarite II which is 0.7" long and 0.25" diameter. 900 standard cubic centimeters of breath sample are passed over the reactive zone at 225 standard cubic centimeters per minute. No developer is required, and the optical subsystem described earlier in this example is used to evaluate the developed color and to correlate that color to the concentration of ammonia in the breath sample.

Example 8

A multi-analyte cartridge with reactive chemistry in a single flow path is described here. In this example, a single cartridge is capable of measuring both ammonia and acetone in a single instance from a single source. In this example, the cartridge is configured to quantitatively assess acetone concentration (for example, between the breath concentration range of 0.5-5 ppm) and to only qualitatively assess ammonia concentration (for example, to assess whether or not the breath ammonia concentration is in excess of 0.5 ppm). The cartridge is comprised of reactive chemistries from Example 1 and Example 3. A pretreatment region is comprised of anhydrous calcium chloride in the column size described in Example 7. Into a 2.7 mm ID column of length 0.3625" is first deposited a layer of 0.05" of ammonia reactive beads. A bead separation plug of porous plastic (1/16" thick, 50-90 micron pores, hydrophilic polyethylene) is placed over the ammonia layer, and then acetone beads are next deposited to a thickness of about 0.25". Alternatively, the bead sizes can be matched to obviate the separation membrane. A developer is contained in a canister (liquid container) above the interactant region. Analysis of the breath sample is as follows: 450 standard cubic centimeters of breath sample are pumped over the analytical column at 150 standard cubic centimeters per minute. After the sample delivery, the optical subsystem comprised of a CMOS camera and white LEDs assesses the color developed in the ammonia beads. Then, the developer is freed to react with the acetone beads. After a set development time, for example 3 minutes, the color in the acetone reactive bed is assessed using the same optical subsystem. Note that addressable LEDs of different spectral emissions can be used to alter the sensitivity of the optical subsystem. It may be beneficial for certain applications, for example, to assess acetone concentration using white LEDs as excitation sources and to assess ammonia concentration using blue LEDs, for example with peak excitation at 470 nm.

A conceptual modification to Example 8 uses multiple reactive chemistries in the same flow path to more accurately measure a single analyte of interest. In this example, the chemistries for carbon dioxide (and/or water) and ammonia are co-immobilized in a 1.2 mm ID column that is approximately 0.5" long. The concentration of carbon dioxide (and/or water) is used to compensate the apparent concentration of ammonia, as the ammonia reaction is a pH reaction that is susceptible to interference from concentrations of water and carbon dioxide that are found in human breath.

Example 9

This example details a means whereby multiple analytes in a single breath sample can be assessed using chemistries contained in multiple flow paths. The multiple flow paths can be contained in a single cartridge or in multiple cartridges, although this example details the case of a single cartridge with multiple flow channels.

The hardware required for this embodiment (based on simultaneous detection of acetone and ammonia) consists of redundant or slight modifications to the hardware systems described earlier. A cartridge is molded with two channels for reactive chemistries and pre-conditioners. As the acetone channel requires a developer and the ammonia does not, the base contains a single ampoule breaking needle, positioned to interact with the acetone channel of the cartridge. The flow handling system is also redundant, with a mass flow meter and pump dedicated to each analytical channel. The ability to independently vary flow rate and delivered volume is preserved. Using a single pump and metering system to split the flow over the two analytical channels is less desirable since the flowrates are not independently variable and variability issues due to column packing impose a lack of control over the delivery volumes. Nevertheless, for some applications a single gas delivery system to drive both analytical channels can be useful. To detect the color development in the two channels, a single camera must either be focused to contain the entire optical sensing zone, the region of interest, (spanning two channels), contain movable optics (a mirror system which 'points' the camera to the appropriate channel), be itself movable (mounted on a sliding rail), or multiple cameras must be used.

Example 10

One method to increase the sensing range for a given column is to vary the volume of breath sample that is flowed through a flow path and into the interactant region. In general, lower detection limits can be achieved by increasing the volume of the breath sample that is flowed over the interactant region. For example, a cartridge may be tuned for 0.5 to 5 ppm acetone sensitivity range using a breath volume of 450 standard cubic centimeters. If the sample to be measured is anticipated to be within a lower range, for example 0.1 to 0.5 ppm acetone, a larger volume of breath sample can be flowed over the interactant region to produce a color change similar to that produced with a lower volume of gas of higher concentration. Thus, for a given flowrate, the concentration of analyte in the breath sample can be determined using a calibration curve appropriate to the sample time. A limitation to this approach, however, is the consumption of pre-conditioning components. Doubling the volume of breath sampled requires a doubling of the desiccant action of anhydrous calcium chloride, for instance. Fortunately, over-packing of anhydrous calcium chloride does not have a dramatically deleterious effect on the acetone concentrations, so if this approach is to be used to extend the measurement range of systems by adjusting sample volumes, then the cartridge should be packed with desiccant appropriate to the lowest desired detection limit.

Reaction time can be used to assess the concentration of a sample. In this approach, the rate of change of color production is used to determine the analyte concentration in the sample. This works because, in general, the rate of chemical reaction, in addition to the final color achieved, is affected by the concentrations of the interactants. Thus, an optical subsystem and appropriate algorithms will make a concentration assessment by taking multiple readings of the color and determining the color production rate. Calibration curves of color production rate vs. analyte concentration (under given conditions, for example sample volume, flowrate, and reaction temperature) can be produced and used to make more rapid assessments of analyte concentration. By adjusting the flowrate of breath sample through the interactant region, this approach enables the selection of various column sensitivities.

Example 11

Figure 76:
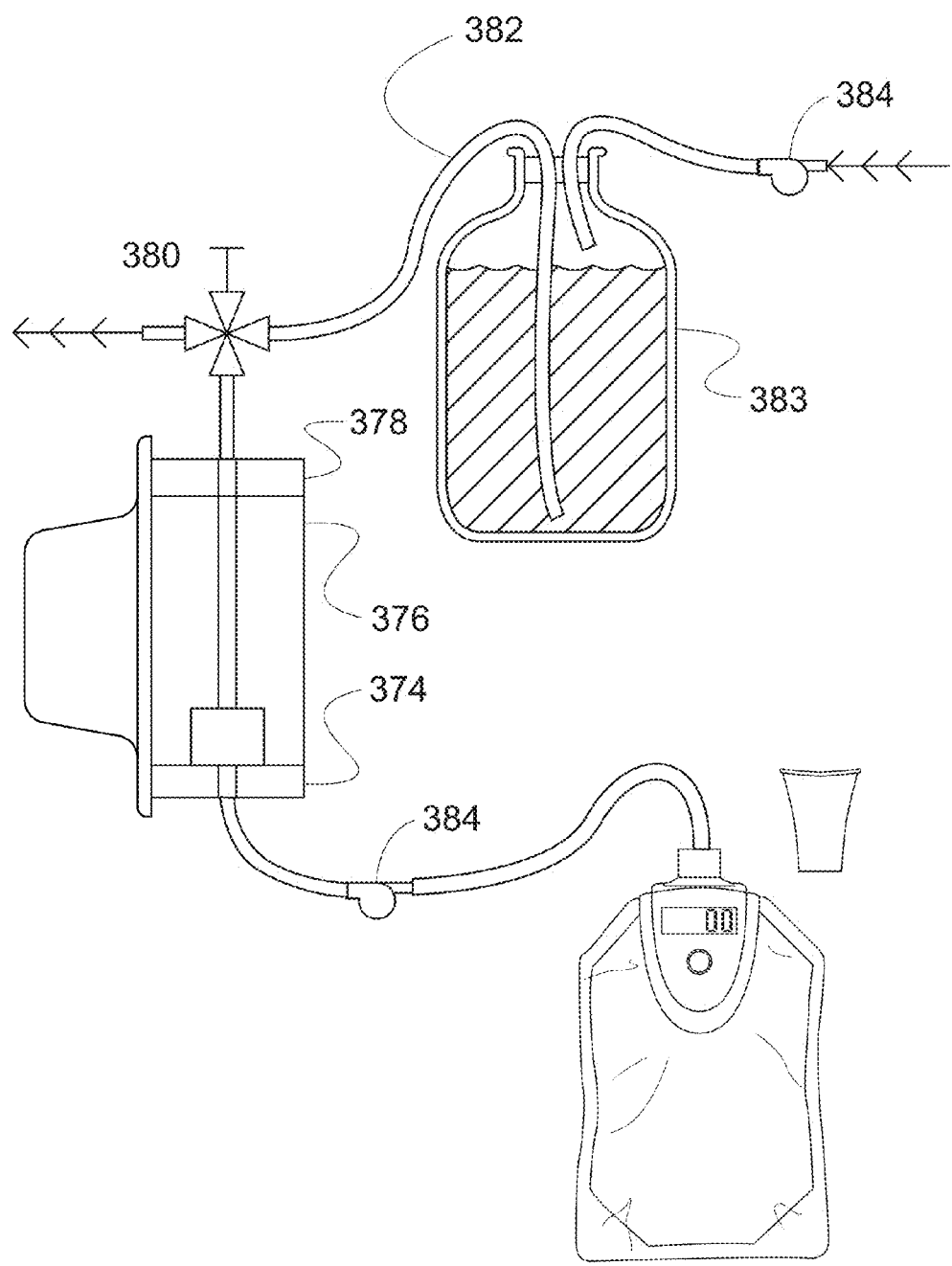
FIG. 76 shows an embodiment of a breath analysis system with the developer inside a replaceable liquid container in the base instead of in disposable cartridges.

Liquid reagents may be housed in a disposable cartridge and made available for reaction with the analyte using a reaction initiator or dispensing device. For some applications, however, it may be preferable to house the liquid developer inside the base and not in the disposable cartridge. A scheme for how this can be accomplished is shown in FIG. 76. In this scheme, a breath sample from a breath bag is evacuated using a first pump (384), which pushes the sample through a lower fixed jaw of a clamping mechanism (374), through the cartridge (376) with appropriate pre-conditioning components, through an upper movable jaw of a clamping mechanism (378), and out a three-way valve (380). When developer is required, the three-way valve (380) position is switched to allow flow of liquid reagent through a feed hose (382) from a pressurized liquid container (383). A second pump (384) is used to apply pressure to the headspace of the container to cause the liquid reagent to be drawn into the feed hose (382) and into the interactant region of the cartridge (376). Alternative configurations of the flow handling system result in different swept volumes and different liquid contact points which may have certain advantages depending on the developer required for a given application. The advantages of this scheme are: a) the flow path of the breath sample is never wetted by developer (that is, when inserting a second cartridge from analysis, the breath sample does not need to flow through tubing that has been wetted by a previous development except downstream of the interactant region), b) the second pump (384) does not contact the developer and thus does not require wettable materials particular to the application, and c) the flow path of the liquid is not exposed to the air (and fluid line drying) due to the three-way valve (5).

Example 12

A method for preparing a cartridge for sensing acetone in a breath sample will now be described. Reagents to pack a cartridge were prepared as follows. APTES beads were made by adding 0.5 g 140 to 170 mesh silica gel to 200 ul APTES and 400 ul propanol. The beads were vortexed thoroughly for 10 seconds. 0.4 ml 1N H2SO4 was added and vortexed for 10 seconds. The beads were incubated at 80 C for 10 minutes and then cured at 110 C for 1 hour.

1.67% and 6.67% solutions of SNP were made by dissolving SNP in 25% DMSO in methanol. Solutions are stored in light-proof containers. 20-30 mesh Ascarite II is available off the shelf and used as a scrubber and desiccant.

A cartridge is prepared for use as follows: a porous polyethylene disk, 1/16" thick is placed into a region in a cartridge with plastic housing. A disk of fibrous polyethylene, also 1/16" thick but compressible to roughly 1/32" thickness is next inserted. 0.9 ml of Ascarite II are then added to a 5/16" diameter pocket. Another disk of porous polyethylene is pressed into the 5/16" diameter pocket to retain the Ascarite II. From the other end of the cartridge, 170 mesh APTES beads, as prepared above, are added to a reactive zone, comprising a region with extruded cross section of roughly 2 mm×4.5 mm, channeled 4 mm deep, spilling over into the retention disk region by approximately 1 mm. A 1/8" thick porous polyethylene disk is firmly pressed into the region to tightly retain the APTES beads. An ampoule is dropped into the region above the 1/8" retention disk. (An ampoule is prepared by filling a 5/16" diameter polyethylene hollow cylinder with 75 microliters of 1.67% SNP in 25% DMSO in methanol, sealed at both ends with laminated polyethylene/foil). A 1/16" thick fibrous polyethylene disk is placed over the ampoule, and the cartridge is sealed on top and bottom with laminated polyethylene/foil barrier materials. The top barrier should compress against the fibrous polyethylene to hold the ampoule in position firmly and preclude the possibility of the ampoule shifting during operation to form an air gap between the bottom of the ampoule and the top of the porous polyethylene which retains the APTES beads into the reactive zone.

Example 13

An embodiment for sensing acetone in a breath sample is provided. A user breaths into a breath bag of approximately 500 ml volume. The breath bag is positioned in the breath bag receiver, and a cartridge, prepared as illustrated above, is inserted into the base. After clicking start on the user interface of the base, the cartridge is sealed such that the flow path of the cartridge is in fluid connection with the flow path of the flow handling system as the linear actuator engages the bottom of the cartridge. A needle in the bottom sealing piston pierces the cartridge's bottom-side outer barrier. A needle from the top of the cartridge is brought down to pierce the cartridge's top-side outer barrier. The pump and other components of the flow handling system deliver approximately 400 ml of the breath sample from the breath bag through the bottom side of the cartridge, with the breath sample passing first through the region of the cartridge containing Ascarite II and then into the region containing the APTES beads. The breath sample flows past the ampoule and exhausts through the holes in the top barrier as recently punctured. After about 3 minutes, with breath samples delivered at about 135 standard cubic centimeters per minute (SCCM), the ampoule is broken with the top needle passing first through the top barrier of the ampoule and then through the bottom barrier. With the porous polyethylene tightly packed against the bottom of the ampoule, the SNP developer wicks easily through the reaction zone containing the APTES beads. After approximately 3 minutes, an image is taken of the reactive zone through the optical sensing zone and the amount of color formation is used to estimate the concentration of acetone that was in the breath sample.

Example 14

The breath analysis system is preferably designed to account for various human factors. Such factors aid users in analyzing their breath with some level of frequency, which may be required for different applications.

An important feature of the embodiment shown in FIG. 48 is the ease by which a user interacts with the base to insert the breath bag and cartridge. The base is designed to receive a breath bag and a cartridge without substantively "moving." Once the accessory components have been attached, by the act of receiving or through actions taken by the base, the accessories are fluidically coupled with the flow handling system. Through this process, information about the analyte may be relayed to the user in a convenient and hassle-free manner.

Minimal Input Pressure. In the embodiment described in FIG. 48, the breath analysis system (410) is used in conjunction with two detachable components, a breath bag (412) and a cartridge (460). The receiving of these components into the base (414) is preferably done ergonomically.

The breath bag requires a small amount of pressure to engage the airtight seal that is made between the breath bag and base. In preferred embodiments, the base (414) is small and lightweight. As such, the pressure to couple the breath bag with the base may cause the base to move. The breath bag receiver is preferably designed such that the receiving of the breath bag into the base does not cause substantial movement of the base. It is also preferable that the user be able to attach (and detach) the breath bag with the base with a single hand (i.e., not a two hand operation).

In FIG. 48, the breath bag receiver (442) is on top of the base (414) so that the force applied by the user when inserting the breath bag is counteracted by the surface on which the base is sitting.

Similarly, the cartridge requires a small amount of pressure to engage with the base. This amount of pressure is preferably low to minimize movement of the base. The cartridge receiver is preferably designed such that the receiving of the cartridge into the base does not cause substantial movement of the base. It is also preferable that the user be able to attach (and remove) the cartridge with the base with a single hand (i.e., not a two hand operation).

In FIG. 48, the cartridge receiver (466) requires only that the user exert minimal effort to gently push the cartridge (460) through a hinged, lightweight door. This force is counteracted by the general weight of the base and does not cause the base to move.

To decrease movement of the base, the base preferably comprises "feet" that increase the coefficient of friction between the base and the surface on which it is placed. The "feet" may be made of material such as rubber or other elastomeric materials.

Receiver Recognition Elements. As described above, the cartridge receiver and the breath bag receiver are components of the base that are subject to frequent interaction by the user. The receivers preferably include user recognition elements. A user recognition element may be a light panel that turns on and off as the base is ready to accept the breath bag or the receiver. Alternatively, the user recognition element may be a colored door or surface that is concave or sloped, as shown in FIG. 48, that lends itself to guiding the user-input accessories into place.

Mechanical and User Interface Interaction. Preferably, the physical interaction of inserting and removing accessories to the base, such as the cartridge (460) and the breath bag (412), and virtual interaction of using the user interface (496), here a touch screen, are grouped. This aids in reducing training time and creating a more intuitive design.

The base is preferably designed for the user to have easy access to the user interface. In FIG. 48, the user interface (496) is a touch screen. As most users are right handed, it is preferable for the touch screen to be on the right hand side of the device. It is also preferable that the steps that require "user interaction" be on the left hand side.

The placement of the breath bag receiver (442) on top of the cartridge receiver (466) (as shown in the drawing figure) is preferable. More preferably, the breath bag receiver center line is centered directly over the cartridge receiver. In so doing, the user has confidence that the contents of the breath bag are evacuated through the cartridge. Functionally, this also helps to reduce the dead volume in the flow handling system.

Angled Surfaces. On the front face of the base (440), the user inserts a cartridge and interacts with the user interface (496), here a touch screen. In FIG. 48, both the cartridge receiver and the user interface are at an angle with regards to the base. Angled insertion aids the user in comfortably inserting the cartridge and interacting with the touch screen. Such insertion also divides the force that the user is applying to the base into a horizontal and vertical component, where the vertical component of the force is counteracted by the surface on which the base is placed.

In a further effort to avoid user-induced force to the base, in FIG. 48, the user interface is flush with the housing of the base. This deters the user from unnecessarily "pushing" into the user interface and maximizes the user's ability to interact with the edges and corners of the touch screen.

Example 15

An embodiment of reactive chemistry for use in sensing carbon dioxide will now be described.

Mix 10 ul of 50% polyethyleneimine in water, 8 ml propanol, and 0.01 g crystal violet with 4 g silica gel (−100+140 mesh). The mixture is dried first at 80° C. for 1 hour and then at 118° C. for 1 additional hour. The dry reagent is loaded into an interactant region of a cartridge.

Example 16

Another embodiment of reactive chemistry for using in sensing carbon dioxide will now be described.

Crush 4-8 mesh soda lime with indicator granules and collect on a 20 mesh sieve. Load dry reagent into an interactant region of a cartridge.

Example 17

An optical non-dispersive infrared (NDIR) sensor for carbon dioxide is retained in a receptacle in fluid communication with the flow handling system, preferably located in the breath input receiver. An example of an NDIR sensor is an Alphasense 20 mm sensor. The connection is made air-tight using an o-ring inside the CO2 sensor receptacle. The gas inlet side of the NDIR CO2 sensor is disposed towards the inside of the breath input receiver but is protected from physical contact during the receiving of the breath bag (or other breath input) by being offset a few millimeters from the interior portion of the breath input receiver. This optical sensor is capable of sensing the amount of CO2 in the breath sample of the breath bag and also capable of producing an electrical signal to interface with a processor. This signal can be used directly or in combination with other information about the breath analyte for signal normalizations, sample quality assessments, and others.

Example 18

Figure 77A:
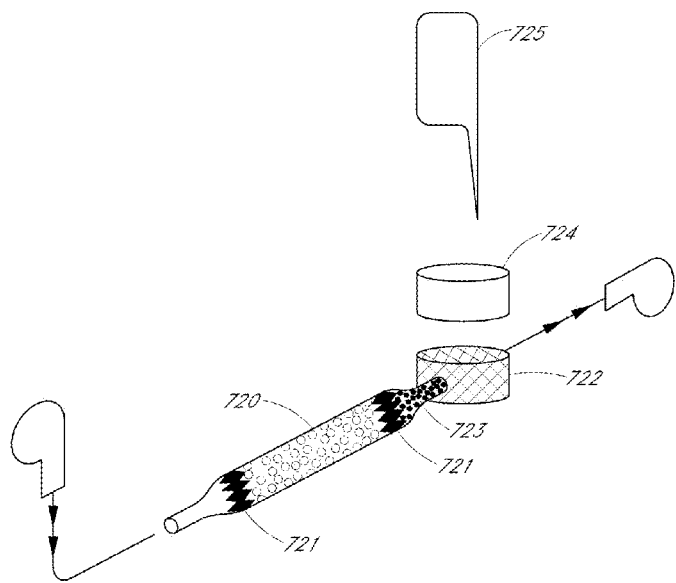
FIG. 77A is a fluid handling system for counter or co-flow gas and liquid handling.
Figure 77B:
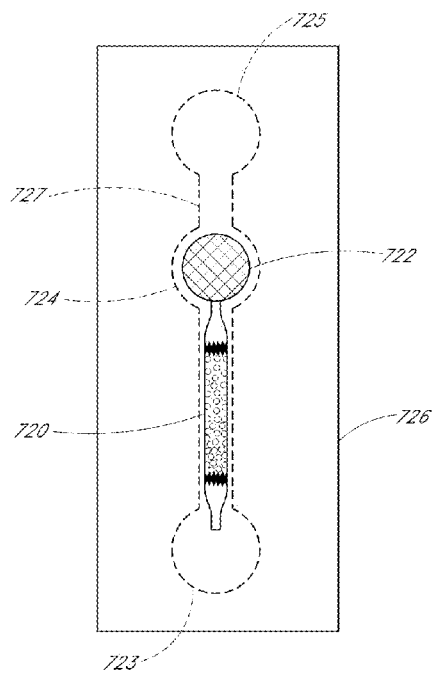
FIG. 77B is a perspective drawing of the same fluid handling system.
Figure 77C:
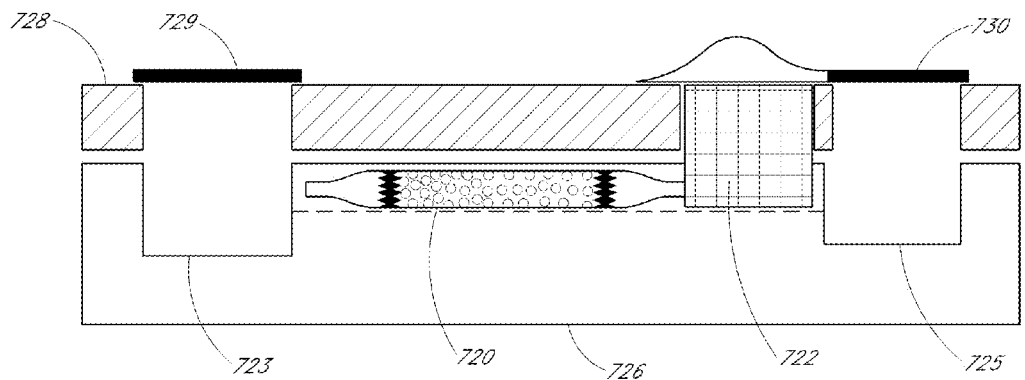
FIG. 77C is a perspective drawing of the same fluid handling system.

FIGS. 77A to 77C show a fluid handling system for counter-flow gas and liquids. FIG. 77A illustrates the main components. An interactant region is disposed within an enclosure, for example a glass capillary tube open on both ends (720). The tube is filled with dry reagents, either singly or in tandem. The dry reagents are immobilized with a porous barrier on either end (721). The enclosure is pressed into a disk of porous polyethylene at one end (722). Interposed between the porous barrier closest to the porous polyethylene is a bed of liquid conductor, for example fine silica (723). A liquid container (724), for example a foil blister pack, is positioned in intimate contact with the porous polyethylene (722). A piercing member (725), for example a needle on a linear actuator, is located close to the liquid container and in-line with both the liquid container and the porous polyethylene. FIG. 77B shows a plan view of the arrangement assembled into a planar substrate (726). The interactant region enclosure (720) is positioned within a channel (727) in the planar substrate. The channel widens to accept three circular regions, one at either end of the interactant region (723, 724) enclosure and one on the more distal end (725). With these pieces assembled, a cover plate (728) is placed over the planar substrate and bonded or otherwise made air-tight with the bottom substrate except through the three circular regions (723, 724, 725). Piercable barrier materials (729, 730) are placed over two circular regions (723, 725) in an air-tight fashion. The liquid container is placed in the corresponding circular region (724) and fastened to the cover plate (728) in an air-tight fashion, for example heat sealing an extended flange. Gas sampling and liquid development through the assembly is as follows. The breath sample is delivered through piercable barriers (729, 730) establishing an air-tight connection between the fluidic source and the interior of the substrate. The breath sample is flown in either direction either via suction or via positive pressure, depending upon the configuration of the pumps. After the appropriate volume of the breath sample is delivered, a piercing member (725) breaks the liquid container (724), and the intimate contact enables the liquid developer to wet the porous polyethylene (722), be drawn through the liquid conductor (723), and into the interactant region. Liquid flow can thus be counter or co-directional with the delivery of the breath sample.

Example 19

Figure 78:
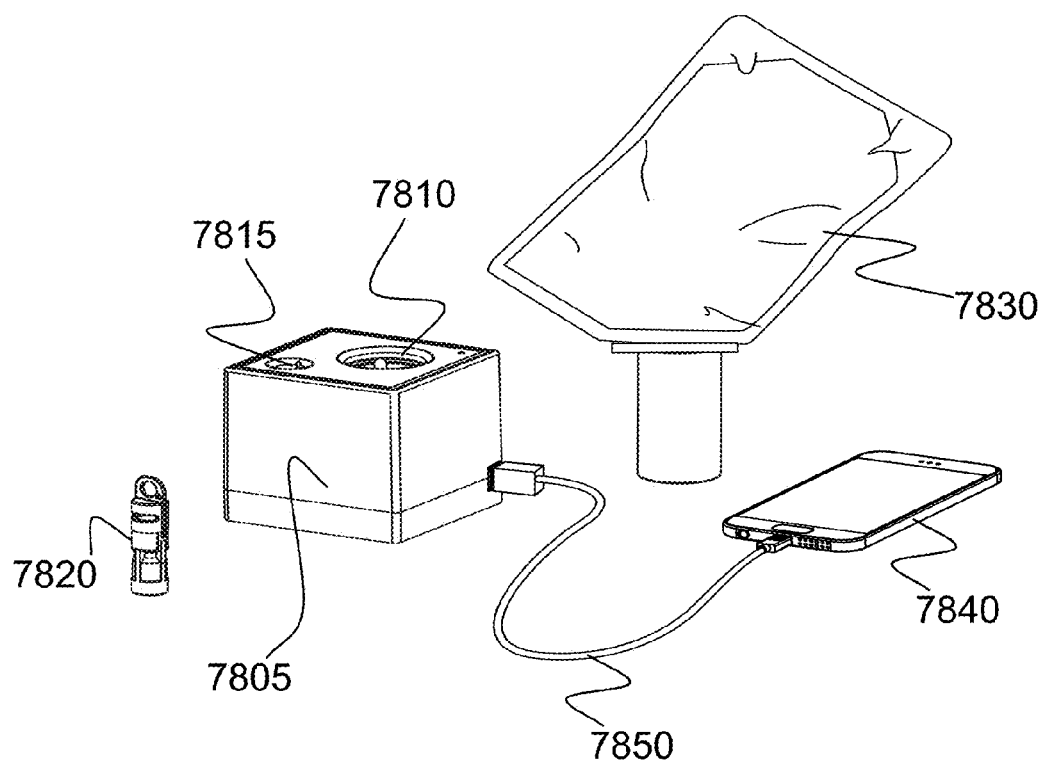
FIG. 78 shows a breath analysis system.

FIG. 78 shows a breath analysis system comprised of a base unit (7805), a cartridge (7820) and a breath bag (7830).

The system communicates with a mobile device (7840) either via wireless or wired means. As described elsewhere in this disclosure, the cartridge and breath bag are inserted into the base unit. In this embodiment, the cartridge is inserted through the cartridge receiving area (7815) and the breath bag through the breath bag receiving area (7810).

Figure 79:
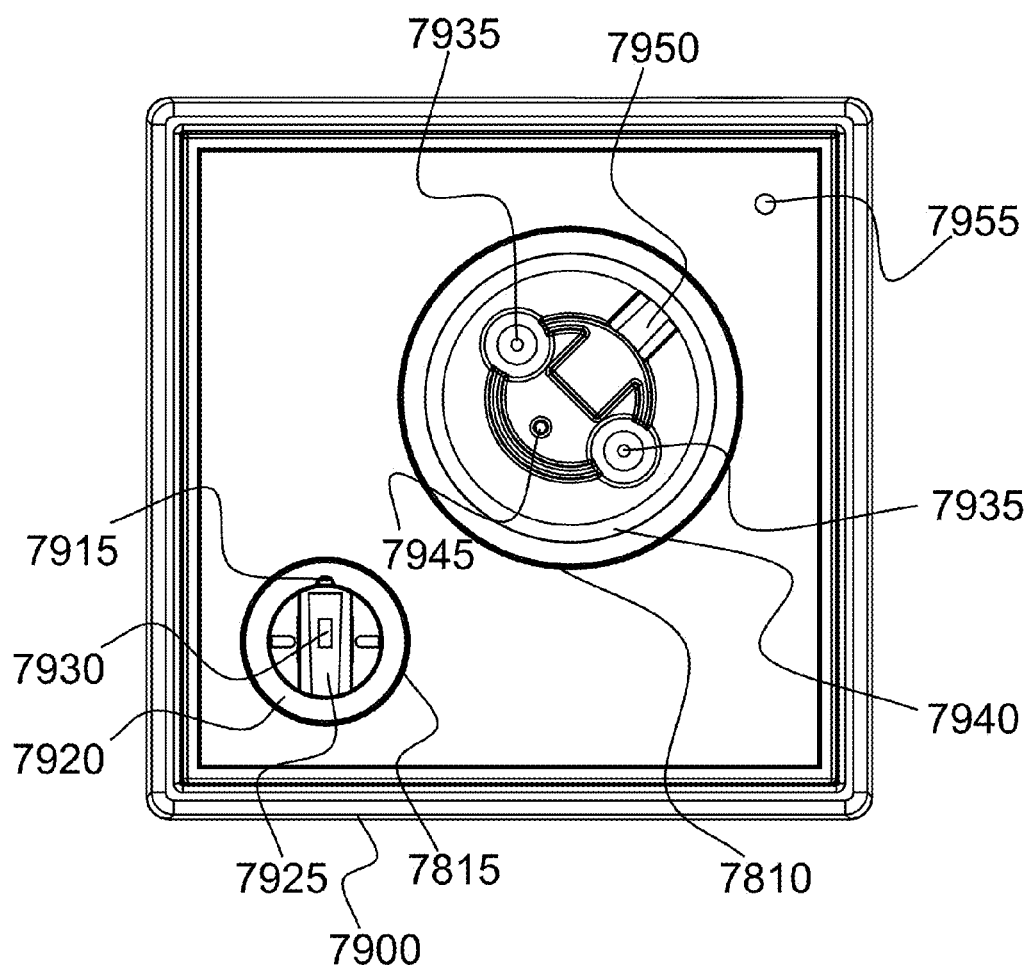
FIG. 79 shows the top face of an embodiment of a base unit.

FIG. 79 shows the top face of the base unit. The device has an exterior facing cartridge receiving area (7815) and a breath bag receiving area (7810). The cartridge insertion area is shown and labeled in other figures. The breath bag receiving area is also shown in FIG. 82, which shows the side view of the cup (8110) into which the breath bag is received. Also externally visible is a light port (7955). This light port is the end portion of a light pipe shown in FIG. 80. The light pipe (8005) is used to direct light from an LED (8010) mounted on the PCB (8015) so that the light is directed to the top plate shown in FIG. 79 as 7955. This indicator may be used to pair the device, details of which are described in U.S. patent application Ser. No. 62/161,753 entitled: "User and Breath Analysis Device Pairing and Communication," which is incorporated by reference. This indicator may further be used to communicate the status or result of the test.

Figure 80:
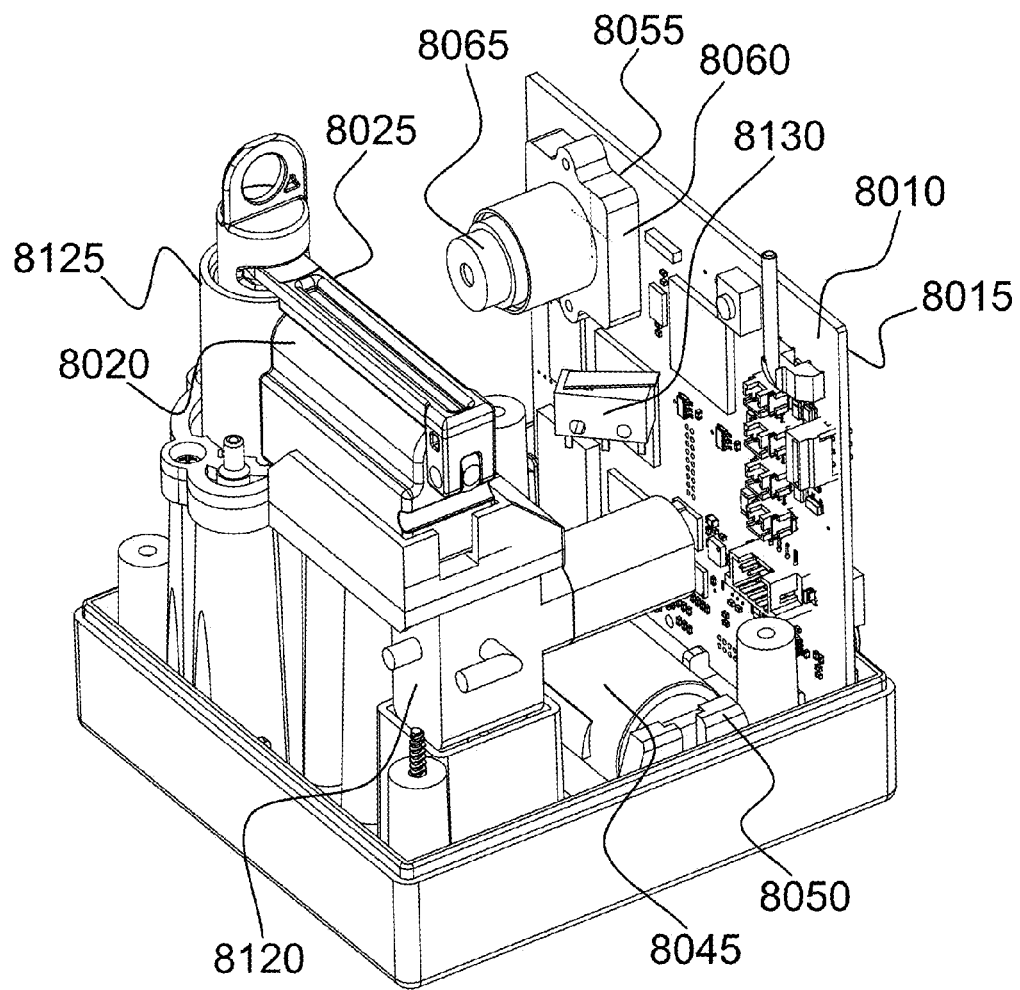
FIG. 80 shows a perspective drawing of the base unit described in FIG. 78.
Figure 81:
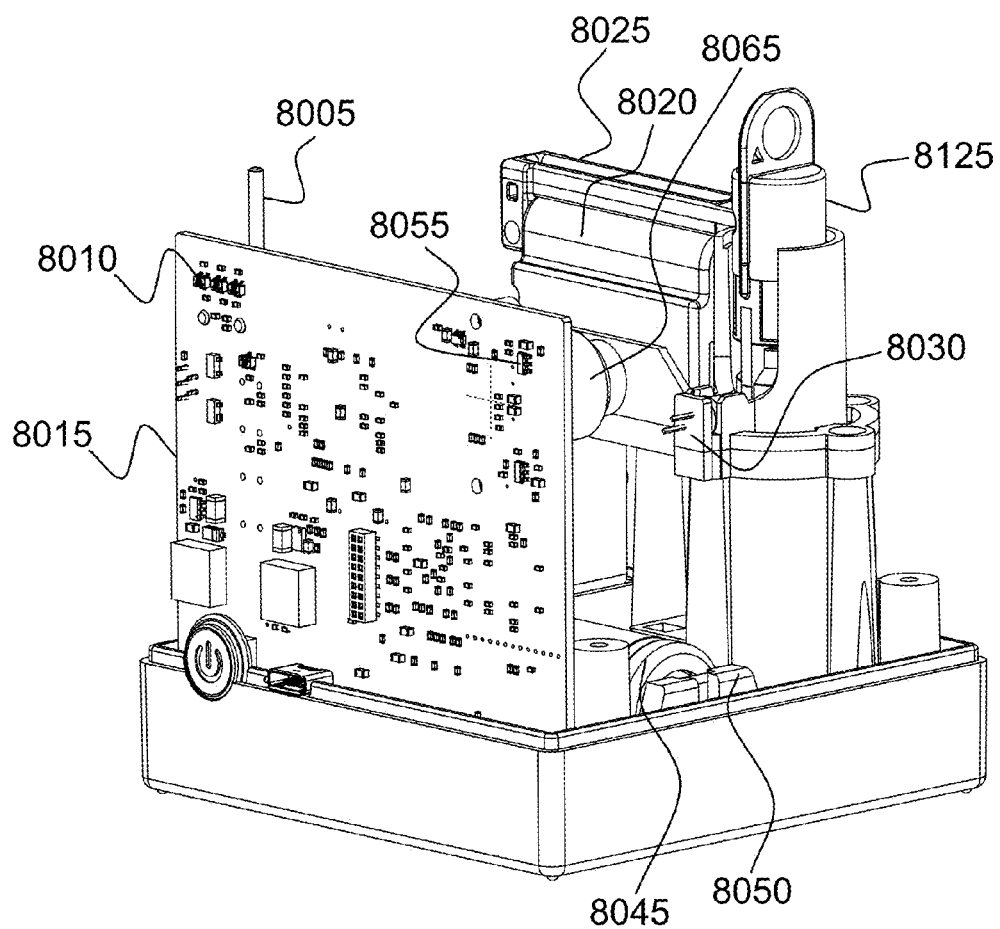
FIG. 81 shows a perspective drawing of the base unit described in FIG. 78.
Figure 83A:
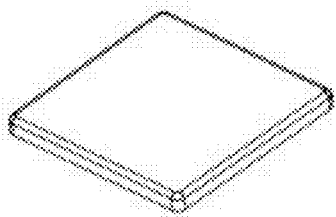
FIGS. 83A, 83B, 83C, 83D, and 83E show five (5) different embodiments of a dust cover that may be used in conjunction with a base unit.
Figure 83B:
Figure 83C:
Figure 83D:
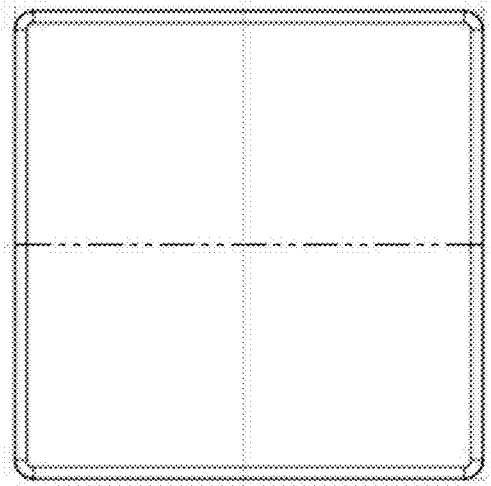
Figure 83E:
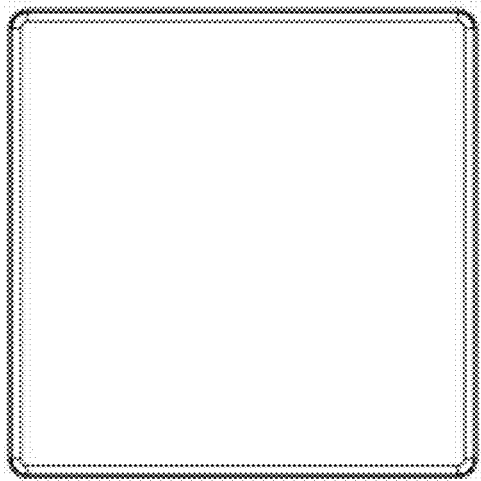

In the present embodiment shown in FIG. 79, the cartridge receiving area (7815) is configured to receive a detachable cartridge (FIG. 80 and FIG. 81 each show a side profile when the cartridge has been inserted). In this embodiment, the cartridge receiving area (7815) includes a key (7915) that ensures that the cartridge is oriented in a specific physical orientation when inserted into the base unit. This key also helps to ensure that the user positions the cartridge correctly into the base unit.

In the present embodiment, the cartridge insertion area further comprises a presence sensor (7925). For example, the presence sensor (7925) may be a bump switch. The presence sensor may be disposed such that the protruding portion of switch (7930) is depressed when the cartridge is pressed into position. Here, the processing unit of the breath acetone measurement device (not shown) monitors the state of the sensor (7925) to determine when it is depressed. Likewise, if the protruding portion of the switch (7930) transitions from a depressed state to an undepressed state, the processing unit detects that the switch is undepressed. To ensure a strong seal in the flow path of the breath sample, it is desirable for the user to press the cartridge all the way into the cartridge receiving area.

It is also desirable that the integrity of the fluid path remain air tight so that the quality and properties of the breath sample are not altered. Accordingly, in breath analysis systems that include a disposable system component comprising at least one of a cartridge and a breath bag, and which systems that further include a base unit that comprises a disposable system component receiving port configured to detachably receive and affix the disposable system component to the base, one may dispose a gasket between the disposable system component and the disposable receiving port to create an air-tight seal.

To illustrate, bump switch (7925) can be fluidically sealed within the cartridge receiving area such that the breath sample does not leak or seep into openings between the enclosing plastics of the base unit and the switch. A gasket (7920) may further facilitate the fluidic sealing.

Other presence sensors may be used. In essence, a presence sensor identifies or recognizes when a detachable, disposable, and/or replaceable accessory component (here a breath bag and a cartridge) is correctly mated with the base unit. In this embodiment, the presence sensor comprises a bump switch. However, this is not meant to be limiting. Examples of presence sensors may include magnetic switches, piezoelectric sensors, proximity sensors (which may include a photodiode), software-coupled image sensors (e.g., a camera that periodically captures an image of a region of interest and processes the image to determine if the detachable component is correctly mated and in place), and/or the like. The presence sensors may also include an electrically conductive material (e.g., a piece of conductive copper tape) that is coupled to the detachable component and that is also embedded within the base unit of the breath analysis system such that when the electrically conductive material and the detachable component are in physical contact with one another, they complete an electrical circuit. The presence sensors may also be a plurality of presence sensors that, alone or in combination, provide more specific guidance to a user (e.g., via a user interface on a mobile application, via a display on a breath acetone measurement device, etc.) on what steps or actions the user may need to perform to correctly insert a detachable component.

Returning to FIG. 79, the top face of the base unit comprises a breath bag receiving area (7810). The breath bag insertion area is configured to receive a replaceable breath bag. The base unit may include two prongs (7935) that protrude into the one-way valve of the breath bag when the breath bag is inserted. A gasket (7940) ensures that the breath sample does not leak or leak above a threshold value. The breath sample may be directed substantially through the hole (7945) in the breath bag receiving area. Once the breath bag is in place, the bump switch (7950) is activated. The processing unit of the breath unit (not shown) may monitor the state of the bump switch. Activation of the bump switch may cause the processing unit (not shown) to sense that the bump switch of the breath acetone measurement device is active and that the breath bag is in place. Likewise, if the breath bag is initially in place, but then slips out of place, the bump switch may be deactivated. Deactivation of the bump switch may cause the processing unit to sense that the bump switch is deactivated and that the breath bag is not in place.

The breath analysis system comprises four main subsystems: (a) flow subsystem, (b) actuation subsystem, (c) image analysis and processing subsystem, and (d) user experience subsystem. Building upon principles and embodiments presented in this disclosure, and with reference to FIGS. 78 to 82D, certain components of each subsystem are pointed out for this embodiment of the base unit.

As shown in FIG. 78, the flow subsystem is configured to transfer the breath sample from the breath bag (7830) to the reactive beads of the cartridge (7820), thereby facilitating a reaction between the acetone in the breath sample with the reactive beads. The flow path starts with a hole (7945) in the breath bag receiving area. The two prongs (7935) protrude into the one-way valve of the breath bag to allow gas flow from the bag through the hole. A gasket (7940) (shown in FIG. 79) ensures a tight seal between the breath bag and the receiving area. The mouthpiece of the breath bag mates with the base unit via a cup (that contains the hole 7945). The "hole" is the top portion of a conduit shown in FIGS. 82A to 82D (8115). Referring to FIGS. 82A to 82D, this conduit connects to tubing (not shown) that is connected to a pump (8120) via a porous metal flow restrictor (8135). The pump is coupled to further tubing to connect it to the base of the cartridge receiving area (8125). In this way, the breath sample is directed into the cartridge. Preferably, a gasket (7920) surrounds the cartridge receiving area such that there is a seal around the cartridge to prevent the breath sample from "leaking" into the interior of the device or ambient environment. An aerial view of the cartridge insertion port and the cartridge gasket are shown in FIGS. 79 (7815 and 7920).

Maintaining an essentially leak-free flow path is important. To ensure that the area surrounding the bump switch (8130) cavities is sealed, a filler material, such as silicone, may be used. In this setup, silicone may also relieve stress from the solder joints (of the bump switch). As a further step to prevent leaks, a gasket (e.g., 7940 or 7920) may be used. This gasket is preferably made of an elastomeric material. The gasket is disposed between two pieces of plastic, where the plastic pieces have a feature (such as a v-shaped protrusion). Screws are used to sandwich the gasket and plastic pieces together such that the features of the plastic "bite" or "tightly mate" with the gasket. This crush ring gasket assembly may be used for both the cartridge gasket and the breath bag gasket.

The pump used in the flow subsystem may generate audible noise. Preferably, an acoustic dampener, such as foam, is used to prevent the pump from "vibrating" against the plastics and also to decrease the noise to ensure a more pleasant user experience.

The actuation subsystem, as shown in FIGS. 6A to 6B and FIG. 80, is configured to release the liquid reagent stored in the cartridge such that it wets the reactive beads (to develop color) at the appropriate time. In this embodiment, the base unit comprises a linear actuator (8020), although this is not meant to be limiting. Other mechanical systems, such as those described elsewhere in this disclosure, may be used to release the liquid reagent. The linear actuator works in combination with a plastic kicker (8025). The actuator moves the kicker into the cartridge receiving area, but more specifically into the window (0475) of the cartridge. The kicker optionally is engaged so that it "locks" the cartridge in place during the test but does not displace the ball (0410) until the appropriate time in the test. The actuator preferably includes positional feedback that allows its movement of the kicker to be controlled, for example, by a microprocessor (8015). The positional feedback is provided by an analog output signal that is generated from a wiper circuit (for instance, as provided by a potentiometer) contained within the actuator electronics.

The system also comprises an image analysis and processing subsystem. Referring to FIGS. 8A to 8B, 80 and 81, the base unit comprises a circuit board that contains a processing unit (8015) that controls various sensors, actuators and components, including a user-facing LED (8010), a cartridge illuminating LED (8030), an actuator (8020), an image sensor mounted on circuit board (8015), a pump (8120), and two bump switches (8130, also shown in FIG. 9). Referring to FIG. 9, the circuit board also comprises a bluetooth chip (0905) that enables communication with the mobile device (0135). The circuit board is powered by a rechargable battery housed in a battery (8045) tray (8050). The pairing and communication process is described in the '753 application.

In this embodiment, the image sensor (8055) is mounted effectively "underneath" the lens mount (8060). Attached to the mount (8060) is a lens (8065). In some embodiments, the lens (8065) is a finite conjugate lens such that it is able to focus better on nearby objects.

After the sample has received time to allow the reaction to develop (after delivering the breath sample into the cartridge), the processing unit turns on the cartridge illuminating LED and directs the image sensor (8055) to take an image to determine the amount of color that is generated from the interaction of the analyte in the breath sample, the liquid reagent (released after the actuator displaces the ball) and the reactive beads contained within the cartridge. In certain embodiments, the LED is illuminated with PWM signals to control its brightness or intensity. These signals are preferably synchronized with the electronic shutter of the image sensor to provide optimal images.

In presently preferred embodiments of the invention, error detection and flagging or notification capabilities are included. Examples of errors or error conditions would include cartridge issues (e.g., incorrect cartridge type, used cartridge, cartridge that is beyond its expiration date, and the like), flow channel integrity issues (e.g., failure to obtain an airtight seal between the breath bag and base unit, e.g., at the gasket or bump switch (8130), failure to obtain an airtight seal between the cartridge and base unit, and the like), liquid dispensing issues, and so on. As an error occurs, it is reported to the processor (8015), e.g., via bump switch or the like, and the processor causes an appropriate error message to be displayed on the display monitor, smart phone (0135), etc. Examples of such error messages would include the following:

Used Cartridge. The base unit detected that a previously-used cartridge was used for this reading. Please remove and discard the cartridge and insert a new one.

Cartridge [or Breath Bag] Removal. The base unit detected that the cartridge or breath bag was removed during this reading. Both the cartridge and the breath bag must remain attached for the duration of the reading. Please re-perform the reading with a new cartridge and a new breath sample.

Wetting Failure. The base unit detected that the cartridge did not wet (from the developer solution) during the test. Please re-perform the reading with a new cartridge and a new breath sample.

Expired Cartridge. The base unit detected that the user is attempting to use an expired cartridge. Please check the expiration date on the cartridge. If expired, please re-perform the reading with a new unexpired cartridge and a new breath sample.

FIGS. 83A to 83E show a dust cover that can be placed on the top of the embodiment described above. This dust cover prevents dust from entering into the breath bag receiving area or the cartridge receiving area.

Example 20

Exemplary reactive chemistry for acetone is described. When used to sense breath acetone, one embodiment of the cartridge shown in FIGS. 4A to 4G comprises three reagents: aminated beads, SNP developer solution and a desiccant.

Aminated Beads. Silica beads (140 mesh to 170 mesh) are coupled with aminopropyltriethoxysilane (APTES). 4 g of silica beads are placed in a mixture of 1.6 mL APTES and 3.2 mL of 2-propanol. Beads are vortexed for a few seconds. 3.2 mL of Sulfuric Acid ($H_2SO_4$) is added to the mixture. Mixture is incubated at 80° C. for 2 hours, and then incubated at 120° C. for 1 hour via hot plate. The overall volume of the synthesis batch can be appropriately scaled.

For certain embodiments, it may be desired to utilize aminated beads of different concentration levels. For the same amount of APTES and propanol, different amounts of silica beads may be used. Examples of different volumes of silica beads include: >8 g, 6 g to 8 g, 4 g to 6 g, 3 g to 4 g, 2.5 g to 3 g, 2 g to 2.5 g, 1.5 g to 2 g, and 1 g to 1.5 g.

Developer Solution. Sodium nitroprusside (SNP) (such as 0.8 g of granules) is added to a solvent solution. The solvent solution may comprise a single solvent or a solvent mixture. The solvent solution may comprise reagents that enhance the color itself or the color-to-background ratio formed when the SNP interacts with the aminated beads. Such reagents are preferably basic. But, they could also be or include diethylamine, diethanolamine, triethylamine and TRIS buffer. The solvent solution may further comprise dimethyl sulfoxide (DMSO) or some reagent to promote solubility.

The solvent solution may be a 75:25 ratio of methanol to DMSO. Depending on the balance between stability and kinetics for a given application and clinical need, the percentage of methanol can vary. The percent composition of methanol can be 100%, 90%-100%, 80%-90%, 70-80%, 60-70%, 50-60% or 30-50%. Decreasing the DMSO concentration reduces the viscosity of the solution, which is desirable in certain applications where rapid "wetting" of the reactive column is needed.

Vortexing the SNP with the solvent solution should allow everything to dissolve.

Desiccant. In this example, the desiccant is calcium chloride. A bulk portion of anhydrous calcium chloride (particle size less than 7.0 mm) is sieved down to range between 12 mesh and 18 mesh. A variation of this formulation would be 4 mesh to 20 mesh.

Ensuring that the desiccant is packed uniformly is desirable. One approach to ensure uniform packing is to pack the desiccant area in fractions, such as thirds.

Additional advantages and modifications will readily occur to those skilled in the art. For example, although the illustrative embodiments, method implementations and examples provided herein above were described primarily in terms of a system comprising a base unit, a breath bag and a cartridge, one may integrate these components. Therefore, the invention in its broader aspects is not limited to the specific details, representative devices and methods, and illustrative examples shown and described. Accordingly, departures may be made from such details without departing from the spirit or scope of the general inventive concept as defined by the appended claims and their equivalents.

We claim:

1. A method for extending an effective working range of an analyzer for measuring an analyte in a breath sample, the method comprising:
    initiating a reaction in the analyzer that produces an optically discernable reaction product having an optical property that is indicative of a concentration of the analyte in the breath sample, wherein initiating the reaction comprises causing a liquid reagent to be brought into contact within a disposable cartridge with an interactant material that has been exposed to the breath sample;
    taking a first reading of the optical property at a first time during the reaction;
    comparing the first reading to a reference and, if the comparison of the first reading to the reference has a first state, determining the concentration using the first reading; and
    if the comparison of the first reading to the reference has a second state different from the first state, determining the concentration of the analyte using a second reading of the optical property, the second reading taken after the first reading.

2. A method as recited in claim 1, wherein the determining of the concentration using the first reading is conducted using a first calibration data set.

3. A method as recited in claim 2, wherein the determining of the concentration using the second reading is conducted using a second calibration data set.

4. A method as recited in claim 3, wherein the first calibration data set calibrates the analyzer to measure the analyte over a first working range of less than 20 ppm and the second calibration data set extends the first working range by at least 100%.

5. A method as recited in claim 2, wherein the first calibration data set calibrates the analyzer to measure the analyte over a working range of 0 to 10 ppm of the analyte.

6. A method as recited in claim 1, further comprising displaying the concentration.

7. A method as recited in claim 1, wherein the optical property comprises intensity.

8. A method as recited in claim 1, wherein the first reading is taken during a kinetic phase of the reaction.

9. A method as recited in claim 1, wherein the method is performed under control of a programmed processor.

10. A method as recited in claim 1, wherein the method is performed automatically by the analyzer.

11. A method as recited in claim 1, wherein the analyzer has an effective working range equal to the sum of at least a first working range and a second working range, wherein the second working range is at least 100% of the first working range.

12. A method as recited in claim 11, wherein the second working range is at least 300% of the first working range.

13. A method for extending an effective working range for measurement of an analyte in a breath sample using a breath analysis device, the method comprising, by a portable breath analysis device:
    initiating a reaction that produces an optically discernable reaction product having an optical property that is indicative of the concentration of the analyte in the breath sample, wherein initiating the reaction comprises causing a liquid reagent to be brought into contact within a disposable cartridge with an interactant material that has been exposed to the breath sample;
    taking a first reading of the optical property at a first time;
    comparing the first reading to a reference and, if the comparison of the first reading to the reference has a first state, determining the concentration using the first reading;
    if the comparison of the first reading to the reference has a second state, adjusting a process parameter of the breath analysis device and taking a second reading of the optical property at a second time subsequent to the adjusting of the process parameter, and using the second reading to determine the concentration of the analyte using a calibration process, the second reading taken after the first reading; and,
    outputting an indication of the concentration of the analyte.

14. A method as recited in claim 13, wherein the first reading is taken during a kinetic phase of the reaction.

15. A method as recited in claim 13, wherein the method is performed under control of a programmed processor of the portable breath analysis device.

16. A method as recited in claim 13, wherein the adjusting of the process parameter comprises adjusting the process parameter to avoid saturation of the reaction.

17. A method as recited in claim 13, wherein the optical property comprises intensity.

18. A method as recited in claim 13, wherein the taking of the second reading is commenced within six minutes following the initiating of the reaction.

19. A method as recited in claim 18, wherein the initiating of the reaction comprises releasing a nitroprusside solution into a reaction volume.

20. A method as recited in claim 19, wherein outputting the indication of the concentration of the analyte comprises displaying a measurement of concentration of acetone within a range of 0 ppm to 120 ppm.

21. A breath analysis device, comprising:
  a breath input port coupled to a flow path;
  an interactant material housed within a reactive region of the flow path such that a breath sample that passes along the flow path is exposed to the interactant material;
  an optical sensor configured to measure a color change produced by a chemical reaction in which a liquid reactant is brought into contact with the interactant material after the interactant material is exposed to the breath sample; and
  a processor programmed to generate a measurement of a concentration of an analyte in the breath sample by a process that comprises:
    generating a first color measurement with the optical sensor at a first time during the chemical reaction;
    determining whether the first color measurement satisfies a predefined condition;
    when the first color measurement satisfies the predefined condition, using the first color measurement to generate the measurement of the concentration of the analyte; and
    when the first color measurement does not satisfy the predefined condition, using a second color measurement generated with the optical sensor after the first optical measurement to generate the measurement of the concentration of the analyte.

22. The breath analysis device of claim 21, wherein the first color measurement is generated during a kinetic of the chemical reaction.

23. The breath analysis device of claim 21, wherein the first color measurement is a color intensity measurement.

* * * * *

UNITED STATES PATENT AND TRADEMARK OFFICE
CERTIFICATE OF CORRECTION

PATENT NO.       : 9,636,044 B2
APPLICATION NO.  : 15/040838
DATED            : May 2, 2017
INVENTOR(S)      : Lubna M. Ahmad It is certified that error appears in the above-identified patent and that said Letters Patent is hereby corrected as shown below:

On the Title Page

In Column 1 at Line 9 (approx.), Change "continuation-in-part" to --continuation--.

In the Specification

In Column 5 at Line 58, Change "nitroprus side," to --nitroprusside,--.

In Column 5 at Lines 59-60, Change "dischloroisocyanourate," to --dichloroisocyanurate,--.

In Columns 21-22 at Line 54 (approx.), Change "bronchiesctasis" to --bronchiectasis--.

In Columns 23 at Line 55, Change "ketoacidocis" to --ketoacidosis--.

In Columns 23-24 at Line 3, Change "mercaptane" to --mercaptan--.

In Column 36 at Line 3, Change "polyethyelene." to --polyethylene.--.

In Column 37 at Lines 7-8, Change "polyethyelene." to --polyethylene.--.

In Column 44 at Lines 43-44, Change "It is The pressed tightly against the interactant beads" to --It is then pressed tightly against the interactant beads--.

In Column 47 at Line 60, Change "aminated and nitroprus side-attached" to --aminated and nitroprusside-attached--.

In Column 53 at Lines 50, Change "Wals" to --Waals--.

In Column 68 at Line 23, Change "C-40)." to --C40).--.

Signed and Sealed this
Twenty-fourth Day of October, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,636,044 B2

In Columns 69-70 at Line 43 (approx.), Change "Dichloroisocyanourate," to --Dichloroisocyanurate,--.

In Column 71 at Lines 27-28, Change "glydoxypropyl" to --glycidoxypropyl--.

In Column 77 at Line 27, Change "fuschin" to --fuchsin--.

In Column 77 at Line 28, Change "fuschin" to --fuchsin--.

In Column 88 at Line 52, Change "(H2504)" to --($H_2SO_4$)--.